United States Patent
Connolly et al.

(10) Patent No.: US 7,244,738 B2
(45) Date of Patent: Jul. 17, 2007

(54) ARYLAMINE-SUBSTITUTED QUINAZOLINONE COMPOUNDS USEFUL AS ALPHA 1A/B ADRENERGIC RECEPTOR ANTAGONISTS

(75) Inventors: Terrence Joseph Connolly, Redwood City, CA (US); Paul Francis Keitz, Redwood City, CA (US); Eun Kyung Lee, San Jose, CA (US); Jim Li, San Jose, CA (US); Francisco Javier Lopez-Tapia, Union City, CA (US); Patrick Finbar McGarry, Mountain View, CA (US); Chris Richard Melville, Palo Alto, CA (US); Dov Nitzan, San Jose, CA (US); Counde O'Yang, Sunnyvale, CA (US); Fernando Padilla, Fremont, CA (US); Klaus Kurt Weinhardt, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 216 days.

(21) Appl. No.: 10/884,768

(22) Filed: Jul. 2, 2004

(65) Prior Publication Data

US 2005/0038016 A1 Feb. 17, 2005

Related U.S. Application Data

(60) Provisional application No. 60/484,570, filed on Jul. 2, 2003.

(51) Int. Cl.
- *A61K 31/517* (2006.01)
- *A01N 43/54* (2006.01)
- *C07D 239/72* (2006.01)
- *A61K 31/549* (2006.01)
- *C07D 417/02* (2006.01)
- *C07D 285/26* (2006.01)

(52) U.S. Cl. .............. 514/266.3; 514/266.2; 544/287

(58) Field of Classification Search ............ 514/266.3, 514/266.2; 544/287
See application file for complete search history.

(56) References Cited

U.S. PATENT DOCUMENTS

| | | | |
|---|---|---|---|
| 4,442,094 A | 4/1984 | Atkinson et al. |
| 5,084,457 A | 1/1992 | Fanshawe et al. |
| 5,869,665 A | 2/1999 | Padia |
| 6,156,758 A | 12/2000 | Kung et al. |
| 6,376,667 B1 | 4/2002 | Castelhano et al. |

FOREIGN PATENT DOCUMENTS

| | | |
|---|---|---|
| DE | 22 58 561 A1 | 6/1973 |
| EP | 0 498723 A1 | 8/1992 |
| WO | WO 95/12592 A1 | 5/1995 |
| WO | WO 99/42456 A2 | 8/1999 |
| WO | WO 99/48878 A1 | 9/1999 |
| WO | WO 01/10860 A2 | 2/2001 |
| WO | WO 01/70737 A2 | 9/2001 |
| WO | WO 01/81340 A2 | 11/2001 |
| WO | WO 02/24667 A1 | 3/2002 |
| WO | WO 02/48152 A2 | 6/2002 |
| WO | WO 02/053558 A1 | 7/2002 |

OTHER PUBLICATIONS

Hess, H. et. al., "Antihypertensive 2-Amino-4(3H)-quinazolinones", J. Med. Chem., 1968, vol. 11, pp. 130-136.*
DeRuiter, et al., Design and Synthesis of 2-(Arylamino)-4(3H)-quinazolinones as Novel Inhibitors of Rat Lens Aldose Reductase, *J. Med. Chemical*, (1986), pp. 627-629, 29(5).
Klopman, et al., "An Artificial Intelligence Approach to the Study of the Structural Moieties Relevant to Drug-Receptor Interactions in Aldose Reductase Inhibitors," *Mol. Pharmacol.*, (1988), pp. 852-862, 34(6).
Hess, et al., "Antihypertensive 2-Amino-4(3H)-quinazolinones," *J. Med. Chemical*, (1968), pp. 130-136, 11(1).
Andrus M.B., et al., "A Modified Synthesis of Iodoazidoaryl Prazosin", Journal Organic Chemistry (2002) pp. 8284-8286, vol. 67.
ABSTRACT Database Beilstein XP002315228 Szabo, Vinkler, S., Acta Chim. Acad. Sci. Hung., (1958) pp. 201-207, vol. 17.

* cited by examiner

*Primary Examiner*—Emily Bernhardt
*Assistant Examiner*—Tamthom N. Truong
(74) *Attorney, Agent, or Firm*—Robert C. Hall

(57) ABSTRACT

Compounds represented by Formula I:

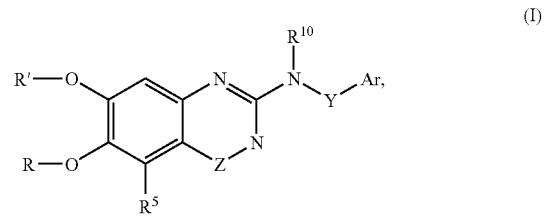

which are useful as are alpha-1A/B adrenoceptor antagonists, to methods of treating conditions associated with the activity of alpha-1A/B adrenoceptors, and to methods of making said compounds, wherein Ar, Z, R, R', $R^5$ and $R^{10}$ are as defined herein.

11 Claims, No Drawings

ARYLAMINE-SUBSTITUTED QUINAZOLINONE COMPOUNDS USEFUL AS ALPHA 1A/B ADRENERGIC RECEPTOR ANTAGONISTS

CROSS REFERENCE TO PRIOR APPLICATION

This application claims benefit under Title 35 U.S.C. 119(e) of U.S. Provisional Application No. 60/484,570, filed Jul. 2, 2003, which is hereby incorporated by reference in its entirety

FIELD OF THE INVENTION

This invention relates to quinazolinone compounds, more particularly, to 2-arylamine substituted quinazolinone compounds and salts thereof which are useful as alpha-1-adrenergic receptor antagonists. The invention further relates to pharmaceutical compositions containing said compounds, to methods for their use as therapeutic agents, and to processes for making said compounds.

BACKGROUND OF THE INVENTION

Alpha-1-adrenergic receptors are G-protein coupled transmembrane receptors that mediate various actions of the sympathetic nervous system through the binding of the catecholamines, epinephrine, and norepinephrine (NE). Currently, several subtypes of the alpha-1 adrenergic receptors are known to exist for which the genes have been cloned: alpha-1A (previously known as alpha-1C), alpha-1B and alpha-1D.

Alpha-1 adrenoceptor antagonists have been shown in numerous clinical studies to be effective in relieving the symptoms associated with benign prostatic hypertrophy, also known as benign prostatic hyperplasia (BPH), an illness typically affecting men over fifty. The symptoms of the condition include, but are not limited to, increased difficulty in urination and sexual dysfunction. Drugs such as prazosin, indoramin, doxazosin and tamsulosin are in common clinical use for BPH, and are effective in reducing both "obstructive" symptoms (e.g. weak stream) and "irritative" symptoms (e.g. nocturia, urinary urge and frequency). However, these compounds are all non-subtype-selective and have the potential to cause significant side-effects, particularly cardiovascular effects such as postural hypotension, dizziness, and syncope, and CNS effects such as aesthenia (tiredness). These effects can limit dosing and the clinical efficacy in reducing symptoms associated with BPH.

Pharmacological studies resulting in the subdivision of alpha-1 adrenoceptors into alpha-1A, alpha-1B, and alpha-1D adrenoceptors have led to the suggestion that development of subtype-selective antagonists may allow for an improved symptomatic treatment of BPH with a lower incidence of dose-limiting side-effects. Recently, much interest has been focused on the role of the alpha-1A adrenoceptor subtype in BPH, as studies have shown that this subtype predominates in the urethra and prostate of man and appears to be the receptor mediating NE-induced smooth muscle contraction in these tissues. See, e.g., Price et al., *J. Urol.* (1993), 150, at 546–551; Faure et al., *Life Sci.* (1994), 54 at 1595–1605; Taniguchi et al., *Naunyn Schmiedeberg's Arch. Pharmacol.* (1997), 355 at 412–416; Forray et al., *Mol. Pharmacol.* (1994), 45 at 703–708; Hatano et al., *Br. J. Pharmacol.* (1994), 113 at 723–728; and Marshall et al., *Br J. Pharmacol.* (1995), 115, at 781–786. Smooth muscle tone is believed to contribute substantially to the total urinary outflow obstruction observed in patients with BPH [Furuya et al., *J. Urol.* (1982), 128 at 836–839]. Increased prostate mass is also a contributing factor. These observations have fuelled the hypothesis that an alpha-1A subtype-selective antagonist may, via a selective and significant decrease in outlet resistance, lead to improved pharmacotherapy for BPH.

However, in BPH, it is often the irritative symptoms which prompt the patient to seek treatment, and these irritative symptoms may be present in patients with no demonstrable obstruction (i.e. normal urine flow rates). Thus, it would be advantageous to provide a therapy for treating patients exhibiting obstructive symptoms and/or irritative symptoms. It is believed that reduction of obstructive and irritative symptoms in patients with BPH may be achieved via a combination of alpha-1A and alpha-1B subtype selectivity in a drug molecule. The lack of alpha-1D adrenoceptor antagonism is expected to lead to reduced or fewer side effects than those associated with the use of non-subtype-selective agents.

The instant invention provides arylamine-substituted quinazolinone compounds that are useful as alpha 1 a/b adrenergic receptor antagonists. Certain arylamine quinazoline compounds useful for other purposes are disclosed in Hess et al., Anti-hypertensive 2-Amino-4(3H)-quinazolinones, *Medical Research Laboratories*, Pfizer & Co. (January 1968); Klopman et al., *Molecular Pharmacology*, "An Artificial Intelligence Approach to the Study of the Structural Moieties Relevant to Drug-Receptor Interactions in Aldose Reductase Inhibitors," Vol. 34, No. 6 (December 1988); DeRuiter et al., "Design and Synthesis of 2-(*Arylamino*)-4 (3*H*)-*quinazolinones as Novel Inhibitors of Rat Lens Aldose Reductase,*" *J. Med. Chem.* Vol. 29 (1986), at pp. 627–29.

All publications, patents, and patent applications cited herein, whether supra or infra, are each hereby incorporated by reference in its entirety.

SUMMARY OF THE INVENTION

The present invention is directed to compounds useful as alpha 1A/B adrenergic receptor antagonists having the Formula (I),

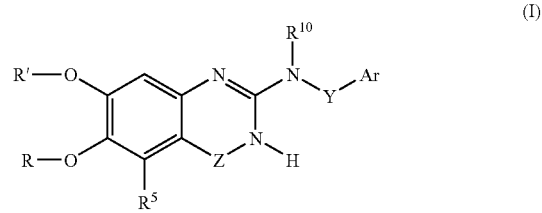

wherein,
Y is optionally-substituted $C_{1-4}$alkylene, $C_{2-4}$alkenylene, heterocyclylene, or heterocyclyl$C_{1-4}$alkylene;
Z is —C(=O)— or —S(=O)$_2$—;
R and R' are alkyl;
$R^5$ is selected from hydrogen, halogen, cyano, hydroxy, —$R^6$, and —$OR^6$;
$R^6$ is selected from alkyl, aryl, heteroaryl, cycloalkyl, and heterocyclyl;
$R^{10}$ is selected from hydrogen, alkyl, hydroxyalkyl, aminoalkyl and aralkyl;
Ar is optionally-substituted aryl or heteroaryl, provided that if $R^5$ is hydrogen, then Y—Ar considered together are not (i) unsubstituted benzyl, (ii) benzyl having a para substituent selected from hydroxy and $CO_2H$, or (iii) benzyl having a hydroxy meta substituent;

or an isomer or pharmaceutically-acceptable salt, hydrate, or prodrug thereof.

The compounds of Formula (I) above are surprisingly advantageous in selectively antagonizing the alpha-1A and alpha-1B subtype receptors with selectively lesser activity in antagonizing the alpha-1D adrenergic receptor, particularly compounds where $R^5$ is other than hydrogen. Accordingly, said compounds of Formula (I) are surprisingly advantageous in methods for treating diseases responsive to alpha-1A and alpha-1B receptor antagonism with reduced side effects.

Another aspect of this invention relates to the methods of treating a subject having a disease state that is alleviated by treatment with an alpha 1A/B adrenergic receptor antagonist, which comprises administering to such a subject in need of treatment therefore, a therapeutically effective amount of at least one compound of Formula I.

Still another aspect of the invention relates to a process for making the claimed compounds. In particular, the inventors herein have discovered a process for making intermediate diones of the formula (II),

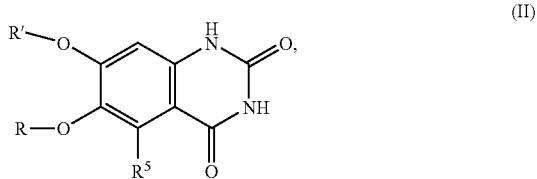

wherein R, R' and $R^5$ are as described above in the Summary of Invention, from nitrobenzoic acid compounds having the formula,

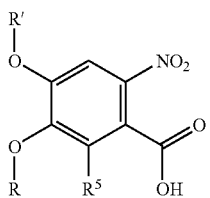

via reduction of the nitro group to an amino group in a water-based solvent, by addition of base, heterogenous catalyst, and exposure to a hydrogen atmosphere. This process is amendable to large-scale synthesis and is high-yielding and environmentally friendly.

DETAILED DESCRIPTION OF THE INVENTION

Definitions

Unless otherwise stated, the following terms used in this application, including the specification and claims, have the definitions given below. As used in the specification and the appended claims, the singular forms "a", "an," and "the" include plural referents unless the context clearly dictates otherwise.

As used herein, the term "alkyl" means a linear or branched, saturated monovalent hydrocarbon moiety of one to eight carbon atoms (preferably one to six carbon atoms), e.g., methyl, ethyl, n-propyl, 2-propyl, tert-butyl, pentyl, and the like. "Lower alkyl" means an alkyl of one to four carbon atoms. When a subscript is used herein following a carbon atom, the subscript refers to the number of carbon atoms that the named group may contain. Thus, for example, $C_{1-4}$alkyl means an alkyl of one to four carbon atoms (i.e., lower alkyl) including methyl, ethyl, propyl, iso-propyl, butyl, and tert-butyl; hydroxy($C_{1-4}$)alkyl means an alkyl of one to four carbon atoms substituted with a hydroxy group; $C_{1-4}$alkoxyalkyl means an alkyl group substituted with an alkoxy group wherein the alkoxy group has one to four carbon atoms; $C_{1-4}$alkoxy($C_{1-4}$)alkyl means an alkyl group of one to four carbon atoms substituted with an alkoxy group wherein the alkoxy group has one to four carbon atoms; and so forth.

"Alkylene" means a linear or branched, saturated bivalent hydrocarbon moiety of one to eight (preferably one to six) carbon atoms, e.g., methylene, ethylene, propylene, and the like.

When the term "alkyl" is used as a suffix following another term, as in "phenylalkyl," or "hydroxyalkyl," this is intended to refer to an alkyl group, as defined above, being substituted with one or two (preferably one) substituent(s) selected from the other, specifically-named group, also as defined herein. For example, "phenylalkyl" includes benzyl, phenylethyl, 2-phenylbutyl, and so forth. "Hydroxyalkyl" includes 2-hydroxyethyl, 1-(hydroxymethyl)-2-methylpropyl, 3,4-dihydroxybutyl, and so forth. "Alkoxyalkyl" refers to an alkyl group substituted with one to two of OR', wherein R' is alkoxy as defined below.

The term "substituted alkyl" refers to an alkyl group as defined above having one, two, three, or four substituents (preferably one to two substituents), independently selected from the group consisting of halo, haloalkoxy, trifluoromethyl, cyano, nitro, —OR$^a$, —SR$^a$, —S(O)R$^c$, —S(O)$_2$R$^c$, —C(=O)R$^a$, —C(=O)NR$^a$R$^b$, —C(O)$_2$R$^a$, —C(O)$_2$NR$^a$R$^b$, —S(O)$_2$NR$^a$R$^b$, —NR$^a$R$^b$, —NR$^a$(C=O)R$^b$, aryl, heteroaryl, cycloalkyl, and/or heterocyclo, wherein R$^a$ and R$^b$ are independently selected from hydrogen, $C_{1-6}$alkyl, aryl, heteroaryl, cycloalkyl, and heterocyclo, and R$^c$ is selected from alkyl, aryl, heteroaryl, cycloalkyl, and heterocyclo, and each of R$^a$, R$^b$, and R$^c$ in turn is optionally substituted with one, two, or three of alkyl, halo, haloalkyl, OR$^e$, haloalkoxy, cyano, —NR$^e$R$^f$, —SO$_2$(alkyl), —CO$_2$R$^e$, —C(=O)R$^e$, and/or —NR$^e$C(=O)R$^f$, and/or a $C_{1-6}$alkyl substituted with one to two of halo, OR$^e$, haloalkoxy, cyano, —NR$^e$R$^f$, —SO$_2$(alkyl), —CO$_2$R$^e$, —C(=O)R$^e$, and/or —NR$^e$C(=O)R$^f$, wherein R$^e$ and R$^f$ are independently selected from hydrogen, alkyl, aminoalkyl, hydroxyalkyl, alkoxyalkyl, cyanoalkyl, haloalkyl, and alkylaminoalkyl. Additionally, when a substituted alkyl group is substituted with a cyclic group such as aryl, heteroaryl, cycloalkyl, or heterocyclo, it is understood said cyclic group in turn may be substituted with one, two or three groups selected from alkyl, halo, haloalkyl, OR$^e$, haloalkoxy, cyano, —NR$^e$R$^f$, —SO$_2$(alkyl), —CO$_2$R$^c$, —C(=O)R$^e$, and/or —NR$^e$C(=O)R$^f$, and/or a $C_{1-6}$alkyl substituted with one to two of halo, OR$^e$, haloalkoxy, cyano, —NR$^e$R$^f$, —SO$_2$(alkyl), —CO$_2$R$^e$, —C(=O)R$^e$, and/or —NR$^e$C(=O)R$^f$, wherein R$^e$ and R$^f$ are as defined immediately above.

The term "substituted alkylene" means an alkylene group as defined above wherein one, two or three carbon atoms of the alkylene straight or branched chain is substituted with a group selected from those recited above for substituted alkyl groups.

The term "substituted lower alkyl" means an alkyl of one to four carbon atoms having one, two, or three substituents selected from those recited above for substituted alkyl.

The term "alkenyl" means a linear or branched, unsaturated monovalent hydrocarbon moiety of two to eight carbon atoms (preferably two to six carbon atoms), having at least one double bond, e.g., ethenyl, propenyl, butenyl, and the like. "Lower alkenyl" means an alkenyl of two to four carbon atoms.

"Alkenylene" means a linear or branched, unsaturated bivalent hydrocarbon moiety of two to eight (preferably two to six) carbon atoms, having at least one double bond, e.g., ethenylene, propenylene, and the like.

The term "substituted alkenyl" refers to an alkenyl group as defined above having one, two, or three substituents, as valence permits (preferably one substituent), independently selected from the group of substituents recited above for "substituted alkyl." A "substituted alkenylene" has one, two, or three substituents, as valence permits (preferably one substituent), independently selected from the group of substituents recited for "substituted alkyl."

"Alkoxy" refers to the group OR, wherein R is alkyl or substituted alkyl. A "lower alkoxy" is a group —OR' wherein R' is $C_{1-4}$alkyl.

When the term "oxy" is used as a suffix following another specifically-named group, as in "aryloxy", "heteroaryloxy," or "arylalkyloxy", this means that an oxygen atom is present as a linker to the other, specifically-named group. Thus, for example, "aryloxy" refers to the group —O—R, wherein R is aryl; "heteroaryloxy" refers to the group —O—R', wherein R' is heteroaryl; and "arylalkyloxy" refers to the group —O—R'', wherein R'' is arylalkyl such as benzyl. Similarly, a "substituted aryloxy" means the group —O—R, wherein R is substituted aryl, and a "substituted heteroaryloxy" means the group —O—R', wherein R' is substituted heteroaryl.

"Amino" refers to the group $NH_2$. Thus, an aminoalkyl refers to an alkyl group having an amino substituent, e.g., —$CH_2$—$NH_2$, —$CH_2$—$CH_2$—$NH_2$, —$CH_2$—$CH(NH_2)$—$CH_3$, and so forth.

"Alkylamino" as used herein refers to monoalkylamino groups having the formula —NHR, as well as dialkylamino groups having the formula —NRR', wherein each R and R' are selected from alkyl and substituted alkyl groups as defined above.

An "alkylaminoalkyl" refers to an alkyl group substituted by one to two of —NHR and/or —NRR', wherein each R and R' is as defined above. A "lower alkylamino" refers to a group —NHR' or —NR'R', wherein each R' is $C_{1-4}$alkyl.

"Aminoalkoxy" means a group —O—R—NHR' or —O—R—NR'R'' wherein R is alkylene as defined herein and R' and R'' each independently are alkyl as defined herein.

As used herein, the term "alkoxyalkylamino" refers to the group —NR$^f$R$^g$, wherein R$^f$ is hydrogen, alkyl, or alkoxyalkyl, and R$^g$ is an alkoxyalkyl (i.e., an alkyl group substituted with an alkoxy).

"Alkoxyalkylaminoalkyl" refers to refers to an alkyl group as defined above that is substituted with an alkoxyalkylamino group as defined above.

A "hydroxyalkylamino" refers to the group —NR$^h$R$^i$, wherein R$^h$ is hydrogen, alkyl, or hydroxyalkyl, and R$^i$ is hydroxyalkyl (i.e., an alkyl group substituted with hydroxy).

"Hydroxyalkylaminoalkyl" refers to refers to an alkyl group as defined above that is substituted with a hydroxyalkylamino group as defined above.

"Aminoalkoxy" means a group —O—R—NHR' or —O—R—NR'R'' wherein R is alkylene as defined above and R' and R'' each independently are alkyl as defined above.

The term "alkylsulfonyl" refers to the group —$SO_2$R, wherein R' is alkyl or substituted alkyl, and "alkylsulfinyl" refers to the group —S(=O)R, wherein R is alkyl or substituted alkyl. Thus, accordingly, methylsulfonyl refers to —$SO_2CH_3$, and methylsulfinyl refers to the group —S(=O)$CH_3$.

"Alkylsulfonylalkyl" means an alkyl group as defined above substituted with an alkylsulfonyl group as defined herein.

"Alkylsulfonylaminoalkyl" means a group —R—NR'—$SO_2$—R'' wherein R is alkylene as defined above and R' and R' each independently are alkyl as defined herein.

"Acetamidinyl" means a group of the formula:

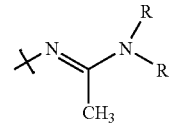

wherein each R is independently hydrogen or alkyl as defined herein.

"Alkoxyalkyl" means a group —R—OR' wherein R is alkylene as defined above and R' is alkyl as defined herein.

"Alkoxyalkoxy" means a group —O—R—OR' wherein R is alkylene as defined above and R' is alkyl as defined herein.

The term "carboxy" refers to the group $CO_2H$. Thus, a carboxyalkyl is an alkyl group as defined above having at least one substituent that is —$CO_2H$.

The term alkoxycarbonyl refers to the group —C(=O)R', wherein R' is alkoxy as defined above, i.e., alkoxycarbonyl is $CO_2R$, wherein R' is alkyl or substituted alkyl, as defined above. A "lower alkoxycarbonyl" refers to the group $CO_2R'$, wherein R' is lower alkyl. Thus, an alkylalkoxycarbonyl is an alkyl group as defined above having at least one substituent that is —$CO_2R$, wherein R' is alkyl or substituted alkyl, as defined above.

"Alkoxyalkylaminocarbonyl" means a group —(C=O)—NR—R'—OR'' wherein R is hydrogen or alkyl as defined herein, R' is alkylene as defined herein, and R'' is alkyl as defined herein.

"Hydoxyalkylaminocarbonyl" means a group —(C=O)—NR—R'—OH'' wherein R is hydrogen or alkyl as defined herein and R' is alkylene as defined herein.

"Aminoalkylaminocarbonyl" means a group —(C=O)—NR—R'—NR''R''' wherein R is hydrogen or alkyl as defined herein, R' is alkylene as defined herein, and each R'' independently is hydrogen or alkyl as defined herein.

"Heterocyclylalkylaminocarbonyl" means a group —(C=O)—NR—R'—R'' wherein R is hydrogen or alkyl as defined herein, R' is alkylene as defined herein, and R'' is heterocyclyl as defined herein.

The term alkylamidyl or alkylamide refers to the group —NH(C=O)R or —NR'(C=O)R, wherein R is alkyl or substituted alkyl, and R' is lower alkyl. A lower alkylamidyl is a group —NH(C=O)R' or —NR'(C=O)R', where R' is lower alkyl.

The term "aryl" refers to a monovalent, monocyclic or bicyclic moiety in which at least one of the rings is an aromatic, carbocyclic moeity. Thus, the term "aryl" includes phenyl, 1-napthyl, and 2-napthyl. The term "aryl" also includes phenyl rings having fused thereto a second nonaromatic carbocyclic ring, or second fused heteroaryl or heterocyclic ring (thus, the term aryl includes groups such as benzothienyl, benzopyrazolyl, benzopiperadinyl, benzocyclohexyl, and the like), with the understanding, however, that in the case of bicyclic aryl groups, the point of attachment will be to the phenyl ring.

A "substituted aryl" is an aryl group as defined above having one to four (preferably one to two) substituents independently selected from the group consisting of halo, haloalkyl, haloalkoxy, cyano, hydroxy, alkoxy, alkyl, substituted alkyl, —SO$_2$R$^r$, —NR$^p$SO$_2$R$^r$, —NR$^p$C(=O)R$^q$, —NR$^p$R$^q$, —C(=O)NR$^p$R$^q$, —SO$_2$NR$^p$R$^q$, —NR$^p$C(=NR$^s$)R$^q$, —N=C(R$^t$)R$^u$, —SO$_2$N=C(R$^t$)R$^u$, —C(=O)R$^p$, —CO$_2$R$^p$, and —OR$^p$, heterocyclo, heteroaryl, phenyl and cycloalkyl, wherein each R$^r$, R$^p$, and R$^q$ is selected from hydrogen, alkyl, substituted alkyl, cycloalkyl, heterocyclo, aryl, and heteroaryl, except R$^r$ is not hydrogen, R$^s$ is selected from hydrogen, alkyl, substituted alkyl, cycloalkyl, and heterocyclo, or alternatively, R$^p$ and R$^q$ when attached to the same nitrogen atom may be taken together to form a heterocyclo or heteroaryl; R$^t$ is selected from hydrogen, alkyl, substituted alkyl, cycloalkyl, and heterocyclo, and R$^u$ is amino or alkylamino, or alternatively, R$^t$ and R$^u$ are taken together to form a cycloalkyl or heterocyclo ring. It should be understood that when an aryl group is substituted by a further ring, and/or when any of R$^p$, R$^q$, R$^r$, R$^s$, R$^t$ and R$^u$ are selected from and/or form a ring, said cyclic groups in turn are optionally substituted with one to three groups selected from alkyl, substituted alkyl, halogen, haloalkoxy, trifluoromethyl, cyano, nitro, —OR$^a$, —SR$^a$, —S(O)R$^c$, —S(O)$_2$R$^c$, —C(=O)R$^a$, —C(=O)NR$^a$R$^b$, —C(O)$_2$R$^a$, —C(O)$_2$NR$^a$R$^b$, —S(O)$_2$NR$^a$R$^b$, —NR$^a$R$^b$, and/or —NR$^a$(C=O)R$^b$, wherein R$^a$, R$^b$ and R$^c$ are as defined above in the definition of substituted alkyl groups.

The term "carbocyclic" means a cyclic moiety in which all ring atoms are carbon atoms, including saturated, partially unsaturated, and unsaturated rings.

"Carbamylalkyl" means a group of the formula:

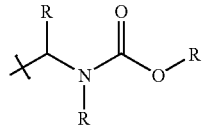

wherein each R is independently hydrogen or alkyl.

The term "cycloalkyl" as used herein refers to saturated or partially unsaturated, monovalent, monocyclic carbocyclic moieties of three to seven ring carbon atoms and further includes such rings having a carbon-carbon bridge of one, two, or three bridgehead carbon atoms, and/or having a second ring fused thereto, with the understanding that the point of attachment will be to the non-aromatic carbocyclic ring moiety. Thus, the term "cycloalkyl" includes such rings as cyclopropyl, cyclopentyl, cyclopentenyl, cyclohexyl, cyclohexenyl, and the like. Additionally, one or two carbon atoms of a cycloalkyl group may optionally contain a carbonyl oxygen group, e.g., one or two atoms in the ring may be a moiety of the formula —C(=O)—.

A "substituted cycloalkyl" is a cycloalkyl group as defined above having one to four (preferably one to two) substituents independently selected from the group consisting of substituents recited above for substituted aryl.

"Formamidinyl" means a group of the formula:

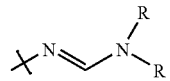

wherein R is hydrogen or alkyl as defined herein. The term "N,N-dimethyl formamidine" or "N,N-dimethyl formamidinyl" refers to the above group wherein R is methyl.

The term "halo," "halide" or "halogen," when referring to a substituent means fluoro, chloro, bromo, or iodo (preferably fluoro or chloro).

The term "haloalkyl" means alkyl substituted with one or more same or different halo atoms, e.g., —CH$_2$Cl, —CF$_3$, —CH$_2$CF$_3$, —CH$_2$CCl$_3$, and the like, and further includes those alkyl groups such as perfluoroalkyl in which all alkyl hydrogen atoms are replaced by fluorine atoms.

The term "haloalkoxy" means a haloalkyl group as defined above linked through an oxygen atom, e.g., it includes —O—CH$_2$Cl, —O—CF$_3$, —O—CH$_2$CF$_3$, —O—CH$_2$CCl$_3$, and the like.

"Haloalkylamino" means a group —NH—R" or —NR'—R" wherein R' is alkyl or haloalkyl as defined herein and R" is haloalkyl as defined herein.

"Haloalkylaminoalkyl" means a group —R—NH—R" or —NR'—R" wherein R is alkylene as defined herein, R' is alkyl or haloalkyl as defined herein and R" is haloalkyl as defined herein.

"Hydroxyalkyl" means a group —R—OH wherein R is alkylene as defined herein.

"Hydroxyalkoxy" means a group —O—R—OH wherein R is alkylene as defined herein.

"Heterocyclo," "heterocyclyl," or "heterocyclic" refers to a saturated or partially-unsaturated non-aromatic monocyclic or bicyclic moiety in which one or two ring atoms are heteroatoms selected from N, O, or S(O)$_x$ (where x is an integer from 0 to 2), the remaining ring atoms being carbon atoms, and additionally, one or two carbon atoms may optionally contain a carbonyl oxygen group, e.g., one or two atoms in the ring may be a moiety of the formula —C(=O)—. Thus, the term heterocyclo includes rings such as tetrahydropyranyl, tetrahydrofuryl, piperidinyl, piperazinyl, morpholinyl, pyrrolidinyl, pyrrolinyl, imidazolidinyl, imidazolinyl, and the like, as well as such rings having a carbonyl oxygen atom in the ring. In the case of a bicyclic heterocyclo, one of the two rings may be a carbocyclic ring with the understanding that in such cases the point of attachment will be to the heterocyclic ring.

"Heterocyclylalkylamino" means a group —NR—R'—R" wherein R is hydrogen or alkyl as defined herein, R' is alkylene as defined herein, and R" is heterocyclyl as defined herein.

When reference is made to an imidazolinyl group, this is intended to refer to both

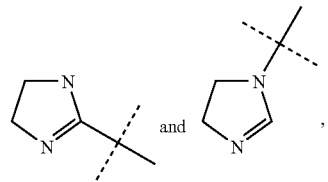

inclusive.

Imidazolinyl groups as defined herein may be optionally substituted with alkyl.

"Imidazolinylalkyl" means a group —R—R' wherein R is alkylene as defined herein and R' is imidazolinyl as defined herein.

A "substituted heterocyclo" or "substituted heterocycle" refers to a heterocyclo group as defined above having one to four substituents (preferably one to two substituents) selected from the group of substituents recited above for substituted aryl.

A "heterocyclylene" means a bivalent heterocyclyl group as defined above, i.e., a heterocyclyl attached to two other groups (e.g., —$NR^{10}$ and Ar in compounds of Formula I).

A "heterocyclyl$C_{1-4}$alkylene" means a group X—R, wherein X is a heterocyclyl as defined above and R is a $C_{1-4}$alkylene as defined above. An optionally-substituted "heterocyclyl$C_{1-4}$alkylene" means a group X—R, wherein X is an optionally-substituted heterocyclyl as defined herein and R is an optionally substituted $C_{1-4}$alkylene as defined herein.

"Heteroaryl" means a monovalent, monocyclic aromatic moiety of 5 to 6 ring atoms containing one, two, three, or four ring heteroatoms, each independently selected from N, O, or S, the remaining ring atoms being carbon, and it also includes such rings having a second ring fused thereto of five to six ring atoms, wherein the second fused ring may be aromatic or nonaromatic and may be carbocyclic, heterocyclic, or a heteroaryl ring, with the understanding, however, that in such cases the point of attachment will be to an aromatic ring containing at least one heteroatom. Thus, the term heteroaryl includes, but is not limited to, pyridyl, furyl, thiophenyl, thiazolyl, isothiazolyl, triazolyl, imidazolyl, isoxazolyl, pyrrolyl, pyrazolyl, pyrimidinyl, benzofuryl, isobenzofuryl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and derivatives thereof.

A "substituted heteroaryl" is a heteroaryl ring as defined above having one to four (preferably one or two) substituents selected from the group of substituents recited above for substituted aryl.

"Optionally substituted pyrrolidinyl" means a group:

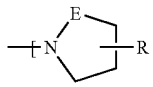

wherein E is —$CH_2$— or —(C═O)— and R is alkyl, alkoxy or hydroxy.

"Optionally substituted pyrrolidinylalkyl" means a group —R—R' wherein R is alkylene as defined herein and R' is imidazolinyl as defined herein.

"Ureidylalkyl" means a group:

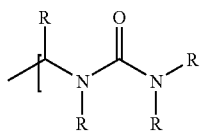

wherein each R is independently hydrogen or methyl.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event may but need not occur, and it includes instances where the event occurs and instances in which it does not. For example, "optionally-substituted cycloalkyl" refers to both cycloalkyl groups and substituted cycloalkyl groups, as defined above. When the term "optionally-substituted" precedes a number of different types of rings in one line or string, e.g., as in "optionally-substituted cycloalkyl or heterocyclo", or "optionally-substituted carbocyclic or heterocyclic ring," or "optionally-substituted aryl, heteroaryl, cycloalkyl, or heterocyclo," it is intended that the term "optionally-substituted" modifies each of the rings identified in the line or string.

When the term "optionally-substituted" is used with respect to a particularly-named cyclic group, such as "optionally-substituted imidazolyl," or "optionally-substituted imidazolidinyl," it should be understood that the optional substituents for such particularly-named rings may be selected from the group of substituents recited above with respect to which the genus of which the particularly-named group is a member. Thus, for example, an "optionally-substituted imidazolyl" may be an unsubstituted imidazolyl or an imidazolyl group having one, two, or three substituents selected from those recited above for substituted heteroaryl groups. An optionally-substituted phenyl or benzyl ring will include an unsubstituted phenyl or benzyl group, and a phenyl or benzyl group having substituents selected from those recited above for substituted aryl groups.

It should be understood that when reference is made to a specific heterocyclo or cycloalkyl group, such as cyclopentyl, pyrrolidinyl, pyrrolinyl, and imidazolinyl, such reference is intended to include such rings wherein optionally one to two carbon atoms of the named ring contain a carbonyl oxygen group, e.g., one or two atoms in the ring may be a moiety of the formula —C(═O)—, as set forth above in the definition of cycloalkyl and heterocyclo.

An optionally-substituted benzyl group means a benzyl group wherein the phenyl portion of the group is unsubstituted or substituted as defined above in the definition for substituted aryl.

A benzyl group having a para substituent selected from hydroxy and $CO_2H$, means a group having the formula

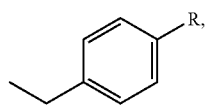

wherein R is hydroxy or $CO_2H$, and benzyl having a hydroxy meta substituent means a group having the formula,

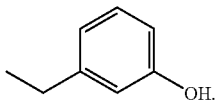

When reference is made herein to substituents on the quinazolinone core, e.g., the "five position substituent," the numbering of the ring atoms is intended to be as follows:

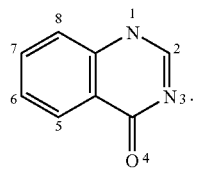

"Pharmaceutically acceptable excipient" means an excipient that is useful in preparing a pharmaceutical composition that is generally safe, non-toxic and neither biologically nor otherwise undesirable. The term includes excipients that are acceptable for veterinary use as well as human pharmaceutical use. A "pharmaceutically acceptable excipient" as used in the specification and claims includes both one and more than one such excipient.

"Pharmaceutically acceptable salt" of a compound means a salt that is generally safe, non-toxic and neither biologically nor otherwise undesirable, and which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, trifluoroacetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, and the like.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I, and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego (1992), Chapter 8: "Prodrugs and Drug delivery Systems" pp. 352–401; *Design of Prodrugs*, edited by H. Bundgaard, Elsevier Science, Amsterdam (1985); *Design of Biopharmaceutical Properties through Prodrugs and Analogs*, Ed. by E. B. Roche, American Pharmaceutical Association, Washington (1977); and *Drug Delivery Systems*, ed. by R. L. Juliano, Oxford Univ. Press, Oxford (1980).

"Solvate" means solvent addition form that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate.

"Protecting group" refers to an atom or group of atoms that is attached to a reactive group in a molecule and masks, reduces, or prevents the reactivity of the group to which it is attached.

Examples of protecting groups can be found in Green and Wuts, *Protective Groups in Organic Chemistry* (Wiley, 2$^{nd}$ ed. 1991), and Harrison and Harrison et al., *Compendium of Synthetic Organic Methods*, Vols. 1–8 (John Wiley and Sons, 1971–1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like. Representative hydroxy protecting groups include those where the hydroxy group is either acylated or alkylated such as with benzyl or lower alkyl and trityl ethers as well as alkyl ethers, tetrahydropyranyl ethers, trialkylsilyl ethers, and allyl ethers.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers," and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the (R) and (S) sequencing rules of Cahn and Prelog, or by the manner in which the molecule rotates the plane of polarized light and designated as dextrorotatory or levorotatory (i.e., as (+) or (−)-isomers respectively). A chiral compound can exist as either an individual enantiomer or as a mixture thereof. A mixture containing different enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures (racemic or otherwise) thereof. The methods for the determination of stereochemistry and the separation of stereoisomers are well-known in the art (see March, *Advanced Organic Chemistry*, Chap. 4, 4th edition, John Wiley and Sons, New York [1992]).

"Tautomers" refers to compounds whose structures differ markedly in arrangement of atoms, but which exist in easy and rapid equilibrium. It is to be understood that compounds of Formula I may be depicted as different tautomers. For example, compounds of Formula I wherein Z is —C(O)—, may be depicted in the following tautomer forms:

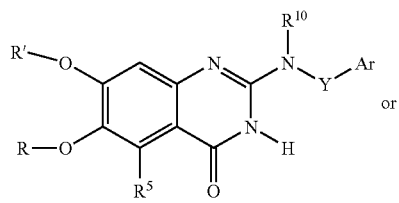

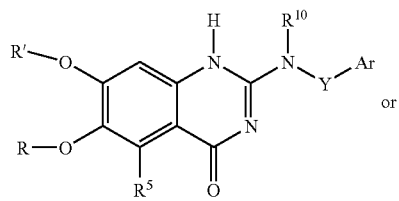

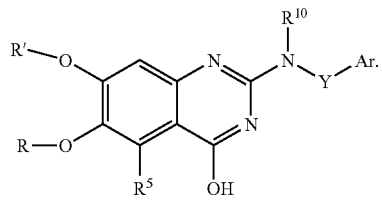

Compounds of Formula I may also contain other groups that exist in tautomeric equilibrium. For example some of the compounds contain an imidazolin-2-yl amino group which may be in equilibrium with an imidazolin-2-ylidenamino group:

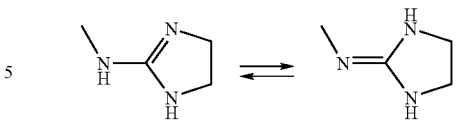

It should also be understood that when compounds have tautomeric forms, all tautomeric forms are intended to be within the scope of the invention, and the naming of the compounds does not exclude any tautomer form.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the progression of the disease, i.e., arresting or reducing the development of the disease or its symptoms; and (3) relieving the disease, i.e., causing regression of the disease or its symptoms.

"A therapeutically effective amount" means the amount of a compound that, when administered to a mammal for treating a disease, is sufficient to effect a treatment for the disease. The "therapeutically effective amount" will vary depending on such factors as the compound being administered, the type of disease being treated, the progression or severity of the disease state, and the age, weight, and general health of the mammal being treated.

"Patient" means mammals and non-mammals. Mammals means any member of the mammalia class including, but not limited to, humans, non-human primates such as chimpanzees and other apes and monkey species; farm animals such as cattle, horses, sheep, goats, and swine; domestic animals such as rabbits, dogs, and cats; and laboratory animals such as rats, mice, and guinea pigs. Examples of non-mammals include, but are not limited to, birds, reptiles, and the like.

"Pharmacological effect" as used herein encompasses effects produced in the patient that achieve the intended purpose of a therapy. In one preferred embodiment, a pharmacological effect means that primary indications of the patient being treated are prevented, alleviated, or reduced. For example, a pharmacological effect would be one that results in the prevention, alleviation or reduction of primary indications in a treated patient. In another preferred embodiment, a pharmacological effect means that disorders or symptoms of the primary indications of the patient being treated are prevented, alleviated, or reduced.

"Disease state" means any disease, condition, symptom, or indication.

"Disorders of the urinary tract" or "uropathy" refer to pathologic changes in the urinary tract and symptoms thereof. Disorders of the urinary tract include overactive bladder (also known as detrusor hyperactivity), outlet obstruction, outlet insufficiency, pelvic hypersensitivity, incontinence, benign prostatic hypertrophy or hyperplasia (BPH), prostatitis, detrusor hyperreflexia, urinary frequency, nocturia, urinary urgency, pelvic hypersensitivity, urge incontinence, urethritis, prostatodynia, cystitis, and idiophatic bladder hypersensitivity.

"Overactive bladder" or "Detrusor hyperactivity" includes, but is not limited to, changes symptomatically manifested as urgency, frequency, reduced bladder capacity, and incontinence episodes; changes urodynamically manifested as changes in bladder capacity, micturition threshold, unstable bladder contractions, and sphincteric spasticity; and symptoms usually manifested in detrusor hyperreflexia (neurogenic bladder), in conditions such as outlet obstruction, outlet insufficency, pelvic hypersensitivity, or in idiopathic conditions such as detrusor instability.

"Outlet obstruction" includes, but is not limited to, benign prostatic hypertrophy or benign prostatic hyperplasia (BPH), urethral stricture disease, tumors and the like. It is usually symptomatically manifested as obstructive (low flow rates, difficulty in initiating urination, and the like), or irritative (urgency, suprapubic pain, and the like).

"Outlet insufficiency" includes, but is not limited to, urethral hypermobility, intrinsic sphincteric deficiency, or mixed incontinence. It is usually symptomatically manifested as stress incontinence.

"Pelvic Hypersensitivity" includes but is not limited to, pelvic pain, interstitial (cell) cystitis, prostadynia, prostatitis, vulvadynia, urethritis, orchidalgia, and the like. It is symptomatically manifested as pain, inflammation or discomfort referred to the pelvic region, and usually includes symptoms of overactive bladder.

"Sexual dysfunction" means the inability to achieve a normal sexual response and includes such conditions in males and females. Thus, it includes male erectile dysfunction (MED) and female sexual dysfunction (FSD).

"Disease states associated with the Central Nervous System (CNS)" or "CNS disease states" mean neurological and/or psychiatric changes in the CNS, e.g., brain and spinal cord, which manifest in a variety of symptoms. Examples of CNS disease states include, but are not limited to, migraine headache; cerebrovascular deficiency; psychoses including paranoia, schizophrenia, attention deficiency, and autism; obsessive/compulsive disorders including anorexia and bulimia; posttraumatic stress disorders, sleep disorders, convulsive disorders including epilepsy and withdrawal from addictive substances; cognitive diseases including Parkinson's disease and dementia; and anxiety/depression disorders such as anticipatory anxiety (e.g., prior to surgery, dental work and the like), depression, mania, seasonal affective disorder (SAD), and convulsions and anxiety caused by withdrawal from addictive substances such as opiates, benzodiazepines, nicotine, alcohol, cocaine, and other substances of abuse; and improper thermoregulation.

PREFERRED EMBODIMENTS

The compounds of this invention demonstrate selectivity for the alpha-1A/B subtype over the alpha-1D subtype. The compounds of this invention may reduce both obstructive and irritative symptoms in patients with BPH. The attenuated antagonism of alpha 1D-adrenoceptor is expected to lead to reduced or fewer side effects than those associated with the use of non-subtype-selective agents. The compounds of the invention are of the Formula (I)

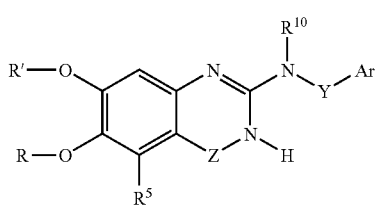

(I)

wherein,
Y is optionally-substituted $C_{1-4}$alkylene, $C_{2-4}$alkenylene, heterocyclylene, or heterocyclyl$C_{1-4}$alkylene;
Z is —C(=O)— or —S(=O)$_2$—;
R and R' are alkyl;
$R^5$ is selected from hydrogen, halogen, cyano, hydroxy, —$R^6$, and —$OR^6$;
$R^6$ is selected from alkyl, aryl, heteroaryl, cycloalkyl, and heterocyclyl;
$R^{10}$ is selected from hydrogen, alkyl, hydroxyalkyl, aminoalkyl and aralkyl;
Ar is optionally substituted aryl or heteroaryl, provided that if $R^5$ is hydrogen, then Y—Ar considered together are not (i) unsubstituted benzyl, (ii) benzyl having a para substituent selected from hydroxy and $CO_2H$, or (iii) benzyl having a hydroxy meta substituent;
or an isomer or pharmaceutically-acceptable salt, hydrate, or prodrug thereof.

Preferred compounds are those compounds having the Formula (Ia),

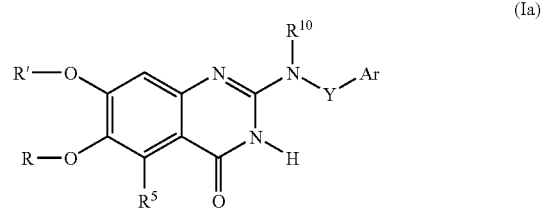

(Ia)

and isomers or pharmaceutically-acceptable salts, hydrates, or prodrugs thereof, wherein:
Y is —(CHR$^1$)— or —(CHR$^2$—CHR$^3$)—;
$R^1$, $R^2$ and $R^3$ are independently selected from hydrogen, lower alkyl, and hydroxy, or $R^2$ and $R^3$ may together form a bond so that Y is ethenylene;
R and R' are lower alkyl;
$R^5$ is selected from halogen, cyano, hydroxy, —$R^6$, and —$OR^6$;
$R^6$ is selected from alkyl, aryl, heteroaryl, and cycloalkyl;
$R^{10}$ is selected from hydrogen, alkyl, hydroxyalkyl, aminoalkyl and aralkyl; and
Ar is optionally-substituted aryl or heteroaryl.

In compounds of Formula (I) as set forth in the description and claims herein, and in Formula (Ia) as set forth above, preferred compounds are those in which $R^5$ is not hydrogen. Even more preferred are compounds where $R^5$ is selected from halogen, hydroxy, cyano, —$R^6$, and —$OR^6$, wherein $R^6$ is selected from $C_{1-4}$alkyl, aminoalkyl, $C_{1-4}$alkylamino ($C_{1-4}$alkyl), hydroxyalkyl, alkoxyalkyl, phenoxyalkyl, benzyloxyalkyl, cycloalkylalkyl, phenyl, benzyl, and cycloalkyl, wherein each of said phenyl, benzyl, and cycloalkyl groups is optionally substituted with one to two of lower alkyl, substituted lower alkyl, cyano, and/or halogen. Even more preferred are compounds wherein $R^5$ is selected from methyl, ethyl, n-propyl, isopropyl, cyano, halogen, methoxy, and ethoxy. Most preferred are compounds wherein $R^5$ is methyl or methoxy.

In compounds of Formulae (I) and (Ia), preferably R and R'are both $CH_3$.

In compounds of Formulae (I) and (Ia), preferably $R^{10}$ is selected from hydrogen, alkyl, amino($C_{1-6}$)alkyl, ($C_{1-6}$)alkylamino($C_{1-6}$)alkyl, hydroxy($C_{1-6}$)alkyl, and an optionally-substituted five or six membered heterocyclo or $C_{3-7}$cycloalkyl. More preferred are compounds wherein $R^{10}$ is selected from hydrogen, lower alkyl, amino($C_{1-4}$)alkyl, ($C_{1-4}$)alkylamino($C_{1-2}$)alkyl, hydroxy($C_{1-4}$)alkyl, and piperidinyl optionally-substituted with lower alkyl or benzyl. Even more preferred are compounds where $R^{10}$ is selected from hydrogen, lower alkyl, hydroxymethyl, hydroxyethyl, —$C_{1-4}$alkylene-$NH_2$, —$C_{1-4}$alkylene-NH($CH_3$), and/or —$C_{1-4}$alkylene-N($CH_3$)$_2$, and most preferred are compounds wherein $R^{10}$ is methyl or ethyl.

In certain embodiments of Formulae (I) and (Ia), Ar is phenyl substituted with a group selected from:

a) optionally substituted alkenyl;

b) optionally-substituted alkyl having one two or three substituents independently selected from —$NR^d(C=O)NR^aR^b$, —$NR^a(C=O)OR^c$ and —$NR^aS(O)_2R^c$ wherein $R^a$, $R^b$, and $R^d$ are independently hydrogen, $C_{1-6}$alkyl, aryl, heteroaryl, cycloalkyl, or heterocyclo, and $R^c$ is alkyl, aryl, heteroaryl, cycloalkyl, or heterocyclo, and each of $R^a$, $R^b$, $R^c$, and $R^d$ in turn is optionally substituted with one, two, or three of alkyl, halo, haloalkyl, $OR^e$, haloalkoxy, cyano, —$NR^eR^f$, —$SO_2$(alkyl), —$CO_2R^e$, —$C(=O)R^e$, and/or —$NR^eC(=O)R^f$, and/or a $C_{1-6}$alkyl substituted with one to two of halo, $OR^e$, halo alkoxy, cyano, —$NR^eR^f$, —$SO_2$(alkyl), —$CO_2R^e$, —$C(=O)R^e$, and/or —$NR^eC(=O)R^f$, wherein $R^e$ and $R^f$ are independently hydrogen, alkyl, aminoalkyl, hydroxyalkyl, alkoxyalkyl, cyanoalkyl, haloalkyl, or alkylaminoalkyl; and c) —$NR^jS(O)_2NR^pR^q$, —$NR^jC(=O)NR^pR^q$, —$NR^pC(=O)OR^r$, —$NR^pC(=O)C(=O)R^q$, and —$NR^jC(=O)NR^p OR^q$ wherein each $R^j$, $R^p$, $R^q$, and $R^r$ is independently hydrogen, alkyl, substituted alkyl, cycloalkyl, heterocyclo, aryl, or heteroaryl, except $R^r$ is not hydrogen, or alternatively, $R^p$ and $R^q$ when attached to the same nitrogen atom may be taken together to form a heterocyclo or heteroaryl. It should be understood that when any of $R^j$, $R^p$, $R^q$, and $R^r$ is and/or forms a ring, said cyclic groups in turn are optionally substituted with one to three substituents selected from the group consisting of alkyl, substituted alkyl, halogen, haloalkoxy, trifluoromethyl, cyano, nitro, —$OR^a$, —$SR^a$, —$S(O)R^c$, —$S(O)_2R^c$, —$C(=O)R^a$, —$C(=O)NR^aR^b$, —$C(O)_2R^a$, —$C(O)_2NR^aR^b$, —$S(O)_2NR^aR^b$, —$NR^aR^b$, and —$NR^aC(=O)R^b$.

In certain embodiments of Formulae (I) and (Ia), Ar is

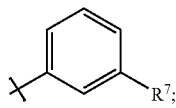

and $R^7$ may be selected from hydroxyalkoxy, optionally substituted pyrrolodinyl, alkylaminoalkyl, alkylsulfonylaminoalkyl, haloalkylaminoalkyl, alkoxyalkylaminoalkyl, hydroxyalkylaminoalkyl, aminoalkoxy, aminoalkyl, ureidylalkyl, carbamylalkyl, acetamidinyl, formamidinyl, optionally substituted imidazolinyl, optionally substituted pyrrolodinylmethyl, optionally substituted imidazolinylmethl, alkoxyalkylaminocarbonyl, hydroxyalkylaminocarbonyl, aminoalkylaminocarbonyl, heterocyclylalkylaminocarbonyl, and heterocyclylalkylamino.

In other embodiments of Formulae (I) and (Ia) where Ar is

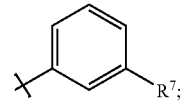

$R^7$ may be selected from methyl-(3,3,3-trifluoro-propyl)-amino-methyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxy-carbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methylamino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxy-ethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyaminocarbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxy-ethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethyl-amino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutane-carboxamidinyl-, imidazolidin-2-ylideneamino-, 1-methyl-pyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-Dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-, 2-oxo-imidazolidin-1-yl-, 3-methyl-2-oxo-imidazolidin-1-yl-, 3-ethyl-2-oxo-imidazolidin-1-yl-, 3-(2-methoxy-ethyl)-2-oxo-imidazolidin-1-yl-, 1H-tetrazol-5-yl-, ethoxy-, 1-pyrrolidin-1-yl-ethyl-, 1-Azetidin-1-yl-ethyl-, aminosulfonyl-, N,N-dimethylamino-acetamidinesulfonyl-, and 1-methanesulfonyl-methylamino)-ethyl-.

In still other embodiments of Formulae (I) and (Ia) where Ar is

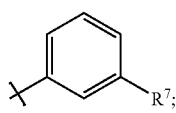

$R^7$ may be selected from:

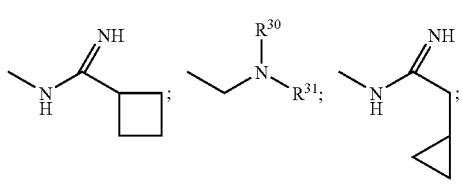

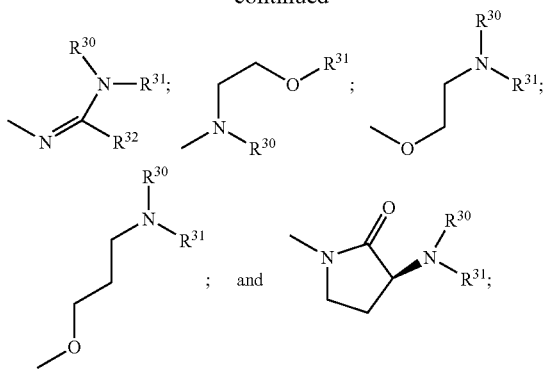

wherein $R^{30}$ and $R^{31}$ each independently is selected from hydrogen, methyl, ethyl, methoxyethyl and hydroxyethyl, and $R^{32}$ is hydrogen, methyl or ethyl.

In yet other embodiments of Formulae (I) and (Ia) where Ar is

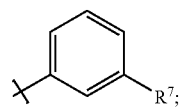

$R^7$ may be selected from:

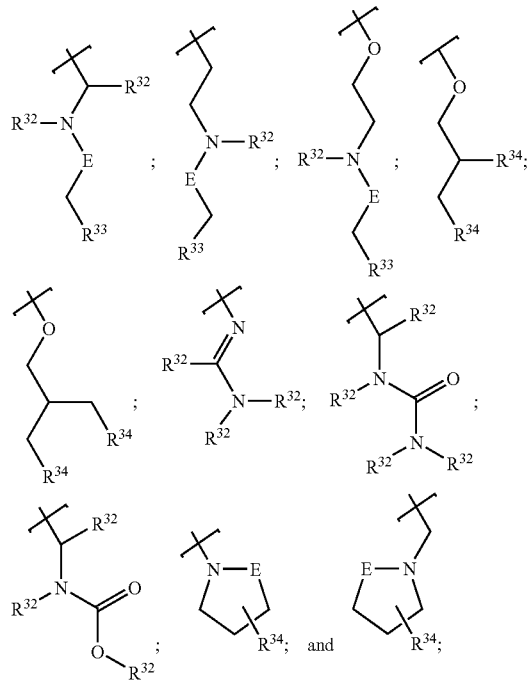

wherein:
each $R^{32}$ independently is hydrogen or alkyl;
each $R^{33}$ independently is hydrogen, alkyl, hydroxy or alkoxy;

each R³⁴ independently is hydroxy or alkoxy; and
E is (C=O) or CH₂.

In certain embodiments of Formulae (I) and (Ia), Ar is

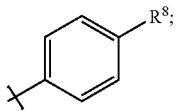

and R⁸ may be selected from hydroxyalkoxy, optionally substituted pyrrolodinyl, alkylaminoalkyl, alkylsulfonylaminoalkyl, haloalkylaminoalkyl, alkoxyalkylaminoalkyl, hydroxyalkylaminoalkyl, aminoalkoxy, aminoalkyl, ureidylalkyl, carbamylalkyl, acetamidinyl, formamidinyl, optionally substituted imidazolinyl, optionally substituted pyrrolodinylmethyl, optionally substituted imidazolinylmethl, alkoxyalkylaminocarbonyl, hydroxyalkylaminocarbonyl, aminoalkylaminocarbonyl, heterocyclylalkylaminocarbonyl, and heterocyclylalkylamino.

In other embodiments of Formulae (I) and (Ia) where Ar is

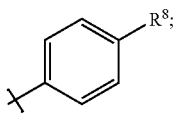

R⁸ may be selected from methyl-(3,3,3-trifluoro-propyl)-amino-methyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxy-carbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methyl-amino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxy-ethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyaminocarbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxyethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethyl-amino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutanecarboxamidinyl-, imidazolidin-2-ylideneamino-, 1-methylpyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-Dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-, 2-oxo-imidazolidin-1-yl-, 3-methyl-2-oxo-imidazolidin-1-yl-, 3-ethyl -2-oxo-imidazolidin-1-yl-, 3-(2-methoxy-ethyl)-2-oxo-imidazolidin-1-yl-, 1H-tetrazol-5-yl-, ethoxy-, 1-pyrrolidin-1-yl-ethyl-, 1-Azetidin-1-ylethyl-, aminosulfonyl-, N,N-dimethylamino-acetamidine-sulfonyl-, and 1-methanesulfonyl-methylamino)-ethyl-.

In still other embodiments of Formulae (I) and (Ia) where Ar is

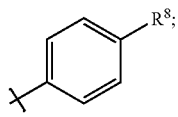

R⁸ may be selected from:

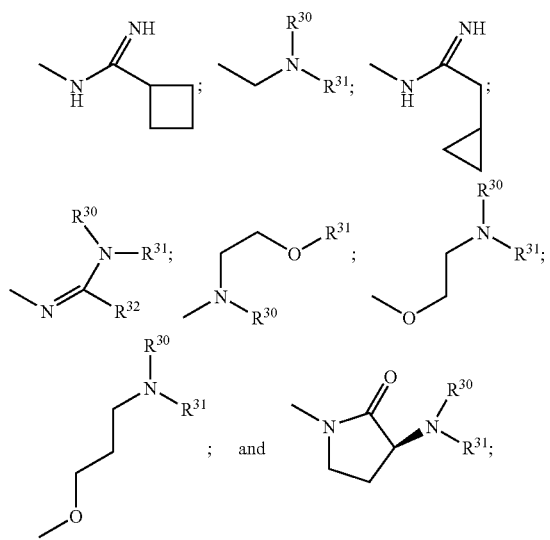

wherein R³⁰ and R³¹ each independently is selected from hydrogen, methyl, ethyl, methoxyethyl and hydroxyethyl, and R³² is hydrogen, methyl or ethyl.

In yet other embodiments of Formulae (I) and (Ia) where Ar is

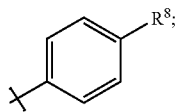

R⁸ may be selected from:

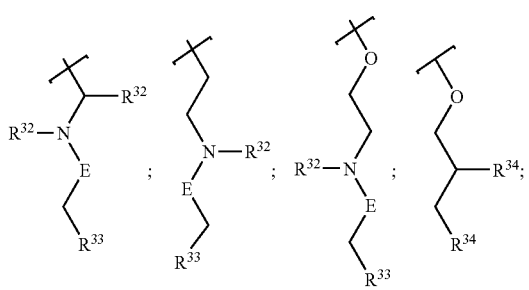

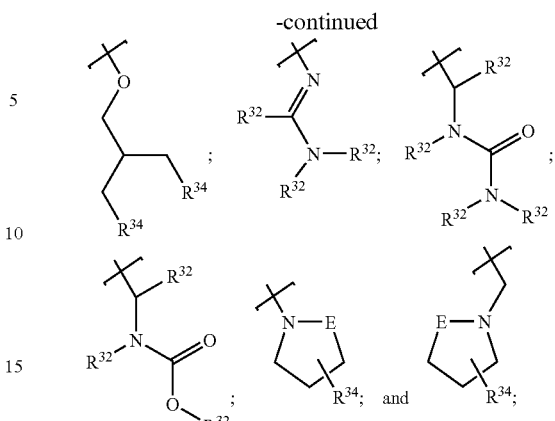

wherein:
each R³² independently is hydrogen or alkyl;
each R³³ independently is hydrogen, alkyl, hydroxy or alkoxy;
each R³⁴ independently is hydroxy or alkoxy; and
E is (C=O) or CH₂.

In certain embodiments of Formulae (I) and (Ia), Y and Ar considered together may be selected from one of (A), (B), (C), or (D):

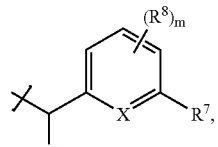
(A)

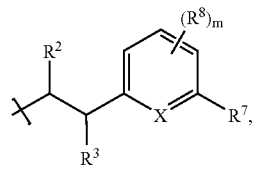
(B)

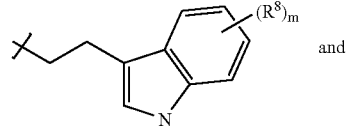
and
(C)

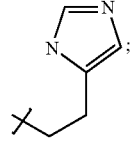
(D)

wherein,
X is N or CH (wherein when X is CH, said hydrogen atom of X is optionally replaced by a substituent R⁸);
R¹, R² and R³ are individually independently selected from hydrogen, lower alkyl, and hydroxy, or R² and R³ together form a bond to define an ethylene group;

R$^7$ is selected from:
a) alkyl, halogen, and cyano;
b) alkyl substituted with one to two of halogen, hydroxy, cyano, —NR$^{12a}$R$^{14a}$, —NR$^{12a}$C(=O)R$^{14a}$, azetidinyl, morpholinyl, pyrrolidinyl, piperidinyl, piperazinyl, imidazolinyl, said rings in turn being optionally substituted with one to two R$^{25}$;
c) —SO$_2$R$^{11}$, —NR$^{12}$SO$_2$R$^{11}$, —NR$^{12}$CO$_2$R$^{11a}$, —NR$^{12}$C(=O)R$^{11a}$, —NR$^{12}$R$^{14}$, —C(=O)NR$^{12}$R$^{14}$, —SO$_2$NR$^{12}$R$^{14}$, —NR$^{12}$C(=NR$^{13}$)R$^{14}$, —N=C(R$^{15}$)R$^{16}$, —SO$_2$N=C(R$^{15}$)R$^{16}$, —C(=O)R$^{17}$, —CO$_2$R$^{17}$, and —OR$^{17}$;
d) heterocyclo or heteroaryl selected from pyrrolidin-2-yl, pyrrolidin-3-yl, imidazolin-2-yl, imidazol-2-yl, piperidinyl, and tetrazolyl, said heterocyclic and heteroaryl rings in turn being optionally substituted as valance permits with one to three of R$^{25}$;

R$^8$ is selected from alkyl, halogen, cyano, alkoxy, amino, alkylamino, alkylsulfonyl, and piperidinyl, each of said R$^8$ groups in turn being optionally substituted with one to two of lower alkyl, lower alkoxy, cyano, and/or halogen;

R$^{11}$ is alkyl, alkylamino, aminoalkyl, or hydroxy(C$_{1-4}$)alkyl;

R$^{11a}$ is alkyl, alkylamino, aminoalkyl, —C(=O)alkyl, N(O)alkyl, or hydroxy(C$_{1-4}$)alkyl;

R$^{12a}$ and R$^{14a}$ are independently selected from hydrogen, alkyl, hydroxyalkyl, lower alkoxyalkyl, haloalkyl, and lower alkylamino(alkyl);

R$^{12}$ and R$^{13}$ are selected from hydrogen, alkyl, and hydroxy(C$_{1-4}$)alkyl;

R$^{14}$ is selected from hydrogen, alkyl, hydroxyalkyl, alkoxyalkyl, aminoalkyl, alkylaminoalkyl, alkylamidylalkyl, cyanoalkyl, pyrrolidinyl, pyrrolinyl, imidazolinyl, pyrimidinyl, tetrahydrofuranyl, furanylalkyl, isothiazolidinyl, oxazolindinyl, tetrahydrofuranylalkyl, morpholinylalkyl, and imidazolylalkyl, said R$^{14}$ cyclic groups in turn being optionally substituted with one, two or three groups where valence allows selected from R$^{25}$;

or alternatively, R$^{12}$ and R$^{14}$ when attached to the same nitrogen atom (as in —NR$^{12}$R$^{14}$, —C(=O)NR$^{12}$R$^{14}$, or —SO$_2$NR$^{12}$R$^{14}$), may be taken together to form pyrrolidinyl, piperidinyl, imidazolinyl, imidazolidinyl, pyrazolyl, or imidazolyl, said rings optionally substituted where valence allows with one, two or three groups selected from R$^{25}$;

R$^{15}$ is selected from hydrogen, alkyl, alkoxyalkyl, and C$_{3-6}$cycloalkyl, and R$^{16}$ is amino or alkylamino, or alternatively, R$^{15}$ and R$^{16}$ are taken together to form a pyrrolidinyl or imidazolidinyl ring optionally substituted with one, two, or three groups selected from R$^{25}$;

R$^{17}$ is selected from hydrogen, alkyl, methylsulfinylalkyl, methylsulfonylalkyl, carboxyalkyl, alkoxycarbonylalkyl, hydroxyalkyl, alkoxyalkyl, aminoalkyl, alkylaminoalkyl, furanyl(C$_{1-4}$)alkyl, tetrahydrofuranyl(C$_{1-4}$)alkyl, morpholinyl(C$_{1-4}$)alkyl, and pyrimidinyl, each R$^{17}$ in turn being optionally substituted where valence allows with one to two groups selected from R$^{25}$;

R$^{25}$ at each occurrence is selected independently of each other R$^{25}$ from lower alkyl, halogen, cyano, alkyl, hydroxy(C$_{1-4}$)alkyl, (C$_{1-4}$)alkoxy(C$_{1-4}$)alkyl, halo(C$_{1-4}$)alkyl, cyano(C$_{1-4}$)alkyl, amino(C$_{1-4}$)alkyl, (C$_{1-4}$)alkylamino(C$_{1-4}$)alkyl, halogen, haloalkoxy, trifluoromethyl, cyano, nitro, —OR$^{26}$, —SR$^{26}$, —S(O)R$^{26}$, —S(O)$_2$R$^{28}$, —C(=O)R$^{26}$, —C(=O)NR$^{26}$R$^{27}$, —C(O)$_2$R$^{26}$, —C(O)$_2$NR$^{26}$R$^{27}$, —S(O)$_2$NR$^{26}$R$^{27}$, —NR$^{26}$R$^{27}$, and/or —NR$^{26}$(C=O)R$^{27}$, wherein R$^{26}$ and R$^{27}$ are selected from hydrogen and C$_{1-4}$alkyl, and R$^{28}$ is C$_{1-4}$alkyl; and m is 0, 1, or 2.

In certain preferred embodiments, Y and Ar considered together may be selected from one of (A) and (B);

R$^5$ is selected from methyl, methoxy, cyano and fluoro; and

R$^7$ is selected from one of pyrrolidinyl, pyrrolinyl, imidazolinyl, —NHC(=NH)R$^{14}$, —N=C(H)(R$^{16}$), —N=C(CH$_3$)(R$^{16}$), —OR$^{17}$, and C$_{1-2}$alkyl optionally substituted with —NR$^{12a}$R$^{14a}$, wherein said pyrrolidinyl, pyrrolinyl and imidazolinyl groups optionally may be substituted with one to two of lower alkyl, hydroxy, lower alkoxy, halogen, cyano, amino, (C$_{1-4}$)alkylamino, hydroxy(C$_{1-4}$)alkyl, amino(C$_{1-4}$)alkyl, and/or (C$_{1-4}$)alkylamino(C$_{1-4}$)alkyl;

R$^{10}$ is methyl;

R$^{14}$ is C$_{3-6}$cycloalkyl or —C$_{1-2}$alkylene-(C$_{3-6}$cycloalkyl);

R$^{16}$ is —NH$_2$, —NH(C$_{1-2}$alkyl), or N(C$_{1-2}$alkyl)$_2$;

R$^{17}$ is —C$_{1-2}$alkylene-NH$_2$, —C$_{1-2}$alkylene-NH(lower alkyl), or —C$_{1-2}$alkylene-N(lower alkyl)$_2$; and R$^{12a}$ and R$^{14a}$ are selected from hydrogen, lower alkyl, hydroxy(C$_{1-4}$alkyl), and —C$_{1-4}$alkylene-O(lower alkyl); and m is 0 or 1.

In certain embodiments of Formulae (I) and (Ia), Y and Ar considered together may be

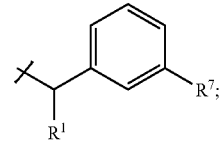

wherein:
R$^1$ is hydrogen, hydroxy, or lower alkyl; and

R$^7$ is selected from one pyrrolidinyl, pyrrolinyl, imidazolinyl, —NR$^{12}$R$^{14}$, —NR$^{12}$C(=NR$^{13}$)R$^{14}$, —N=C(R$^{15}$)(R$^{16}$), —OR$^{17}$, and C$_{1-4}$alkyl optionally substituted with pyrrolidinyl, pyrrolinyl, imidazolinyl, —NR$^{12a}$R$^{14a}$, and/or —OR$^{17a}$, wherein said pyrrolidinyl, pyrrolinyl and imidazolinyl groups in turn optionally may be substituted with one to three groups selected from R$^{25}$;

R$^{12a}$, R$^{14a}$, R$^{17}$, and R$^{17a}$ are independently selected from hydrogen, lower alkyl, hydroxy(C$_{1-4}$alkyl), —C$_{1-4}$alkylene-O(lower alkyl), —C$_{1-4}$alkylene-NH$_2$, —C$_{1-4}$alkylene-NH(lower alkyl), —C$_{1-4}$alkylene-N(lower alkyl)$_2$, and —C$_{1-4}$alkylene-(C$_{3-6}$cycloalkyl);

R$^{12}$ is hydrogen, alkyl, or hydroxy(C$_{1-4}$)alkyl;

R$^{14}$ is selected from hydrogen, alkyl, hydroxyalkyl, alkoxyalkyl, aminoalkyl, alkylaminoalkyl, alkylamidylalkyl, cyanoalkyl, pyrrolidinyl, pyrrolinyl, imidazolinyl, pyrimidinyl, tetrahydrofuranyl, furanylalkyl, isothiazolidinyl, oxazolindinyl, tetrahydrofuranylalkyl, morpholinylalkyl, and imidazolylalkyl, said R$^{14}$ cyclic groups in turn being optionally substituted with one, two or three groups where valence allows selected from R$^{25}$;

or alternatively, R$^{12}$ and R$^{14}$ may be taken together to form pyrrolidinyl, piperidinyl, imidazolinyl, imidazolidinyl, pyrazolyl, or imidazolyl, said rings optionally substituted where valence allows with one, two or three groups selected from R$^{25}$;

R$^{15}$ is independently selected from hydrogen, lower alkyl, hydroxy(C$_{1-4}$)alkyl, and C$_{3-6}$cycloalkyl;

R$^{16}$ is independently amino or (C$_{1-4}$)alkylamino;

or alternatively, R$^{15}$ and R$^{16}$ may be taken together to form a pyrrolidinyl or imidazolinyl ring, wherein said pyrrolidinyl, pyrrolinyl and imidazolinyl groups optionally may be substituted with one to three groups selected from $R^{25}$; and $R^{25}$ at each occurrence is independently selected from lower alkyl, halogen, cyano, hydroxy($C_{1-4}$)alkyl, and ($C_{1-4}$) alkoxy($C_{1-4}$)alkyl.

In certain embodiments of Formulae (I) and (Ia), Ar is 2,3-dihydro-1H-isoindol-5-yl optionally substituted at the 2-position with methyl or 2-methoxyethyl.

In certain embodiments of Formulae (I) and (Ia), Ar is 1H-indol-3-yl.

In certain embodiments of Formulae (I) and (Ia), Y is heterocyclylene such as piperazin-1,4-di-yl or piperidin-1-3-di-yl.

In certain embodiments of Formulae (I) and (Ia), Ar is pyridin 2-yl optionally substituted at the 4-position or 6-position with hydroxyalkoxy, optionally substituted pyrrolodinyl, alkylaminoalkyl, alkylsulfonylaminoalkyl, haloalkylaminoalkyl, alkoxyalkylaminoalkyl, hydroxyalkylaminoalkyl, aminoalkoxy, aminoalkyl, ureidylalkyl, carbamylalkyl, acetamidinyl, formamidinyl, optionally substituted imidazolinyl, optionally substituted pyrrolodinylmethyl, optionally substituted imidazolinylmethl, alkoxyalkylaminocarbonyl, hydroxyalkylaminocarbonyl, aminoalkylaminocarbonyl, heterocyclylalkylaminocarbonyl, or heterocyclylalkylamino.

According to another aspect of the invention, preferred compounds are those compounds having the Formula (Ib),

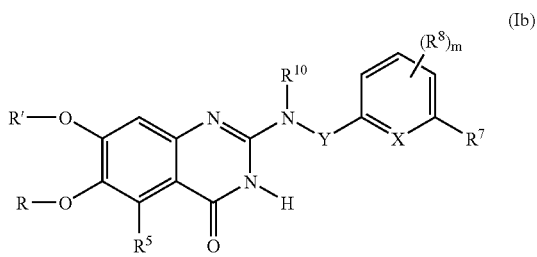

and isomers or pharmaceutically-acceptable salts, hydrates, or prodrugs thereof, wherein:

Y, $R^1$, $R^2$, $R^3$, R, R', $R^5$, and $R^6$ are as defined above for compounds of Formula (Ia);

X is N or CH (wherein when X is CH, said hydrogen atom of X is optionally replaced by a substituent $R^8$);

$R^7$ is selected from alkyl, substituted alkyl, halogen, cyano, $-SO_2R^{11}$, $-NR^{12}SO_2R^{11}$, $-NR^{12}CO_2R^{11a}$, $-NR^{12}C(=O)R^{11a}$, $-NR^{12}R^{14}$, $-C(=O)NR^{12}R^{14}$, $-SO_2NR^{12}R^{14}$, $-NR^{12}C(=NR^{13})R^{14}$, $-N=C(R^{15})R^{16}$, $-SO_2N=C(R^{15})R^{16}$, $-C(=O)R^{17}$, $-CO_2R^{17}$, $-OR^{17}$, heterocyclo, heteroaryl, phenyl, and cycloalkyl, wherein said heterocyclo, heteroaryl, phenyl, and cycloalkyl groups are optionally substituted with up to three $R^{25}$;

$R^8$ is selected from alkyl, lower alkyl, halogen, cyano, halo($C_{1-4}$)alkyl, hydroxy, lower alkoxy, amino, ($C_{1-4}$) alkylamino, ($C_{1-4}$)alkylamino($C_{1-4}$)alkyl, hydroxy($C_{1-4}$) alkyl, ($C_{1-4}$)alkoxy)($C_{1-4}$)alkyl, pyrrolidinyl, and piperidinyl (said pyrrolidinyl and piperidinyl in turn being optionally substituted with one to two of lower alkyl, lower alkoxy, cyano, and/or halogen);

$R^{10}$ is selected from hydrogen, $C_4$alkyl, hydroxy($C_{1-4}$)alkyl, and carboxy($C_{1-4}$)alkyl;

$R^{11}$, $R^{12}$, $R^{13}$, and $R^{15}$ are independently selected from hydrogen, alkyl, hydroxyalkyl, alkoxyalkyl, and cycloalkyl, except $R^{11}$ is not hydrogen;

$R^{11a}$ is selected from alkyl, alkylamino, aminoalkyl, $-C(=O)$alkyl, N(O)alkyl, and hydroxyalkyl;

$R^{16}$ is independently amino or alkylamino; or alternatively, $R^{15}$ and $R^{16}$ may be taken together to form a heterocyclo ring optionally substituted with up to three groups selected from $R^{25}$;

$R^{14}$ and $R^{17}$ are independently selected from hydrogen, alkyl, substituted alkyl, and heterocyclo or heteroaryl optionally substituted with up to three groups selected from $R^{25}$;

or alternatively, $R^{12}$ and $R^{14}$ when attached to the same nitrogen atom (as in $-NR^{12}R^{14}$, $-C(=O)NR^{12}R^{14}$, and $-SO_2NR^{12}R^{14}$), may be taken together to form heterocyclo or heteroaryl ring optionally substituted with up to three groups selected from $R^{25}$;

$R^{25}$ is at each occurrence independently selected as valence permits from alkyl, substituted alkyl, halogen, haloalkoxy, trifluoromethyl, cyano, nitro, $-OR^{26}$, $-SR^{26}$, $-S(O)R^{26}$, $-S(O)_2R^{28}$, $-C(=O)R^{26}$, $-C(=O)NR^{26}R^{27}$, $-C(O)_2R^{26}$, $-C(O)_2NR^{26}R^{27}$, $-S(O)_2NR^{26}R^{27}$, $-NR^{26}R^{27}$, and/or $-NR^{26}(C=O)R^{27}$, wherein $R^{26}$ and $R^{27}$ are selected from hydrogen, $C_{1-6}$alkyl, aryl, heteroaryl, cycloalkyl and heterocyclo, and $R^{28}$ is selected from $C_{1-6}$alkyl, aryl, heteroaryl, cycloalkyl and heterocyclo; and m is 0, 1, or 2.

Even more preferred are compounds of Formula (Ib), as immediately defined above, in which X is CH, m is 0, and $R^7$ is selected from pyrrolidinyl, pyrrolinyl, imidazolinyl, $-NR^{12}R^{14}$, $-NR^{12}C(=NR^{13})R^{14}$, $-N=C(R^{15})(R^{16})$, $-OR^{17}$, and $C_{1-4}$alkyl optionally substituted with pyrrolidinyl, pyrrolinyl, imidazolinyl, $-NR^{12a}R^{14a}$, and/or $-OR^{17a}$, wherein said pyrrolidinyl, pyrrolinyl and imidazolinyl groups in turn optionally may be substituted with one to three of lower alkyl, halogen, cyano, and/or hydroxy ($C_{1-4}$)alkyl; $R^{12}$, $R^{12a}$, $R^{13}$, $R^{14}$, $R^{14a}$, $R^{17}$, and $R^{17a}$ are independently selected from hydrogen, lower alkyl, hydroxy ($C_{1-4}$alkyl), $-C_{1-4}$alkylene-O(lower alkyl), $-C_{1-4}$alkylene-$NH_2$, $-C_{1-4}$alkylene-NH(lower alkyl), $-C_{1-4}$alkylene-N (lower alkyl)$_2$, and $-C_{1-4}$alkylene-($C_{3-6}$cycloalkyl); $R^{15}$ is independently selected from hydrogen, lower alkyl, hydroxy ($C_{1-4}$)alkyl, and $C_{3-6}$cycloalkyl; $R^{16}$ is independently amino or ($C_{1-4}$)alkylamino; or alternatively, $R^{15}$ and $R^{16}$ may be taken together to form a pyrrolidinyl, pyrrolinyl, or imidazolinyl ring, wherein said pyrrolidinyl, pyrrolinyl and imidazolinyl groups optionally may be substituted with one to three of lower alkyl, hydroxy, lower alkoxy, halogen, cyano, amino, ($C_{1-4}$)alkylamino, hydroxy($C_{1-4}$)alkyl, amino($C_{1-4}$) alkyl, and/or ($C_{1-4}$)alkylamino($C_{1-4}$)alkyl.

In certain embodiments of Formula (Ib):

Y is methylene;

R and R' are methyl;

$R^5$ is methoxy or methyl;

one of $R^7$ and $R^8$ is hydrogen, or methoxy, and the other is selected from methyl-(3,3,3-trifluoro-propyl)-amino-methyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxy-carbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methyl-amino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxy-ethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyaminocarbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxyethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethyl-amino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutane-carboxamidinyl-, imidazolidin-2-ylideneamino-, 1-methyl-pyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-, 2-oxo-imidazolidin-1-yl-, 3-methyl-2-oxo-imidazolidin-1-yl-, 3-ethyl-2-oxo-imidazolidin-1-yl-, 3-(2-methoxy-ethyl)-2-oxo-imidazolidin-1-yl-, 1H-tetrazol-5-yl-, ethoxy-, 1-pyrrolidin-1-yl-ethyl-, 1-Azetidin-1-yl-ethyl-, aminosulfonyl-, N,N-dimethylamino-acetamidinesulfonyl-, and 1-methanesulfonyl-methylamino)-ethyl-; and R$^{10}$ is hydrogen or methyl.

According to another aspect of the invention, preferred are those compounds having the Formula (Ic),

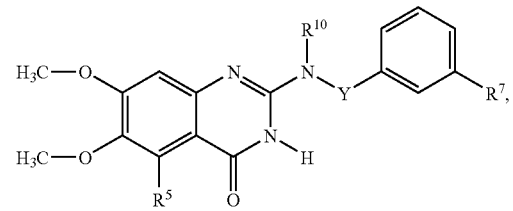

(Ic)

and isomers or pharmaceutically-acceptable salts, hydrates, or prodrugs thereof, wherein:

Y is —(CHR$^1$)— or —(CHR$^2$—CHR$^3$)—;

R$^1$, R$^2$ and R$^3$ are independently selected from hydrogen, lower alkyl, and hydroxy;

R$^5$ is selected from C$_{1-4}$alkyl, halogen, cyano, hydroxy, C$_{1-4}$alkoxy, —O(CH$_2$)$_r$NH$_2$, —O(CH$_2$)$_r$NH(C$_{1-4}$alkyl), —O(CH$_2$)$_r$N(C$_{1-4}$alkyl)$_2$, —O(CH$_2$)$_r$OH, and —O(CH$_2$)$_r$O(C$_{1-4}$alkyl);

R$^7$ is selected from pyrrolidinyl, pyrrolinyl, imidazolinyl, —NR$^{12}$R$^{14}$, —NR$^{12}$C(=NR$^{13}$)R$^{14}$, —N=C(R$^{15}$)(R$^{16}$), —OR$^{17}$, and C$_{1-4}$alkyl optionally substituted with pyrrolidinyl, pyrrolinyl, imidazolinyl, —NR$^{12a}$R$^{14a}$, and/or —OR$^{17a}$, wherein said pyrrolidinyl, pyrrolinyl and imidazolinyl groups optionally may be substituted with one to two of lower alkyl, hydroxy, lower alkoxy, halogen, cyano, amino, (C$_{1-4}$)alkylamino, hydroxy(C$_{1-4}$)alkyl, amino(C$_{1-4}$)alkyl, and/or (C$_{1-4}$)alkylamino(C$_{1-4}$)alkyl;

R$^{10}$ is methyl;

R$^{12}$, R$^{12a}$, R$^{13}$, R$^{14}$, R$^{14a}$, R$^{17}$, and R$^{17a}$ are independently selected from hydrogen, lower alkyl, hydroxy(C$_{1-4}$alkyl), —C$_{1-4}$alkylene-O(lower alkyl), —C$_{1-4}$alkylene-NH$_2$, —C₄alkylene-NH(lower alkyl), —C₁₋₄alkylene-N(lower alkyl)₂, C₃₋₆cycloalkyl, and —C₁₋₄alkylene-(C₃₋₆cycloalkyl);

R$^{15}$ is hydrogen, lower alkyl, hydroxyC₁₋₄alkyl, or C₃₋₆cycloalkyl;

R$^{16}$ is independently amino or (C₁₋₄)alkylamino;

or alternatively, R$^{15}$ and R$^{16}$ may be taken together to form a pyrrolidinyl, pyrrolinyl, or imidazolinyl ring, wherein said pyrrolidinyl, pyrrolinyl and imidazolinyl groups optionally may be substituted with one to three of lower alkyl, halogen, cyano, —C(=O)H, —C(=O) (C₁₋₄)alkyl, amino, (C₁₋₄)alkylamino, hydroxy(C₁₋₄)alkyl, amino (C₁₋₄)alkyl, and (C₁₋₄)alkylamino(C₁₋₄)alkyl; and r is 1, 2, 3, or 4.

Within the above group of compounds according to Formula (Ic), more preferred are compounds having the Formula (Id),

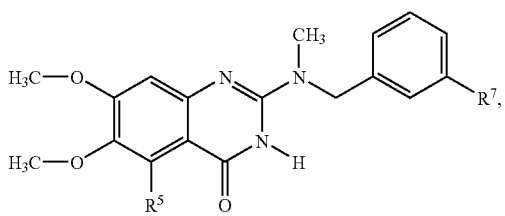

(Id)

wherein R$^5$ is selected from methyl, methoxy, cyano and fluoro; and

R$^7$ is selected from one of pyrrolidinyl, pyrrolinyl, imidazolinyl, —NHC(=NH)R$^{14}$, —N=C(H)(R$^{16}$), —N=C(CH₃)(R$^{16}$), —OR$^{17}$, and C₁₋₂alkyl optionally substituted with —NR$^{12a}$R$^{14a}$, wherein said pyrrolidinyl, pyrrolinyl and imidazolinyl groups optionally may be substituted with one to two of lower alkyl, hydroxy, lower alkoxy, halogen, cyano, amino, (C₁₋₄)alkylamino, hydroxy(C₁₋₄)alkyl, amino(C₁₋₄)alkyl, and/or (C₁₋₄)alkylamino(C₁₋₄)alkyl;

R$^{14}$ is C₃₋₆cycloalkyl or —C₁₋₂alkylene-(C₃₋₆cycloalkyl);

R$^{16}$ is —NH₂, —NH(C₁₋₂alkyl), or N(C₁₋₂alkyl)₂;

R$^{17}$ is —C₁₋₂alkylene-NH₂, —C₁₋₂alkylene-NH(lower alkyl), or —C₁₋₂alkylene-N(lower alkyl)₂; and R$^{12a}$ and R$^{14a}$ are selected from hydrogen, lower alkyl, hydroxy(C₁₋₄alkyl), and —C₁₋₄alkylene-O(lower alkyl).

Within the above group of preferred compounds, more preferred are those compounds as immediately defined above wherein R$^7$ is selected from one of:

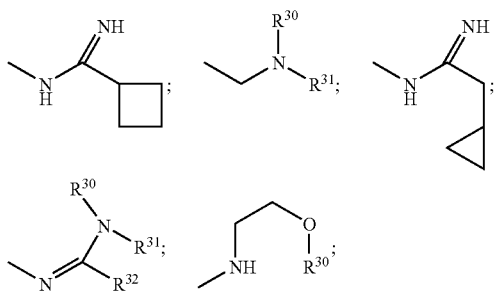

-continued

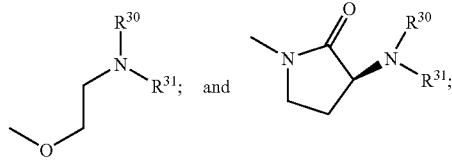

wherein R$^{30}$, R$^{31}$, and R$^{32}$ are independently selected from hydrogen and methyl.

According to another aspect of the invention, combinations of the preferred groups described herein form other preferred embodiments. In this manner, a variety of preferred compounds are embodied within the present invention. For example, another group of preferred compounds, selected from a combination of preferred groups recited above, are those compounds having the formula (Ic), as immediately defined above, wherein R$^5$ is fluoro, cyano, methyl, or methoxy, and R$^{10}$ is methyl. Thus, further combinations of preferred compounds may be selected from the preferred groups recited above.

Among other discoveries, the inventors herein have discovered that a 5-position substituent on the quinazolinone core produces an unexpected and/or surprising advantage with regard to the compounds' effectiveness as selective antagonists of the alpha-1A and alpha-1B adrenoceptors. The 5-position substituent advantageously affects the metabolic pathway for the claimed quinazolinone compounds and increases their bioavailability, thus enhancing their pharmacological effects.

Utility

Alpha-1 adrenoceptors mediate the contractile state of smooth muscle tissue and are present in the human prostate, bladder neck and urethra. Alpha-1 adrenoceptor stimulation also produces contraction of urethral and bladder neck smooth muscle, leading to increased resistance in urinary outflow. Thus, alpha-1 adrenoceptor antagonists may be useful in treating disorders of the urinary tract, as previously defined.

Alpha-1B adrenoceptors are present in the liver, heart and cerebral cortex and are believed to be involved in mediating vascular contractile and blood pressure responses. Alpha-1B adrenoceptors are also present in areas of the spinal cord which receive input from sympathetic neurons originating in the pontine micturition center and are presumed to be involved in the regulation of bladder function. Additionally, alpha-1B adrenoceptor antagonists are useful as analgesic/antihyperalgesic therapies for treating pain, including symptoms of acute pain, inflammatory pain, neuropathic pain (including thermal and mechanical hyperalgesia as well as thermal and mechanical allodynia), complex regional pain syndromes (including reflex sympathetic dystrophy, causalgia and sympathetically maintained pain and the like).

However, it must be noted that in BPH, it is often the irritative symptoms which prompt the patient to seek treatment, and that these irritative symptoms may be present even in patients with no demonstrable obstruction (i.e. normal urine flow rates). By combining both alpha-1A and alpha-1B subtype selectivity in a compound, a reduction of both obstructive and irritative symptoms in patients with BPH may be achieved. Lower levels or lack of alpha-1D adrenoceptor antagonism should lead to reduced or fewer side effects than those associated with the use of non-subtype-selective agents.

In a preferred embodiment, the compounds of this invention are useful for treating disorders and symptoms which can be ameliorated by blockade of alpha 1A/B adrenoceptors, such as reduction or alleviation of urinary tract disorders, for example, pelvic hypersensitivity (including interstitial cystitis, prostatitis, pelvic pain syndrome, infectious cystitis, prostatodynia, and the like), overactive bladder, urinary frequency, nocturia, urinary urgency, detrusor hyperreflexia, outlet obstruction, BPH, prostatitis, urge incontinence, urethritis, idiophatic bladder hypersensitivity, sexual dysfunction, and the like.

In another preferred embodiment, the compounds of this invention are useful for treating disorders and symptoms which can be ameliorated by blockade of alpha-1A/B adrenoceptors, such as reduction or alleviation of pain disorders, for example inflammatory pain, neuropathic pain, cancer pain, acute pain, chronic pain or complex regional pain syndromes.

In a more preferred embodiment, the compounds of this invention are useful for treating disorders and symptoms which can be ameliorated by blockade of both alpha-1A and alpha-1B adrenoceptors with diminished blockade of alpha-1D adrenoceptors, such as reduction or alleviation of both outlet obstruction, such as benign prostatic hypertrophy, and irritative symptoms associated with it, such as pain.

In another preferred embodiment, the compounds of this invention are useful for the improvement of sexual dysfunction including male erectile dysfunction (MED) and female sexual dysfunction (FSD).

These and other therapeutic uses are described, for example, in *Goodman & Gilman's, The Pharmacological Basis of Therapeutics*, ninth edition, McGraw-Hill, New York, 1996, Chapter 26, 601–616; and Coleman, R. A., *Pharmacological Reviews*, 1994, 46, 205–229.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sublingual), rectal, nasal, topical, vaginal, or parenteral (including intramuscular, intraarterial, intrathecal, subcutaneous and intravenous) administration or pulmonary in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) to about 20 milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays may contain in addition to the active ingredient, such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the case of a dropper or pipette, dosing may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example on the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, and starch derivatives such as hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples below.

Abbreviations

Throughout the disclosure, and in the following Schemes and Examples herein, the following abbreviations are used for ease of reference:

| | |
|---|---|
| BOC | tert-butoxycarbonyl |
| BPH | Benign prostatic hypertrophy or benign prostatic hyperplasia |
| CBZ | carbobenzyloxy |
| CNS | Central nervous system |
| DCM | dichloromethane |
| DMF | N,N-Dimethylformamide |
| DMSO | Dimethylsulfoxide |
| EtOH | ethanol |

| | |
|---|---|
| EtOAc | Ethyl Acetate |
| Hal | Halogen or halide |
| KOH | Potassium hydroxide |
| L | Leaving group |
| MeOH | methanol |
| P | Protective group |
| Pd/C | Palladium on carbon |
| THF | Tetrahydrofuran |

General Synthetic Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this application.

The starting materials and the intermediates of the synthetic reaction schemes may be isolated and purified if desired using conventional techniques including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −78° C. to about 150° C., more preferably from about 0° C. to reflux, and most preferably and conveniently at about room (or ambient) temperature, e.g., about 20° C.

Scheme 1

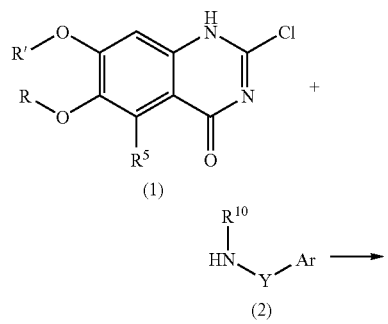

Compounds of formula (Ia) can be prepared by coupling 2-chloro-quinazoline-4-one compounds (1) with amine compounds (2), in a solvent such as EtOH, with or without additives such as diisopropylethylamine. Quinazolin-4-ones can be prepared as described in Cronin et al., *J. Med. Chem*, Vol. 11 (1968), at pp. 130–136, and WO 02/053558 A1, which are incorporated herein by reference. Alternatively, 2-chloro-quinazoline-4-one compounds (1) can be prepared as described below using the method described in Scheme 3.

Scheme 2

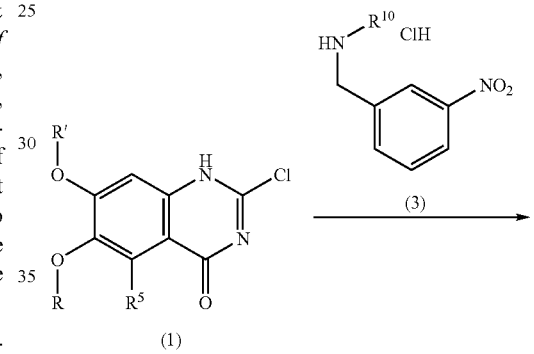

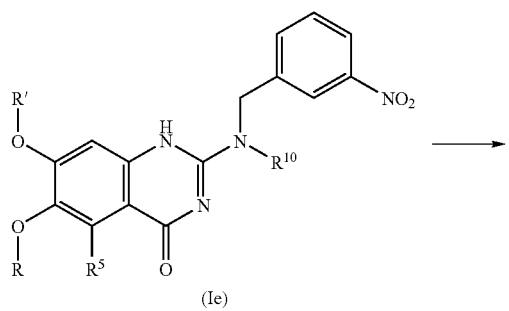

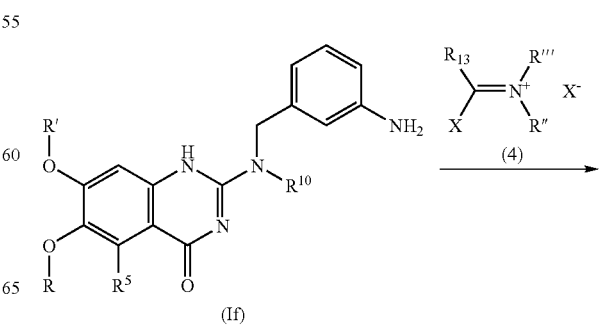

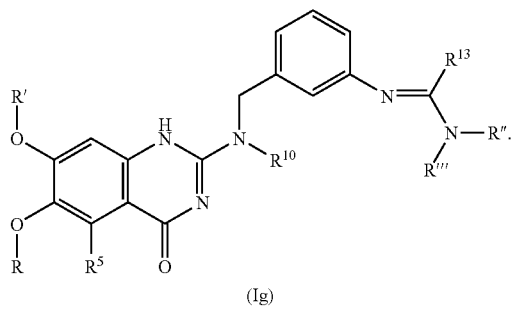

(Ig)

Compounds of formula (Ie), (If), and (Ig) can be prepared from 2-chloro-quinazoline-4-one compounds (1) using the process shown in Scheme 2.

Compounds of formula (Ie), (If), and (Ig) can be also prepared from 2-chloro-quinazoline compounds (1) using the process shown in Scheme 2.

2-Chloro-quinazolin-4-one compounds (1) can be converted to compounds of formula (Ie) by combining amines such as (3) (or a suitable salt of such amines, e.g. HCl salt thereof) with compounds (1) in a solvent, such as isopropanol, and heating the reaction mixture in the presence or absence of an additive like diisopropylethylamine. Compounds (Ie) can be isolated by cooling and filtering the reaction mixture. In some cases, the recovery of product can be increased by adding an anti-solvent (e.g. water) prior to performing the filtration.

Compounds of formula (1f) can be prepared by combining compounds (Ie), a heterogenous catalyst on an inert support (e.g. palladium on carbon), an organic solvent (e.g. ethanol), water, and base (e.g. NaOH). Then, to this reaction mixture, hydrogen is introduced either directly or indirectly (e.g., via transfer hydrogenation using formate salts, hydrazine, etc.), and the nitro group is reduced to an amino group. The catalyst and support are removed, and the reaction mixture is neutralized by addition of acid (e.g. acetic, trifluoroacetic, hydrochloric acid, etc). The precipitated compound of formula (1f) is then collected via filtration.

Compounds of formula (1g) can be prepared by combining compounds of formula (1f) in an organic solvent (methylene chloride, acetonitrile, etc) and a solution of iminium salt (4) (prepared by activation of the appropriate acetamide or formamide with phosphorous oxychloride or trifluoromethanesulfonic anhydride as described by Fabio et al, *J. Med. Chem*, Vol. 21, 273–276 (1978); Campbell et al, *Tetrahedron Letters*, Vol 25, 4813–4816 (1984), and Sforza et al, *Tetrahedron Letters*, Vol 39, 711–714 (1998).) The reaction is quenched by the addition of water, cooled, and then the pH is adjusted to ~8.5 with a base (e.g. NaOH, KOH, etc). The aqueous layer is extracted with an organic solvent (e.g. methylene chloride), then the organic solvent is converted to an alcohol (e.g. isopropanol), heated, cooled then filtered to provide compounds of formula (Ig).

Quinazolin-4-ones (1) can be prepared as described in Cronin et al. or WO 02/053558 A1, cited above, or using the method described in Scheme 3.

Scheme 3

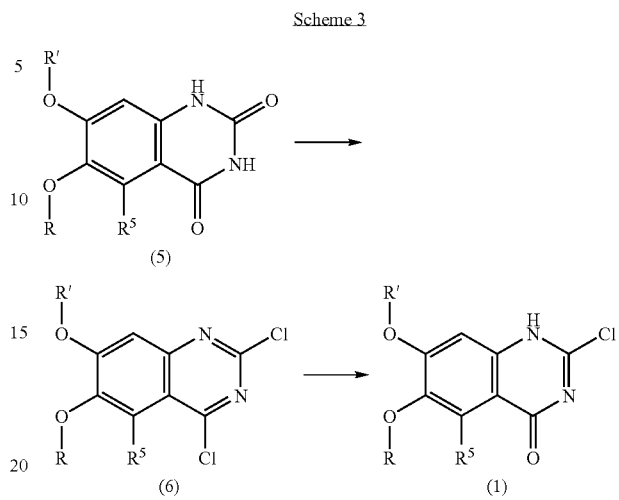

Scheme 3 illustrates an alternate method for making 2-chloro-quinazolin-4-one compounds (1), used as starting material in Schemes 1 and 2.

Dione intermediate (5) is converted to dichloroquinazoline (6) by combining (5) with a chlorinating and dehydrating agent (e.g., phosphorous oxychloride) in an organic solvent (e.g. acetonitrile) and heating the reaction mixture. The dichloroquinazoline (6) is isolated by quenching the reaction mixture into water and filtering the precipitated product, or by quenching the reaction mixture into a mixture of water and a water-immiscible solvent (e.g. methylene chloride), and extracting the product into the organic solvent. The solvent is evaporated to provide compound (6).

Compound (6) is then combined with a base (e.g., KOH, NaOH) in a mixture of water and a solvent like THF. At the end of the reaction, the organic solvent is partially removed by distillation, an acid (e.g. HOAc) is added, and the compound (1) is collected via filtration.

Dione intermediates (5) are commercially available or can be readily prepared by one skilled in the field, e.g., as described in Mizuno et al., *Heteroatom Chemistry*, Vol. 11 (6) (2000), at pp. 428–433; Mizuno et al., *Tetrahedron Letters*, Vol. 41 (7) (2000), at pp. 1051–51; U.S. Pat. No. 6,376,667-B1; U.S. Pat. No. 6,048,864; WO 97/23462; EP Pat. 775697-A1; and so forth.

Alternatively, dione intermediates (5) may be prepared as described in Scheme 4.

Scheme 4

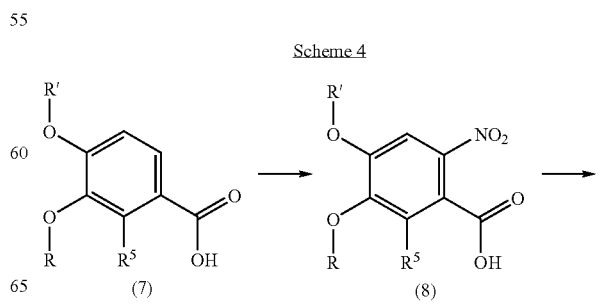

-continued

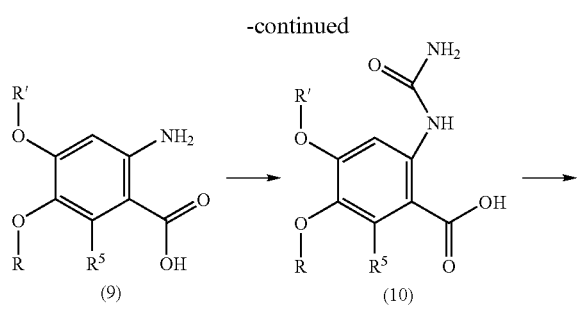

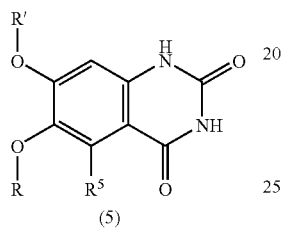

Scheme 4 illustrates an alternative method for making of diones (5), used in Scheme 3 to prepare 2-chloro-quinazolin-4-one compounds (1).

Nitro-acids (8) are commercially available, or can be readily prepared by one skilled in the field from carboxylic acids (7) using several methods, including that of Kowalczyk et al., *Organic Process Research and Development*, Vol. 1 (1997), at pp. 355–358. Carboxylic acids (7) are commercially available.

Nitro acids (8) are dissolved in water by addition of base (e.g., NaOH, KOH, LiOH). Typically, the amount of base used to dissolve the acids is in the range of a 1.3 to 1.5 molar equivalent, e.g., at a pH≧12. A heterogenous catalyst on an inert support is added (e.g., palladium on carbon), and the reaction mixture is exposed to a hydrogen atmosphere either directly (hydrogen gas) or indirectly (via transfer hydrogenation technique using, e.g., formate salts, hydrazine, etc., as the hydrogen source). The nitro-group is thereby converted to an amino group to provide compounds (9).

Compounds (9) can be converted to urea (10) by addition of a cyanate salt (e.g., KOCN, NaOCN) and an acid (e.g., HCl, HOAc). For this urea-forming step, the pH is preferably maintained in the range of 6.0 to 8.0, more preferably between 6.8 and 8.0. At pH greater than 8, the urea formation step may slow down, and when the pH is between 5.6 and 6.0, an undesirable side reaction may occur. Degradation occurs at lower pH, e.g., at pH of ~3.9. The urea (10) is then cyclized to a dione derivative (5) by adding a base (e.g., NaOH, KOH), wherein the pH is typically maintained at ≧12, and heating the reaction mixture. The results of this cyclization step may be improved as the pH is increased. The dione (5) is precipitated by adding an acid (e.g., HCl, HOAc) to the reaction mixture, to achieve a pH of about less than 8.2, more preferably in the range of 6.5 to 7.5, and the dione (5) may be isolated such as by filtration. Other acids also may be used, e.g., any acid that will generate HOCN in-situ from the cyanate salt and the acid.

The process of Scheme 4 is particularly advantageous in that the water-insoluble compounds (8)–(5) are converted into water-soluble compounds by conversion to their respective salts (by addition of base) and then the pH is adjusted to allow the desired reaction to occur in a water-based solvent system.

EXAMPLES

The following preparations and examples are provided to enable those skilled in the art to more clearly understand and to practice the present invention. However, these Examples should not be considered as limiting the scope of the invention, but merely as being illustrative and representative thereof.

Example A-1

6,7-Dimethoxy-2-[methyl-(3-pyrrolidin-1-yl-benzyl)-amino]-1H-quinazolin-4-one

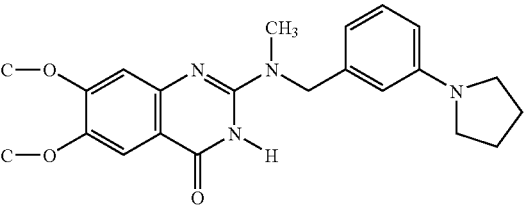

Step 1:

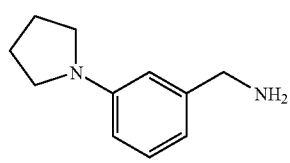

(1)

Benzylamine (1) was prepared following the procedure of Sznaidman et al., *Bioorg. Med. Chem. Lett.*, 6(5) (1996), at pp. 565–568.

Step 2:

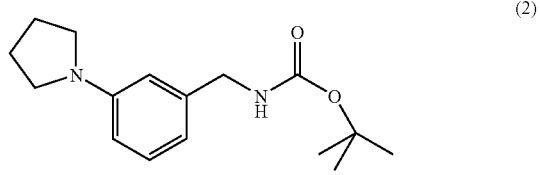

(2)

Benzylamine (1) (4.8 g, 27.3 mmol) in 100 mL DCM was reacted with 6.1 g (28 mmol) of di-tert-butyl dicarbonate for 2 h. The solvent was evaporated under reduced pressure and the remaining solid was dried at 60° C. in vacuo to afford 7.7 g of the carbamate (2) (Mp=106.8–107.5° C.).

Step 3:

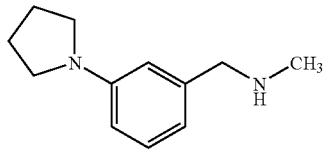
(3)

The carbamate (2) from Step 2 (7.6 g, 27.5 mmol) was dissolved in 70 mL THF and added over a period of 30 min. to a stirred slurry of 3 g (75 mmol) of LAH in 300 mL of diethyl ether. The mixture was stirred at reflux for 8 h and allowed to stand at ambient temperature for 16 h. The reaction was quenched while stirring by sequential addition of 1—water; 2—15% NaOH and 3—water until all solids appeared to be white. The solids were removed by filtration and washed once with THF. The filtrates were combined, concentrated under reduced pressure, and the remaining oil was distilled to yield 4.1 g (78%) of the N-methylbenzylamine (3). Bp 140° C./1 mm.

Step 4:

A sample of 2-chloro-6,7-dimethoxyquinazolin-4-one (300 mg, 1.25 mmol) in 4–5 mL of 1,2-dihydroxypropane was allowed to react with (400 mg, 2.1 mmol) of benzylamine (3) for 16 h at 110° C. The solvent was removed in vacuo and the remaining solid was chromatographed (EM Science silica gel 60; 2% MeOH in DCM) to yield 300 mg (60%) of the above titled-compound Example A-1. Mp 238–40° C.; MS m/z 395 (M+H). The bis HCl salt was obtained when the free base in hot EtOH was treated with an excess of 10% HCl in EtOH, and was crystallized by addition of diethyl ether. Mp 220–223° C. Anal. ($C_{22}H_{26}N_4O_3 \cdot 2HCl$), Calcd.: C, 56.54; H, 6.04; N, 11.99. Found: C, 56.20; H, 6.01; N, 11.95.

Example A-2

2-[Benzyl-(1-benzyl-piperidin-4-yl)-amino]-6,7-dimethoxy-1H-quinazolin-4-one; compound with trifluoro-acetic acid

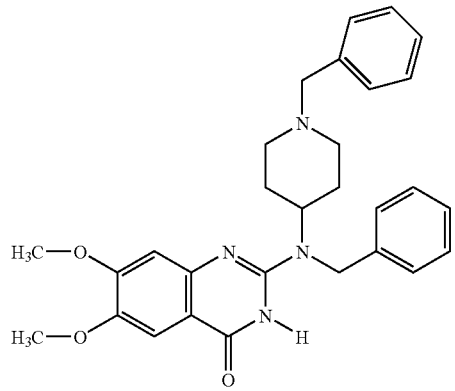

Step 1:

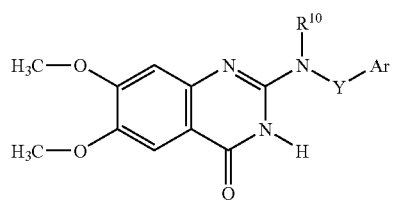
(1)

Benzylamine (1) was prepared following the procedure of Harper et al., *Journal of Medicinal Chemistry*, Vol. 7(6) (1964), at pp. 729–32.

Step 2:

The benzylamine (1) (14 mg) and 2-chloro-6,7-dimethoxyquinazolin-4-one (12 mg) were heated together in NMP at 80° C. for 3 d. Purification by RP-HPLC provided the title compound: m/z 485 (M+H)$^+$.

Examples A-3 to A-16

(Ih)

Compounds having the above formula (Ih), wherein $R^{10}$ and Y—Ar considered together have the values reported in Table 1, were prepared following the same or similar method as described above for Example A-1, except the appropriately-substituted amine was used in place of N-methyl-(3-pyrrolidin-1-yl-benzyl)-amine.

TABLE 1

| Ex. | R¹⁰ | —Y—Ar | Compound Name | Mp ° C. | MS (M + H)⁺ |
|---|---|---|---|---|---|
| A-3 | —CH$_3$ | (6-methylpyridin-2-ylmethyl) | 6,7-Dimethoxy-2-[methyl-(6-methyl-pyridin-2-ylmethyl)-amino]-1H-quinazolin-4-one | | 341 |
| A-4 | —CH$_3$ | (2-(1H-indol-3-yl)ethyl) | 2-{[2-(1H-Indol-3-yl)-ethyl]-methyl-amino}-6,7-dimethoxy-1H-quinazolin-4-one | | 379 |
| A-5 | —CH$_3$ | [3-(4-methyl-piperazin-1-yl)benzyl] | 6,7-Dimethoxy-2-{methyl-[3-(4-methyl-piperazin-1-yl)-benzyl]-amino}-1H-quinazolin-4-one | | 424 |
| A-6 | —H | [2-(4-methyl-piperazin-1-yl)benzyl] | 6,7-Dimethoxy-5-methyl-2-[2-(4-methyl-piperazin-1-yl)-benzylamino]-1H-quinazolin-4-one | | 424 |
| A-7 | -isoPr | benzyl | 2-(Benzyl-isopropyl-amino)-6,7-dimethoxy-1H-quinazolin-4-one | 168–170.5 | 354 |
| A-8 | —CH$_3$ | [3-(N,N-dimethylformamidine)phenyl]methyl | N'-(3-{[(6,7-Dimethoxy-4-oxo-1,4-dihydro-quinazolin-2-yl)-methyl-amino]-methyl}-phenyl)-N,N-dimethyl-formamidine, hydrochloride salt | 242–245 | 395.4 M⁺ |
| A-9 | —CH$_3$ | [3-(4,5-dihydro-3H-pyrrol-2-ylamino)benzyl] | 2-{[3-(4,5-Dihydro-3H-pyrrol-2-ylamino)-benzyl]-methyl-amino}-6,7-dimethoxy-1H-quinazolin-4-one | 211–14 | 407.5 M⁺ |
| A-10 | —CH$_3$ | [3-(acetamidine)phenyl]methyl | N-(3-{[(6,7-Dimethoxy-4-oxo-1,4-dihydro-quinazolin-2-yl)-methyl-amino]-methyl}-phenyl)-acetamidine, hydrogen bromide salt | 263–66 | 381.4 M⁺ |

TABLE 1-continued

| Ex. | R¹⁰ | —Y—Ar | Compound Name | Mp ° C. | MS (M + H)⁺ |
|---|---|---|---|---|---|
| A-11 | —CH₃ | (3-(4,5-dihydro-1H-imidazol-2-ylamino)benzyl group) | 2-{[3-(4,5-Dihydro-1H-imidazol-2-ylamino)-benzyl]-methyl-amino}-6,7-dimethoxy-1H-quinazolin-4-one | | 409 |
| A-12 | —CH₃ | (3-(4,4-dimethyl-4,5-dihydroimidazol-1-yl)benzyl group) | 2-{[3-(4,4-Dimethyl-4,5-dihydro-imidazol-1-yl)-benzyl]-methyl-amino}-6,7-dimethoxy-1H-quinazolin-4-one | 240–244 | 422 |
| A-13 | —CH₃ | (3-(N,N-dimethylacetamidino)phenethyl group) | N'-(3-{2-[(6,7-Dimethoxy-4-oxo-1,4-dihydro-quinazolin-2-yl)-methyl-amino]-ethyl}-phenyl)-N,N-dimethyl-acetamidine | 135–138.1 | 423.5 M⁺ |
| A-14 | —CH₃ | (3-(pyrimidin-2-ylamino)phenethyl group) | 6,7-Dimethoxy-2-(methyl-{2-[3-(pyrimidin-2-ylamino)-phenyl]-ethyl}-amino)-1H-quinazolin-4-one | | 433 |
| A-15 | —CH₃ | (3-((1H-imidazol-2-ylmethyl)amino)phenethyl group) | 2-[(2-{3-[(1H-Imidazol-2-ylmethyl)-amino]-phenyl}-ethyl)-methyl-amino]-6,7-dimethoxy-1H-quinazolin-4-one | | 435 |
| A-16 | —CH₃ | (2-(3,4-dimethoxyphenyl)ethyl group) | 2-{[2-(3,4-Dimethoxy-phenyl)-ethyl]-methyl-amino}-6,7-dimethoxy-1H-quinazolin-4-one | | 400 |

Additional compounds prepared according to the procedure of Example A-1 using various aralkylamines with 2-chloro-6,7-dimethoxyquinazolin-4-one are shown in Table 11.

Example B-1

2-[(3-Amino-benzyl)-methyl-amino]-6,7-dimethoxy-5-methyl-1H-quinazolin-4-one

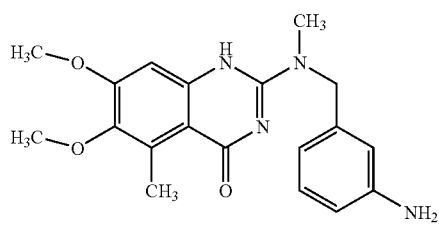

Step 1: 2-Chloro-6,7-dimethoxy-5-methyl-quinazolin-4-one

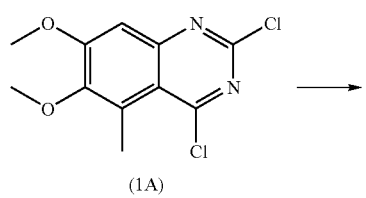

A solution of 3 g (11 mmol) of the dichloroquinazoline (1A) in 50 mL THF was stirred with 30 mL of 40% aqueous KOH and 3 mL of 40% aqueous tetrabutylammonium hydroxide for 3 days. The layers were allowed to separate and the upper layer was concentrated to give a white solid. This was treated with dilute acetic acid and the solid was collected and washed with water, then dried at 65° C. in vacuo to afford 2.4 g (86%) of the 2-chloroquinazolin-4-one (1). Mp 251–251.7° C.; MS (ES+) m/z 255 (M+H)$^+$. Anal. ($C_{11}H_{11}ClN_2O_3$) Calcd.: C, 51.88; H, 4.35; N, 11.00. Found: C, 51.94; H, 4.34; N, 10.95.

Step 2:

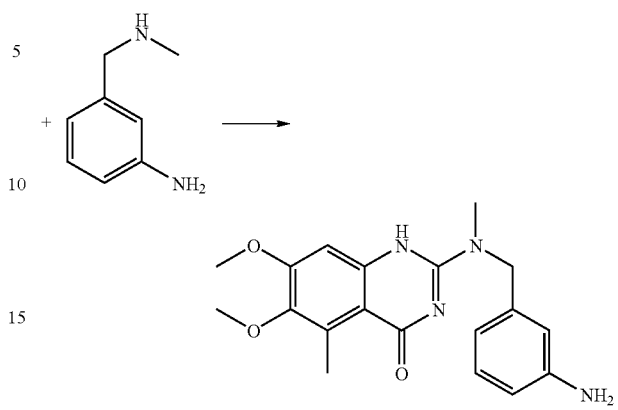

A mixture consisting of the 2-chloroquinazolin-4-one (1) from Step 1 (2.95 g, 11.6 mmol), the above benzylamine (2) (1.65 g, 12.2 mmol), and N,N-diisopropylethylamine (1.5 g, 11.6 mmol) in 45 mL of EtOH was placed in a heavy-walled glass reaction vessel. A magnetic stirring bar was added and the reaction vessel was closed. The reaction mixture formed a slurry, and it was stirred while the reaction vessel was kept partially immersed in an 120° C. bath for 2 h. The mixture was allowed to remain at ambient temperature without stirring for 16 h. The solid product was collected, washed twice with EtOH, and dried at 65° C. in vacuo furnishing 3.7 g (90%) of Example B-1 as an off-white solid. Mp 268–269.5° C.; Anal. ($C_{19}H_{22}N_4O_3$) Calcd.: C, 64.39; H, 6.26; N, 15.81. Found: C, 64.05; H, 6.25; N, 15.49.

Example B-2

3-{[(6,7-Dimethoxy-5-methyl-4-oxo-1,4-dihydro-quinazolin-2-yl)-methyl-amino]-methyl}-benzonitrile

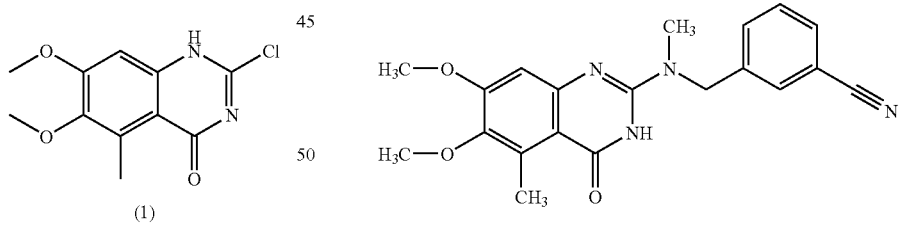

Diisopropylethylamine (0.82 mL, 4.71 mmol) was added to a mixture of 2-chloro-6,7-dimethoxy-5-methylquinazolin-4-one (1.0 g, 3.92 mmol) and N-methyl-(3-cyano-benzyl)-amine (0.68 g, 4.71 mmol) in EtOH (50 mL). The mixture was heated at 120° C. for 1.5 h in a sealed tube. After cooling, the resulting white solid was filtered and washed with MeOH to provide the arylnitrile of Example B-2. Mp 279.9–281.5° C.; $^1$H NMR (DMSO-$d_6$) δ 2.6 (s, 3H), 3.05 (s, 3H), 3.62 (s, 3H), 3.84 (s, 3H), 4.86 (s, 2H), 6.62 (s, 1H), 7.5–7.7.78 (m, 4H); $^{13}$C NMR (DMSO-$d_6$) δ 13.89, 35.58, 51.52, 55.93, 60.22, 104.79, 111.78, 119.15, 130.12, 131.19, 131.28, 131.96, 132.51, 140.04, 142.96, 150.51, 157.71. MW=365.

Examples B-3 to B-10

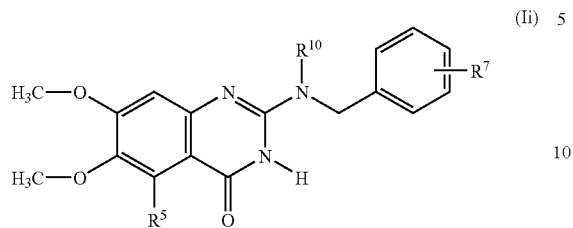

Compounds having the above formula (Ii), wherein $R^5$, $R^7$ and $R^{10}$ have the values reported in Table 2 were prepared following the same or similar method as described for Examples B-1 and B-2.

TABLE 2

| Ex. | $R^5$ | $R^7$ | $R^{10}$ | Compound Name | Mp ° C. | MS $(M + H)^+$ |
|---|---|---|---|---|---|---|
| B-3 | —CH$_3$ | —H | H$_3$C—N(CH$_3$)—CH$_2$CH$_2$— | 2-[Benzyl-(2-dimethylamino-ethyl)-amino]-6,7-dimethoxy-5-methyl-1H-quinazolin-4-one | | 397 |
| B-4 | —CH$_3$ | 3-Br | —CH$_3$ | 2-[(3-Bromo-benzyl)-methyl-amino]-6,7-dimethoxy-5-methyl-1H-quinazolin-4-one | | 419 |
| B-5 | —O—CH$_3$ | 3-Br | —CH$_3$ | 2-[(3-Bromo-benzyl)-methyl-amino]-5,6,7-trimethoxy-1H-quinazolin-4-one | | 435 |
| B-6 | —CH$_3$ | 2-F | —CH$_2$CH$_2$OH | 2-[(2-Fluoro-benzyl)-(2-hydroxy-ethyl)-amino]-6,7-dimethoxy-5-methyl-1H-quinazolin-4-one | | 388 |
| B-7 | —O—CH$_3$ | 3-cyano | —CH$_3$ | 3-{[Methyl-(5,6,7-trimethoxy-4-oxo-1,4-dihydro-quinazolin-2-yl)-amino]-methyl}-benzonitrile | | 381 |
| B-8 | —CH$_3$ | 3-NH(CH$_3$) | —CH$_3$ | 6,7-Dimethoxy-5-methyl-2-[methyl-(3-methylamino-benzyl)-amino]-1H-quinazolin-4-one | | 368.4M$^+$ |
| B-9 | —O—CH$_3$ | 3-NH$_2$ | —CH$_3$ | 2-[(3-Amino-benzyl)-methyl-amino]-5,6,7-trimethoxy-1H-quinazolin-4-one | 225–226.5 | 370.4M$^+$ |
| B-10 | —CH$_3$ | 2-NH$_2$ | —CH$_3$ | 2-[(2-Amino-benzyl)-methyl-amino]-5,6,7-trimethoxy-1H-quinazolin-4-one; | | 370.4M$^+$ |

Additional compounds prepared according to the procedure of Examples B-2 and B-3 are shown in Table 11.

Example C-1

6,7-Dimethoxy-5-methyl-2-[methyl-(3-methylaminomethyl-benzyl)-amino]-1H-quinazolin-4-one

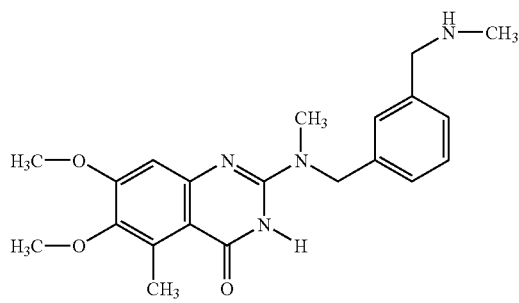

Step 1:

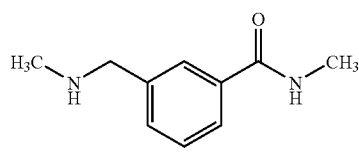

3-(Bromomethyl)benzoate (5.0 g, 21.83 mmol) and 40% methylamine in water (40.0 mL, 515.2 mmol) in EtOH (17 mL) were heated at 80° C. for 6 h. The solvent was concentrated to dryness. Purification by flash chromatography ($CH_2Cl_2$:MeOH:$NH_4OH$/300:10:1) gave 2.71 g (70%) of compound (1) above as a clear oil.

Step 2:

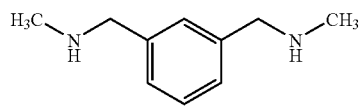

1.0 M $LiAlH_4$ in THF (30.32 mL, 30.42 mmol) was added to compound (1) (2.71 g, 15.01 mmol) in THF (20 mL), and the mixture was heated at reflux for 16 h. After cooling to rt, $Na_2SO_4 \cdot 0.8H_2O$ (ca. 5 g) was added, and the heterogeneous solution was stirred at rt for 0.5 h. The white solid was filtered off and the filtrate was concentrated to dryness. Purification by flash chromatography ($CH_2Cl_2$: MeOH: $NH_4OH$/60:10:1) gave 1.17 g (48%) of the above compound (2) as a clear oil.

Step 3:

2-Chloro-6,7-dimethoxy-5-methyl-1H-quinazolin-4-one (0.805 g, 3.16 mmol) and compound (2) (0.675 g, 4.109 mmol) in EtOH (10 mL) were heated in a sealed tube at 120° C. for 3 h. The solvent was evaporated to dryness under reduced pressure. Purification by flash chromatography ($CH_2Cl_2$: MeOH: $NH_4OH$/320:10:1) followed by recrystallization ($CH_2Cl_2$/ether) gave 0.468 g (39%) of the above Example C-1 as a white solid. mp 179.0–181.3° C.; $^1H$ NMR (DMSO-$d_6$, 2.49) δ 1.74 (s, 3H), 2.54 (t, 2H), 2.80 (s, 3H), 2.97 (s, 6H), 3.62 (s, 3H), 3.75 (t, 2H), 3.86 (2, 3H), 4.72 (s, 2H), 6.40 (d, 1H), 6.67 (s, 1H), 6.75 (d, 2H), 7.05 (t, 1H), 10.99 (s, 1H); IR (KBr) $v_{max}$ 1589 $cm^{-1}$; MS (ES+) m/z 383 (M+H); Anal. ($C_{21}H_{26}N_4O_3$)C: calcd, 65.95; found, 65.75; H: calcd, 6.85; found, 6.76; N: calcd, 14.65; found, 14.66.

Examples C-2 to C-24

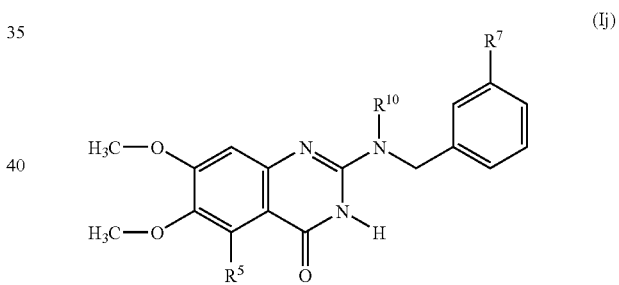

Compounds having the above formula (Ij), wherein $R^5$, $R^7$ and $R^{10}$ have the values reported in Table 3, were prepared following the same or similar method as described for Example C-1.

TABLE 3

| Ex. | $R^5$ | —$R^7$ | $R^{10}$ | Compound Name | Mp° C. | MS (M + H) |
|---|---|---|---|---|---|---|
| C-2 | —$CH_3$ | —$CH_2$—$NH_2$ | —$CH_3$ | 2-[(3-Aminomethyl-benzyl)-methyl-amino]-6,7-dimethoxy-5-methyl-1H-quinazolin-4-one | | 369 |
| C-3 | —O—$CH_3$ | —$CH_2CN$ | —$CH_3$ | (3-{[Methyl-(5,6,7-trimethoxy-4-oxo-1,4-dihydro-quinazolin-2-yl)-amino]-methyl}-phenyl)-acetonitrile | | 395 |
| C-4 | —O—$CH_3$ | —$CH_2OH$ | —$CH_3$ | 2-[(3-Hydroxymethyl-benzyl)-methyl-amino]- | | 386 |

TABLE 3-continued

| Ex. | R⁵ | —R⁷ | R¹⁰ | Compound Name | Mp° C. | MS (M + H) |
|---|---|---|---|---|---|---|
| C-5 | —OH | —CH₂OH | —CH₃ | 5,6,7-trimethoxy-1H-quinazolin-4-one 5-Hydroxy-2-[(3-hydroxymethyl-benzyl)-methyl-amino]-6,7-dimethoxy-1H-quinazolin-4-one | | 372 |
| C-6 | —O—CH₃ | 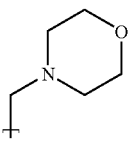 | —CH₃ | 5,6,7-Trimethoxy-2-[methyl-(3-morpholin-4-ylmethyl-benzyl)-amino]-1H-quinazolin-4-one | | 455 |
| C-7 | —O—CH₃ | —CH₂NH(CH₃) | —CH₃ | 5,6,7-Trimethoxy-2-[methyl-(3-methylaminomethyl-benzyl)-amino]-1H-quinazolin-4-one | 124.9–127.6 | 398.5 M⁺ |
| C-8 | —CH₃ |  | —CH₂CH₃ | 2-[Ethyl-(3-methylaminomethyl-benzyl)-amino]-6,7-dimethoxy-5-methyl-1H-quinazolin-4-one | | 396.5 M⁺ |
| C-9 | —CH₃ |  | —CH₃ | 2-[(3-Ethylaminomethyl-benzyl)-methyl-amino]-6,7-dimethoxy-5-methyl-1H-quinazolin-4-one | | 396.5 M⁺ |
| C-10 | —O—CH₃ | 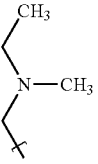 | —CH₃ | 2-({3-[(Ethyl-methyl-amino)-methyl]-benzyl}-methyl-amino)-5,6,7-trimethoxy-1H-quinazolin-4-one | | 426.5 M⁺ |
| C-11 | —CH₃ | 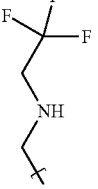 | —CH₃ | 6,7-Dimethoxy-5-methyl-2-(methyl-{3-[(2,2,2-trifluoro-ethylamino)-methyl]-benzyl}-amino)-1H-quinazolin-4-one | | 450.5 M⁺ |
| C-12 | —O—CH₃ | 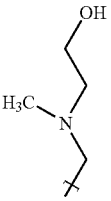 | —CH₃ | 2-[(3-{[(2-Hydroxy-ethyl)-methyl-amino]-methyl}-benzyl)-methyl-amino]-5,6,7-trimethoxy-1H-quinazolin-4-one hydrochloride salt | 169.0–171.9 | 456.5 M⁺ |
| C-13 | —CH₃ | 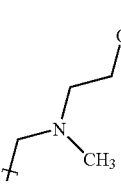 | —CH₃ | 6,7-dimethoxy-5-methyl-2-[(3-{[(2-methoxy-ethyl)-methyl-amino]methyl}-benzyl)-methyl-amino]-1H-quinazolin-4-one | | 426.5 M⁺ |

TABLE 3-continued

| Ex. | R[5] | —R[7] | R[10] | Compound Name | Mp° C. | MS (M + H) |
|---|---|---|---|---|---|---|
| C-14 | —O—CH$_3$ | 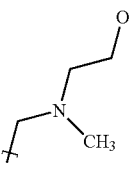 | —CH$_3$ | 5,6,7-Trimethoxy-2-[(3-{[(2-methoxy-ethyl)-methyl-amino]-methyl}-benzyl)-methyl-amino]-1H-quinazolin-4-one hydrogen chloride salt | 162.9–164.5 | 470.6 M$^+$ |
| C-15 | —O—CH$_3$ | 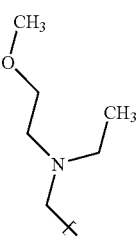 | —CH$_3$ | 2-[(3-{[Ethyl-(2-methoxy-ethyl)-amino]-methyl}-benzyl)-methyl-amino]-5,6,7-trimethoxy-1H-quinazolin-4-one hydrogen chloride salt | | 470.6 M$^+$ |
| C-16 | —CH$_3$ | 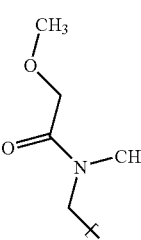 | —CH$_3$ | N-(3-{[(6,7-Dimethoxy-5-methyl-4-oxo-1,4-dihydro-quinazolin-2-yl)-methyl-amino]-methyl}-benzyl)-2-methoxy-N-methyl-acetamide | | 454.5 M$^+$ |
| C-17 | —O—CH$_3$ | 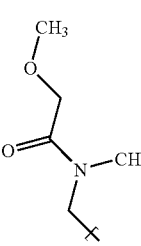 | —CH$_3$ | 2-Methoxy-N-methyl-N-(3-{[methyl-(5,6,7-trimethoxy-4-oxo-1,4-dihydro-quinazolin-2-yl)-amino]-methyl}-benzyl)-acetamide | 115–117 | 470.5 M$^+$ |
| C-18 | —CH$_3$ | 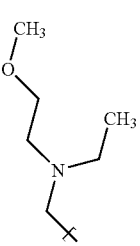 | —CH$_3$ | 2-[(3-{[Ethyl-(2-methoxy-ethyl)-amino]-methyl}-benzyl)-methyl-amino]-6,7-dimethoxy-5-methyl-1H-quinazolin-4-one | | 454.6 M$^+$ |
| C-19 | —CH$_3$ | 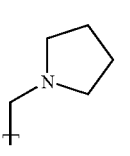 | —CH$_3$ | 6,7-Dimethoxy-5-methyl-2-[methyl-(3-pyrrolidin-1-ylmethyl-benzyl)-amino]-1H-quinazolin-4-one | | 422.5 M$^+$ |
| C-20 | —OH | 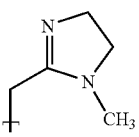 | —CH$_3$ | 5-Hydroxy-6,7-dimethoxy-2-{methyl-[3-(1-methyl-4,5-dihydro-1H-imidazol-2-ylmethyl)-benzyl]-amino}-1H-quinazolin-4-one | | 438 |

TABLE 3-continued

| Ex. | R⁵ | —R⁷ | R¹⁰ | Compound Name | Mp° C. | MS (M + H) |
|---|---|---|---|---|---|---|
| C-21 | —O—CH₃ | 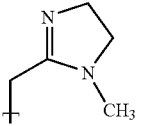 | —CH₃ | 5,6,7-Trimethoxy-2-{methyl-[3-(1-methyl-4,5-dihydro-1H-imidazol-2-ylmethyl)-benzyl]-amino}-1H-quinazolin-4-one | | 452 |
| C-22 | —OH | 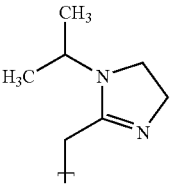 | —CH₃ | 5-Hydroxy-2-{[3-(1-isopropyl-4,5-dihydro-1H-imidazol-2-ylmethyl)-benzyl]-methyl-amino}-6,7-dimethoxy-1H-quinazolin-4-one | | 466 |
| C-23 | —O—CH₃ | 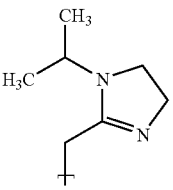 | —CH₃ | 2-{[3-(1-Isopropyl-4,5-dihydro-1H-imidazol-2-ylmethyl)-benzyl]-methyl-amino}-5,6,7-trimethoxy-1H-quinazolin-4-one | | 480 |
| C-24 | —O—CH₃ | 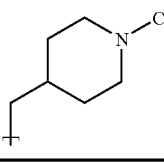 | —CH₃ | 5,6,7-Trimethoxy-2-{methyl-[3-(1-methyl-piperidin-4-ylmethyl)-benzyl]-amino}-1H-quinazolin-4-one | | 466.6 M⁺ |

Additional compounds prepared according to the procedure of Example C-1 are shown in Table 11.

Examples D-1 to D-8, E-1 to E-15

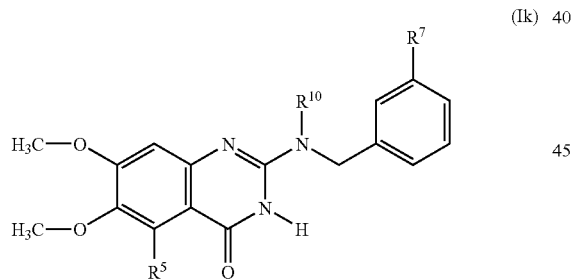

Compounds having the above formula (Ik), wherein R⁵, R⁷ and R¹⁰ have the values reported in Tables 4 and 5, were prepared following the same or similar method as described for the above Examples.

TABLE 4

| Ex. | R⁵ | R⁷ | R¹⁰ | Compound Name | Mp ° C. | MS (M⁺) |
|---|---|---|---|---|---|---|
| D-1 | —CH₃ | —SO₂CH₃ | —CH₃ | 2-[(3-Methanesulfonyl-benzyl)-methyl-amino]-6,7-dimethoxy-5-methyl-1H-quinazolin-4-one | 269.5–271.5 | 417.5 |
| D-2 | —O—CH₃ | —SO₂CH₃ | —CH₃ | 2-[(3-Methanesulfonyl-benzyl)-methyl-amino]-5,6,7-trimethoxy-1H-quinazolin-4-one | 231.5–232.9 | 433.5 |

TABLE 4-continued

| Ex. | R⁵ | R⁷ | R¹⁰ | Compound Name | Mp ° C. | MS (M⁺) |
|---|---|---|---|---|---|---|
| D-3 | —O—CH₃ | 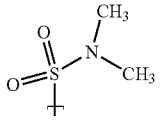 | —CH₃ | N,N-Dimethyl-3-{[methyl-(5,6,7-trimethoxy-4-oxo-1,4-dihydro-quinazolin-2-yl)-amino]-methyl}-benzenesulfonamide | | 462.5 |
| D-4 | —CH₃ | 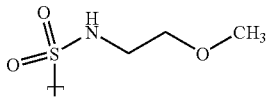 | —CH₃ | 3-{[(6,7-Dimethoxy-5-methyl-4-oxo-1,4-dihydro-quinazolin-2-yl)-methyl-amino]-methyl}-N-(2-methoxy-ethyl)-benzenesulfonamide | | 476.6 |
| D-5 | —O—CH₃ | 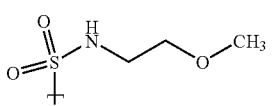 | —CH₃ | N-(2-Methoxy-ethyl)-3-{[methyl-(5,6,7-trimethoxy-4-oxo-1,4-dihydro-quinazolin-2-yl)-amino]-methyl}-benzenesulfonamide | | 492.6 |
| D-6 | —CH₃ | 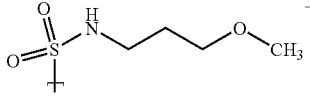 | —CH₃ | 3-{[(6,7-Dimethoxy-5-methyl-4-oxo-1,4-dihydro-quinazolin-2-yl)-methyl-amino]-methyl}-N-(3-methoxy-propyl)-benzenesulfonamide | | 490.6 |
| D-7 | —CH₃ | —CO₂H | —CH₃ | 3-{[(6,7-Dimethoxy-5-methyl-4-oxo-1,4-dihydro-quinazolin-2-yl)-methyl-amino]-methyl}-benzoic acid | | 383.4 |
| D-8 | —O—CH₃ | —CO₂H | —CH₃ | 3-{[Methyl-(5,6,7-trimethoxy-4-oxo-1,4-dihydro-quinazolin-2-yl)-amino]-methyl}-benzoic acid | | 400 (M + H)⁺ |

TABLE 5

| Ex. | R⁵ | R⁷ | R¹⁰ | Compound Name | Mp ° C. | MS (M + H)⁺ |
|---|---|---|---|---|---|---|
| E-1 | —CH₃ | —C(=O)NHCH₃ | —CH₃ | 3-{[(6,7-Dimethoxy-5-methyl-4-oxo-1,4-dihydro-quinazolin-2-yl)-methyl-amino]-methyl}-N-methyl-benzamide | 243.3–245.1 | 396.4 M⁺ |
| E-2 | —O—CH₃ | —C(=O)NHCH₃ | —CH₃ | N-Methyl-3-{[methyl-(5,6,7-trimethoxy-4-oxo-1,4-dihydro-quinazolin-2-yl)-amino]-methyl}-benzamide | 217.9–219.1 | 412.4 M⁺ |
| E-3 | —O—CH₃ | 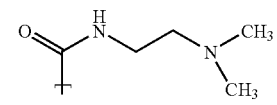 | —CH₃ | N-(2-Dimethylamino-ethyl)-3-{[methyl-(5,6,7-trimethoxy-4-oxo-1,4-dihydro-quinazolin-2-yl)-amino]-methyl}-benzamide | | 470 |
| E-4 | —O—CH₃ | 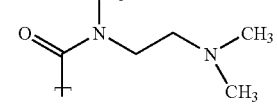 | —CH₃ | N-(2-Dimethylamino-ethyl)-N-methyl-3-{[methyl-(5,6,7-trimethoxy-4-oxo-1,4-dihydro-quinazolin-2-yl)-amino]-methyl}-benzamide | | 484 |

TABLE 5-continued

| Ex. | R$^5$ | R$^7$ | R$^{10}$ | Compound Name | Mp °C. | MS (M + H)$^+$ |
|---|---|---|---|---|---|---|
| E-5 | —O—CH$_3$ | C(=O)N(CH$_3$)CH$_2$CH$_2$CH$_2$N(CH$_3$)$_2$ | —CH$_3$ | N-(3-Dimethylamino-propyl)-N-methyl-3-{[methyl-(5,6,7-trimethoxy-4-oxo-1,4-dihydro-quinazolin-2-yl)-amino]-methyl}-benzamide | | 498 |
| E-6 | —O—CH$_3$ | C(=O)NHCH$_2$CH$_2$OH | —CH$_3$ | N-(2-Hydroxy-ethyl)-3-{[methyl-(5,6,7-trimethoxy-4-oxo-1,4-dihydro-quinazolin-2-yl)-amino]-methyl}-benzamide | | 443 |
| E-7 | —O—CH$_3$ | C(=O)NHCH$_2$CH(OH)CH$_3$ | —CH$_3$ | N-(2-Hydroxy-propyl)-3-{[methyl-(5,6,7-trimethoxy-4-oxo-1,4-dihydro-quinazolin-2-yl)-amino]-methyl}-benzamide | | 457 |
| E-8 | —O—CH$_3$ | C(=O)CH(CH$_3$)CH$_2$CH$_2$OH | —CH$_3$ | N-(2-Hydroxy-ethyl)-N-methyl-3-{[methyl-(5,6,7-trimethoxy-4-oxo-1,4-dihydro-quinazolin-2-yl)-amino]-methyl}-benzamide | | 457 |
| E-9 | —O—CH$_3$ | C(=O)NHCH$_2$CH$_2$OCH$_3$ | —CH$_3$ | N-(2-Methoxy-ethyl)-3-{[methyl-(5,6,7-trimethoxy-4-oxo-1,4-dihydro-quinazolin-2-yl)-amino]-methyl}-benzamide | | 457 |
| E-10 | —O—CH$_3$ | C(=O)NHCH$_2$CH$_2$CH$_2$OCH$_3$ | —CH$_3$ | N-(3-Methoxy-propyl)-3-{[methyl-(5,6,7-trimethoxy-4-oxo-1,4-dihydro-quinazolin-2-yl)-amino]-methyl}-benzamide | | 471 |
| E-11 | —O—CH$_3$ | C(=O)NHCH$_2$CN | —CH$_3$ | N-Cyanomethyl-3-{[methyl-(5,6,7-trimethoxy-4-oxo-1,4-dihydro-quinazolin-2-yl)-amino]-methyl}-benzamide | | 438 |
| E-12 | —O—CH$_3$ | C(=O)NH-CH$_2$-(tetrahydrofuran-2-yl) | —CH$_3$ | 3-{[Methyl-(5,6,7-trimethoxy-4-oxo-1,4-dihydro-quinazolin-2-yl)-amino]-methyl}-N-(tetrahydro-furan-2-ylmethyl)-benzamide | | 483 |
| E-13 | —O—CH$_3$ | C(=O)NH-CH$_2$-(furan-2-yl) | —CH$_3$ | N-Furan-2-ylmethyl-3-{[methyl-(5,6,7-trimethoxy-4-oxo-1,4-dihydro-quinazolin-2-yl)-amino]-methyl}-benzamide | | 483 |
| E-14 | —O—CH$_3$ | C(=O)NHCH$_2$CH$_2$-(morpholin-4-yl) | —CH$_3$ | 3-{[Methyl-(5,6,7-trimethoxy-4-oxo-1,4-dihydro-quinazolin-2-yl)-amino]-methyl}-N-(2-morpholin-4-yl-ethyl)-benzamide | | 512 |

TABLE 5-continued

| Ex. | R⁵ | R⁷ | R¹⁰ | Compound Name | Mp °C | MS (M + H)⁺ |
|---|---|---|---|---|---|---|
| E-15 | —O—CH₃ | 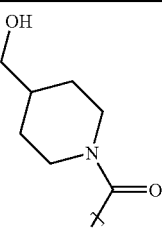 | —CH₃ | 2-{[3-(4-Hydroxymethyl-piperidine-1-carbonyl)-benzyl]-methyl-amino}-5,6,7-trimethoxy-1H-quinazolin-4-one | | 497 |

Example F-1

2-{[3-(2-Hydroxy-ethoxy)-benzyl]-methyl-amino}-5,6,7-trimethoxy-1H-quinazolin-4-one

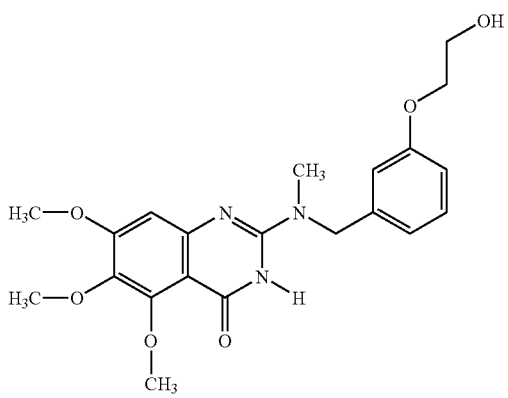

Step 1: 3-[2-(tert-Butyl-dimethyl-silanyloxy)-ethoxy]-benzaldehyde.

TBDMSCl silylation reagent in DMF (60 mL) was added to 3-(2-hydroxy-ethoxy)-benzaldehyde (4.985 g, 30.00 mmol). The mixture was stirred at room temperature for 72 h. The mixture was diluted with water and extracted with diethyl ether. The ethereal extracts were dried over Na$_2$SO$_4$ and concentrated in vacuo. The residue was purified by SiO$_2$ eluted with 95:5 CH$_2$Cl$_2$/MeOH to give 2.38 g (28%) of a clear oil.

Step 2: {3-[2-(tert-Butyl-dimethyl-silanyloxy)-ethoxy]-benzylidene}-methyl-amine.

3-[2-(tert-Butyl-dimethyl-silanyloxy)-ethoxy]-benzaldehyde (2.375 g, 8.47 mmol) was dissolved in 10 mL EtOH. MeNH$_2$ (1.2 mL, 40% in H$_2$O) was added and the mixture was heated to 40° C. for 30 min. The mixture was then concentrated in vacuo. The aqueous residue was diluted with isopropanol and then concentrated in vacuo. This was repeated twice more giving 2.184 g (87.89%) of a dry white powder.

Step 3: {3-[2-(tert-Butyl-dimethyl-silanyloxy)-ethoxy]-benzyl}-methyl-amine.

{3-[2-(tert-Butyl-dimethyl-silanyloxy)-ethoxy]-benzylidene}-methyl-amine (1.174 g, 4.00 mmol) was dissolved in EtOH and cooled to 0° C. NaBH$_4$ (189 mg, 5.00 mmol) was added and the mixture was allowed to stir for 4 h. The reaction was carefully quenched with water. The EtOH was removed in vacuo. The aqueous residue was extracted with CH$_2$Cl$_2$. The organic extracts were dried over Na$_2$SO$_4$ and concentrated in vacuo to give 1.185 g (quant) of a white powder.

Step 4: 2-({3-[2-(tert-Butyl-dimethyl-silanyloxy)-ethoxy]-benzyl}-methyl-amino)-5,6,7-trimethoxy-1H-quinazolin-4-one.

{3-[2-(tert-Butyl-dimethyl-silanyloxy)-ethoxy]-benzyl}-methyl-amine from Step 3 (294 mg, 1.00 mmol) and 2-chloro-5,6,7-trimethoxy-1H-quinazolin-4-one (prepared as described previously) (270 mg, 1.00 mmol) were dissolved in dry DMSO. Et$_3$N (0.14 mL, 1.00 mmol) was added and the mixture was heated to 120° C. overnight. Upon cooling, the mixture was poured into water and extracted with diethyl ether. The ethereal extracts were dried over Na$_2$SO$_4$ and concentrated in vacuo. The residue was purified by SiO$_2$ eluted with 99:1 CH$_2$Cl$_2$/MeOH to give 435 mg (82.12%) of a white crystalline solid.

Step 5: 2-{[3-(2-Hydroxy-ethoxy)-benzyl]-methyl-amino}-5,6,7-trimethoxy-1H-quinazolin-4-one.

Compound from step 4 (431 mg, 0.82 mmol) was dissolved in dry THF (15 mL). Bu$_4$NF (0.82 mL, 1.0 M in THF) was added and the mixture was stirred overnight. The mixture was concentrated in vacuo. The residue was dissolved in hot MeOH and allowed to stand for crystallization. A small fraction of diethyl ether was added to induce crystallization. The solid was filtered and dried to give 56 mg (16.57%) of a white crystalline solid. mp 146.0–147.5° C.; $^1$H NMR (D$_2$O-d$_2$) δ 3.19 (s, 3 H), 3.86 (s, 3 H), 3.88 (s, 3 H), 3.89 (t, 2 H, J=4.4), 3.92 (s, 3H), 4.04 (t, 2 H, J=4.4), 4.85 (s, 2 H), 6.63 (s, 1 H), 6.83 (m, 3 H), 7.23 (t, 1 H, J=7.8); $^{13}$C NMR (DMSO-d$_6$, 39.50) δ 35.57, 52.90, 56.37, 61.81, 61.83, 62.16, 69.55, 102.77, 104.74, 113.65, 114.35, 120.55, 130.24, 138.86, 139.30, 150.96, 151.03, 153.47, 159.45, 159.56, 162.81; MS (ES+) m/z 416 (M+H); Anal. (C$_{21}$H$_{25}$N$_3$O$_6$)C: calcd, 60.71; found, 60.39; H: calcd, 6.07; found, 5.97; N: calcd, 10.11; found, 10.01.

Example F-2

2-[(3-Methanesulfinylmethoxy-benzyl)-methyl-amino]-6,7-dimethoxy-5-methyl-1H-quinazolin-4-one

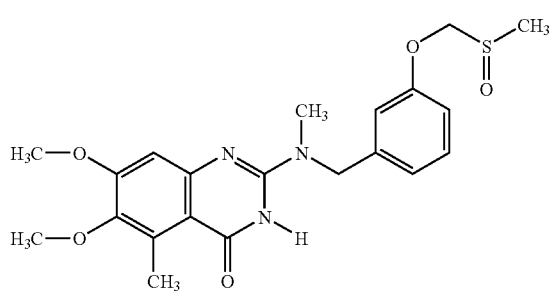

Step 1: 3-Methylsulfanylmethoxy-benzaldehyde.

3-Hydroxybenzaldehyde (6.106 g, 50.00 mmol) was dissolved in acetone at room temperature. K$_2$CO$_3$ (13.821 g, 100.00 mmol), NaI (7.569 g, 50.00 mmol) and chloromethyl methyl sulfide (4.19 mL, 50.00 mmol) were added, and the mixture was allowed to stir for 80 h. The mixture was filtered, the filtrate concentrated to an oil, and the residue purified by SiO$_2$ eluted with 99:1 CH$_2$Cl$_2$/MeOH to give 3.309 g (36.31%) of a yellow oil.

Step 2: Methyl-(3-methylsulfanylmethoxy-benzylidene)-amine.

3-Methylsulfanylmethoxy-benzaldehyde from step 1 (3.309 g, 18.16 mmol) was dissolved in EtOH (9 mL). MeNH$_2$ (2.55 mL, 40% in H$_2$O) was added and the mixture was heated to 40° C. for 30 min. Upon cooling, the mixture was concentrated in vacuo. The aqueous residue was diluted with isopropanol and then concentrated in vacuo. This was repeated twice more giving 3.55 g (quant) of a pale yellow oil.

Step 3: Methyl-(3-methylsulfanylmethoxy-benzyl)-amine.

Compound from step 2 (3.546 g, 18.16 mmol) was dissolved in EtOH (50 mL) and cooled to 0° C. NaBH$_4$ (859 mg, 22.70 mmol) was added and the mixture was allowed to stir for 4 h. The reaction was carefully quenched with water. The EtOH was removed in vacuo. The aqueous residue was extracted with CH$_2$Cl$_2$. The organic extracts were dried over Na$_2$SO$_4$ and concentrated in vacuo to give 2.044 g (57%) of a clear yellow oil.

Step 4: (3-Methanesulfinylmethoxy-benzyl)-methyl-amine.

Compound from step 3 (592 mg, 3.00 mmol) was dissolved in glacial acetic acid (4 mL) and cooled to 0° C. H$_2$O$_2$ (0.34 mL, 3.00 mmol) was added drop-wise. The mixture was allowed to stir for 6 h. The mixture was then diluted with CH$_2$Cl$_2$ and neutralized with K$_2$CO$_3$. The solids were filtered off. The filtrate was dried over Na$_2$SO$_4$ and concentrated in vacuo to give 640 mg (quant) of a yellow crystalline solid.

Step 5: 2-[(3-Methanesulfinylmethoxy-benzyl)-methyl-amino]-6,7-dimethoxy-5-methyl-1 H-quinazolin-4-one.

Compound from step 4 (213 mg, 1.00 mmol) and 2-chloro-6,7-dimethoxy-5-methyl-1H-quinazolin-4-one (254 mg, 1.00 mmol) were dissolved in dry DMSO. Et$_3$N (0.14 mL, 1.00 mmol) was added, and the mixture was heated to 120° C. overnight. Upon cooling, the mixture was poured into water and extracted with diethyl ether. The ethereal extracts were dried over Na$_2$SO$_4$ and concentrated in vacuo. The residue was recrystallized from MeOH to give 54 mg (12.53%) of the above Example F-2 as a white crystalline powder. mp 191.0–193.5° C.; $^1$H NMR (DMSO-d$_6$, 2.49) δ 2.59 (s, 3 H), 2.60 (s, 3 H), 3.03 (s, 3 H), 3.62 (s, 3 H), 3.84 (s, 3 H), 4.79 (s, 2 H), 5.02 (d, 1 H, J=10.6), 5.22 (d, 1 H, J=10.6), 6.64 (s, 1 H), 6.90 (d, 1 H, J=7.6), 7.01 (m, 2 H), 7.30 (t, 1 H, J=7.9); $^{13}$C NMR (DMSO-d$_6$, 39.50) δ 13.90, 34.66, 35.59, 51.90, 55.93, 60.23, 84.92, 104.81, 108.46, 114.18, 115.02, 121.22, 130.13, 131.94, 140.10, 142.90, 150.63, 150.97, 157.71, 157.97, 163.67; MS (ES+) m/z 432 (M+H); Anal. (C$_{21}$H$_{25}$N$_3$O$_5$S)C: calcd, 58.45; found, 58.32; H: calcd, 5.84; found, 5.74; N: calcd, 9.74; found, 9.77.

Example F-3

6,7-Dimethoxy-5-methyl-2-{methyl-[3-(pyrimidin-2-yloxy)-benzyl]-amino}-1H-quinazolin-4-one

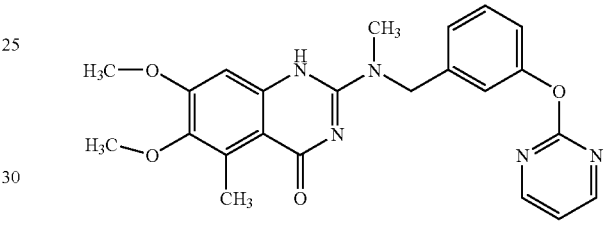

Step 1:

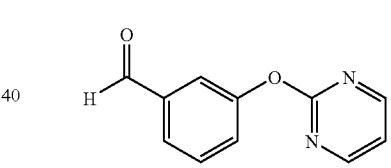

(1)

A mixture of 3-hydroxybenzaldehyde (2.00 g, 16.38 mmol), 2-chloropyrimidine (1.88 g, 16.38 mmol) and $^i$Pr$_2$NEt (5.71 mL, 32.75 mmol), under N$_2$ atmosphere was heated at 105° C. for 24 h. The reaction mixture was allowed to cool to room temperature. The crude was subjected to column chromatography (silica gel, 20% EtOAc in hexanes) to furnish 1.62 g of the desired aryl ether (1) as an off-white solid.

Step 2:

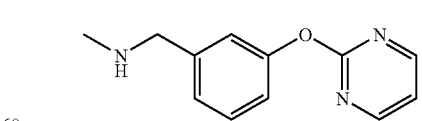

(2)

To a solution of the aryl ether (1) from Step 1 (1.00 g, 5.00 mmol) and MeNH$_2$ (3.00 mL, 2.0 M in THF, 5.99 mmol) in MeOH (75 mL) at room temperature was added NaCNBH$_3$ (377 mg, 5.99 mmol). The reaction was stirred for 7 h before it was concentrated under reduced pressure. The residue was taken-up in a mixture of 1 N aq. HCl (20 mL) and CH$_2$Cl$_2$ (5 mL). The aq. layer was separated, adjusted to pH 10, and extracted with $CH_2Cl_2$. The $CH_2Cl_2$ extract was washed with brine, dried over $MgSO_4$, and concentrated. The residue was purified by column chromatography (silica gel, 10% MeOH in $CH_2Cl_2$) to furnish 363 mg of the benzylamine (2) as a faintly-colored oil.

Step 3:

A mixture of the benzylamine (2) from Step 2 (152 mg, 0.71 mmol), 2-chloro-6,7-dimethoxy-5-methyl-quinazolin-4-one (150 mg, 0.59 mmol) and $^iPr_2NEt$ (205 μL, 1.18 mmol) in anhydrous EtOH (5 mL) in a sealed tube was heated at 65° C. for 16 h before it was allowed to cool to room temperature slowly. The precipitate was collected by suction filtration, washed with EtOH, and dried in the oven at 60° C. to provide 57 mg of Example F-3 as an off-white solid. Mp 224.0–227.8° C.; TLC $R_f$ 0.52 (5% MeOH in $CH_2Cl_2$); $^1H$ NMR (DMSO-$d_6$, 2.49) δ 2.60 (s, 3 H), 3.05 (s, 3 H), 3.62 (s, 3 H), 3.83 (s, 3 H), 4.85 (s, 2 H), 6.62 (br s, 1 H), 7.08–7.13 (m, 3 H), 7.24 (t, 1 H, J=4.8 Hz), 7.40 (t, 1 H, J=7.7 Hz), 8.60 (d, 2 H, J=4.8 Hz), 10.84 (br s, 1 H); MS (ES+) m/z 434 (M+H); Anal. ($C_{23}H_{23}N_5O_4 \cdot 2HCl \cdot 0.5H_2O$) C: calcd, 53.60; found, 53.55; H: calcd, 13.58; found, 13.52; N: calcd, 5.08; found, 4.48.

Examples F-4 to F-16

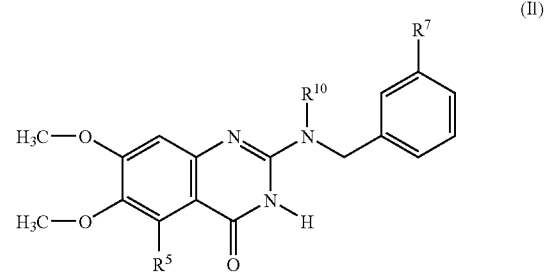

(II)

Compounds having the above formula (II), wherein $R^5$, $R^7$ and $R^{10}$ have the values reported in Table 6 were prepared following the same or similar method as described for Examples F-1 through F-3.

TABLE 6

| Ex. | $R^5$ | $R^7$ | $R^{10}$ | Compound Name | Mp ° C. | MSM+ |
| --- | --- | --- | --- | --- | --- | --- |
| F-4 | —$CH_3$ | —OH | —$CH_3$ | 2-[(3-Hydroxy-benzyl)-methyl-amino]-6,7-dimethoxy-5-methyl-1H-quinazolin-4-one | | 355.4 |
| F-5 | —O—$CH_3$ | —OH | —$CH_3$ | 2-[(3-Hydroxy-benzyl)-methyl-amino]-5,6,7-trimethoxy-1H quinazolin-4-one | | 371.4 |
| F-6 | —O—$CH_3$ | methanesulfonylmethoxy group | —$CH_3$ | 2-[(3-Methanesulfonylmethoxy-benzyl)-methyl-amino]-5,6,7-trimethoxy-1H-quinazolin-4-one | 183.9–185.4 | 463.5 |
| F-7 | —$CH_3$ | carboxymethoxy group | —$CH_3$ | (3-{[(6,7-Dimethoxy-5-methyl-4-oxo-1,4-dihydro-quinazolin-2-yl)-methyl-amino]-methyl}-phenoxy)-acetic acid | | 413.4 |
| F-8 | —O—$CH_3$ | carboxymethoxy group | —$CH_3$ | (3-{[Methyl-(5,6,7-trimethoxy-yl)-amino]-methyl}-phenoxy)-4-oxo-1,4-dihydro-quinazolin-2-acetic acid | | 429.4 |
| F-9 | —$CH_3$ | 2-hydroxyethoxy group | —$CH_3$ | 2-{[3-(2-Hydroxy-ethoxy)-benzyl]-methyl-amino}-6,7-dimethoxy-5-methyl-1H-quinazolin-4-one | 180.5–183.1 | 399.4 |

TABLE 6-continued

| Ex. | R⁵ | R⁷ | R¹⁰ | Compound Name | Mp °C. | MSM⁺ |
|---|---|---|---|---|---|---|
| F-10 | —CH₃ | 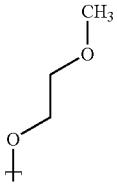 | —CH₃ | 6,7-Dimethoxy-2-{[3-(2-methoxy-ethoxy)-benzyl]-methyl-amino}-5-methyl-1H-quinazolin-4-one | 144.8–145.9 | 413.5 |
| F-11 | —O—CH₃ | 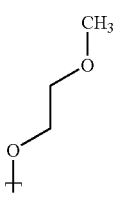 | —CH₃ | 5,6,7-Trimethoxy-2-{[3-(2-methoxy-ethoxy)-benzyl]-methyl-amino}-1H-quinazolin-4-one | 144.8–145.9 | 429.5 |
| F-12 | —CH₃ | 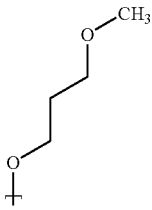 | —CH₃ | 6,7-Dimethoxy-2-{[3-(3-methoxy-propoxy)-benzyl]-methyl-amino}-5-methyl-1H-quinazolin-4-one | | 427.5 |
| F-13 | —O—CH₃ | 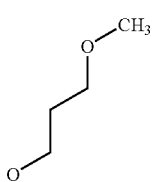 | —CH₃ | 5,6,7-Trimethoxy-2-{[3-(3-methoxy-propoxy)-benzyl]-methyl-amino}-1H-quinazolin-4-one | | 443.5 |
| F-14 | —CH₃ | 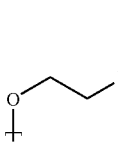 | —CH₃ | 2-([3-(2-Dimethylamino-ethoxy)-benzyl]-methyl-amino}-6,7-dimethoxy-5-methyl-1H-quinazolin-4-one | | 426.5 |
| F-15 | —CH₃ | 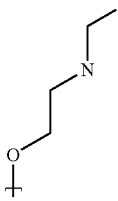 | —CH₃ | 2-([3-(2-Ethylamino-ethoxy)-benzyl]-methyl-amino}-6,7-dimethoxy-5-methyl-1H-quinazolin-4-one | | 426.5 |
| F-16 | —O—CH₃ | 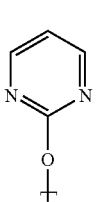 | —CH₃ | 5,6,7-Trimethoxy-2-{methyl-[3-(pyrimidin-2-yloxy)-benzyl]-amino}-1H-quinazolin-4-one | 191–192.9 | 449.5 |

Additional compounds prepared according to the procedure of Examples F-1 through F-3 are shown in Table 11.

Example G-1

N'-(3-{[(6,7-Dimethoxy-5-methyl-4-oxo-1,4-dihydro-quinazolin-2-yl)-methyl-amino]-methyl}-phenyl)-N,N-dimethyl-acetamidine

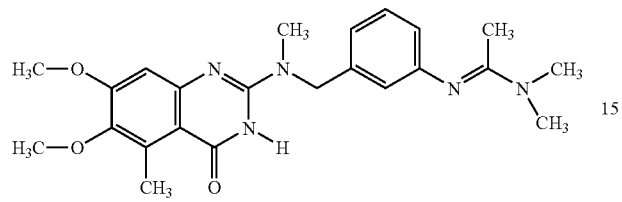

The aniline of Example B-1 (600 mg, 1.7 mmol), the dimethylacetal of DMF (330 mg, 2.23 mmol), and DMF (2 mL) was kept at 100° C. for 35 min and then stored at ambient temperature for 16 h. The precipitated product was collected and washed with diethyl ether affording 340 mg of product. This material was further purified by chromatography (EM Science silica gel 60; 3% MeOH in DCM containing 0.5% of ammonium hydroxide) to yield 250 mg (35%) of the above compound as a white solid. Mp 174.4–174.8° C.; ms 424 (M+H). The HCl salt of the above compound was prepared mixing 600 mg (1.4 mmol) of the free base with 8 mL hot EtOH, and then adding to this solution 2.7 mL of a 1.4 M solution of HCl in EtOH (3.7 mmol). The HCl salt was crystallized by addition of diethyl ether. The collected product was dried at 80° C. in vacuo to furnish 620 mg. Mp 170.6–172.5° C.; Anal. ($C_{23}H_{29}N_5O_3 \cdot 2HCl \cdot 0.5H_2O$) Calcd.: C, 54.65; H, 6.38; N, 13.86. Found: C, 54.40; H, 6.14; N, 13.81.

Examples G-2 to G-55

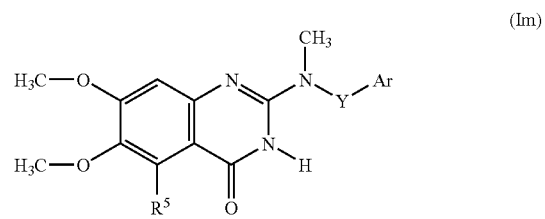

(Im)

Compounds having the above formula (Im), wherein $R^5$, $R^{10}$ and Y—Ar taken together have the values reported in Table 7, were prepared following the same or similar method as described for Example G-1.

TABLE 7

| Ex. No | $R^5$ | —Y—Ar | Compound Name | Mp ° C. | MW |
|---|---|---|---|---|---|
| G-2 | IsoPr | ![structure] | N-(3-{[(5-Isopropyl-6,7-dimethoxy-4-oxo-1,4-dihydro-quinazolin-2-yl)-methyl-amino]-methyl}-phenyl)-methanesulfonamide | 215–17 | 460.55 |
| G-3 | —CH₃ | ![structure] | 6,7-Dimethoxy-5-methyl-2-[methyl-(3-[(dimethylamino)sulfonyl]amino]-benzyl)-amino]-1H-quinazolin-4-one | | 461.54 |
| G-4 | —CH₃ | ![structure] | 6,7-Dimethoxy-5-methyl-2-[methyl-(3-[(dimethylamino)sulfonyl]methyl-amino]-benzyl)-amino]-1H-quinazolin-4-one | | 475.57 |
| G-5 | —O—CH₃ | ![structure] | 5,6,7-Trimethoxy-2-[methyl-(3-[(dimethylamino)sulfonyl]methyl-amino]-benzyl)-amino]-1H-quinazolin-4-one | | 477.54 |

TABLE 7-continued

| Ex. No | R⁵ | —Y—Ar | Compound Name | Mp °C. | MW |
|---|---|---|---|---|---|
| G-6 | —O—CH₃ | (3-[N,N-dimethyl-sulfamoyl-N-methyl]aminobenzyl) | 5,6,7-Trimethoxy-2-[methyl-(3-[(dimethylamino)sulfonyl]methyl-amino]-benzyl)-amino]-1H-quinazolin-4-one | | 491.57 |
| G-7 | —CH₃ | (3-acetamidobenzyl) | N-(3-{[(6,7-Dimethoxy-5-methyl-4-oxo-1,4-dihydro-quinazolin-2-yl)-methyl-amino]-methyl}-phenyl)-acetamide | | 396.45 |
| G-8 | —O—CH₃ | (3-acetamidobenzyl) | N-(3-{[Methyl-(5,6,7-trimethoxy-4-oxo-1,4-dihydro-quinazolin-2-yl)-amino]-methyl}-phenyl)-acetamide | | 412.44 |
| G-9 | —O—CH₃ | (4-chloro-3-acetamidobenzyl) | N-(4-Chloro-3-{[methyl-(5,6,7-trimethoxy-4-oxo-1,4-dihydro-quinazolin-2-yl)-amino]-methyl}-phenyl)-acetamide | | 446.89 |
| G-10 | —O—CH₃ | (3-(3,3-dimethylureido)benzyl) | 1,1-Dimethyl-3-(3-{[methyl-(5,6,7-trimethoxy-4-oxo-1,4-dihydro-quinazolin-2-yl)-amino]-methyl}-phenyl)-urea | | 441.49 |
| G-11 | —O—CH₃ | (3-(methoxycarbonylamino)benzyl) | (3-{[Methyl-(5,6,7-trimethoxy-4-oxo-1,4-dihydro-quinazolin-2-yl)-amino[-methyl}-phenyl)-carbamic acid methyl ester | | 428.44 |

TABLE 7-continued

| Ex. No | R⁵ | —Y—Ar | Compound Name | Mp °C. | MW |
|---|---|---|---|---|---|
| G-12 | —CH₃ | | (3-{[(6,7-Dimethoxy-5-methyl-4-oxo-1,4-dihydro-quinazolin-2-yl)-methyl-amino]-methyl}-phenyl)-methyl-carbamic acid methyl ester | | 426.47 |
| G-13 | —CH₃ | | N-(3-{[(6,7-Dimethoxy-5-methyl-4-oxo-1,4-dihydro-quinazolin-2-yl)-methyl-amino]-methyl}-phenyl)-N-methyl-2-oxo-propionamide | | 438.48 |
| G-14 | —CH₃ | | 3-(3-{[(6,7-Dimethoxy-5-methyl-4-oxo-1,4-dihydro-quinazolin-2-yl)-methyl-amino]-methyl}-phenyl)-1,1-dimethyl-urea | | 425.49 |
| G-15 | —O—CH₃ | | 1-Methoxy-3-(3-{[methyl-(5,6,7-trimethoxy-4-oxo-1,4-dihydro-quinazolin-2-yl)-amino]-methyl}-phenyl)-urea | | 443.46 |
| G-16 | —O—CH₃ | | 2-{[3-(2-Hydroxy-ethylamino)-benzyl]-methyl-amino}-5,6,7-trimethoxy-1H-quinazolin-4-one | 60.5–61.4 | 414.46 |
| G-17 | —OH | | 5-Hydroxy-2-({3-[(3-hydroxy-propyl)-methyl-amino]-benzyl}-methyl-amino)-6,7-dimethoxy-1H-quinazolin-4-one | | 428.49 |
| G-18 | —O—CH₃ | | 2-{[3-(3-Hydroxy-propylamino)-benzyl]-methyl-amino}-5,6,7-trimethoxy-1H-quinazolin-4-one | 47–48.5 | 428.49 |
| G-19 | —O—CH₃ | | 5,6,7-Trimethoxy-2-{[3-(2-methoxy-ethylamino)-benzyl]-methyl-amino}-1H-quinazolin-4-one | 178.9–179.9 | 428.49 |

TABLE 7-continued

| Ex. No | R⁵ | —Y—Ar | Compound Name | Mp ° C. | MW |
|---|---|---|---|---|---|
| G-20 | —OCH₃ | (structure) | 5,6,7-Trimethoxy-2-({3-[(2-methoxy-ethyl)-methyl-amino]-benzyl}-methyl-amino)-1H-quinazolin-4-one | 179.3–181.2 | 442.51 |
| G-21 | —OCH₃ | (structure) | 2-({3-[(3-Hydroxy-propyl)-methyl-amino]-benzyl-}methyl-amino)-5,6,7-trimethoxy-1H-quinazolin-4-one | 156–157.2 | 442.51 |
| G-22 | —OCH₃ | (structure) | 5,6,7-Trimethoxy-2-{[3-(3-methoxy-propylamino)-benzyl]-methyl-amino}-1H-quinazolin-4-one, hydrochloride salt | | 442.51 |
| G-23 | —OCH₃ | (structure) | (3-{[(6,7-Dimethoxy-5-methyl-4-oxo-1,4-dihydro-quinazolin-2-yl)-methyl-amino]-methyl}-phenyl)-methyl-carbamic acid methyl ester | | 455.5 |
| G-24 | —OCH₃ | (structure) | 2-({3-[Bis-(2-hydroxy-ethyl)-amino]-benzyl}-methyl-amino)-5,6,7-trimethoxy-1H-quinazolin-4-one | | 458.51 |
| G-25 | —CH₃ | (structure) | N-[2-(3-{1-[(6,7-Dimethoxy-5-methyl-4-oxo-1,4-dihydro-quinazolin-2-yl)-methyl-amino]-ethyl}-phenylamino)-ethyl]-acetamide | | 453.54 |
| G-26 | —CH₃ | (structure) | N-(3-{[(6,7-Dimethoxy-5-methyl-4-oxo-1,4-dihydro-quinazolin-2-yl)-methyl-amino]-methyl}-phenyl)-acetamidine | 155–58 | 395.46 |

TABLE 7-continued

| Ex. No | R⁵ | —Y—Ar | Compound Name | Mp ° C. | MW |
|---|---|---|---|---|---|
| G-27 | —O—CH₃ | | N-(3-{[Methyl-(5,6,7-trimethoxy-4-oxo-1,4-dihydro-quinazolin-2-yl)-amino]-methyl}-phenyl)-acetamidine | | 411.46 |
| G-28 | —CH₃ | | N-(3-{[(6,7-Dimethoxy-5-methyl-4-oxo-1,4-dihydro-quinazolin-2-yl)-methyl--pbenyl)-N,N'-amino]-methyl} dimethyl-acetamidine | | 423.51 |
| G-29 | —CH₃ | | N-(3-{[(6,7-Dimethoxy-5-methyl-4-oxo-1,4-dihydro-quinazolin-2-yl)-methyl-amino]-methyl}-phenyl)-N'-methyl-acetamidine | | 409.49 |
| G-30 | —CH₃ | | N'-(3-{[(6,7-Dimethoxy-5-methyl-4-oxo-1,4-dihydro-quinazolin-2-yl)-methyl-amino]-methyl}-phenyl)-N,N-dimethyl-formamidine | 185–86 | 409.49 |
| G-31 | —O—CH₃ | | N,N-Dimethyl-N'-(3-{[methyl-(5,6,7-trimethoxy-4-oxo-1,4-dihydro-quinazotin-2-yl)-amino]-methyl}-phenyl)-acetamidine | 199–201 | 439.51 |
| G-32 | —O—CH₃ | | N,N-Dimethyl-N'-(3-{[methyl-(5,6,7-trimethoxy-4-oxo-1,4-dihydro-quinazolin-2-yl)-amino]-methyl}-phenyl)-isobutyramidine | 148–50 | 467.57 |
| G-33 | —CH₂CH₃ | | N'-(3-{[(5-Ethyl-6,7-dimethoxy-4-oxo-1,4-dihydro-quinazolin-2-yl)-methyl-amino]-methyl}-phenyl)-N,N-dimethyl-acetamidine | 224.6–225.5 | 437.54 |
| G-34 | -isoPr | | N'-(3-{[(5-Isopropyl-6,7-dimethoxy-4-oxo-1,4-dihydro-quinazolin-2-yl)-methyl-amino]-methyl}-phenyl)-N,N-dimethyl-acetamidine | | 451.57 |
| G-35 | —OH | | N'-(3-{[(5-Hydroxy-6,7-dimethoxy-4-oxo-1,4-dihydro-quinazolin-2-yl)-methyl-amino]-methyl}-phenyl)-N,N-dimethyl-acetamidine | | 425.49 |

TABLE 7-continued

| Ex. No | R⁵ | —Y—Ar | Compound Name | Mp °C. | MW |
|---|---|---|---|---|---|
| G-36 | —OCH₃ | | 3-Methoxy-N,N-dimethyl-N'-(3-{[methyl-(5,6,7-trimethoxy-4-oxo-1,4-dihydro-quinazolin-2-yl)-amino]-methyl}-phenyl)-propionamidine | 145 | 483.57 |
| G-37 | —OCH₃ | | N,N-Dimethyl-N'-(3-{[methyl-(5,6,7-trimethoxy-4-oxo-1,4-dihydro-quinazolin-2-yl)-amino]-methyl}-phenyl)-cyclobutanecarboxamidine | | 479.57 |
| G-38 | —CH₃ | | 2-{[3-(Imidazolidin-2-ylideneamino)-benzyl]-methyl-amino}-6,7-dimethoxy-5-methyl-1H-quinazolin-4-one | 141.3–144.7 | 422.49 |
| G-39 | —OCH₃ | | 5,6,7-Trimethoxy-2-{methyl-[3-(1-methyl-pyrrolidin-2-ylideneamino)-benzyl]-amino}-1H-quinazolin-4-one | 130–133 | 451.52 |
| G-40 | —OCH₃ | | 2-{[2-Chloro-5-(1,3-dimethyl-imidazolidin-2-ylideneamino)-benzyl]-methyl-amino}-5,6,7-trimethoxy-1H-quinazolin-4-one | | 500.98 |
| G-41 | —CH₂CH₃ | | 2-{[3-(1,3-dimethyl-imidazolidin-2-ylideneamino)-benzyl]-methyl-amino}-6,7-diimethoxy-5-ethyl-1H-quinazolin-4-one, hexafluorophosphate | 212.5–219.9 | 464.57 |
| G-42 | —CH₃ | | 2-{[3-(4,5-Dihydro-3H-pyrrol-2-ylamino)-benzyl]-methyl-amino}-6,7-dimethoxy-5-methyl-1H-quinazolin-4-one | 175.4–177.2 | 421.50 |
| G-43 | —OCH₃ | | 2-{[3-(4,5-Dihydro-3H-pyrrol-2-ylamino)-benzyl]-methyl-amino}-5,6,7-trimethoxy-1H-quinazolin-4-one | 207–209 | 437.50 |

TABLE 7-continued

| Ex. No | R[5] | —Y—Ar | Compound Name | Mp ° C. | MW |
|---|---|---|---|---|---|
| G-44 | —O—CH₃ | | 5,6,7-Trimethoxy-2-{methyl-[3-(2-oxo-tetrahydro-furan-3-ylamino)-benzyl]-amino}-1H-quinazolin-4-one | | 454.48 |
| G-45 | —OH | | 2-({5-[(4,5-Dihydro-3H-pyrrol-2-yl)-methyl-amino]-2-fluoro-benzyl}-methyl-amino)-5-hydroxy-6,7-dimethoxy-1H-quinazolin-4-one | | 455.49 |
| G-46 | —CH₃ | | 6,7-Dimethoxy-5-methyl-2-{methyl-[3-(pyrimidin-2-ylamino)-benzyl]-amino}-1H-quinazolin-4-one | | 432.48 |
| G-47 | —O—CH₃ | | 5,6,7-Trimethoxy-2-{methyl-[3-(pyrimidin-2-ylamino)-benzyl]-amino}-1H-quinazolin-4-one | | 448.48 |
| G-48 | —O—CH₃ | | 2-{[3-(2-Chloro-pyrimidin-4-ylamino)-benzyl]-methyl-amino}-5,6,7-trimethoxy-1H-quinazolin-4-one | | 482.93 |
| G-49 | —O—CH₃ | | 2-{[3-(4-Chloro-pyrimidin-2-ylamino)-benzyl]-methyl-amino}-5,6,7-trimethoxy-1H-quinazolin-4-one | | 482.93 |

TABLE 7-continued

| Ex. No | R⁵ | —Y—Ar | Compound Name | Mp °C. | MW |
|---|---|---|---|---|---|
| G-50 | —CH₃ | | 2-{[3-(4-Chloro-pyrimidin-2-ylamino)-benzyl]-methyl-amino}-6,7-dimethoxy-5-methyl-1H-quinazolin-4-one | | 466.93 |
| G-51 | —OCH₃ | | 2-{[3-(2-Chloro-5-methyl-pyrimidin-4-ylamino)-benzyl]-methyl-amino}-5,6,7-trimethoxy-1H-quinazolin-4-one | | 496.95 |
| G-52 | —OCH₃ | | 2-{[3-(2-Chloro-6-methyl-pyrimidin-4-ylamino)-benzyl]-methyl-amino}-5,6,7-trimethoxy-1H-quinazolin-4-one | | 496.95 |
| G-53 | —OCH₃ | | 2-{[3-(4-Chloro-6-methyl-pyrimidin-2-ylamino)-benzyl]-methyl-amino}-5,6,7-trimethoxy-1H-quinazolin-4-one | | 496.95 |
| G-54 | —OCH₃ | | 2-({3-[(1H-Imidazol-2-ylmethyl)-amino]-benzyl}-methyl-amino)-5,6,7-trimethoxy-1H-quinazolin-4-one | | 450.50 |
| G-55 | —F | | N'-(3-{[(5-Fluoro-6,7-dimethoxy-4-oxo-1,4-dihydro-quinazolin-2-yl)-methyl-amino]-methyl}-phenyl)-N,N-dimethyl-acetamidine | | 427.48 |

Additional compounds prepared according to the procedure of Example G-1 are shown in Table 11.

Example H-1

5,6,7-Trimethoxy-2-{methyl-[3-(2-oxo-pyrrolidin-1-yl)-benzyl]-amino}-1H-quinazolin-4-one

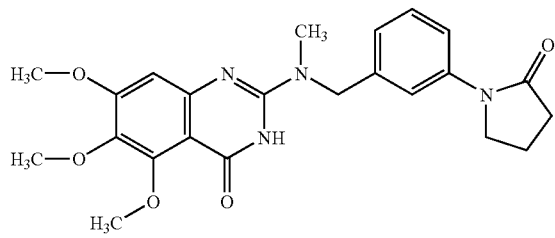

Step 1:

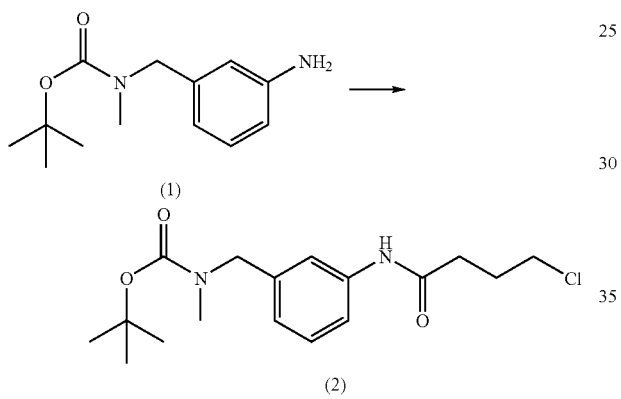

To a solution of aniline (1) (1.39 g, 5.88 mmol) and $^i$Pr$_2$NEt (1.13 mL, 6.42 mmol) in THF (7 mL) at 0° C. was added dropwise a solution of 4-chlorobutyryl chloride (659 □L, 5.88 mmol) in THF (3 mL). The reaction mixture was then allowed to warm to room temperature and stirred for 1 h before it was poured into a mixture of EtOAc and saturated aq. NH$_4$Cl. The organic layer was separated and concentrated under reduced pressure to provide the crude amide intermediate (2).

Step 2:

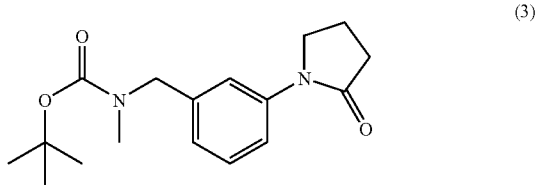

To a solution of the amide intermediate (2) from Step 1 in MeCN (150 mL) at room temperature was added dropwise a solution of 50% aq. NaOH (0.94 mL, 11.76 mmol). The reaction mixture was stirred for 1 h before it was concentrated under reduced pressure. The residue was partitioned between EtOAc and H$_2$O. The organic layer was washed with brine, dried over MgSO$_4$, and concentrated. The residue was purified (silica gel, EtOAc) to furnish 1.80 g of lactam (3) as colorless oil.

Step 3:

Trifluoroacetic acid (375 μL, 4.87 mmol) was added via syringe to a stirred solution of (3) from Step 2 (189 mg, 0.62 mmol) at 0° C. After 3 hours, the solution was concentrated under reduced pressure, then pumped under vacuum for 1 hour. The crude residue was dissolved in EtOH (2 mL), and added to a sealed tube containing 2-chloro-5,6,7-trimethoxy-1H-quinazolin-4-one (132 mg, 0.49 mmol), diisopropylethylamine (425 μL, 2.44 mmol), and EtOH (3 mL). The suspension was heated at 110° C. for 2 hours, then cooled to room temperature and stirred overnight. The reaction mixture was concentrated under reduced pressure, and purified by chromatography to give 128 mg (60%) of the above Example H-1 as a cream colored solid. mp 165.5–166.5° C.; TLC Rf 0.5 (5% MeOH/DCM); IR (KBr) $v_{max}$ 3429, 2933, 1657, 1592, 1481, 1452, 1120, 1047, 933; $^1$H NMR (DMSO-d$_6$, 2.49) 2.04 (m, 2H), 2.50 (t, 2H, J=1.9), 3.03 (s, 3H), 3.70 (s, 3H), 3.77 (s, 1H), 3.81 (t, 2H, J=6.9), 3.84 (s, 3H), 4.81 (s, 2H), 6.57 (s, 2H), 6.99 (d, 1H, J=7.7), 7.32 (t, 1H, J=7.8), 7.49 (dd, 1H, J=2.1, 7.4), 7.65 (s, 1H), 10.83 (s, 1H); MS (ES+) m/z 439 (M+H); Anal. (C$_{23}$H$_{26}$N$_4$O$_5$ w/0.25M CH$_2$Cl$_2$): calcd 60.75; found: 60.65; H: calcd, 5.81; found: 5.79; N: calcd, 12.19; found, 11.98).

Example H-2

6,7-Dimethoxy-5-methyl-2-{methyl-[3-(1-methyl-4,5-dihydro-1H-imidazol-2-yl)-benzyl]-amino}-1H-quinazolin-4-one

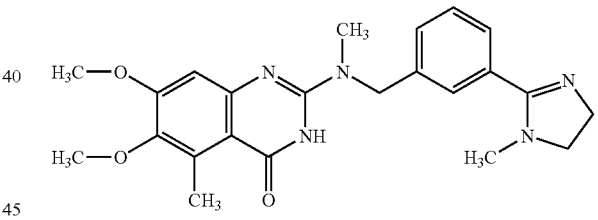

Step 1:

Diisopropylethylamine (0.82 mL, 4.71 mmol) was added to the mixture of 2-chloro-6,7-dimethoxy-5-methyl-quinazolin-4-one (1.0 g, 3.92 mmol) and N-methyl-(3-cyano-benzyl)-amine (0.68 g, 4.71 mmol) in EtOH (50 mL). It was heated at 120° C. for 1.5 h in the sealed tube. After cooling down, the resulting white solid was filtered and washed with MeOH: mp 279.9–281.5° C.; $^1$H NMR (DMSO-d$_6$) δ 2.6 (s, 3H), 3.05 (s, 3H), 3.62 (s, 3H), 3.84 (s, 3H), 4.86 (s, 2H), 6.62 (s, 1H), 7.5–7.7.78 (m, 4H); $^{13}$C NMR (DMSO-d$_6$) δ 13.89, 35.58, 51.52, 55.93, 60.22, 104.79, 111.78, 119.15, 130.12, 131.19, 131.28, 131.96, 132.51, 140.04, 142.96, 150.51, 157.71;

Step 2:

α-Bromo-m-cyanotoluene (1.0 g, 5.1 mmol) in 2M MeNH$_2$/MeOH (25.5 mL, 51 mmol) was refluxed for 1 h. After evaporating most of solvent, the resulting solid was filtered. The mother liquor was concentrated in vacuo and it was purified by chromatography.

Step 3:

A few drops of carbondisulfide was added to a solution of the arylnitrile of Example B-2, above (0.08 g, 0.219 mol) in 1 mL of N-methylethylendiamine. The mixture was allowed to stir at 120° C. for 2 h. The excess amine was evaporated under reduced pressure and purified by flash column chromatography to provide the above Example H-2. Mp 145–148° C.; IR (KBr) $v_{max}$ 2931, 1660, 1306 cm$^{-1}$; $^1$H NMR (DMSO-d$_6$) δ 2.6 (s, 3H), 2.7 (s, 3H), 3.05 (s, 3H), 3.45 (t, 2H), 3.62 (s, 3H), 3.68 (t, 2H), 3.84 (s, 3H), 4.86 (s, 2H), 6.65 (s, 1H), 7.3–7.45 (m, 4H); $^{13}$C NMR (DMSO-d$_6$) δ 13.89, 35.60, 36.48, 39.05, 39.33, 39.60, 39.88, 51.82, 52.54, 53.90, 55.93, 60.23, 127.01, 127.10, 128.97, 129.04, 131.40, 131.98, 138.36, 142.94, 167.08; MS (ES+) m/z 422 (M+H); Anal. (C$_{23}$H$_{27}$N$_5$O$_3$. 0.30M CH$_2$Cl$_2$) C; calcd, 62.61; found, 62.71; H; calcd, 6.22; found, 6.28; N; calcd, 15.67; found, 15.83.

Example H-3

6,7-Dimethoxy-5-methyl-2-{methyl-[3-(1-methyl-piperidin-4-yl)-benzyl]-amino}-1H-quinazolin-4-one

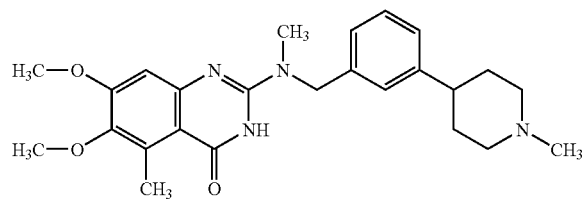

Step 1: 4-(3-Methylcarbamoylphenyl)piperidine-1-methyl-carboxamide.

To a solution of 4-(3-carboxyphenyl)piperidine-1-carboxylic acid tert-butyl ester (1.0 g, 3.27 mmol) in 4 mL of DMF, was added CDI (0.63 g, 3.92 mmol) and the reaction mixture warmed to 60° C. for two hours. After that time, the mixture was cooled to 0–5° C. and, a 2 M solution of methylamine in THF (4.91 mL, 9.82 mmol) was added via syringe and the mixture allowed to warm to room temperature overnight. The mixture was poured into a saturated solution of ammonium chloride, and the product was extracted with ethyl ether (3×50 mL). Organics were washed with water (3×30 mL) and brine (1×15 mL), then dried with magnesium sulfate and concentrated. The dense liquid, crude product, was used into the next step without further treatment. Yield 1.05 g (100%). $^1$H NMR (CDCl$_3$, 7.26) δ 1.48 (s, 9 H), 1.63 (m, 2 H), 1.75 (m, 2 H), 2.69 (m, 1 H), 2.80 (m, 2 H), 3.01 (d, 3 H), 4.23 (br s, 2H), 6.15 (br s, D$_2$O, 1H), 7.32 (dt, 1H, J=6.87, 1.71), 7.34 (t, 1H, J=6.72), 7.55 (dt, 1H, J=6.87, 1.71), 7.64 (t, 1H, J=1.71); MS (ES+) m/z 319 (M+H), 341.2 (M+Na).

Step 2: Methyl-[3-(1-methylpiperidin-4-yl)benzyl]amine.

To a solution of 4-(3-methylcarbamoylphenyl)piperidine-1-methylcarboxamide (1.05 g, 3.29 mmol) in 50 mL of THF, was added portion-wise LiAlH$_4$ (0.625 g, 16.48 mmol). The reaction mixture was stirred at room temperature for 18 hours and then warmed to 50° C. for 24 hours. Then, the mixture was cooled to room temperature and Na$_2$SO$_4$.10H$_2$O (10 g) was added portion-wise (very slowly), and the mixture stirred for two hours. Solids were removed by filtration (celite pad), rinsed with 10% MeOH/CH$_2$Cl$_2$ (100 mL), and the filtrate concentrated. The residue was purified by flash chromatography, eluting with CH$_2$Cl$_2$: MeOH:NH$_4$OH (60:10:1). Yield 0.59 g (81.9%). $^1$H NMR (CDCl$_3$, 7.26) δ 1.64 (br s, D$_2$O, 1H), 1.82 (m, 4 H), 2.04 (m, 2H), 2.32 (s, 3 H), 2.45 (s, 3 H), 2.47 (m, 1 H), 2.97 (m, 2H), 3.72 (s, 2H), 7.13–7.18 (m, 3H), 7.26 (t, 1H, J=7.08); MS (ES+) m/z 219.2 (M+H).

Step 3: 6,7-Dimethoxy-5-methyl-2-{methyl-[3-(1-methylpi-peridin-4-yl)benzyl]amino}-1H-quinazolin-4-one In a heavy-walled pressure tube, a mixture of methyl-[3-(1-methylpiperidin-4-yl)benzyl]amine (0.14 g, 0.64 mmol) and 2-chloro-6,7-dimethoxy-5-methyl-1H-quinazolin-4-one (0.155 g, 0.60 mmol) in 4 mL of EtOH, was heated to 120° C. for 5 hours. After solvent removal, the residue was purified by flash chromatography eluting with CH$_2$Cl$_2$: MeOH:NH$_4$OH (94.5:5:0.5), and the above-titled Example H-3 crystallized from CH$_2$Cl$_2$/cyclohexane. mp 155.7–158° C.; IR (KBr) $v_{max}$ 2933, 1651, 1590 cm$^{-1}$; $^1$H NMR (DMSO-d$_6$, 2.49) δ 1.59–1.71 (m, 4H), 1.93 (m, 2H), 2.16 (s, 3H), 2.42 (m, 1 H), 2.60 (s, 3H), 2.82 (m, 2 H), 3.01 (s, 3H), 3.62 (s, 3H), 3.84 (s, 3H), 4.78 (s, 2H), 6.63 (br s, 1H), 7.03 (d, 1H, J=7.44), 7.11–7.13 (m, 2 H), 7.25 (t, 1H, J=7.74), 10.81 (br s, D$_2$O, 1H); $^{13}$C NMR (DMSO-d$_6$, 39.50) δ 13.44, 32.94, 35.12, 41.08, 46.09, 51.64, 55.44, 55.65, 59.76, 124.61, 125.32, 125.65, 128.44, 137.54, 146.43; MS (ES+) m/z 437 (M+H); Anal. (C$_{25}$H$_{32}$N$_4$O$_3$.0.25H$_2$O)C: calcd, 68.08; found, 68.02; H: calcd, 7.43; found, 7.19; N: calcd, 12.70; found, 12.69.

Examples H-4 to H-47

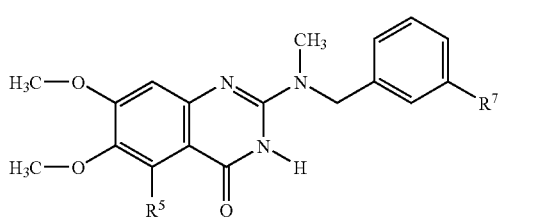

(In)

Compounds having the above formula (In), wherein R$^5$ and R$^7$ have the values reported in Table 8, were prepared following the same or similar method as described for Examples H-1 to H-3, except using an appropriately substituted benzyl amine.

TABLE 8

| Ex. No | —R⁵ | —R⁷ | Compound Name | Mp ° C. | MW |
|---|---|---|---|---|---|
| H-4 | —CH₃ | 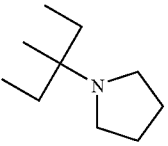 | 6,7-Dimethoxy-5-methyl-2-[meethyl-(3-pyrrolidin-1-yl-benzyl)-amino]-1H-quinazolin-4-one | | 408.50 |
| H-5 | —O—CH₃ | 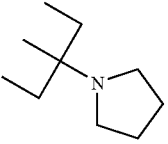 | 5,6,7-Trimethoxy-2-[methyl-(3-pyrrolidin-1-yl-benzyl)-amino]-1H-quinazolin-4-one | | 424.50 |
| H-6 | —CH₃ | 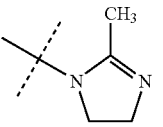 | 6,7-Dimethoxy-5-methyl-2-{methyl-[3-(2-methyl-4,5-dihydro-imidazol-1-yl)-benzyl]-amino}-1H-quinazolin-4-one | 177–180 | 421.50 |
| H-7 | —CH₃ | 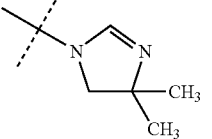 | 2-{[3-(4,4-Dimethyl-4,5-dihydro-imidazol-1-yl)-benzyl]-methyl-amino}-6,7-dimethoxy-5-methyl-1H-quinazolin-4-one | | 435.53 |
| H-8 | —CH₃ | 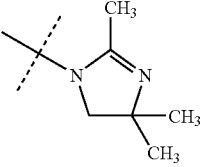 | 6,7-Dimethoxy-5-methyl-2-{methyl-[3-(2,4,4-trimethyl-4,5-dihydro-imidazol-1-yl)-benzyl]-amino}-1H-quinazolin-4-one | | 449.55 |
| H-9 | —CH₃ | 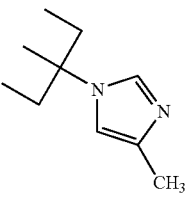 | 6,7-Dimethoxy-5-methyl-2-{methyl-[3-(4-methyl-imidazol-1-yl)-benzyl]-amino}-1H-quinazolin-4-one | | 419.48 |
| H-10 | —CH₃ | 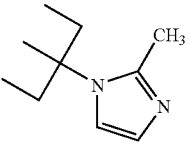 | 6,7-Dimethoxy-5-methyl-2-{methyl-[3-(2-methyl-imidazol-1-yl)-benzyl]-amino}-1H-quinazolin-4-one | | 419.48 |
| H-11 | —CH₃ | 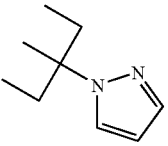 | 6,7-Dimethoxy-5-methyl-2-[methyl-(3-pyrazol-1-yl-benzyl)-amino]-1H-quinazolin-4-one | | 405.46 |
| H-12 | —CH₃ | 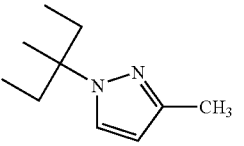 | 6,7-Dimethoxy-5-meethyl-2-{methyl-[3-(3-methyl-pyrazol-1-yl)-benzyl]-amino}-1H-quinazolin-4-one | 220–223.5 | 419.48 |

TABLE 8-continued

| Ex. No | —R⁵ | —R⁷ | Compound Name | Mp ° C. | MW |
|---|---|---|---|---|---|
| H-13 | —CH₃ | (structure) | 2-{[3-(3,5-Dimethyl-pyrazol-1-yl)-benzyl]-methyl-amino}-6,7-dimethoxy-5-methyl-1H-quinazolin-4-one | | 433.51 |
| H-14 | —CH₃ | (structure) | 6,7-Dimethoxy-5-methyl-2-[methyl-(3-pyrrolidin-2-yl-benzyl)-amino]-1H-quinazolin-4-one | | 408.50 |
| H-15 | —OCH₃ | (structure) | 5,6,7-Trimethoxy-2-[methyl-(3-pyrrolidin-3-yl-benzyl)-amino]-1H-quinazolin-4-one | | 424.50 |
| H-16 | —CH₃ | (structure) | 6,7-Dimethoxy-5-methyl-2-{methyl-[4-(1-medthyl-4,5-dihydro-1H-imidazol-2-yl)-benzyl]-amino}-1H-quinazolin-4-one | | 421.50 |
| H-17 | —O—CH₃ | (structure) | 5,6,7-Trimethoxy-2-‡meethyl-[3-(1-methyl-4,5-dihydro-1H-imidazol-2-yl)-benzyl]-amino}-1H-quinazolin-4-one | | 437.5 |
| H-18 | —CH₃ | (structure) | 2-{[3-(1-Ethyl-4,5-dihydro-1H-imidazol-2-yl)-benzyl]-methyl-amino}-6,7-dimethoxy-5-methyl-1H-quinazolin-4-one | | 435.52 |
| H-19 | —O—CH₃ | (structure) | 2-0{[3-(1-Ethyl-4,5-dihydro-1H-imidazol-2-yl)-benzyl]-methyl-amino}-5,6,7-trimethoxy-1H-quinazolin-4-one | | 451.52 |
| H-20 | —O—CH₃ | (structure) | 2-{[3-(1-Isopropyl-4,5-dihydro-1H-imidazol-2-yl)-benzyl]-methyl-amino}-5,6,7-trimethoxy-1H-quinazolin-4-one | | 465.55 |
| H-21 | —CH₃ | (structure) | 2-{[4-(1-Isopropyl-4,5-dihydro-1H-imidazol-2-yl)-benzyl]-methyl-amino}-6,7-dimethoxy-5-methyl-1H-quinazolin-4-one | | 449.55 |

TABLE 8-continued

| Ex. No | —R⁵ | —R⁷ | Compound Name | Mp ° C. | MW |
|---|---|---|---|---|---|
| H-22 | —OH | 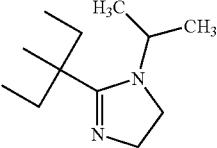 | 5-Hydroxy-2-{[3-(1-isopropyl-4,5-dihydro-1H-imidazol-2-yl)-benzyl]-methyl-amino}-6,7-dimethoxy-1H-quinazolin-4-one | | 451.52 |
| H-23 | —CH₃ | 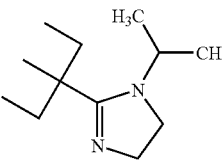 | 2-{[4-(1-Isopropyl-4,5-dihydro-1H-imidazol-2-yl)-benzyl]-methyl-amino}-6,7-dimethoxy-5-methyl-1H-quinazolin-4-one | | 449.55 |
| H-24 | —CH₃ | 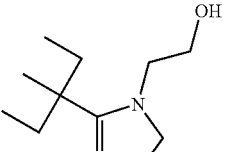 | 2-({3-[1-(2-Hydroxy-ethyl)-4,5-dihydro-1H-imidazol-2-yl]-benzyl}-methyl-amino)-6,7-dimethoxy-5-methyl-1H-quinazolin-4-one | | 451.52 |
| H-25 | —O—CH₃ | 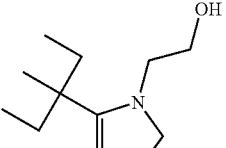 2-({3-[1-(2-Hydroxy-ethyl)-4,5-di-hydro-1H-imidazol-2-ylk]-benzyl}-me-ethyl-amino)-5,6,7-trimethoxy-1H-quinazolin-4-one | | 467.52 | |
| H-26 | —CH₃ | 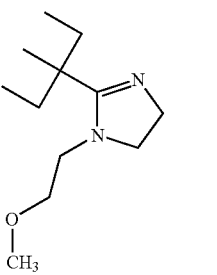 | 6,7-Dimethoxy-2-({3-[1-(2-methoxy-ethyl)-4,5-dihydro-1H-imidazol-2-yl]-benzyl}-methyl-amino)-5-methyl-1H-quinazolin-4-one | | 465.55 |
| H-27 | —O—CH₃ | 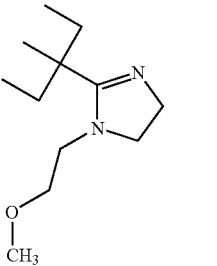 | 5,6,7-Trimethoxy--({3-[1-(2-meethoxy-ethyl)-4,5-dihydro-1H-imidazol-2-yl]-benzyl}-methyl-0amino)-1H-quinazolin-4-one | | 481.55 |

TABLE 8-continued

| Ex. No | —R⁵ | —R⁷ | Compound Name | Mp ° C. | MW |
|---|---|---|---|---|---|
| H-28 | —CH₃ | 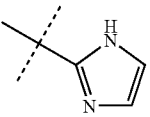 | 2-{[3-(1H-Imidazol-2-yl)-benzyl]-methyl-amino}-6,7-dimethopxy-5-methyl-1H-quinazolin-4-one | | 405.46 |
| H-29 | —CH₃ | 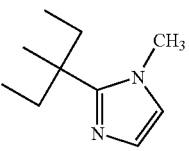 | 6,7-Dimethoxy-5-methyl-2-{methyl-[3-(1-methyl-1H-imidazol-2-yl)-benzyl]-amino}-1H-quinazolin-4-one | | 419.48 |
| H-30 | —CH₃ | 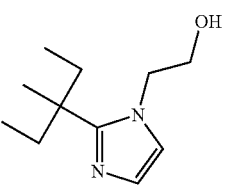 | 2-({3-[1-(2-Hydroxy-ethyl)-1H-imidazol-2-yl]-benzyl}-methyl-amino)-6,7-dimeethoxy-5-methyl-1H-quinazolin-4-one | | 449.51 |
| H-31 | —CH₃ | 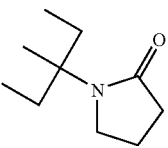 | 6,7-Dimethoxy-5-methyl-2-{methyl-[3-(2-oxo-pyrrolidin-1-yl)-benzyl]-amino}-1H-quinazolin-4-one | | 422.48 |
| H-32 | —CH₃ | 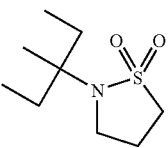 | 2-{[3-(1,1-Dioxo-11 6-isothiazolidin-2-yl)-benzyl]-methyl-amino}-6,7-dimeethoxy-5-methyl-1H-quinazolin-4-one | | 458.54 |
| H-33 | —OCH₃ | 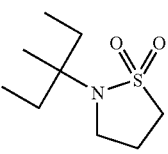 | 2-{[3-(1,1-Dioxo-11 6-isothiazolidin-2-yl)-benzyl]-methyl-amino}-5,6,7-trimethoxy-1H-quinazolin-4-one | | 474.54 |
| H-34 | —CH₃ | 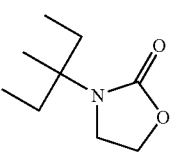 | 6,7-Dimethoxy-5-methyl-02-{methyl-[3-(2-oxo-oxazolidin-3-yl)-benzyl]-amino}-1H-quinazolin-4-one | | 424.45 |
| H-35 | —OCH₃ | 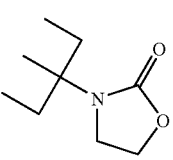 | 5,6,7-Trimethoxy-2-{methyl-[3-(2-oxo-oxazolidin-3-yl)-benzyl]-amino}-1H-quinazolin-4-one | | 440.45 |
| H-36 | —CH₃ | 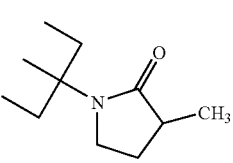 | 6,7-Dimethoxy-5-methyl-2-{methyl-[3-(3-methyl-2-oxo-pyrrolidin-1-yl)-benzyl]-amino}-1H-quinazolin-4-one | | 436.51 |

TABLE 8-continued

| Ex. No | —R⁵ | —R⁷ | Compound Name | Mp ° C. | MW |
|---|---|---|---|---|---|
| H-37 | —CH₃ | 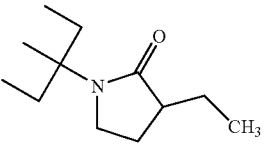 | 2-{[3-(3-Ethyl-2-oxo-pyrrolidin-1-yl)-benzyl]-methyl-amino)-6,7-dimethoxy-5-methyl-1H-quinazolin-4-one | | 450.54 |
| H-38 | —OCH₃ | 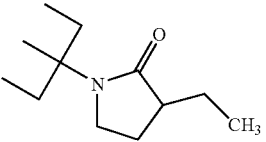 | 2-{[3-(3-Ethyl-2-oxo-pyrrolidin-1-yl)-benzyl]-methyl-amino}-5,6,7-trimethoxy-1H-quiniazolin-4-one | | 466.54 |
| H-39 | —CH₃ | 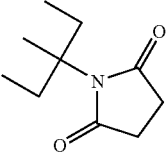 | 1-(3-{[(6,7-Dimethoxy-5-methyl-4-oxo-1,4-dihydro-quinazolin-2-yl)-methyl-amino]-methyl}-phenyl)-pyrrolidine-2,5-dione | | 436.47 |
| H-40 | —OCH₃ | 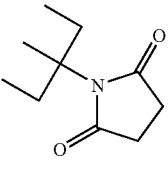 | 1-(3-{[Methyl-(5,6,7-trimethoxy-4-oxo-1,4-dihydro-quinazolin-2-yl)-amino]-methyl}-phenyl)-pyrrolidin-2,5-dione | | 452.47 |
| H-41 | —OCH₃ | 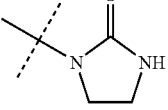 | 5,6,7-Trimethoxy-2-{methyl-[3-(2-oxo-imidazolidin-1-yl)-beenzyl]-amino}-1H-quinazolin-4-one | | 439.47 |
| H-42 | —CH₃ | 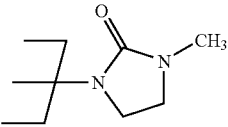 | 6,7-Dimethoxy-5-methyl-2-{methyl-[3-(3-methyl-2-oxo-imidazolidin-1-yl)-benzyl]-amino}-1H-quinazolin-4-one | | 437.50 |
| H-43 | —OCH₃ | 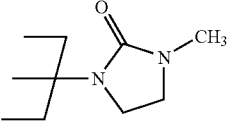 | 5,6,7-Trimethoxy-2-{methyl-[3-(3-methyl-2-oxo-imidazolidin-1-yl)-benzyl]-amino}-1H-quinazolin-4-one | | 453.49 |
| H-44 | —CH₃ | 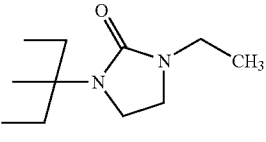 | 2-{[3-(3-Ethyl-2-oxo-imidazolidin-1-yl)-benzyl]-methyl-amino}-6,7-dimethoxy-5-methyl-1H-quinazolin-4-one | | 451.52 |
| H-45 | —OCH₃ | 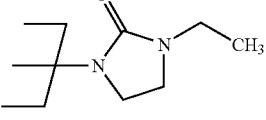 | 2-{[3-(3-Ethyl-2-oxo-imidazolidin-1-yl)-benzyl]-meethyl-amino}-5,6,7-trimethoxy-1H-quinazolin-4-one | | 467.52 |

TABLE 8-continued

| Ex. No | —R⁵ | —R⁷ | Compound Name | Mp ° C. | MW |
|---|---|---|---|---|---|
| H-46 | —OCH₃ | 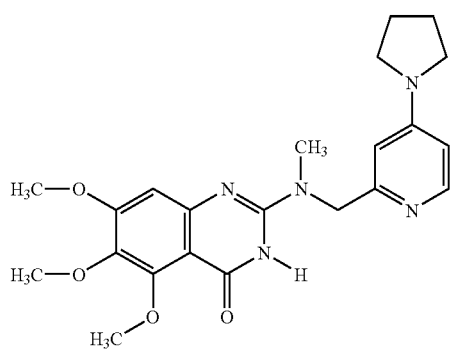 | 5,6,7-Trimeethoxy-2-({3-[3-(2-methoxy-ethyl)-2-oxo-imidazolidin-1-yl]-benzyl}-methyl-amino)-1H-quinazolin-4-one | | 497.55 |
| H-47 | —CH₃ | 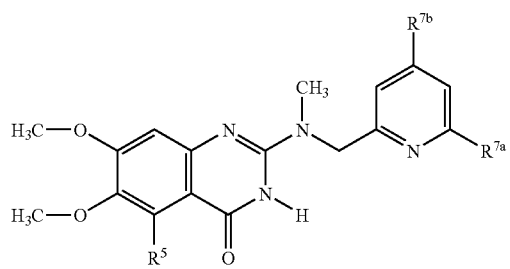 | 6,7-Dimethoxy-5-methyl-2-{methyl-[3-(1H-tetrazol-5-yl)-benzyl]-amino}-1H-quinazolin-4-one | | 407.43 |

Additional compounds prepared according to the procedure of Example H-1 through H-3 are shown in Table 11.

Example I-1

6,7-Dimethoxy-5-methyl-2-[methyl-(4-pyrrolidin-1-yl-pyridin-2-ylmethyl)-amino]-1H-quinazolin-4-one Step 1:

To a 2 N solution of methylamine (6.15 mL, 12.3 mmol) in MeOH was added 4-chloro-2-chloromethylpyridine (0.2 g, 1.23 mmol). The resulting solution was allowed to stir for overnight at rt. After evaporation of the solvent, 4-chloro-2-methylaminomethylpyridine was purified by flash column chromatography. The starting material (4-chloro-2-chloromethylpyridine) was prepared according to Tamura et al., *Chem. Pharm. Bull.*, Vol. 48(10) (2000), at pp. 1514–1518.

Step 2:

Diisopropylethylamine (0.15 mL, 0.86 mmol) was added to a mixture of 2-chloro-5,6,7-trimethoxy-1H-quinazolin-4-one (0.2 g, 0.78 mmol) and 4-chloro-2-methylaminomethylpyridine (0.13 g, 0.86 mmol) in EtOH (8 mL). The mixture was heated at 90° C. for 5 h. After cooling, the resulting white solid was filtered and washed with MeOH to provide quinazolino-pyridine compound.

Step 3:

4-chloropyridine compound from Step 2 (20 mg, 0.05 mmol) in pyrrolidine (0.5 mL) was heated at 130° C. overnight in a sealed tube. The mixture was filtered, concentrated, and purified by preparative reversed-phase HPLC to afford the above Example I-1. ¹H NMR (DMSO-d₆) δ: 2.0 (br, 2H), 2.62 (s, 3H), 3.15 (s, 3H), 3.50 (m, 2H), 3.62 (s, 3H), 3.84 (s, 3H), 4.90 (s, 2H), 6.72 (m, 1H), 6.79 (dd, 1H), 7.54 (s, 1H), 8.17 (dd, 1H) (as the TFA salt). MS (ES+) m/z 410 (M+H)⁺.

Examples I-2 to I-13

(Io)

Compounds I-3 through I-8 and I-13 having the above formula (Io), wherein R⁵, R⁷ᵃ and R⁷ᵇ have the values reported in Table 9, were prepared following the same or similar method as described for Example I-1, replacing the pyrrolidine in step 3 with the desired substituent. The remaining compounds were prepared by condensation of the appropriate amine and carbonyl compounds according to procedures in Abdel-Magid et al. *J. Organic Chemistry* Vol. 61 (1996), at pp. 3849–3862.

TABLE 9

| Ex. No | R⁵ | —R⁷ᵃ | —R⁷ᵇ | Compound Name | MW |
|---|---|---|---|---|---|
| 1-2 | —OCH₃ | 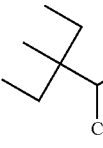 | —H | 5,6,7-Trimethoxy-2-[(6-{1-[(2-methoxy-ethyl)-methyl-amino]-ethyl}-pyridin-2-ylmethyl)-methyl-amino]-1H-quinazolin-4-one | 471.56 |
| I-3 | —O—CH₃ | —H | —Cl | 2-[(4-Chloro-pyridin-2-ylmethyl)-methyl-amino]-5,6,7-trimethoxy-1H-quinazolin-4-one | 390.83 |
| I-4 | —OH | —H | 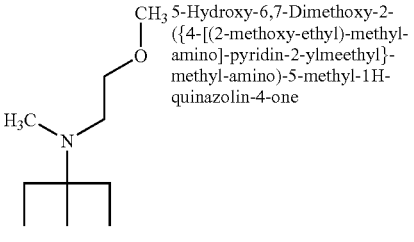 | 5-Hydroxy-6,7-Dimethoxy-2-({4-[(2-methoxy-ethyl)-methyl-amino]-pyridin-2-ylmeethyl}-methyl-amino)-5-methyl-1H-quinazolin-4-one | 429.47 |
| I-5 | —CH₃ | —H | 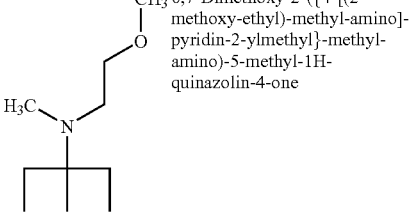 | 6,7-Dimethoxy-2-({4-[(2-methoxy-ethyl)-methyl-amino]-pyridin-2-ylmethyl}-methyl-amino)-5-methyl-1H-quinazolin-4-one | 427.50 |
| I-6 | —O—HC₃ | —H | 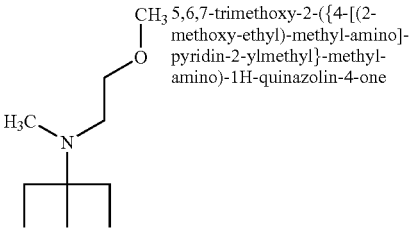 | 5,6,7-trimethoxy-2-({4-[(2-methoxy-ethyl)-methyl-amino]-pyridin-2-ylmethyl}-methyl-amino)-1H-quinazolin-4-one | 443.50 |
| I-7 | —O—HC₃ | —H | 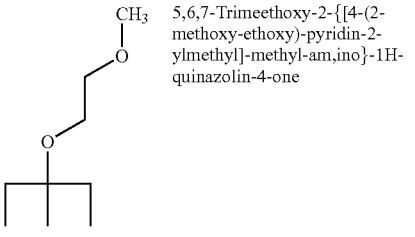 | 5,6,7-Trimeethoxy-2-{[4-(2-methoxy-ethoxy)-pyridin-2-ylmethyl]-methyl-am,ino}-1H-quinazolin-4-one | 430.46 |

TABLE 9-continued

| Ex. No | R⁵ | —R⁷ᵃ | —R⁷ᵇ | Compound Name | MW |
|---|---|---|---|---|---|
| I-8 | —OCH₃ | —H | OEt | 2-[(4-Ethoxy-pyridin-2-ylmethyl)-meethyl-amino]-5,6,7-trimethoxy-1H-quinazolin-4-one | 400.43 |
| I-9 | —CH₃ | 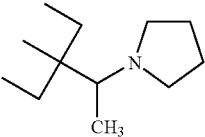 | —H | 6,7-Dimethoxy-5-methyl-2-{methyl-[6-(1-pyrrolidin-1-yl-ethyl)-pyridin-2-ylmethyl]-amino}-1H-quinazolin-4-one | 437.54 |
| I-10 | —OCH₃ | 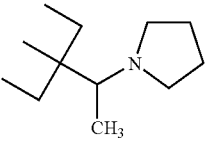 | —H | 5,6,7-Trimethoxy-2-{methyl-[6-(1-pyrrolidin-1-yl-ethyl)-pyridin-2-ylmethyl]-amino}-1H-quinazolin-4-one | 453.54 |
| I-11 | —CH₃ | 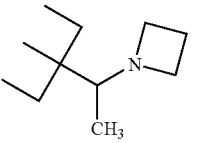 | —H | 2-{[6-(1-Azetidin-1-yl-ethyl)-pyridin-2-ylmethyl]-methyl-amino}-6,7-dimethoxy-5-methyl-1H-quinazolin-4-one | 423.51 |
| I-12 | —O—CH₃ | 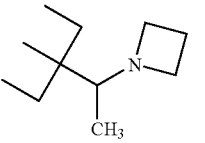 | —H | 2-{[6-(1-Azetidin-1-yl-ethyl)-pyridin-2-ylmethyl]-meethyl-amino}-5,6,7-trimethoxy-1H-quinazolin-4-one | 439.51 |
| I-13 | —CH₃ | —H | 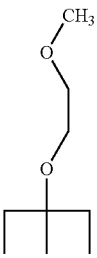 | 6,7-Dimethoxy-23-{[4-(2-methoxy-ethoxy)-pyridin-2-ylmethyl]-methyl-amino}-5-methyl-1H-quinazolin-4-one | 414.46 |

Additional compounds prepared according to the procedure of Example I-1 are shown in Table 11.

Examples J-1 to J-7

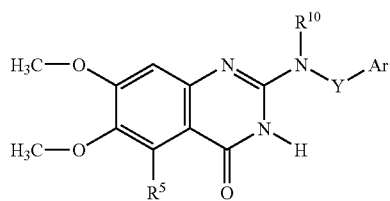

Compounds having the above formula (Ip), wherein $R^5$, $R^{10}$ and Y—Ar taken together have the values reported in Table 10, were prepared following the same or similar method as described above, e.g., upon coupling compounds having the desired aryl or heteroaryl groups with 2-chloro-6,7-dimethoxy-5-methyl-1H-quinazolin-4-one, or 2-chloro-5,6,7-trimethoxy-1H-quinazolin-4-one.

TABLE 10

| Ex. No | $R^5$ | $R^{10}$ | —Y—Ar | | MW |
|---|---|---|---|---|---|
| J-1 | —O—CH₃ | —CH₃ | [structure] | N,N-Dimethyl-N'-(3-{2-[methyl-(5,6,7-trimethoxy-4-oxo-1,4-dihydro-quinazolin-2-yl)-amino]-ethyl}-phenyl)-acetamidine | 453.54 |
| J-2 | —CH₃ | H | [structure] | 5-[2-(6,7-Dimethoxy-5-methyl-4-oxo-1,4-dihydro-quinazolin-2-ylamino)-propyl]-2-methoxy-benzenesulfonamide | 462.52 |
| J-3 | —CH₃ | H | [structure] | 5-[2-(6,7-Dimethoxy-5-methyl-4-oxo-1,4-dihydro-quinazolin-2-ylamino)-propyl]-2-methoxy-N-(1-dimethylamino-ethylidene)-benzenesulfonamide | 531.63 |
| J-4 | —CH₃ | —CH₃ | [structure] | N'-(3-{2-[(6,7-Dimethoxy-5-methyl-4-oxo-1,4-dihydro-quinazolin-2-yl)-methyl-amino]-1-hydroxy-ethyl}-phenyl)-N,N-dimethyl-acetamidine | 453.54 |
| J-5 | —CH₃ | —CH₃ | [structure] | N'-(3-{2-[(6,7-Dimethoxy-5-methyl-4-oxo-1,4-dihydro-quinazolin-2-yl)-methyl-amino]-vinyl}-phenyl)-N,N-dimethyl-acetamidine; | 435.53 |
| J-6 | —CH₃ | —CH₃ | [structure] | 2-{[2-(3H-Imidazol-4-yl)-ethyl]-methyl-amino}-6,7-dimethoxy-5-methyl-1H-quinazolin-4-one | 343.39 |

TABLE 10-continued

| Ex. No | $R^5$ | $R^{10}$ | —Y—Ar | | MW |
|---|---|---|---|---|---|
| J-7 | —O—CH$_3$ | —CH$_3$ | | 2-{[2-(3H-Imidazol-4-yl)-ethyl]-meethyl-amino}-5,6,7-trimethoxy-1H-quinazolin-4-one | 359.38 |
| J-8 | —CH$_3$ | —CH$_3$ | | 2-[(1-Benzyl-piperidin-3-yl)-methyl-amino]-6,7-dimethoxy-5-methyl-1H-quinazolin-4-one | 422.53 |

Example K-1

N,N-Dimethyl-N'-(3-{[methyl-(6,7,8-trimethoxy-1,1-dioxo-1,4-dihydro-1l6-benzo[1,2,4]thiadiazin-3-yl)-amino]-methyl}-phenyl)-acetamidine

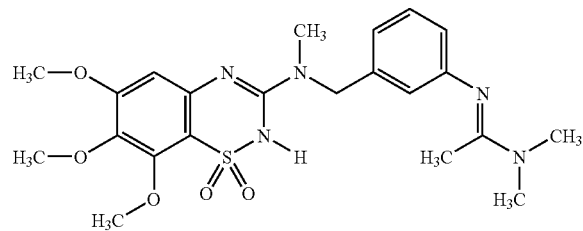

Step 1: 6,7,8-Trimethoxy benzothiadiazine-3-one-1,1-dioxide

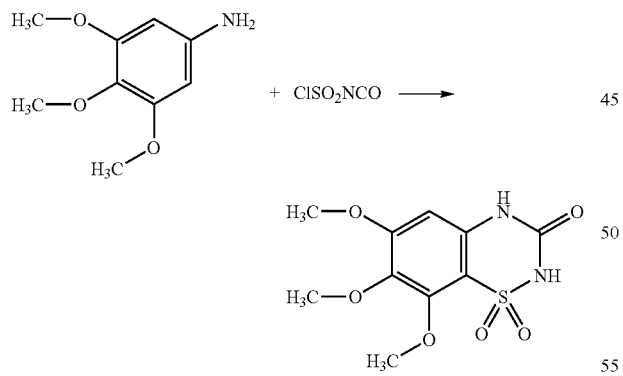

Step 1: 6,7,8-Trimethoxy-1,1-dioxo-1,4-dihydro-2H-1lambda*6*-benzo[1,2,4]thiadiazin-3-one To 45 mL nitroethane was added chlorosulfonylisocyanate (3 mL, 34 mmol). The solution was cooled to −70° C. A solution of trimethoxyaniline (4.5 g, 24.5 mmol) in nitroethane (15 mL) was added over 5 minutes. The temperature of the solution rose to −64° C. The solution was removed from the ice bath and allowed to warm to −5° C. while a heavy precipitate formed. In one portion, AlCl$_3$ (5 g, 37.6 mmol) was added. The precipitate went into solution as the temperature rose to 25° C. The resulting solution was placed in a 110° C. oil bath and stirred for 30 min. The resulting mixture was cooled to rt and poured into ice water. The aqueous layer was removed from the resulting black gum, which contained some of the desired material, as well as starting material and side products. The aqueous layer was shaken with EtOAc and the layers separated. The organic layer was evaporated in vacuo and the residue crystallized from a small amount of EtOAc to yield 6,7,8-trimethoxy benzothiadiazine-3-one-1,1-dioxide. (3.4 g): mp 220–223 □C; MS (ES+) m/z 289 (M+H); 1H NMR (DMSO-d6, 2.49)), 3.75(s, 3H), 3.83(s, 3H), 3.89 (s, 3H), 6.58 (s, 1H), 11 (s, 1H).

Step 2: 6,7,8-trimethoxy-3-chloro-benzothiadiazine-3-1,1-dioxide

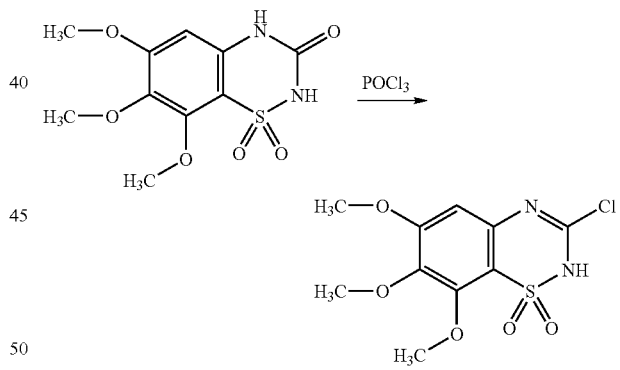

To 6,7,8-trimethoxy benzothiadiazine-3-one-1,1-dioxide (2.4 g, 8.3 mmol) was added phosphorous oxychloride (22 mL). The resulting mixture was cooled to 5 □C and N,N-diethylaniline (2.6 mL, 20 mmol) was added. The mixture was allowed to warm to rt, and then heated at 80° C. for 8 h. The solvent was removed by distillation under reduced pressure. The resulting syrup was poured into ice water. After rapid stirring the precipitate was filtered. The aqueous mother liquors were extracted with methylene chloride. The resulting organic layer was dried over Na$_2$SO$_4$, the drying agent removed by filtration and the solvent removed under reduced pressure, to afford 6,7,8-trimethoxy-3-chloro-benzothiadiazine-3-1,1-dioxide 920 mg. MS (ES+) m/z 307 (M+H); 1H NMR (DMSO-d6, 2.49)), 3.75(s, 3H), 3.83(s, 3H), 3.89 (s, 3H), 6.58 (s, 1H), 11 (s, 1H).

Step 3:

The chlorobenzothiadiazine dioxide from Step B (130 mg, 0.42 mmol) and N,N-dimethyl-N'-(3-methylaminomethyl-phenyl)-acetamidine (90 mg, 0.43 mmol) in EtOH (5 mL) were heated in a sealed tube at 100° C. for 18 h. The mixture was cooled and the suspension filtered. The desired product was found in both the filter cake and the mother liquors so these were combined and the solvent removed under reduced pressure. The resulting material was chromatographed on silica gel to yield a partially purified fraction which was then further purified by reverse phase HPLC to provide the above-titled Example K-1. (M+H)+ 477.

Example K-2

N'-(3-{[(6,7-Dimethoxy-1,1-dioxo-1,4-dihydrobenzo[1,2,4]thiadiazin-3-yl)-methyl-amino]-methyl}-phenyl)-N,N-dimethyl-acetamidine

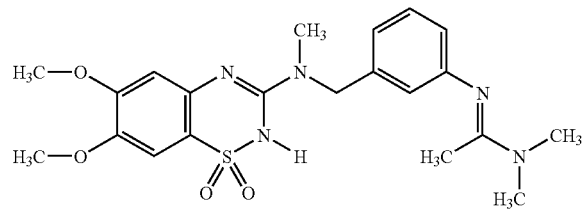

Step 1: 6,7-Dimethoxy-3-(methylaminomethyl-3-nitrophenyl)benzothiadiazine-3-one-1,1-dioxide

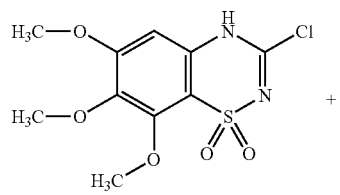

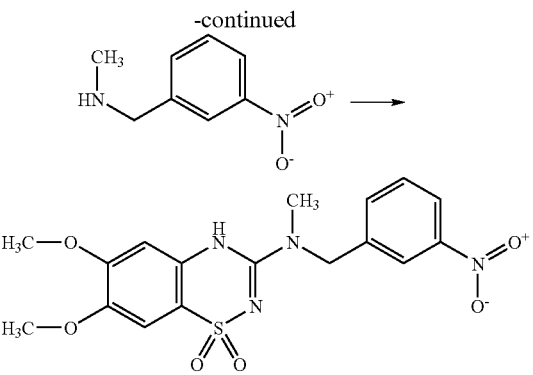

A solution of 3-chloro-6,7-dimethoxy-4H-benzo[1,2,4]thiadiazine 1,1-dioxide (404 mg, 1.5 mmol), methyl-(3-nitrobenzyl)-amine hydrochloride (400 mg, 2 mmol), DBU (0.25 mL, excess) and dimethoxyethanol (5 mL) was heated at 80° C. 18 h. The solvent was removed under reduced pressure. The resulting gum was chromatagraphed on silica gel in 3% MeOH in DCM to yield white crystals (250 mg): MS (ES+) m/z 407 (M+H). Substituted 2H-benzo[1,2,4]thiadiazine-1,1-dioxides were prepared as described in Ref. WO 02/053558 A1. The nitro compound (250 mg, 0.6 mmol), 10% Pd/C (32 mg) and EtOH (60 mL) were hydrogenated on a Parr apparatus at 45 psi for 18 h. The reaction mixture was then filtered under nitrogen through a glass fiber paper and the solvent removed under reduced pressure to yield the aniline as a white solid (210 mg). MS (ES+) m/z 377 (M+H).

Step, 2:

The aniline from Step 1 (210 mg, 0.56 mmol), dimethylacetamide dimethyl acetal (80 uL, excess) and dimethylacetamide (2 mL) were heated at 80° C. for 18 h. The solvent was removed under reduced pressure. The resulting gum was dissolved in DCM and chromatographed over silica gel in 4% MeOH in DCM to yield the above-titled Example K-2 as an off white solid.

Representative compounds in accordance with the invention are shown in Table 11, together with corresponding melting point or low resolution Mass Spectrum data.

TABLE 11

| # | Structure | Systematic Name | MP ° C. | M + H |
|---|---|---|---|---|
| 1 | 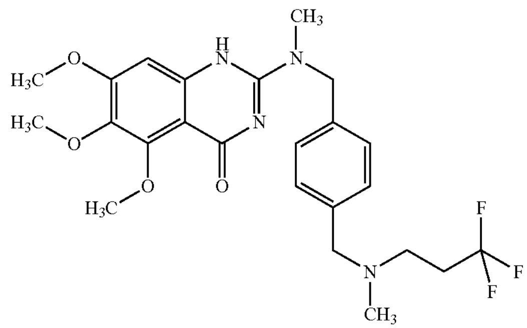 | 5,6,7-Trimethoxy-2-[methyl-(4-{[methyl-(3,3,3-trifluoro-propyl)-amino]-methyl}-benzyl)-amino]-1H-quinazolin-4-one | 97.8–101.9 | |
| 2 | 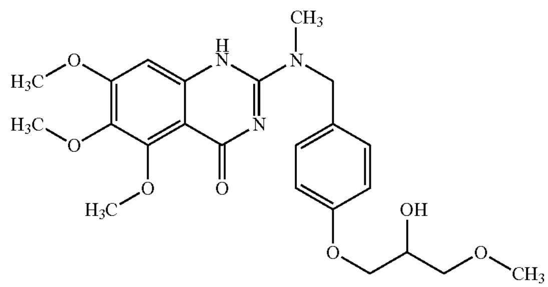 | 2-{[4-(2-Hydroxy-3-methoxy-propoxy)-benzyl]-methyl-amino}-5,6,7-trimethoxy-1H-quinazolin-4-one | 108.1–111.5 | |
| 3 | 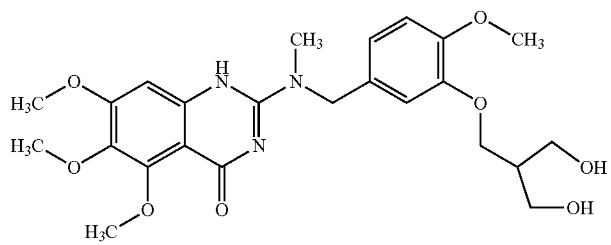 | 2-{[[3-(3-Hydroxy-2-hydroxymethyl-propoxy)-4-methoxy-benzyl]-methyl-amino]}-5,6,7-trimethoxy-1H-quinazolin-4-one | 139.7–146.6 (HCl salt) | |

TABLE 11-continued

| # | Structure | Systematic Name | MP ° C. | M + H |
|---|---|---|---|---|
| 4 | 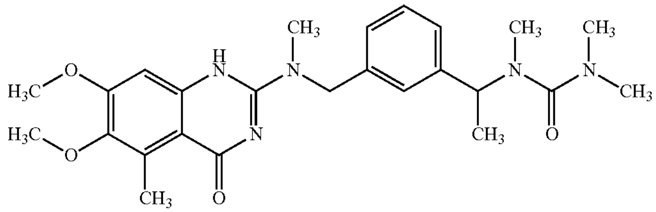 | 1-[1-(3-{[(6,7-Dimethoxy-5-methyl-4-oxo-1,4-dihydro-quinazolin-2-yl)-methyl-amino]-methyl}-phenyl)-ethyl]-1,3,3-trimethyl-urea | 125.9–128.0 | |
| 5 | 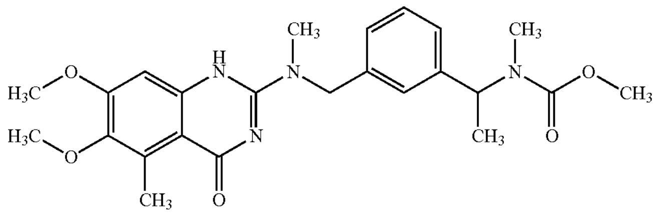 | [1-(3-{[(6,7-Dimethoxy-5-methyl-4-oxo-1,4-dihydro-quinazolin-2-yl)(methyl-amino]-methyl}-phenyl)-ethyl]-methyl-carbamic acid methyl ester | 117.9–120.1 | |
| 6 | 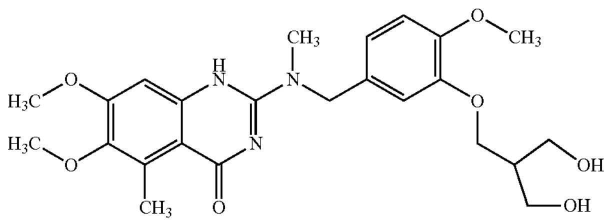 | 2-{[3-(3-Hydroxy-2-hydroxymethyl-propoxy)-4-methoxy-benzyl]-methyl-amino}-6,7-dimethoxy-5-methyl-1H-quinazolin-4-one | 210.8–215.4 | |
| 7 | 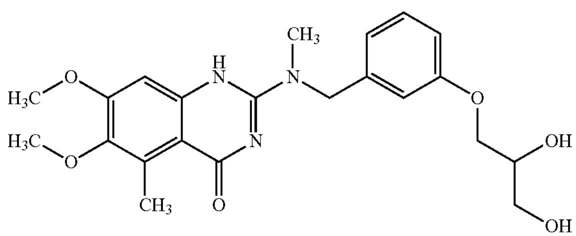 | 2-{[3-(2,3-Dihydroxy-propoxy)-benzyl]-methyl-amino}-6,7-dimethoxy-5-methyl-1H-quinazolin-4-one | 220–224 (HCl salt) | |

TABLE 11-continued

| # | Structure | Systematic Name | MP °C. | M + H |
|---|---|---|---|---|
| 8 | 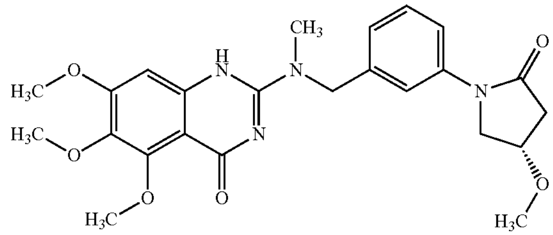 | 5,6,7-Trimethoxy-2-{[3-((S)-4-methoxy-2-oxo-pyrrolidin-1-yl)-benzyl]-methyl-amino}-1H-quinazolin-4-one | 142.5–147.4 | |
| 9 | 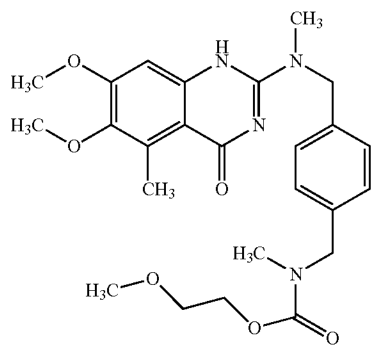 | (4-{[(6,7-Dimethoxy-5-methyl-4-oxo-1,4-dihydro-quinazolin-2-yl)-methyl-amino]-methyl}-benzyl)-methyl-carbamic acid 2-methoxy-ethyl ester | 159.4–160.4 | |
| 10 | 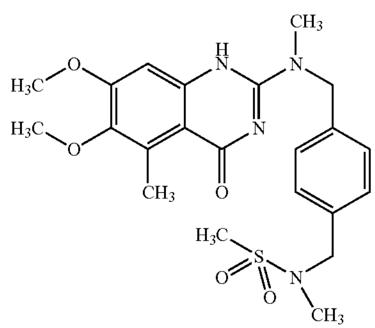 | N-(4-{[(6,7-Dimethoxy-5-methyl-4-oxo-1,4-dihydro-quinazolin-2-yl)-methyl-amino]-methyl}-benzyl)-N-methyl-methanesulfonamide | 238–240 | |

TABLE 11-continued

| # | Structure | Systematic Name | MP °C. | M + H |
|---|---|---|---|---|
| 11 | 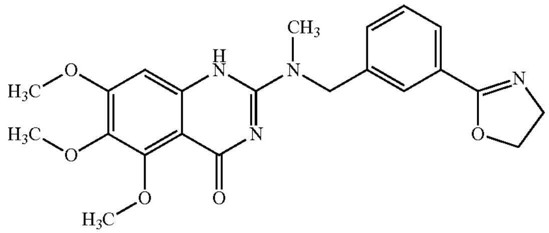 | 2-{[3-(4,5-Dihydro-oxazol-2-yl)-benzyl]-methyl-amino}-5,6,7-trimethoxy-1H-quinazolin-4-one | 202.3–203.4 | |
| 12 | 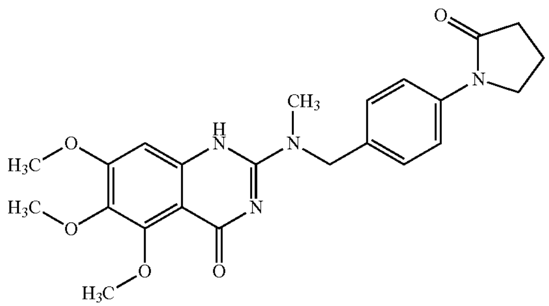 | 5,6,7-Trimethoxy-2-{methyl-[4-(2-oxo-pyrrolidin-1-yl)-benzyl]-amino}-1H-quinazolin-4-one | 195.9–197.4 | |
| 13 | 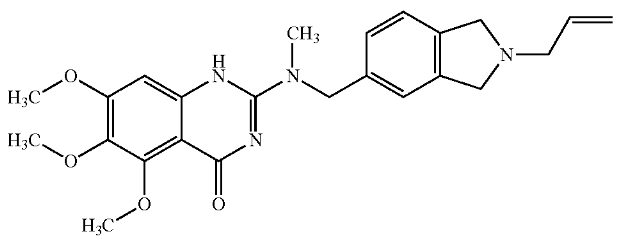 | 2-[(2-Allyl-2,3-dihydro-1H-isoindol-5-ylmethyl)-methyl-amino]-5,6,7-trimethoxy-1H-quinazolin-4-one | 133.7–136.6 | |

TABLE 11-continued

| # | Structure | Systematic Name | MP ° C. | M + H |
|---|---|---|---|---|
| 14 | 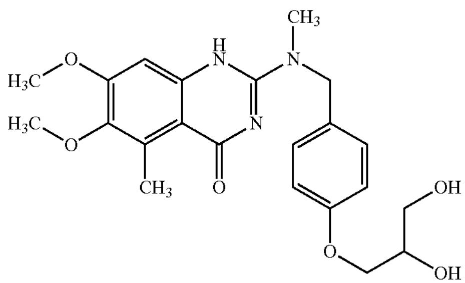 | 2-[{4-(2,3-Dihydroxy-propoxy)-benzyl]-methyl-amino}-6,7-dimethoxy-5-methyl-1H-quinazolin-4-one | 199.7–201.9 | |
| 15 | 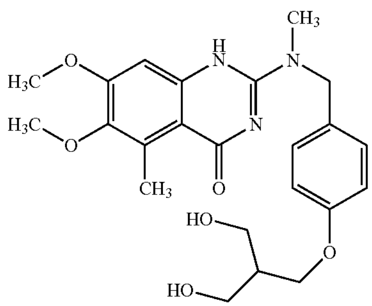 | 2-[{4-(3-Hydroxy-2-hydroxymethyl-propoxy)-benzyl]-methyl-amino}-6,7-dimethoxy-5-methyl-1H-quinazolin-4-one | 197.5–199 (HCl salt) | |
| 16 | 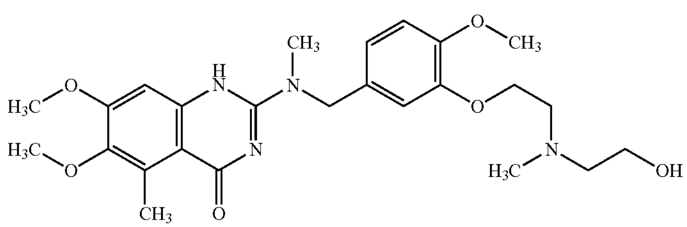 | 2-[(3-{2-[(2-Hydroxy-ethyl)-methyl-amino]-ethoxy}-4-methoxy-benzyl)-methyl-amino]-6,7-dimethoxy-5-methyl-1H-quinazolin-4-one | 144.8–146.2 | |
| 17 | 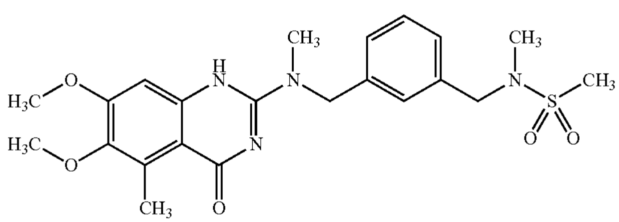 | N-(3-{[(6,7-Dimethoxy-5-methyl-4-oxo-1,4-dihydro-quinazolin-2-yl)-methyl-amino]-methyl}-benzyl)-N-methyl-methanesulfonamide | 223.9–225.9 | |

TABLE 11-continued

| # | Structure | Systematic Name | MP °C. | M + H |
|---|---|---|---|---|
| 18 | 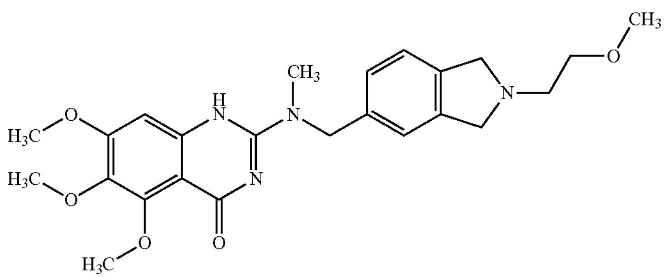 | 5,6,7-Trimethoxxy-2-{[2-(2-methoxy-ethyl)-2,3-dihydro-1H-isoindol-5-ylmethyl]-methyl-amino}-1H-quinazolin-4-one | 133.3–136.6 | |
| 19 | 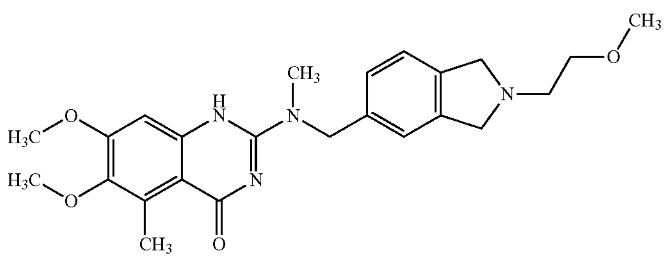 | 6,7-Dimethoxy-2-{[2-(2-methoxy-ethyl)-2,3-dihydro-1H-isoindol-5-ylmethyl]-methyl-amino}-5-methyl-1H-quinazolin-4-one | 173.3–177.9 | |
| 20 | 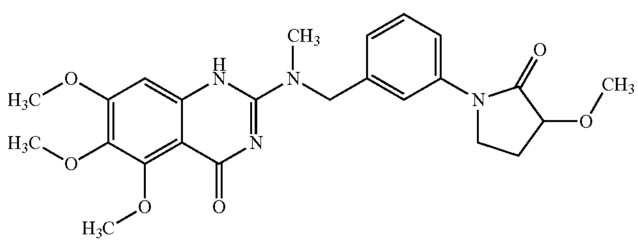 | 5,6,7-Trimethoxy-2-{[3-(3-methoxy-2-oxo-pyrrolidin-1-yl)-benzyl]-methyl-amino}-1H-quinazolin-4-one | 90.2–94.7 | |

TABLE 11-continued

| # | Structure | Systematic Name | MP ° C. | M + H |
|---|---|---|---|---|
| 21 | 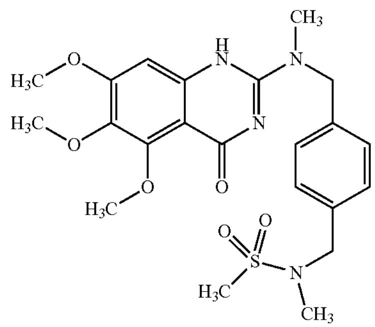 | N-Methyl-N-(4-{[methyl-(5,6,7-trimethoxy-4-oxo-1,4-dihydro-quinazolin-2-yl)-amino]-methyl}-benzyl)-methanesulfonamide | 148.8–151 | |
| 22 | 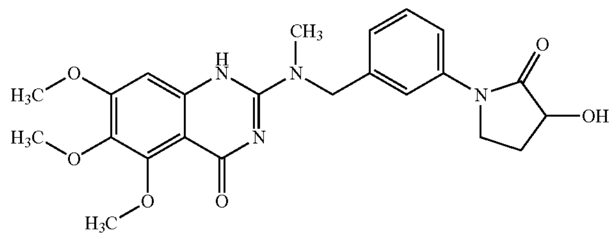 | 2-{[3-(3-Hydroxy-2-oxo-pyrrolidin-1-yl)-benzyl]-methyl-amino}-5,6,7-trimethoxy-1H-quinazolin-4-one | 172.9–175.9 (HCl salt) | |
| 23 | 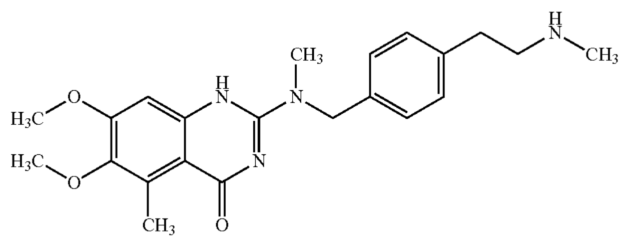 | 6,7-Dimethoxy-5-methyl-2-{methyl-[4-(2-methylamino-ethyl)-benzyl]-amino}-1H-quinazolin-4-onbe | 154.6–159.0 | |

TABLE 11-continued

| # | Structure | Systematic Name | MP °C. | M + H |
|---|---|---|---|---|
| 24 | 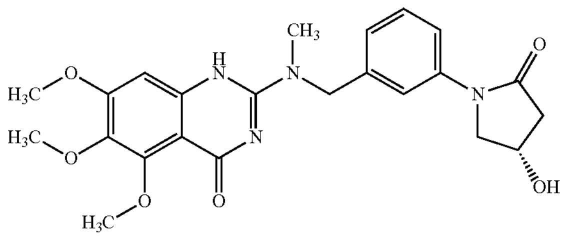 | 2-{[3-((S)-4-Hydroxy-2-oxo-pyrrolidin-1-yl)-benzyl]-methyl-amino}-5,6,7-trimethoxy-1H-quinazolin-4-one | 207.5–209.9 | |
| 25 | 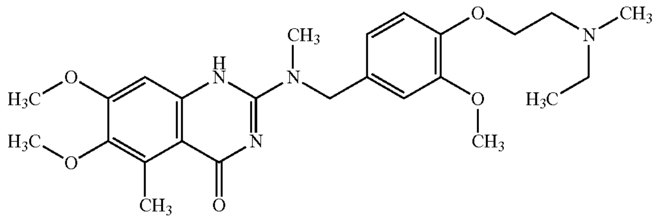 | 2-({4-[2-(Ethyl-methyl-amino)-ethoxy]-3-methoxy-benzyl}-methyl-amino)-6,7-dimethoxy-5-methyl-1H-quinazolin-4-one | 158.1–159.2 | |
| 26 | 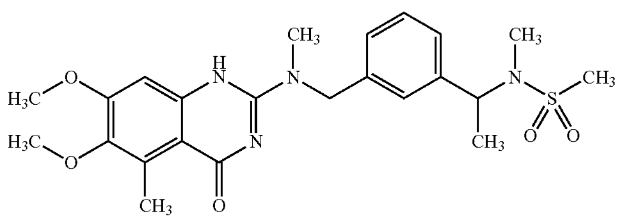 | N-[1-(3-{[(6,7-Dimethoxy-5-methyl-4-oxo-1,4-dihydro-quinazolin-2-yl)-methyl-amino]-methyl}-phenyl)-ethyl]-N-methyl-methanesulfonamide | 130.0–133.8 | |
| 27 | 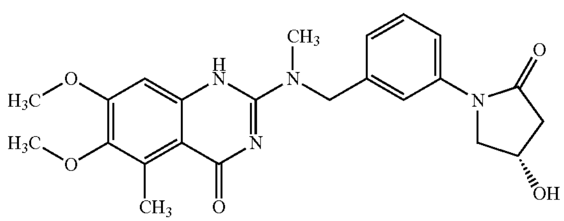 | 2-{[3-((S)-4-Hydroxy-2-oxo-pyrrolidin-1-yl)-benzyl]-methyl-amino}-6,7-dimethoxy-5-methyl-1H-quinazolin-4-one | 230.8–232.5 | |

TABLE 11-continued

| # | Structure | Systematic Name | MP °C. | M + H |
|---|---|---|---|---|
| 28 | 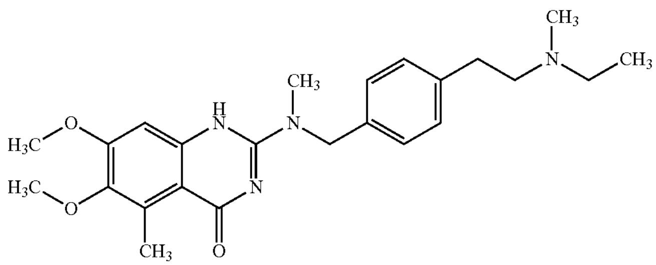 | 2-({4-[2-(Ethyl-methyl-amino)-ethyl]-benzyl}-methyl-amino)-6,7-dimethoxy-5-methyl-1H-quinazolin-4-one | 172.4–173.2 | |
| 29 | 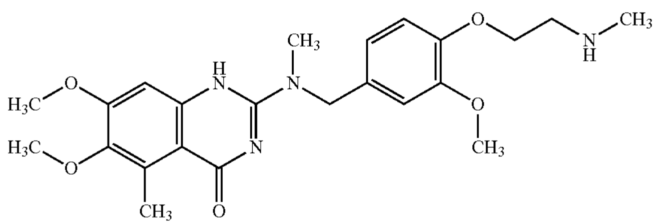 | 6,7-Dimethoxy-2-{[3-methoxy-4-(2-methylamino-ethoxy)-benzyl]-methyl-amino}-5-methyl-1H-quinazolin-4-one | 168.9–169.8 | |
| 30 | 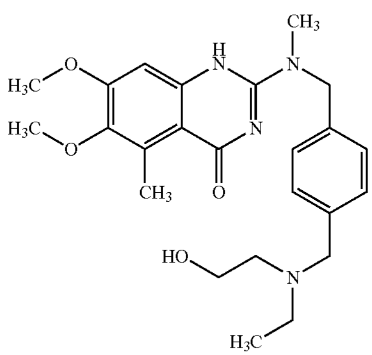 | 2-[(4-{[Ethyl-(2-hydroxy-ethyl)-amino]-methyl}-benzyl)-methyl-amino]-6,7-dimethoxy-5-methyl-1H-quinazolin-4-one | 142–5 | |

TABLE 11-continued

| # | Structure | Systematic Name | MP ° C. | M + H |
|---|---|---|---|---|
| 31 | 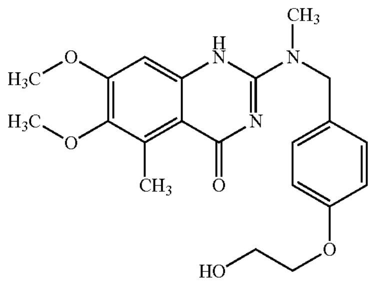 | 2-{[4-(2-Hydroxy-ethoxy)-benzyl]-methylamino}-6,7-dimethoxy-5-methyl-1H-quinazolin-4-one | 198.5–199.5 | |
| 32 | 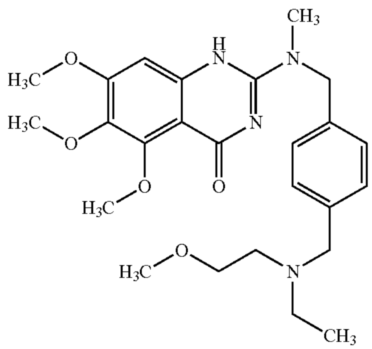 | 2-[(4-{[Ethyl(2-methoxy-ethyl)-amino]-methyl}-benzyl)-methyl-amino]-5,6,7-trimethoxy-1H-quinazolin-4-one | 120–122.4 | |
| 33 | 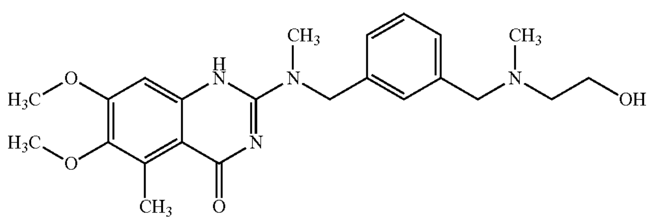 | 2-[(3-{[(2-Hydroxy-ethyl)-methyl-amino]-methyl}-benzyl)-methyl-amino]-6,7-dimethoxy-5-methyl-1H-quinazolin-4-one | 123.8–125.6 | |

TABLE 11-continued

| # | Structure | Systematic Name | MP °C. | M + H |
|---|---|---|---|---|
| 34 | 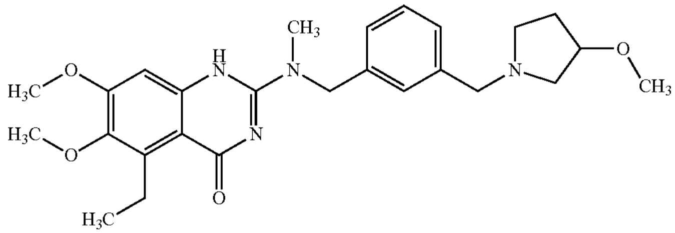 | 5,6,7-Trimethoxy-2-{[3-(3-methoxy-pyrrolidin-1-ylmethyl)-benzyl]-methyl-amino}-1H-quinazolin-4-one | 89.6–90.2 | |
| 35 | 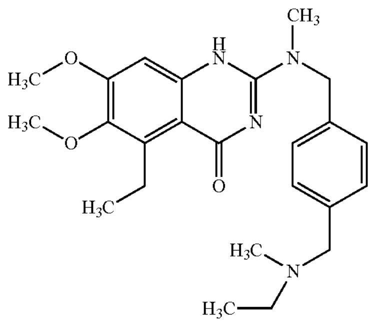 | 2-({4-[(Ethyl-methyl-amino)-methyl]-benzyl}-methyl-amino)-5,6,7-trimethoxy-1H-quinazolin-4-one | 172.3–174.4 (HCl salt) | 427 |
| 36 | 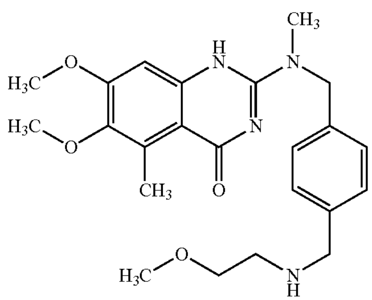 | 6,7-Dimethoxy-2-({4-[(2-methoxy-ethylamino)-methyl]-benzyl}-methyl-amino)-5-methyl-1H-quinazolin-4-one | 265–268 (HCl salt) | |

TABLE 11-continued

| # | Structure | Systematic Name | MP ° C. | M + H |
|---|---|---|---|---|
| 37 | 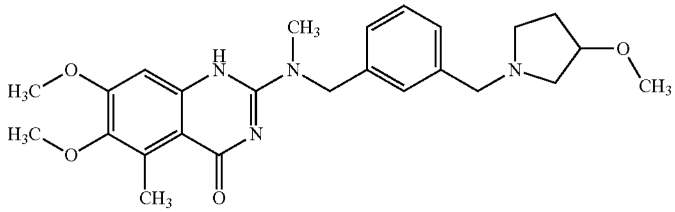 | 6,7-Dimethoxy-2-{[3-(3-methoxy-pyrrolidin-1-ylmethyl)-benzyl]-methyl-amino}-5-methyl-1H-quinazolin-4-one | 151.2–152.9 | |
| 38 | 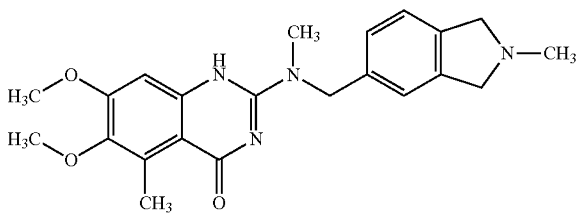 | 6,7-Dimethoxy-5-methyl-2-[methyl-(2-methyl-2,3-dihydro-1H-isoindol-5-ylmethyl)-amino]-1H-quinazolin-4-one | 214.9–224.8 | |
| 39 | 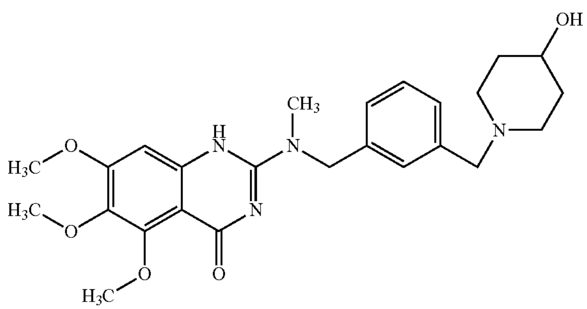 | 2-{[3-(4-Hydroxy-piperidin-1-ylmethyl)-benzyl]-methyl-amino}-5,6,7-trimethoxy-1H-quinazolin-4-one | 97.5–104.7 | |

TABLE 11-continued

| # | Structure | Systematic Name | MP ° C. | M + H |
|---|---|---|---|---|
| 40 | 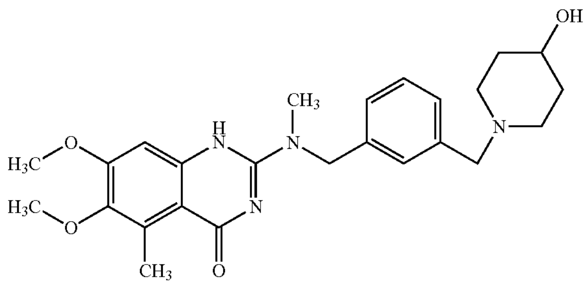 | 2-{[3-(4-Hydroxy-piperidin-1-ylmethyl)-benzyl]-methyl-amino}-6,7-dimethoxy-5-methyl-1H-quinazolin-4-one | 159.2–159.6 | |
| 41 | 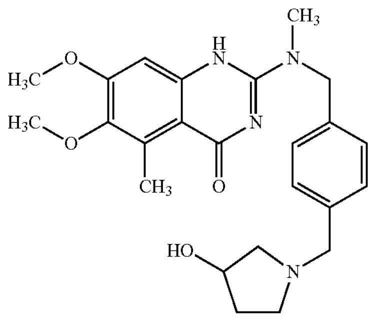 | 2-{[[4-(3-Hydroxy-pyrrolidin-1-ylmethyl)-benzyl]-methyl-amino}-6,7-dimethoxy-5-methyl-1H-quinazolin-4-one | 166–169 | |
| 42 | 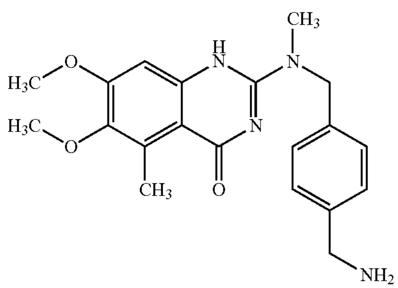 | 2-[((4-Aminomethyl-benzyl)-methyl-amino]-6,7-dimethoxy-5-methyl-1H-quinazolin-4-one | 248.2–249.4 (HCl salt) | |

TABLE 11-continued

| # | Structure | Systematic Name | MP ° C. | M + H |
|---|---|---|---|---|
| 43 | 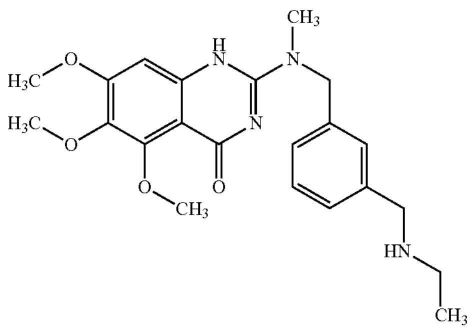 | 2-[(3-Ethylaminomethyl-benzyl)-methyl-amino]-5,6,7-trimethoxy-1H-quinazolin-4-one | 133.9–134.7 | |
| 44 | 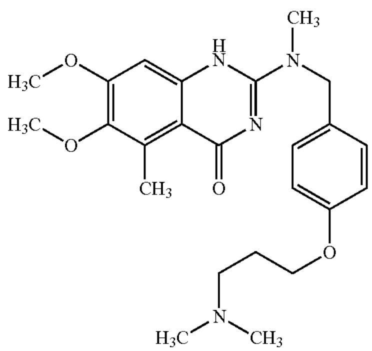 | 2-{[4-(3-Dimethylamino-propoxy)-benzyl]-methyl-amino}-6,7-dimethoxy-5-methyl-1H-quinazolin-4-one h | 191–192.2 (HCl salt) | |
| 45 | 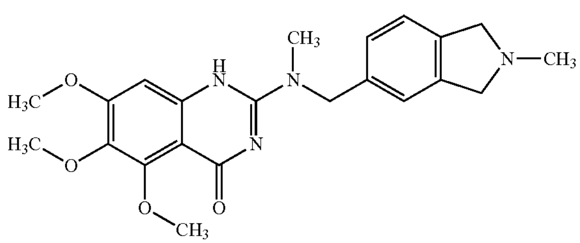 | 5,6,7-Trimethoxy-2-[methyl-(2-methyl-2,3-dihydro-1H-isoindol-5-ylmethyl)-amino]-1H-quinazolin-4-one | 165.5–166.5 | |

TABLE 11-continued

| # | Structure | Systematic Name | MP °C. | M + H |
|---|---|---|---|---|
| 46 | 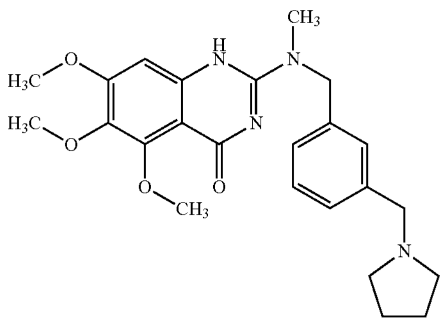 | 5,6,7-Trimethoxy-2-[methyl-(3-pyrrolidin-1-ylmethyl-benzyl)-amino]-1H-quinazolin-4-one | 127.0–129.9 | |
| 47 | 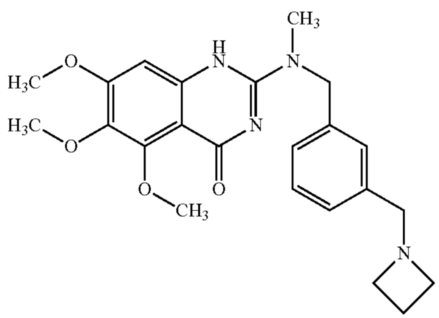 | 2-[(3-Azetidin-1-ylmethyl-benzyl)-methyl-amino]-5,6,7-trimethoxy-1H-quinazolin-4-one | 131.3–133.1 | |
| 48 | 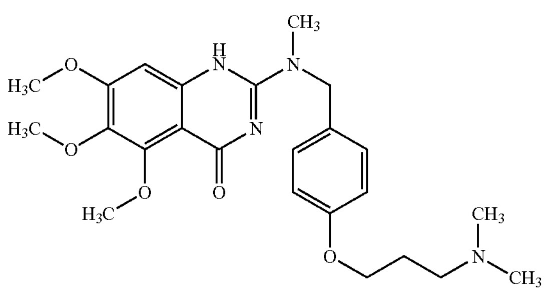 | 2-[[4-(3-Dimethylamino-propoxy)-benzyl]-methyl-amino]-5,6,7-trimethoxy-1H-quinazolin-4-one | 108–111 | |

TABLE 11-continued

| # | Structure | Systematic Name | MP °C. | M + H |
|---|---|---|---|---|
| 49 | 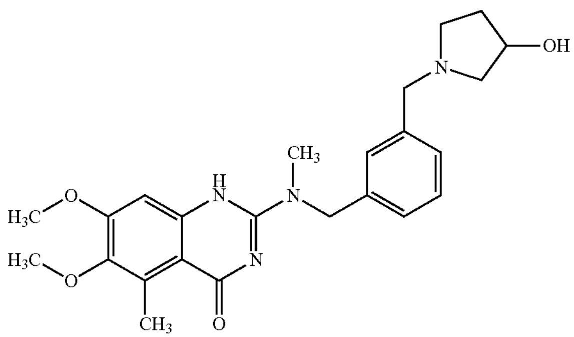 | 2-{[3-(3-Hydroxy-pyrrolidin-1-ylmethyl)-benzyl]-methyl-amino}-6,7-dimethoxy-5-methyl-1H-quinazolin-4-one | 148.0–149.8 | |
| 50 | 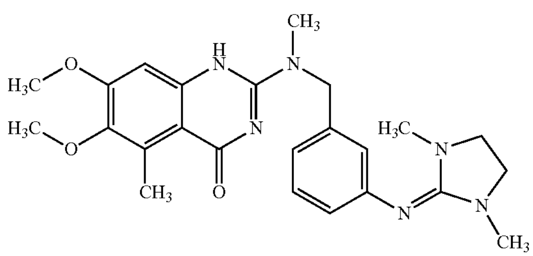 | 2-{[3-(1,3-Dimethyl-imidazolidin-2-ylidenemamino)-benzyl]-methyl-amino}-6,7-dimethoxy-5-methyl-1H-quinazoline-4-one | 200.2–204.4 | |
| 51 | 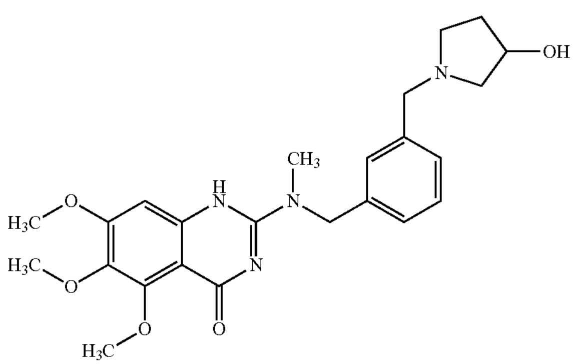 | 2-{[3-(3-Hydroxy-pyrrolidin-1-ylmethyl)-benzyl]-methyl-amino}-5,6,7-trimethoxy-1H-quinazolin-4-one | 174.3–176.4 | |

TABLE 11-continued

| # | Structure | Systematic Name | MP ° C. | M + H |
|---|---|---|---|---|
| 52 | 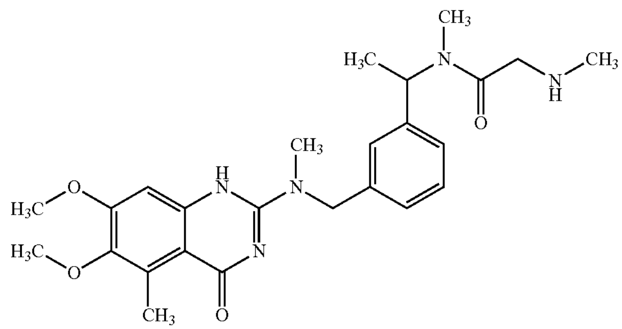 | N-[1-(3-{[(6,7-Dimethoxy-5-methyl-4-oxo-1,4-dihydro-quinazolin-2-yl)-methyl-amino]-methyl}-phenyl)-ethyl]-N-methyl-2-methylamino-acetamide | 118.1–120.8 | |
| 53 | 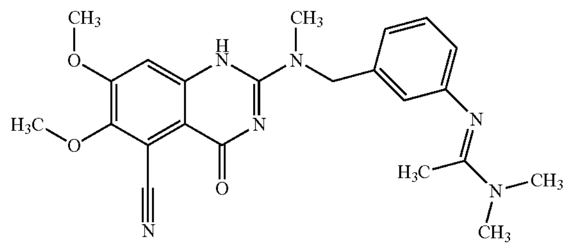 | N'-(3-{[(5-Cyano-6,7-dimethoxy-4-oxo-1,4-dihydro-quinazolin-2-yl)-methyl-amino]-methyl}-phenyl)-N,N-dimethyl-acetamide | 222.1–226.9 | |
| 54 | 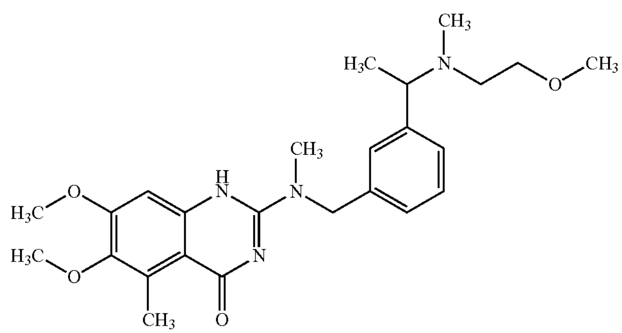 | 6,7-Dimedthoxy-2-{(3-{1-[(2-methoxy-ethyl)-methyl-amino]-ethyl}-benzyl)-methyl-amino]-5-methyl-1H-quinazolin-4-one | 114.5–116.9 | |

TABLE 11-continued

| # | Structure | Systematic Name | MP °C. | M + H |
|---|---|---|---|---|
| 55 | 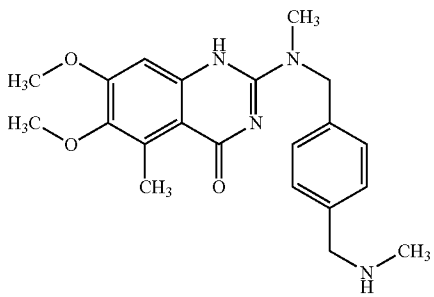 | 6,7-Dimethoxy-5-methyl-2-[methyl-(4-methylaminomethyl-benzyl)-amino]-1H-quinazolin-4-one | 264–268 (HCL salt) | |
| 56 | 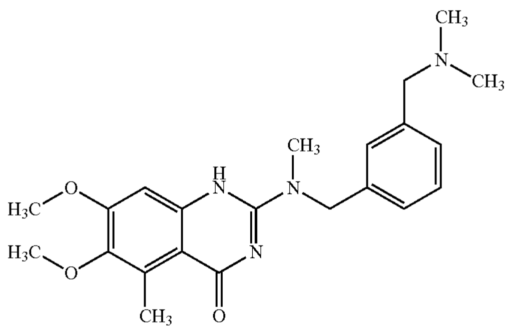 | 2-[(3-Dimethylaminomethyl-benzyl)-methyl-amino]-6,7-dimethoxy-5-methyl-1H-quinazolin-4-one | 174.9–176.0 | |
| 57 | 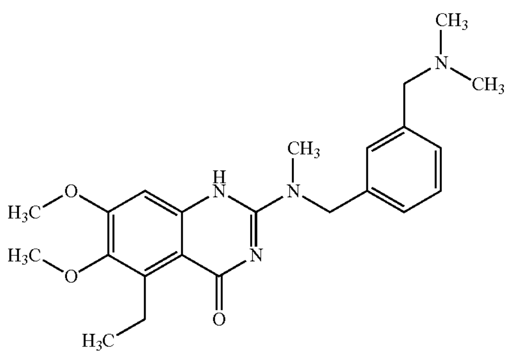 | 2-[(3-Dimethylaminomethyl-benzyl)-methyl-amino]-5,6,7-trimethoxy-1H-quinazolin-4-one | 110.0–113.1 | |

TABLE 11-continued

| # | Structure | Systematic Name | MP °C. | M + H |
|---|---|---|---|---|
| 58 | 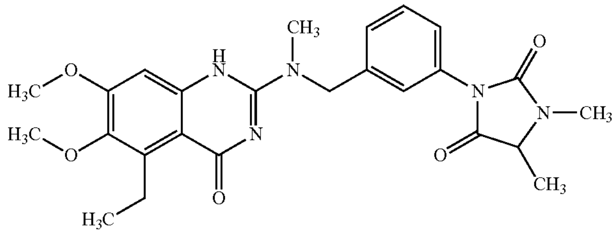 | 1,5-Dimethyl-3-(3-{[methyl-(5,6,7-trimethoxy-4-oxo-1,4-dihydro-quinazolin-2-yl)-amino]-methyl}-phenyl)-imidazolidine-2,4-dione | 179.1–179.9 | |
| 59 | 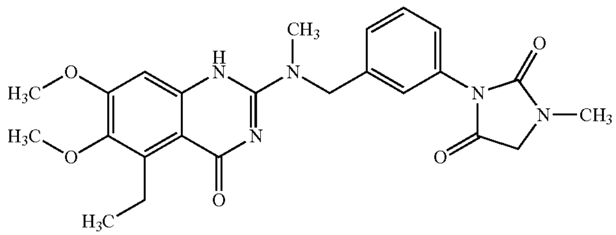 | 1-Methyl-3-(3-{[methyl-(5,6,7-trimethoxy-4-oxo-1,4-dihydro-quinazolin-2-yl)-amino]-methyl}-phenyl)-imidazolidine-2,4-dione | 130.0–137.0 | |
| 60 | 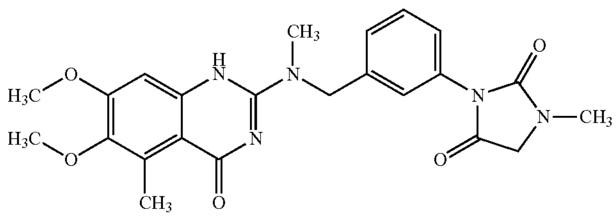 | 3-(3-{[((6,7-Dimethoxy-5-methyl-4-oxo-1,4-dihydro-quinazolin-2-yl)-methyl-amino]-methyl}-phenyl)-1-methyl-imidazolidine-2,4-dione | 209.3–210.8 | |
| 61 | 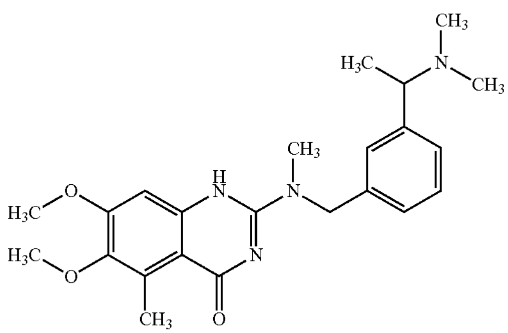 | 2-{[3-(1-Dimethylamino-ethyl)-benzyl]-methyl-amino}-6,7-dimethoxy-5-methyl-1H-quinazolin-4-one | 137.0–140.1 | |

TABLE 11-continued

| # | Structure | Systematic Name | MP °C. | M + H |
|---|---|---|---|---|
| 62 | 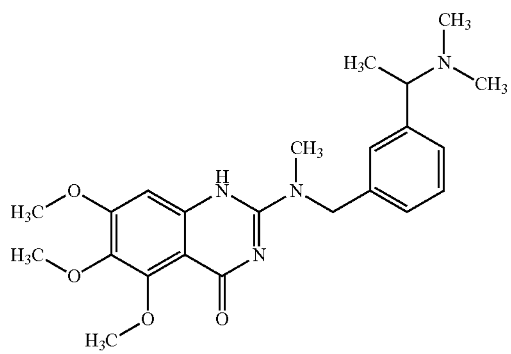 | 2-{[3-(1-Dimethylamino-ethyl)-benzyl]-methyl-amino}-5,6,7-trimethoxy-1H-quinazolin-4-one | 122.6–125.5 | |
| 63 | 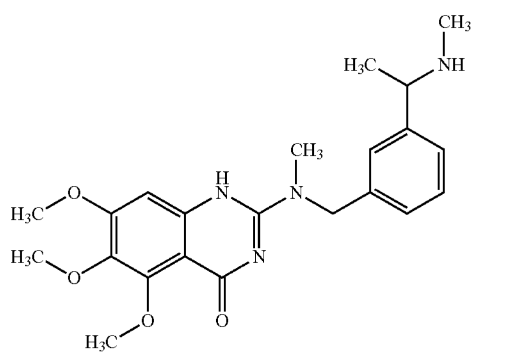 | 5,6,7-Trimethoxy-2-{methyl-[3-(1-methylamino-ethyl)-benzyl]-amino}-1H-quinazolin-4-one | 131.8–134.4 | |

TABLE 11-continued
| # | Structure | Systematic Name | MP ° C. | M + H |
|---|---|---|---|---|
| 64 | 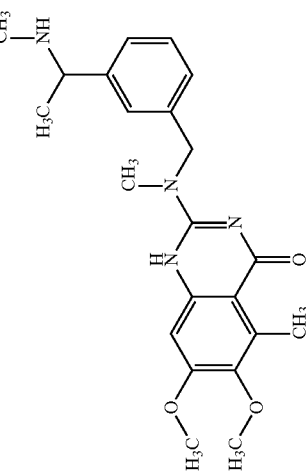 | 6,7-Dimethoxy-5-methyl-2-{methyl[3-(1-methylamino-ethyl)-benzyl]-amino}-1H-quinazolin-4-one | 161.6–164.1 | |
| 65 | 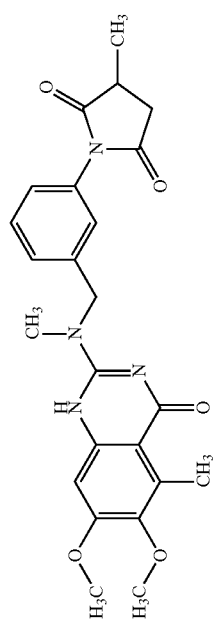 | 1-(3-{[(6,7-Dimethoxy-5-methyl-4-oxo-1,4-dihydro-quinazolin-2-yl)-methyl-amino]-methyl}-phenyl)-3-methyl-pyrrolidine-2,5-dione | 217.8–219.2 | |
| 66 | 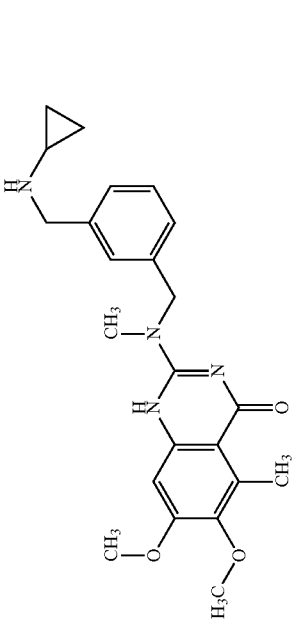 | 2-[(3-Cyclopropylaminomethyl-benzyl)-methyl-amino]-6,7-dimethoxy-5-methyl-1H-quinazolin-4-one | 144.5–147.6 | |

TABLE 11-continued

| # | Structure | Systematic Name | MP ° C. | M + H |
|---|---|---|---|---|
| 67 | 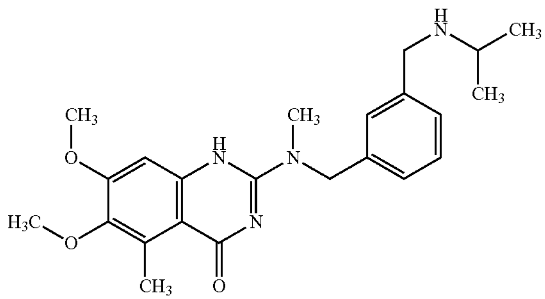 | 2-{[3-(Isopropylamino-methyl)-benzyl]-methyl-amino}-6,7-dimethoxy-5-methyl-1H-quinazolin-4-one | 143.3–144.4 | |
| 68 | 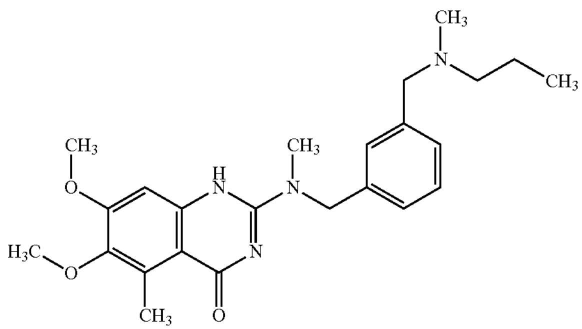 | 6,7-Dimethoxy-5-methyl-2-(methyl-{3-[(methyl-propyl-amino)-methyl]-benzyl}-amino)-1H-quinazolin-4-one | 128.1–129.1 | |
| 69 | 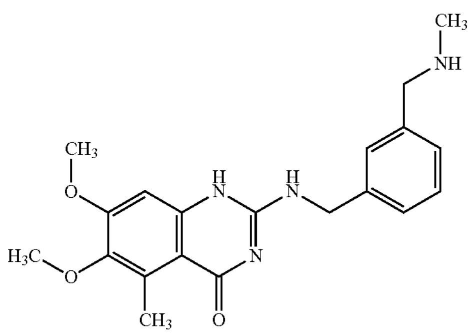 | 6,7-Dimethoxy-5-methyl-2-(3-methylaminomethyl-benzylamino)-1H-quinazolin-4-one | 142.5–142.9 | |

TABLE 11-continued
| # | Structure | Systematic Name | MP °C. | M + H |
|---|---|---|---|---|
| 70 | 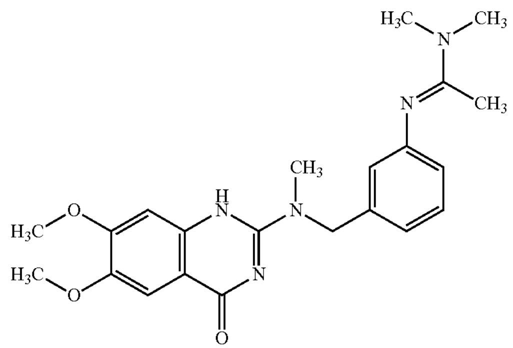 | N'-(3-{[(6,7-Dimethoxy-4-oxo-1,4-dihydro-quinazolin-2-yl)-methyl-amino]-methyl}-phenyl)-N,N-dimethyl-acetamidine | 221.8–223 | |
| 71 | 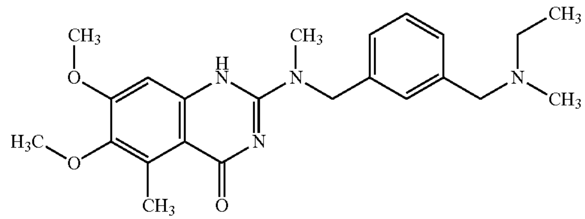 | 2-({3-[(Ethyl-methyl-amino)-methyl]-benzyl}-methyl-amino)-6,7-dimethoxy-5-methyl-1H-quinazolin-4-one | 146.7–150.8 | |
| 72 | 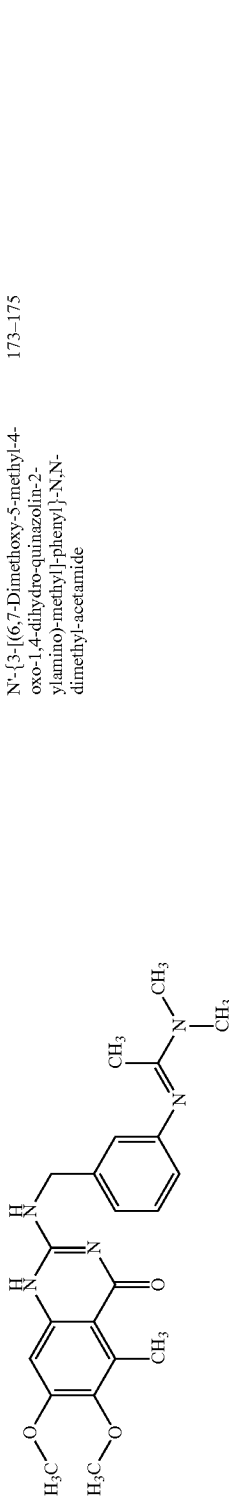 | N'-{3-[(6,7-Dimethoxy-5-methyl-4-oxo-1,4-dihydro-quinazolin-2-ylamino)-methyl]-phenyl}-N,N-dimethyl-acetamide | 173–175 | |

TABLE 11-continued

| # | Structure | Systematic Name | MP ° C. | M + H |
|---|---|---|---|---|
| 73 | 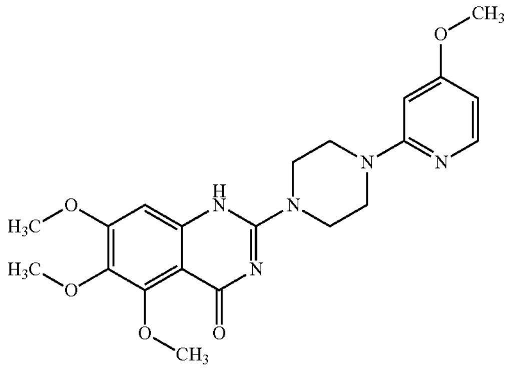 | 5,6,7-Trimethoxy-2-[4-(4-methoxy-pyridin-2-yl)-piperazin-1-yl]-1H-quinazolin-4-one | 229–231 | |
| 74 | 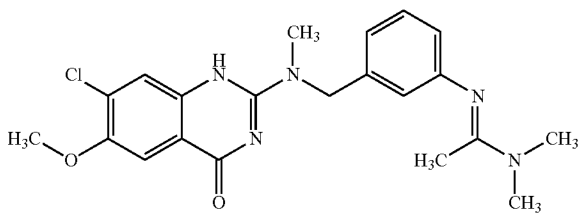 | N'-(3-{[(7-Chloro-6-methoxy-4-oxo-1,4-dihydro-quinazolin-2-yl)-methyl-amino]-methyl}-phenyl)-N,N-dimethyl-acetamide | 185.4–191.9 | |
| 75 | 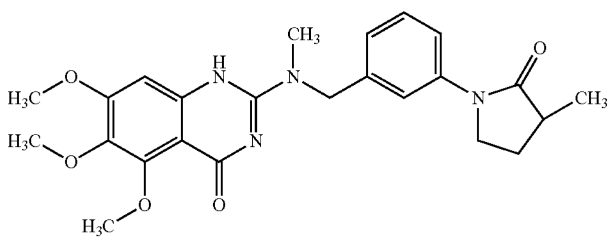 | 5,6,7-Trimethoxy-2-{methyl-[3-(3-methyl-2-oxo-pyrrolidin-1-yl)-benzyl]-amino}-1H-quinazolin-4-one | 156.4–162.0 | |

TABLE 11-continued

| # | Structure | Systematic Name | MP ° C. | M + H |
|---|---|---|---|---|
| 76 | 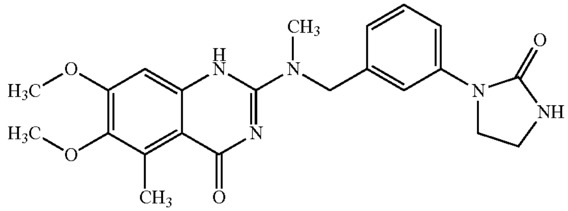 | 6,7-Dimethoxy-5-methyl-2-{methyl-[3-(2-oxo-imidazolidin-1-yl)-benzyl]-amino}-1H-quinazolin-4-one | 265.0–266.0 | |
| 77 | 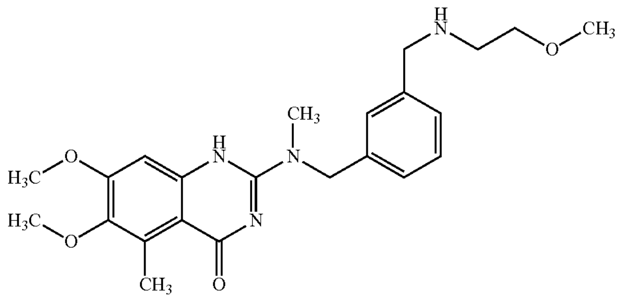 | 6,7-Dimethoxy-2-({3-[(2-methoxy-ethylamino)-methyl]-benzyl}-methyl-amino)-5-methyl-1H-quinazolin-4-one | 150.0–152.1 | |
| 78 | 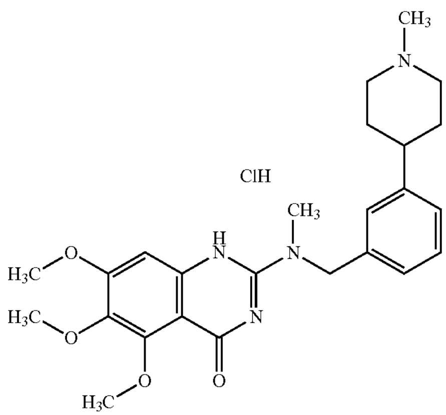 | 5,6,7-Trimethoxy-2-{methyl-[3-(1-methyl-piperidin-4-yl)-benzyl]-amino}-1H-quinazolin-4-one | 181.5–189.4 | |

TABLE 11-continued

| # | Structure | Systematic Name | MP °C. | M + H |
|---|---|---|---|---|
| 79 | 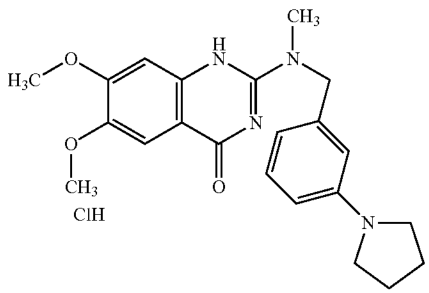 | 6,7-Dimethoxy-2-[methyl-(3-pyrrolidin-1-yl-benzyl)-amino]-1H-quinazolin-4-one | 220–223 | |
| 80 | 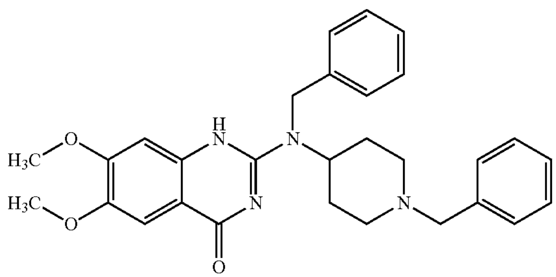 | 2-[Benzyl-(1-benzyl-piperidin-4-yl)-amino]-6,7-dimethoxy-1H-quinazolin-4-one | | 485 |
| 81 | 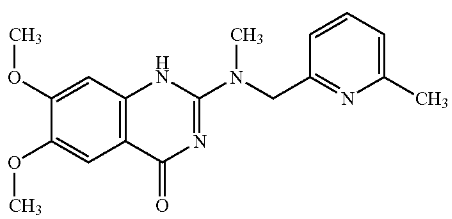 | 6,7-Dimethoxy-22-[methyl-(6-methyl-pyridin-2-ylmethyl)-amino]-1H-quinazolin-4-one | | 341 |
| 82 | 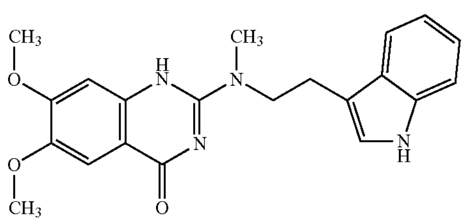 | 2-{[2-(1H-Indol-3-yl)-ethyl]-methyl-amino}-6,7-dimethoxy-1H-quinazolin-4-one | | 379 |

TABLE 11-continued
| # | Structure | Systematic Name | MP °C. | M + H |
|---|---|---|---|---|
| 83 | 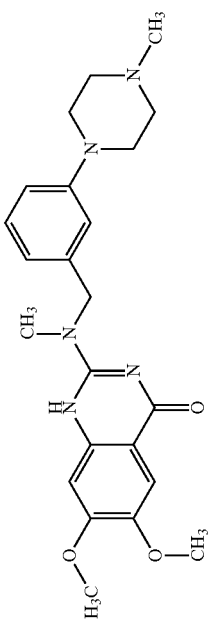 | 6,7-Dimethoxy-2-{methyl-[3-(4-methyl-piperazin-1-yl)-benzyl]-amino}-1H-quinazolin-4-one | | 424 |
| 84 | 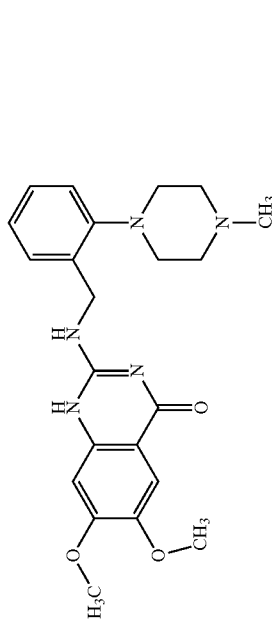 ClH | 6,7-Dimethoxy-2-[2-(4-methyl-piperazin-1-yl)-benzylamino]-1H-quinazolin-4-one | | |
| 85 | 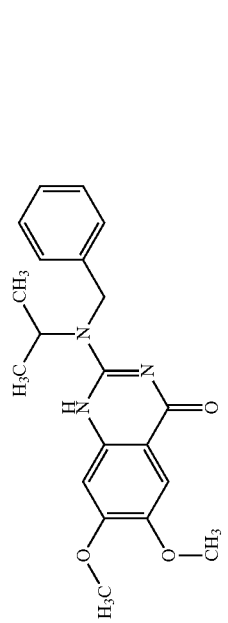 | 2-(Benzyl-isopropyl-amino)-6,7-dimethoxy-1H-quinazolin-4-one | 168–170.5 | 354 |
| 86 | 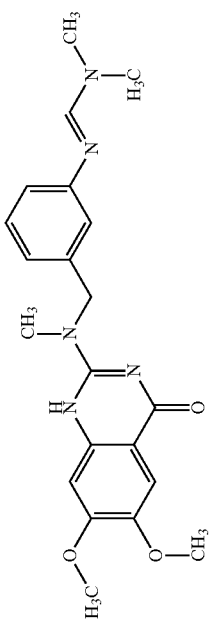 | N'-(3-{[(6,7-Dimethoxy-4-oxo-1,4-dihydro-quinazolin-2-yl)-methyl-amino]-methyl}-phenyl)-N,N-dimethyl-formamidine | 242–245 (HCl salt) | 395.4 M⁺ |

TABLE 11-continued

| # | Structure | Systematic Name | MP ° C. | M + H |
|---|---|---|---|---|
| 87 | 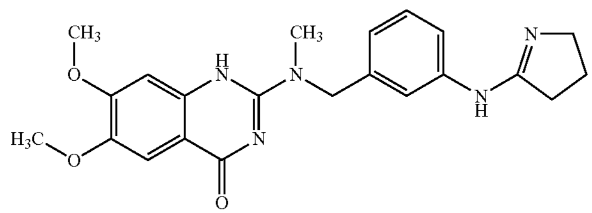 | 2-{[3-(4,5-Dihydro-3H-pyrrol-2-yl)amino)-benzyl]-methyl-amino}-6,7-dimethoxy-1H-quinazolin-4-one | 211–14 | 407.5 M[+] |
| 88 | 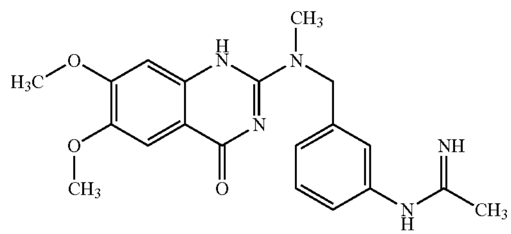 | N-(3-{[(6,7-Dimethoxy-4-oxo-1,4-dihydro-quinazolin-2-yl)-methyl-amino]-methyl}-phenyl)-acetamide | 263–266 (HBr salt) | 381.4 M[+] |
| 89 | 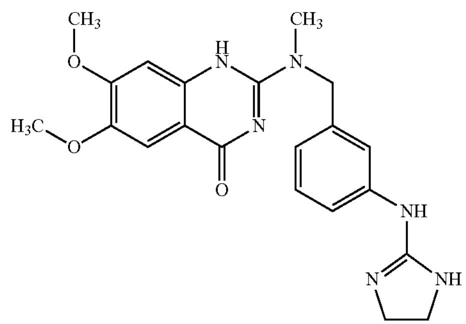 | 2-{[3-(4,5-Dihydro-1H-imidazol-2-yl)amino)-benzyl]-methyl-amino}-6,7-dimethoxy-1H-quinazolin-4-one | 163.8–176.9 | 409 |
| 90 | 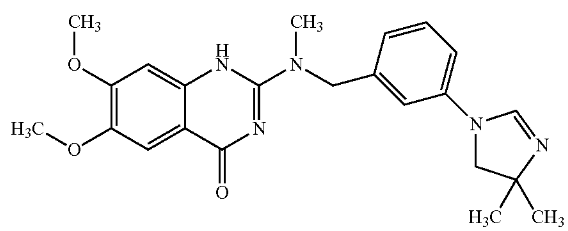 | 2-{[3-(4,4-Dimethyl-4,5-dihydro-imidazol-1-yl)-benzyl]-methyl-amino}-6,7-dimethoxy-1H-quinazolin-4-one | 240–242 | 422 |

TABLE 11-continued

| # | Structure | Systematic Name | MP ° C. | M + H |
|---|---|---|---|---|
| 91 | 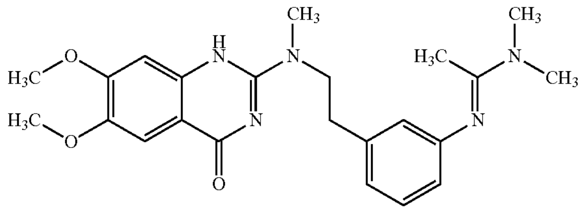 | N'-(3-{2-[((6,7-Dimethoxy-4-oxo-1,4-dihydro-quinazolin-2-yl)-methyl-amino]-ethyl}-phenyl)-N,N-dimethyl-acetamidine | 135–138.1 | 423.5 M+ |
| 92 | 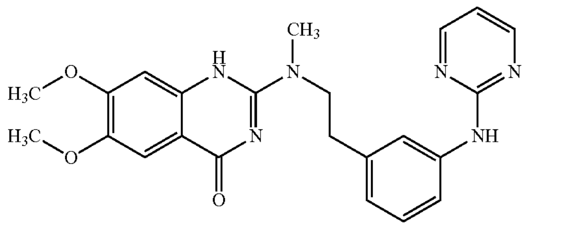 | 6,7-Dimethoxy-2-(methyl-‡2-[3-(pyrimidin-2-ylamino)phen yl]-ethyl}-amino)-1H-quinazolin-4-one | | 433 |
| 93 | 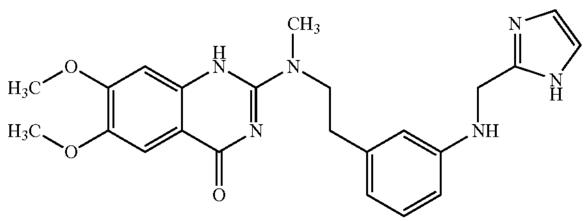 | 2-[(2-{3-[(1H-Imidazol-2-ylmethyl)-amino]-phenyl}-ethyl)-methyl-amino]-6,7-dimethoxy-1H-quinazolin-4-one | | 435 |
| 94 | 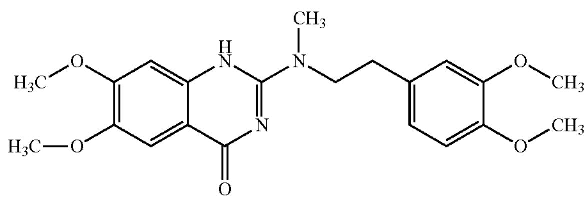 | 2-{[2-(3,4-Dimethoxy-phenyl)-ethyl]-methyl-amino}-6,7-dimethoxy-1H-quinazolin-4-one | | 400 |

TABLE 11-continued

| # | Structure | Systematic Name | MP ° C. | M + H |
|---|---|---|---|---|
| 95 | 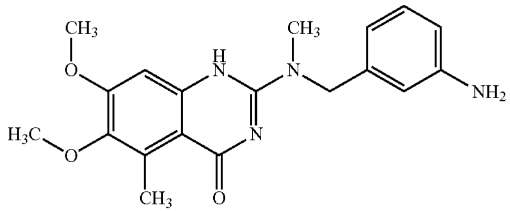 | 2-[(3-Amino-benzyl)-methyl-amino]-6,7-dimethoxy-5-methyl-1H-quinazolin-4-one | 268–269.5 | |
| 96 | 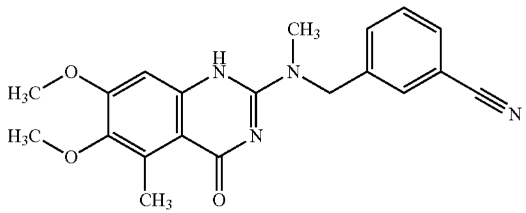 | 3-{[(6,7-Dimethoxy-5-methyl-4-oxo-1,4-dihydro-quinazolin-2-yl)-methyl-amino]-methyl}-benzonitrile | 279.9–281.5 (TFA salt) | 365 |
| 97 | 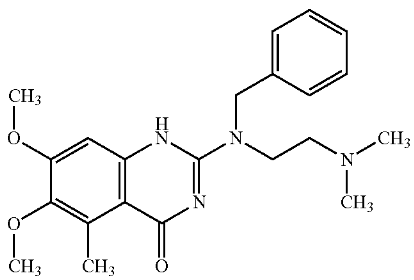 | 2-[Benzyl-(2-dimethylamino-ethyl)-amino]-6,7-dimethoxy-5-methyl-1H-quinazolin-4-one | | 397 |
| 98 | 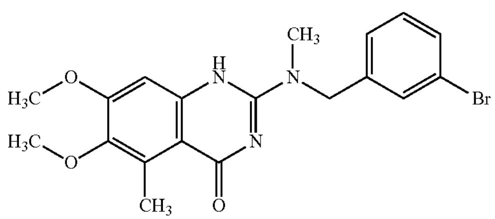 | 2-[(3-Bromobenzyl)-methyl-amino]-6,7-dimethoxy-5-methyl-1H-quinazolin-4-one | 232.9–234 | 419 |

TABLE 11-continued

| # | Structure | Systematic Name | MP °C. | M + H |
|---|---|---|---|---|
| 99 | 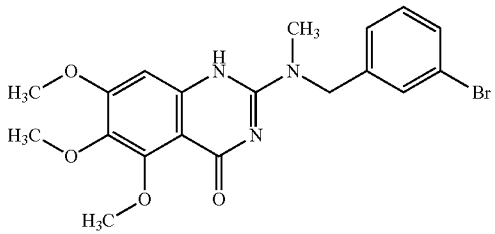 | 2-[(3-Bromo-benzyl)-methyl-amino]-5,6,7-trimethoxy-1qH-quinazolin-4-one | | 435 |
| 100 | 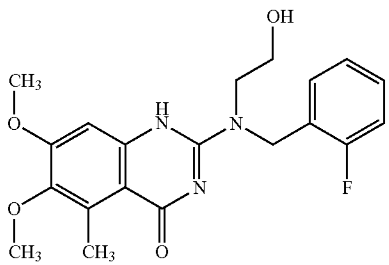 | 2-[(2-Fluoro-benzyl)-(2-hydroxy-ethyl)-amino]-6,7-dimethoxy-5-methyl-1H-quinazolin-4-one | | 388 |
| 101 | 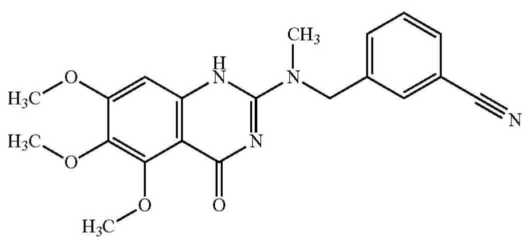 | 3-[[Methyl-(5,6,7-trimethoxy-4-oxo-1,4-dihydro-quinazolin-2-yl)-amino]-medethyl-]-benzonitrile | | 381 |
| 102 | 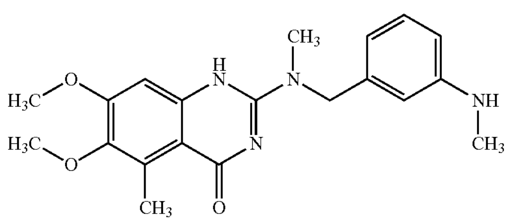 | 6,7-Dimethoxy-5-methyl-2-[methyl-(3-methylamino-benzyl)-amino]-1H-quinazolin-4-one | 195.9–197.9 | 368.4 M+ |

TABLE 11-continued

| # | Structure | Systematic Name | MP ° C. | M + H |
|---|---|---|---|---|
| 103 | 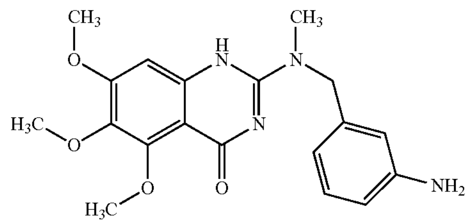 | 2-[(3-Amino-benzyl)-methyl-amino]-5,6,7-trimethoxy-1H-quinazolin-4-one | 225–226.5 | 370.4 M+ |
| 104 | 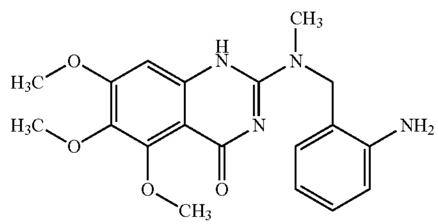 | 2-[(2-Amino-benzyl)-methyl-amino]-5,6,7-trimethoxy-1H-quinazolin-4-one | >300 (deco mp) (HCl salt) | 370.4 M+ |
| 105 | 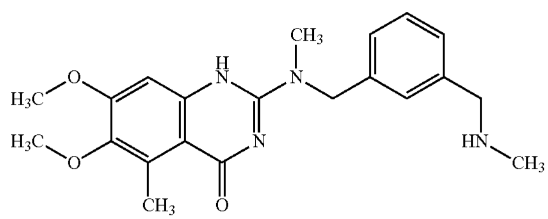 | 6,7-Dimethoxy-5-methyl-2-[methyl-(3-methylaminomethyl-benzyl)-amino]-1H-quinazolin-4-one | 179.0–181.3 | 383 |
| 106 | 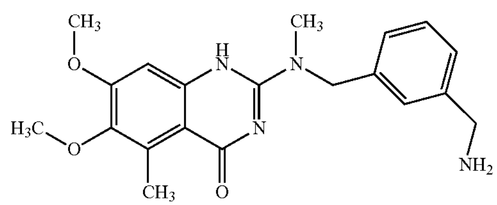 | 2-[(3-Aminomethyl-benzyl)-methyl-amino]-6,7-dimethoxy-5-methyl-1H-quinazolin-4-one | | 369 |

TABLE 11-continued

| # | Structure | Systematic Name | MP ° C. | M + H |
|---|---|---|---|---|
| 107 | 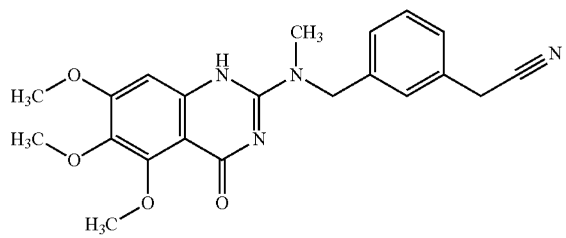 | (3-{[Methyl-(5,6,7-trimethoxy-4-oxo-1,4-dihydro-quinazolin-2-yl)-amino]-methyl}-phenyl)-acetonitrile | 149.5–153.3 | 395 |
| 108 | 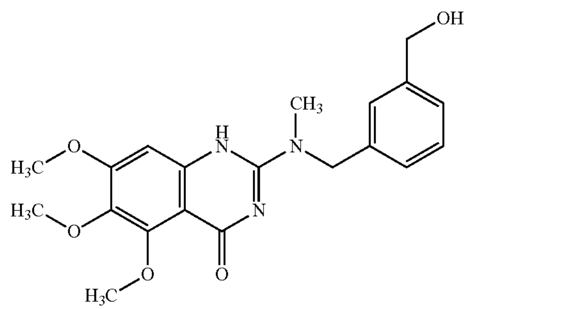 | 2-[(3-Hydroxymethyl-benzyl)-methyl-amino]-5,6,7-trimethoxy-1H-quinazolin-4-one | | 386 |
| 109 | 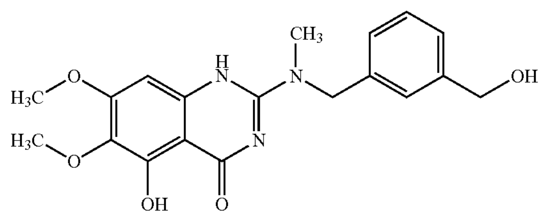 | 5-Hydroxy-2-[(3-hydroxymethyl-benzyl)-metrhyl-amino]-6,7-dimethoxy-1H-quinazolin-4-one | | 372 |
| 110 | 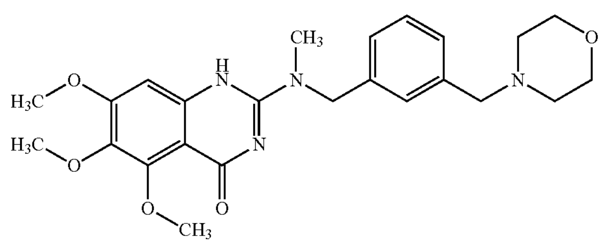 | 5,6,7-Trimethoxy-2-[methyl-(3-morpholin-4-ylmethyl-benzyl)-amino]-1H-quinazolin-4-one | 160.0–162.1 | 455 |

TABLE 11-continued

| # | Structure | Systematic Name | MP ° C. | M + H |
|---|---|---|---|---|
| 111 | 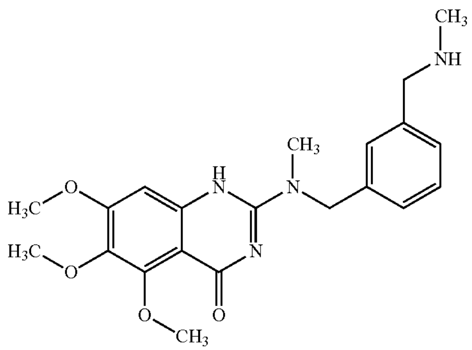 | 5,6,7-Trimethoxy-2-[methyl-(3-methylaminomethyl-benzyl)-amino]-1H-quinazolin-4-one | 124.9–127.6 | 398.5 M+ |
| 112 | 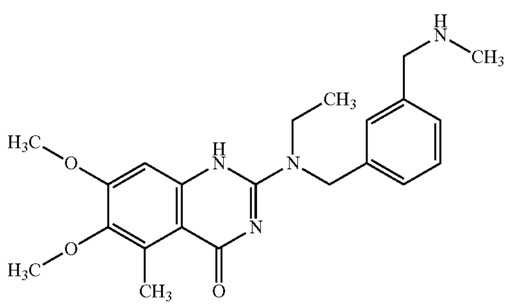 | 2-[Ethyl-(3-methylaminomethyl-benzyl)-amino]-6,7-dimethoxy-5-methyl-1H-quinazolin-4-one | 159.3–164.1 | 386.5 M+ |
| 113 | 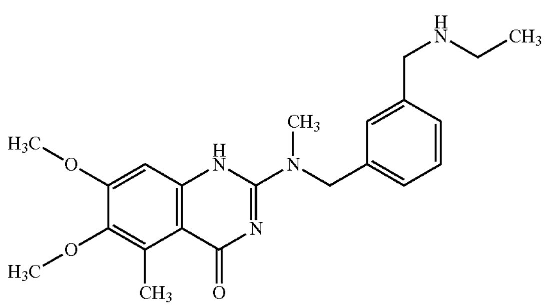 | 2-[(3-Ethylaminomethyl-benzyl)-methyl-amino]-6,7-dimethoxy-5-methyl-1H-quinazolin-4-one | 158.2–158.9 | 396.5 M+ |

TABLE 11-continued

| # | Structure | Systematic Name | MP ° C. | M + H |
|---|---|---|---|---|
| 114 | 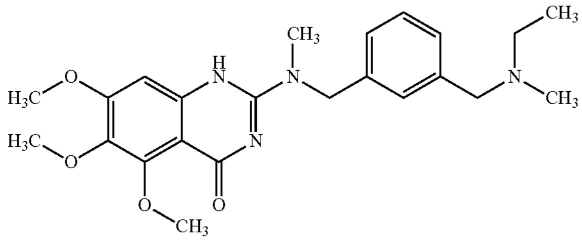 | 2-({3-[(Ethyl-methyl-amino)-methyl]-benzyl}-methyl-amino)-5,6,7-trimethoxy-1H-quinazolin-4-one | 106.5–108.9 | 426.5 M+ |
| 115 | 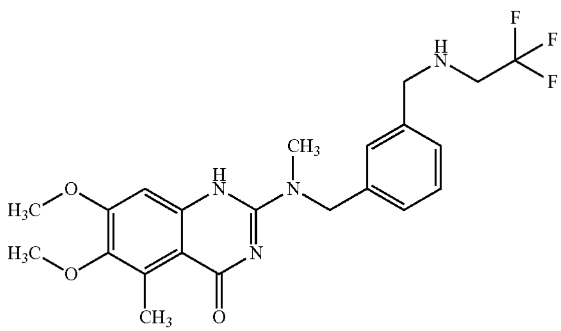 | 6,7-Dimethoxy-5-methyl-2-(methyl-{3-[(2,2,2-trifluoro-ethylamino)-methyl]-benzyl}-amino)-1H-quinazolin-4-one | 1800.4–181.5 | 450.5 M+ |
| 116 | 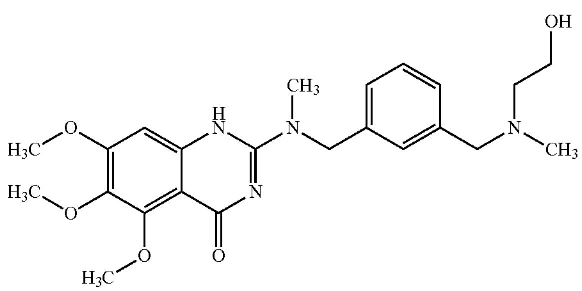 | 2-[(3-{[(2-Hydroxy-ethyl)-methyl-amino]-methyl}-benzyl)-methyl-amino]-5,6,7-trimethoxy-1H-quinazolin-4-one | 169.0–171.9 (HCl salt) | 443 |

TABLE 11-continued

| # | Structure | Systematic Name | MP ° C. | M + H |
|---|---|---|---|---|
| 117 | 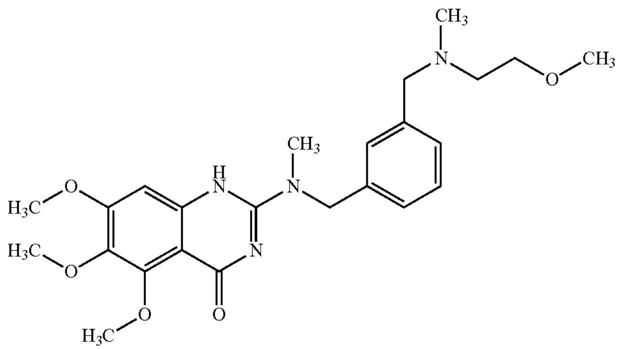 | 5,6,7-Trimethoxy-2-[(3-{[(2-methoxy-ethyl)-methyl-amino]-methyl}-benzyl)-methyl-amino]-1H-quinazolin-4-one | 162.9–164.5 (bishydrochloride salt) | 457 |
| 118 | 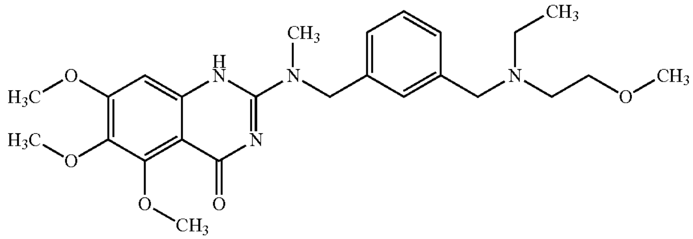 | 2-[(3-{[Ethyl-(2-methoxy-ethyl)-amino]-methyl}-benzyl)-methyl-amino]-5,6,7-trimethoxy-1H-quinazolin-4-one | 164.5–166.0 (HCl salt) | 407.6 M+ |
| 119 | 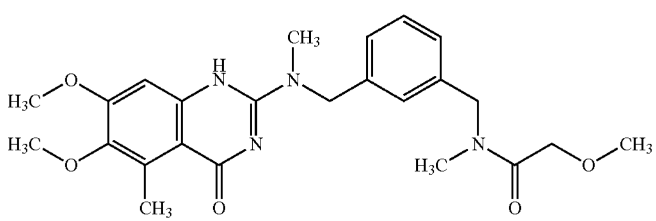 | N-(3-{[((6,7-Dimethoxy-5-methyl-4-oxo-1,4-dihydro-quinazolin-2-yl)-methyl-amino]-methyl}-benzyl)-2-methoxy-N-methyl-acetamide | 150.0–151.2 | 454.5 M+ |

TABLE 11-continued

| # | Structure | Systematic Name | MP °C. | M + H |
|---|---|---|---|---|
| 120 | 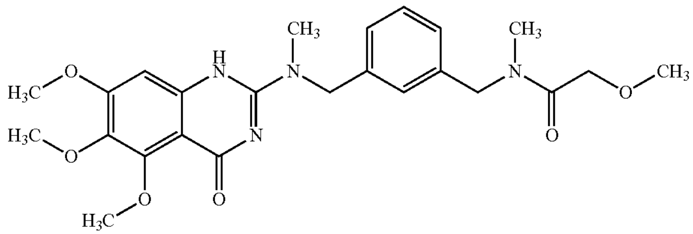 | 2-Methoxy-N-methyl-N-(3-{[methyl-(5,6,7-trimethoxy-4-oxo-1,4-dihydro-quinazolin-2-yl)-amino]-methyl}-benzyl)-acetamide | 115–117 | 470.5 M+ |
| 121 | 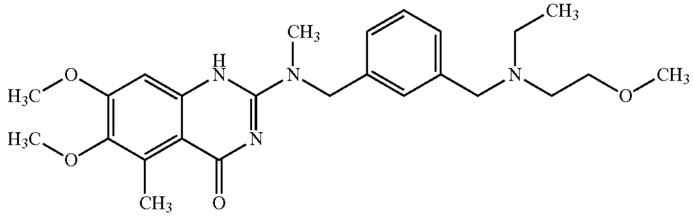 | 2-[(3-{[Ethyl(2-methoxy-ethyl)-amino]-methyl}-benzyl)-methyl-azmino]-6,7-dimethoxy-5-methyl-1H-quinazolin-4-one | 121.8–122.3 | 454.6 M+ |
| 122 | 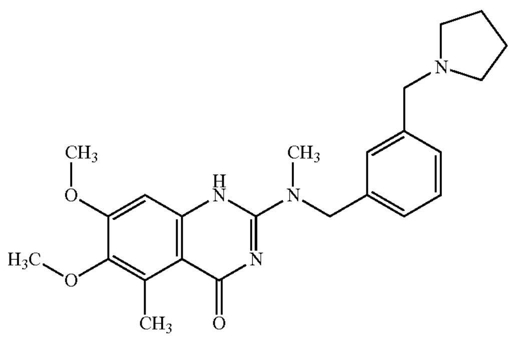 | 6,7-Dimethoxy-5-methyl-2-[methyl-(3-pyrrolidin-1-ylmethyl-benzyl)-amino]-1H-quinazolin-4-one | 163.9–164.5 | 422.5 M+ |
| 123 | 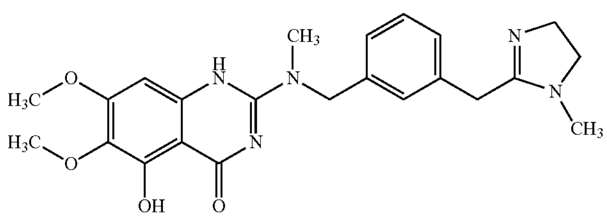 | 5-Hydroxy-6,7-dimethoxy-2-{methyl-[3-(1-methyl-4,5-dihydro-1H-imidazol-2-ylmethyl)-benzyl]-amino}-1H-quinazolin-4-one | | 438 |

TABLE 11-continued

| # | Structure | Systematic Name | MP ° C. | M + H |
|---|---|---|---|---|
| 124 | 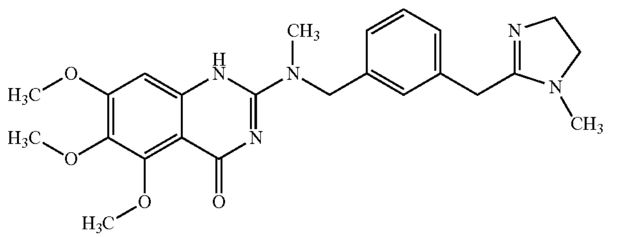 | 5,6,7-Trimethoxy-2-{methyl-[3-(1-methyl-4,5-dihydro-1H-imidazol-2-ylmethyl)-benzyl]-amino}-1H-quinazolin-4-one | | 452 |
| 125 | 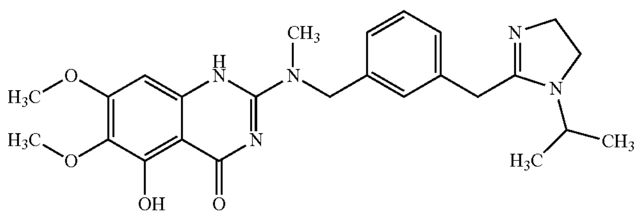 | 5-Hydroxy-2-{[3-(1-isopropyl-4,5-dihydro-1H-imidazol-2-ylmethyl)-benzyl]-methyl-amino}-6,7-dimethoxy-1H-quinazolin-4-one | | 466 |
| 126 | 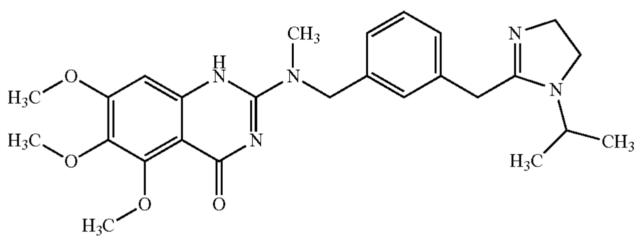 | 2-{[3-(1-Isopropyl-4,5-dihydro-1H-imidazol-2-ylmethyl)-benzyl]-methyl-amino}-5,6,7-trimethoxy-1H-quinazolin-4-one | | 480 |

TABLE 11-continued

| # | Structure | Systematic Name | MP °C. | M + H |
|---|---|---|---|---|
| 127 | 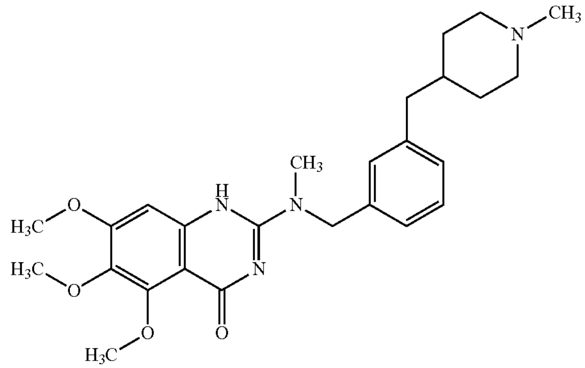 | 5,6,7-Trimethoxy-2-{methyl-[3-(1-methyl-piperidin-4-ylmethyl)-benzyl]-amino}-1H-quinazolin-4-one | 175–195 (HCl salt) | 466.6 M+ |
| 128 | 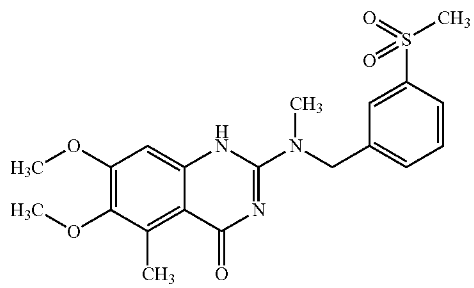 | 2-[(3-Methanesulfonyl-benzyl)-methyl-amino]-6,7-dimethoxy-5-methyl-1H-quinazolin-4-one | 269.5–271.5 | 417.5 M+ |
| 129 | 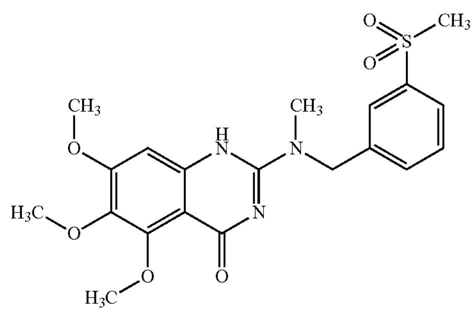 | 2-[(3-Methanesulfonyl-benzyl)-methyl-amino]-5,6,7-trimethoxy-1H-quinazolin-4-one | 231.5–232.9 | 433.5 M+ |

TABLE 11-continued

| # | Structure | Systematic Name | MP °C. | M + H |
|---|---|---|---|---|
| 130 | 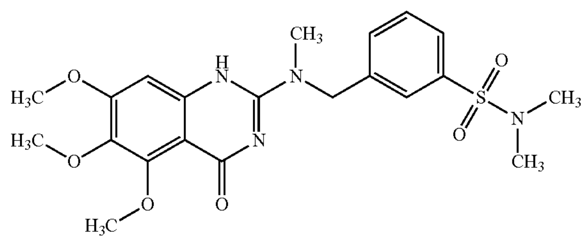 | N,N-Dimethyl-3-{[methyl-5,6,7-trimethoxy-4-oxo-1,4-dihydro-quinazolin-2-yl)-amino]-methyl}-benzenesulfonamide | 199.9 to 204.0 | 462.5 M+ |
| 131 | 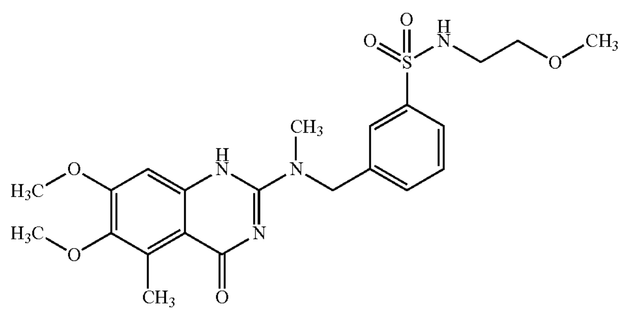 | 3-{[(6,7-Dimethoxy-5-methyl-4-oxo-1,4-dihydro-quinazolin-2-yl)-methyl-amino]-methyl}-N-(2-methoxy-ethyl)-benzenesulfonamide | 163.0–164.9 | 476.6 M+ |
| 132 | 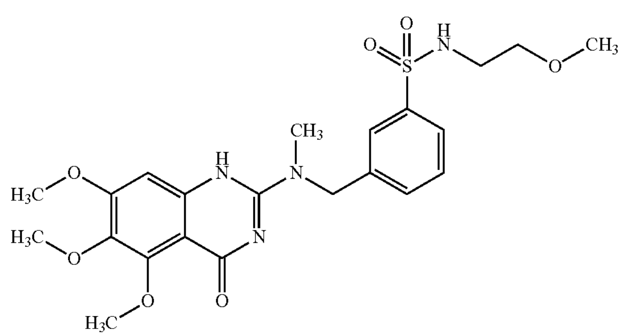 | N-(2-Methoxy-ethyl)-3-{[methyl-(5,6,7-trimethoxy-4-oxo-1,4-dihydro-quinazolin-2-yl)-amino]-methyl}-benzenesulfonamide | 176.9–179.1 | 492.6 M+ |

TABLE 11-continued

| # | Structure | Systematic Name | MP °C. | M + H |
|---|---|---|---|---|
| 133 | 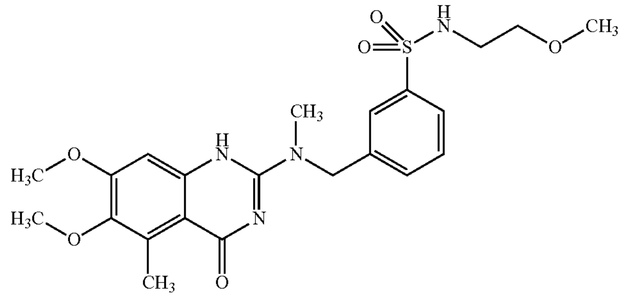 | 3-{[(6,7-Dimethoxy-5-methyl-4-oxo-1,4-dihydro-quinazolin-2-yl)-methyl-amino]-methyl}-N-(3-methoxy-propyl)-benzenesulfonamide | 169.0–171.9 | 490.6 M+ |
| 134 | 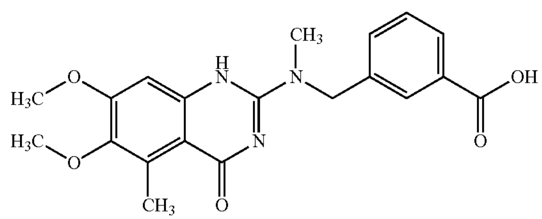 | 3-{[(6,7-Dimethoxy-5-methyl-4-oxo-1,4-dihydro-quinazolin-2-yl)-methyl-amino]-methyl}-benzoic acid | 283.1–286.2 | 383.4 M+ |
| 135 | 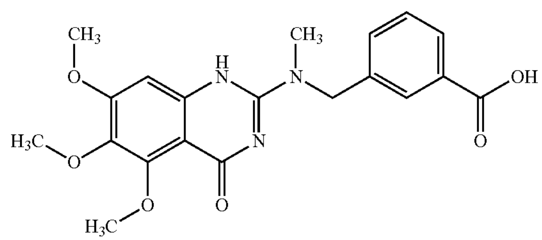 | 3-{[Methyl-(5,6,7-trimethoxy-4-oxo-1,4-dihydro-quinazolin-2-yl)-amino]-methyl}-benzoic acid | | 400 |
| 136 | 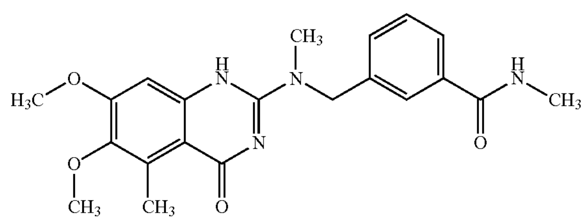 | 3-{[(6,7-Dimethoxy-5-methyl-44-oxo-1,4-dihydro-quinazolin-2-yl)-methyl-amino]-methyl}-N-methyl-benzamide | 243.3–245.1 | 396.4 M+ |

TABLE 11-continued

| # | Structure | Systematic Name | MP ° C. | M + H |
|---|---|---|---|---|
| 137 | 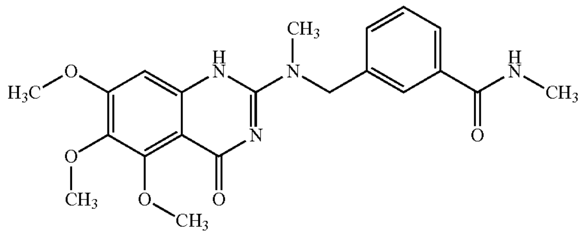 | N-Methyl-3-{[methyl-(5,6,7-trimethoxy-4-oxo-1,4-dihydro-quinazolin-2-yl)-amino]-methyl}-benzamide | 217.9–219.1 | 412.4 M+ |
| 138 | 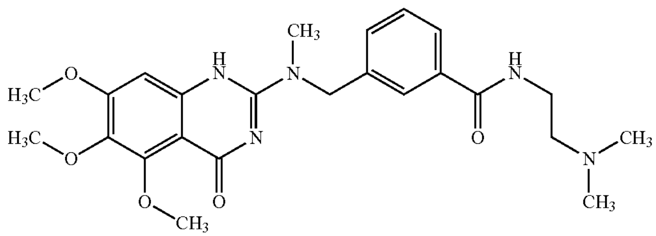 | N-(2-Dimethylamino-ethyl)-3-{[methyl-(5,6,7-trimethoxy-4-oxo-1,4-dihydro-quinazolin-2-yl)-amino]-methyl}-benzamide | | 470 |
| 139 | 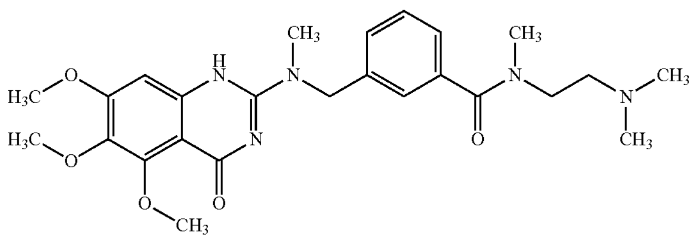 | N-(2-Dimethylamino-ethyl)-N-methyl-3-{[methyl-(5,6,7-trimethoxy-4-oxo-1,4-dihydro-quinazolin-2-yl)-amino]-methyl}-benzamide | | 484 |
| 140 | 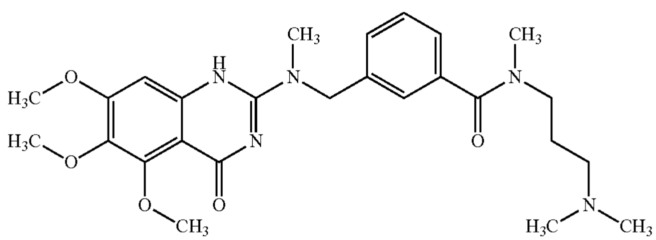 | N-(3-Dimethylamino-propyl)-N-methyl-3-{[methyl-(5,6,7-trimethoxy-4-oxo-1,4-dihydro-quinazolin-2-yl)-amino]-methyl}-benzamide | | 498 |

TABLE 11-continued

| # | Structure | Systematic Name | MP ° C. | M + H |
|---|---|---|---|---|
| 141 | 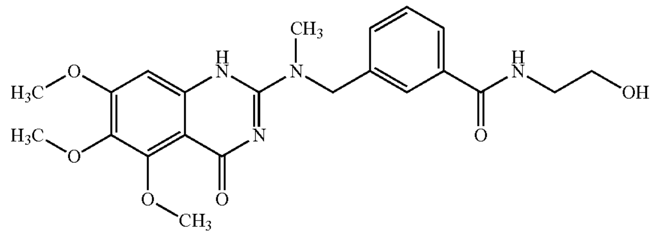 | N-(2-Hydroxy-ethyl)-3-{[methyl-(5,6,7-trimethoxy-4-oxo-1,4-dihydro-quinazolin-2-yl)-amino]-methyl}-benzamide | | 443 |
| 142 | 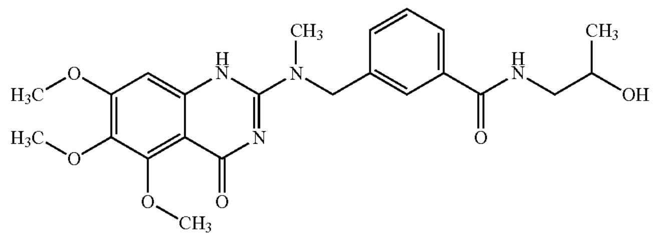 | N-(2-Hydroxy-propyl)-3-{[methyl-(5,6,7-trimethoxy-4-oxo-1,4-dihydro-quinazolin-2-yl)-amino]-methyl}-benzamide | | 457 |
| 143 | 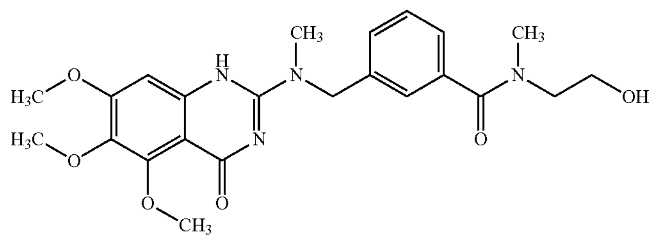 | N-(2-Hydroxy-ethyl)-N-methyl-3-{[methyl-(5,6,7-trimethoxy-4-oxo-1,4-dihydro-quinazolin-2-yl)-amino]-methyl}-benzamide | | 457 |
| 144 | 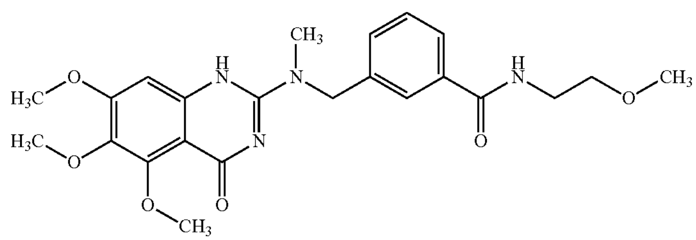 | N-(2-Methoxy-ethyl)-3-{[methyl-(5,6,7-trimethoxy-4-oxo-1,4-dihydro-quinazolin-2-yl-amino]-methyl}-benzamide | | 457 |

TABLE 11-continued

| # | Structure | Systematic Name | MP °C. | M + H |
|---|---|---|---|---|
| 145 | 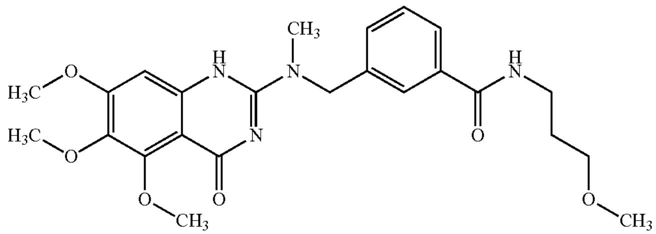 | N-(3-Methoxy-propyl)(-3-{[methyl-(5,6,7-trimethoxy-4-oxo-1,4-dihydro-quinazolin-2-yl)-amino]-methyl}-benzamide | | 471 |
| 146 | 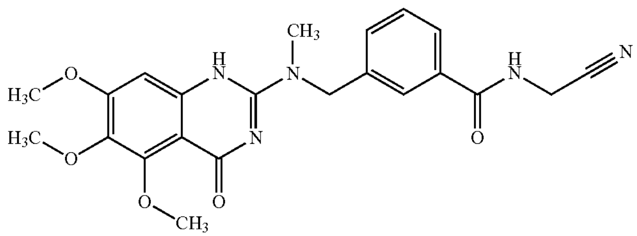 | N-Cyanomethyl-3-{[methyl-(5,6,7-trimethoxy-4-oxo-1,4-dihydro-quinazolin-2-yl)-amino]-methyl}-benzamide | | 438 |
| 147 | 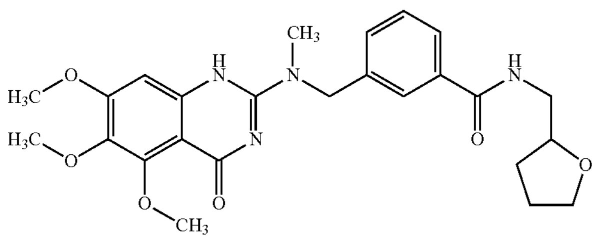 | 3-{[Methyl-(5,6,7-trimethoxy-4-oxo-1,4-dihydro-quinazolin-2-yl)-amino]-methyl}-N-(tetrahydro-furan-2-ylmethyl)-benzamide | | 483 |
| 148 | 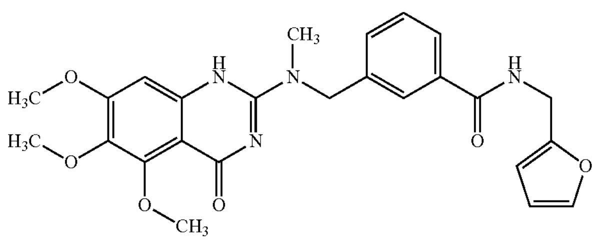 | N-Furan-2-ylmethyl-3-{[methyl-(5,6,7-trimethoxy-4-oxo-1,4-dihydro-quinazolin-2-yl)-amino]-methyl}-benzamide | | 479 |

TABLE 11-continued
| # | Structure | Systematic Name | MP °C. | M + H |
|---|---|---|---|---|
| 149 | 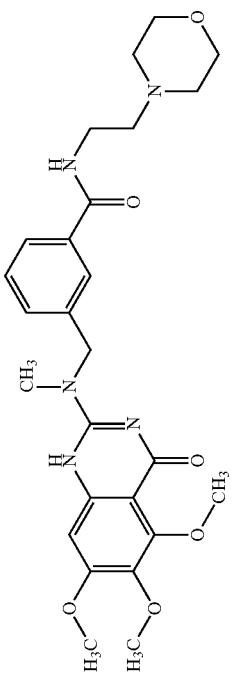 | 3-{[Methyl-(5,6,7-trimethoxy-4-oxo-1,4-dihydro-quinazolin-2-yl)-amino]-methyl}-N-(2-morpholin-4-yl-ethyl,)-benzamide | | 512 |
| 150 | 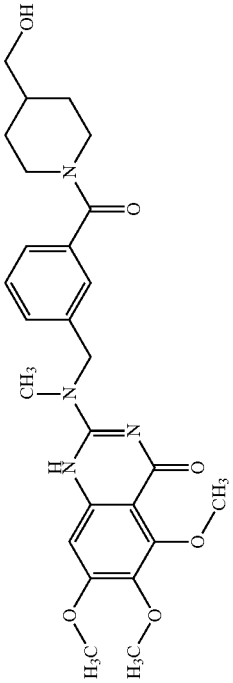 | 2-{[3-(4-Hydroxymethyl-piperidine-1-carbonyl)-benzyl]-methyl-amino}-5,6,7-trimethoxy-1H-quinazolin-4-one | | 497 |
| 151 | 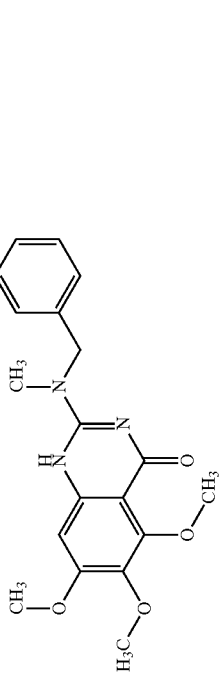 | 2-{[3-(2-Hydroxy-ethoxy)-benzyl]-methyl-amino}-5,6,7-trimethoxy-1H-quinazolin-4-one | 146.0–1247.5 | 416 |

TABLE 11-continued

| # | Structure | Systematic Name | MP ° C. | M + H |
|---|---|---|---|---|
| 152 | 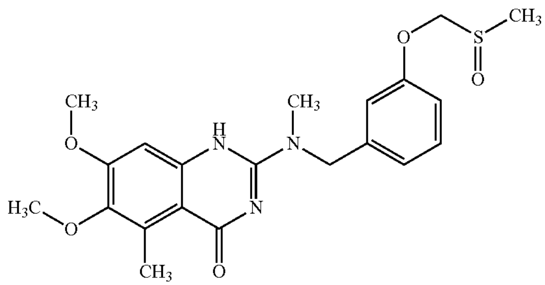 | 2-[(3-Methanesulfinylmethoxy-benzyl)-methyl-amino]-6,7-dimethoxy-5-methyl-1H-quinazolin-4-one | 191.0–193.5 | 432 |
| 153 | 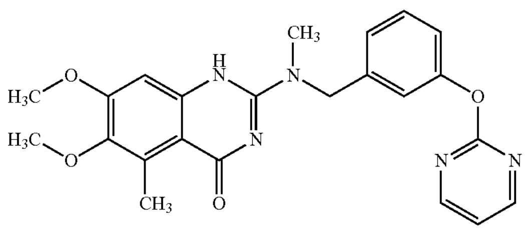 | 6,7-Dimethoxy-5-methyl-2-{methyl-[3-(pyrimidin-2-yloxy)-benzyl]-amino}-1H-quinazolin-4-one | 224.0–227.8 | 434 |
| 154 | 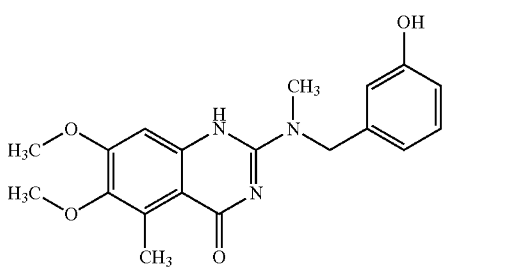 | 2-[(3-Hydroxy-benzyl)-methyl-amino]-6,7-dimethoxy-5-methyl-1H-quinazolin-4-one | 252.9–254.35 | 355.4 M+ |

TABLE 11-continued

| # | Structure | Systematic Name | MP ° C. | M + H |
|---|---|---|---|---|
| 155 | 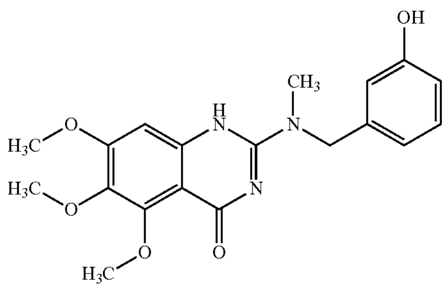 | 2-[(3-Hydroxy-benzyl)-methyl-amino]-5,6,7-trimethoxy-1H-quinazolin-4-one | 212.3–215.1 | 371.4 M+ |
| 156 | 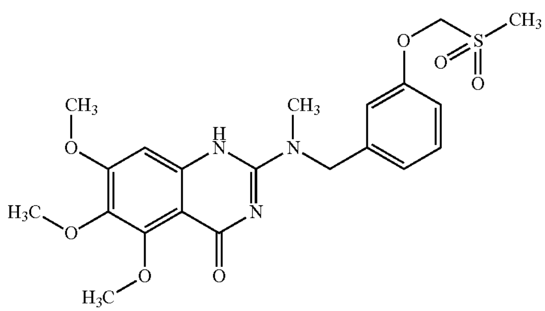 | 2-[(3-Methanesulfonylmethoxy-benzyl)-methyl-amino]-5,6,7-trimethoxy-1H-quinazolin-4-one | 183.9–185.4 | 463.5 M+ |
| 157 | 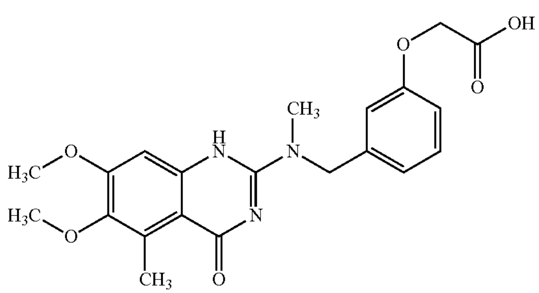 | (3-{[(6,7-Dimethoxy-5-methyl-4-oxo-1,4-dihydro-quinazolin-2-yl)-methyl-amino]-methyl}-phenoxy)-acetic acid | >300 | 413.4 M+ |

TABLE 11-continued

| # | Structure | Systematic Name | MP ° C. | M + H |
|---|---|---|---|---|
| 158 | 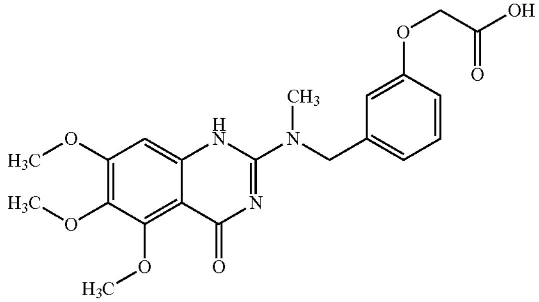 | (3-{[Methyl-(5,6,7-trimethoxy-4-oxo-1,4-dihydro-quinazolin-2-yl)-amino]-methyl}-phenoxy)-acetic acid | >300 | 429.4 M+ |
| 159 | 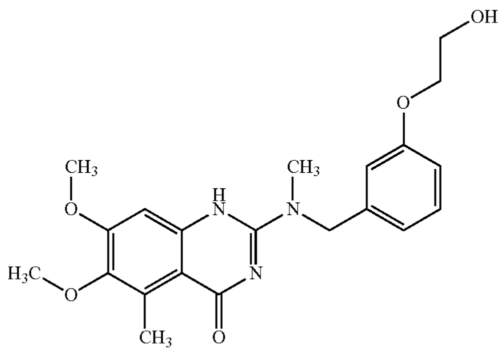 | 2-{[3-(2-Hydroxy-ethoxy)-benzyl]-methyl-amino}-6,7-dimethoxy-5-methyl-1H-quinazolin-4-one | 180.5–183.1 | 399.4 M+ |

TABLE 11-continued

| # | Structure | Systematic Name | MP ° C. | M + H |
|---|---|---|---|---|
| 160 | 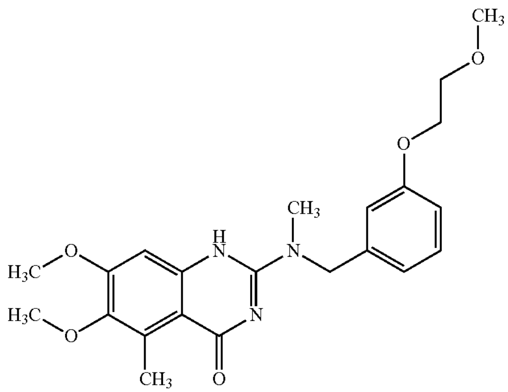 | 6,7-Dimethoxy-2-{[3-(2-methoxy-ethoxy)-benzyl]-methyl-amino}-5-methyl-1H-quinazolin-4-one | 176.6–177.9 | 413.5 M+ |
| 161 | 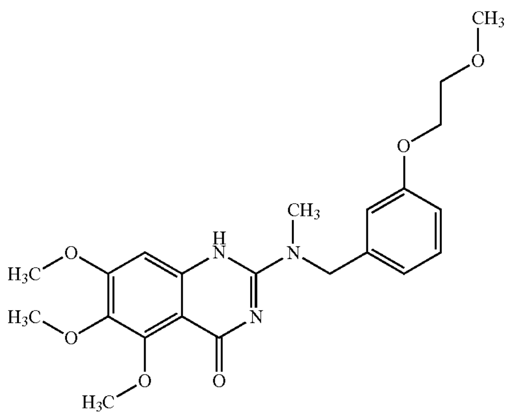 | 5,6,7-Trimethoxy-2-{[3-(2-methoxy-ethoxy)-benzyl]-methyl-amino}-1H-quinazolin-4-one | 144.8–145.9 | 429.5 M+ |

TABLE 11-continued

| # | Structure | Systematic Name | MP °C. | M + H |
|---|---|---|---|---|
| 162 | 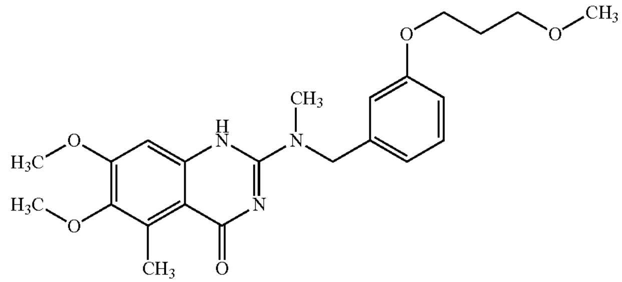 | 6,7-Dimethoxy-2-{[3-(3-methoxy-propoxy)-benzyl]-methyl-amino}-5-methyl-1H-quinazolin-4-one | 150.1–152.0 | 427.5 M+ |
| 163 | 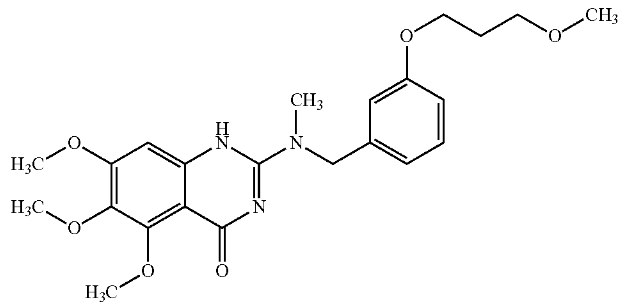 | 5,6,7-Trimethoxy-2-{[2-(3-methoxy-propoxy)-benzyl]-methyl-amino}-1H-quinazolin-4-one | 147.5–149.1 | 443.5 M+ |
| 164 | 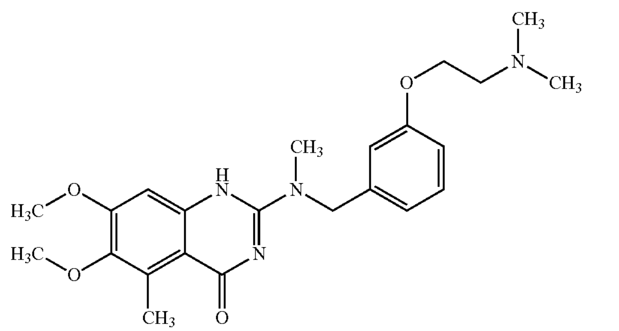 | 2-{[3-(2-Dimethylamino-ethoxy)-benzyl]-methyl-amino}-6,7-dimethoxy-5-methyl-1H-quinazolin-4-one | 137.9–141.9 | 426.5 M+ |

TABLE 11-continued

| # | Structure | Systematic Name | MP °C. | M + H |
|---|---|---|---|---|
| 165 | 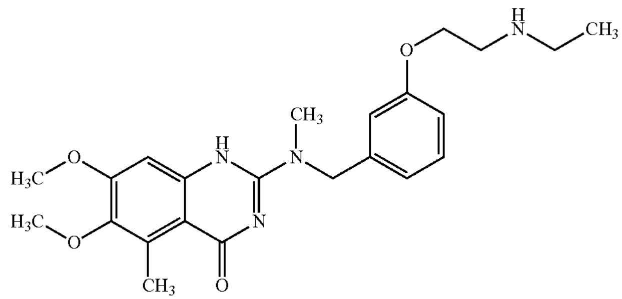 | 2-{[3-(2-Ethylamino-ethoxy)-benzyl]-methyl-amino}-6,7-dimethoxy-5-methyl-1H-quinazolin-4-one | 264.6–266.5 | 426.5 M+ |
| 166 | 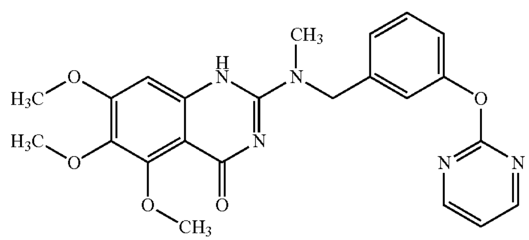 | 5,6,7-Trimethoxy-2-{methyl-[3-(pyrimidin-2-yloxy)-benzyl]-amino}-1H-quinazolin-4-one | 191–192.9 | 449.5 M+ |
| 167 | 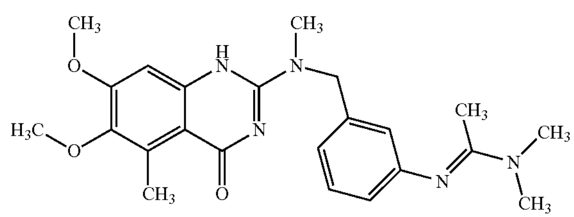 | N'-(3-{[(6,7-Dimethoxy-5-methyl-4-oxo-1,4-dihydro-quinazolin-2-yl)-methyl-amino]-methyl}-phenyl)-N,N-dimethyl-acetamide | 174.4–174.8 | 424 |
| 168 | 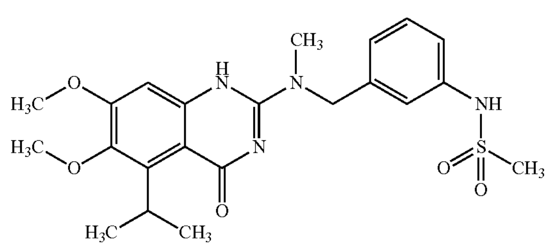 | N-(3-{[(5-Isopropyl-6,7-dimethoxy-4-oxo-1,4-dihydro-quinazolin-2-yl)-methyl-amino]-methyl}-phenyl)-methanesulfonamide | 215–17 | |

TABLE 11-continued

| # | Structure | Systematic Name | MP ° C. | M + H |
|---|---|---|---|---|
| 169 | 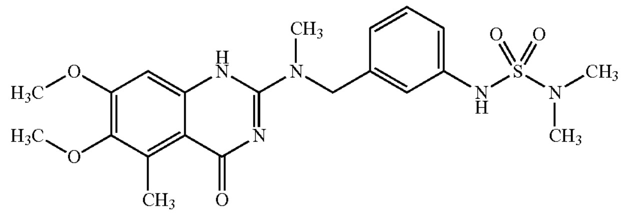 | N'-(3-{[(6,7-dimethoxy-5-methyl-4-oxo-1,4-dihydro-quinazolin-2-yl)-methyl-amino]-methyl}-phenyl)-N,N-dimethylsulfamide | 195.3–199.0 | |
| 170 | 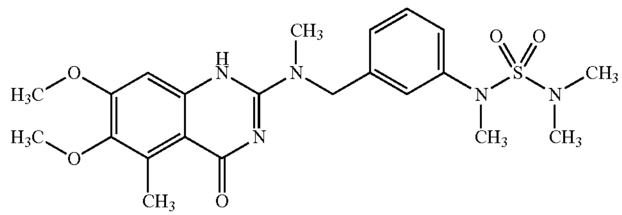 | N-(3-{[(6,7-dimethoxy-5-methyl-4-oxo-1,4-dihydro-quinazolin-2-yl)-methyl-amino]-methyl}-phenyl)-N,N',N'-trimethylsulfamide | 160.0–161.7 | |
| 171 | 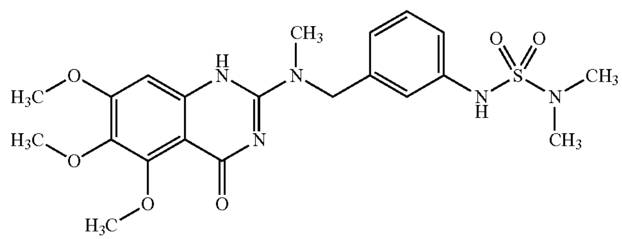 | N,N-Dimethyl-N'-(3-{[methyl-(5,6,7-trimethoxy-4-oxo-1,4-dihydro-quinazolin-2-yl)-amino]-methyl}-phenyl)-sulfamide | 176.5–179.7 | |
| 172 | 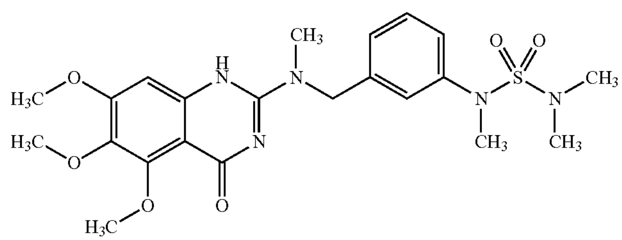 | N,N,N'-Trimethyl-N'-(3-{[methyl-(5,6,7-trimethoxy-4-oxo-1,4-dihydro-quinazolin-2-yl)-amino]-methyl}-phenyl)-sulfamide | 170.3–172.3 | |

TABLE 11-continued

| # | Structure | Systematic Name | MP ° C. | M + H |
|---|---|---|---|---|
| 173 | 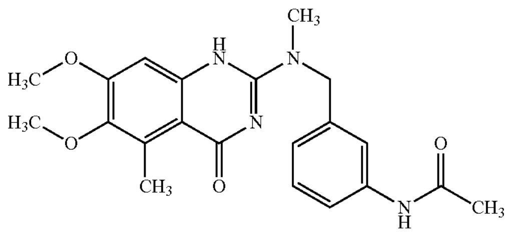 | N-(3-{[(6,7-Dimethoxy-5-methyl-4-oxo-1,4-dihydro-quinazolin-2-yl)-methyl]-amino]-methyl}-phenyl)-sulfamide | 170.3–172.3 | |
| 174 | 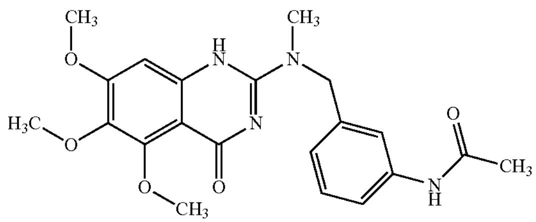 | N-(3-{[Methyl-(5,6,7-trimethoxy-4-oxo-1,4-dihydro-quinazolin-2-yl)-amino]-methyl}-phenyl)-acetamide | 166.5–172.9 (HCl Salt) | |
| 175 | 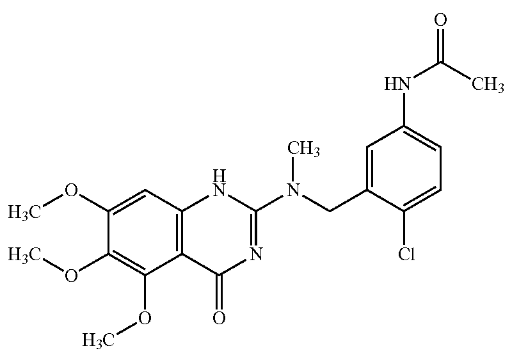 | N-(4-Chloro-3-{[methyl-(5,6,7-trimethoxy-4-oxo-1,4-dihydro-quinazolin-2-yl)-amino]-methyl}-phenyl)-acetamide | | 447, M+ |

TABLE 11-continued

| # | Structure | Systematic Name | MP °C. | M + H |
|---|---|---|---|---|
| 176 | 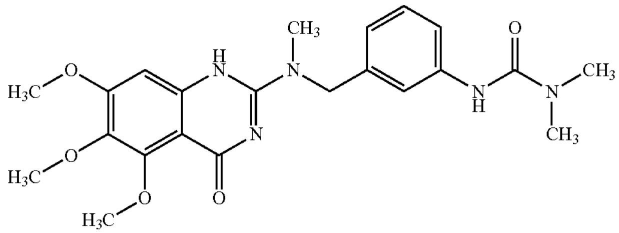 | 1,1-Dimethyyl-3-(3-{[methyl-(5,6,7-trimethoxy-4-oxo-1,4-dihydro-quinaolin-2-yl)-amino]-methyl}-phenyl)-urea | | 442 |
| 177 | 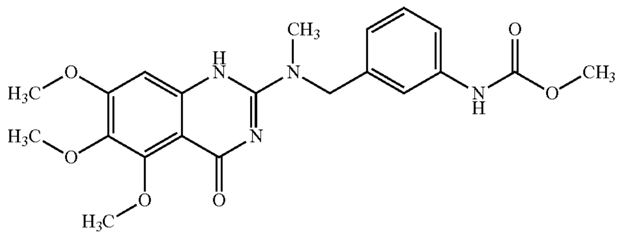 | (3-{[Methyl-(5,6,7-trimethoxy-4-oxo-1,4-dihydro-quinazolin-2-yl)-amino]-methyl}-phenyl)-carbamic acid methyl ester | 230.9–232.1 | |
| 178 | 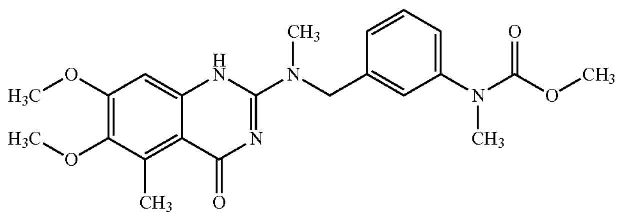 | (3-{[(6,7-Dimethoxy-5-methyl-4-oxo-1,4-dihydro-quinazolin-2-yl)-methyl-amino]-methyl}-phenyl)-methyl-carbamic acid methyl ester | 191.9–194.1 | |
| 179 | 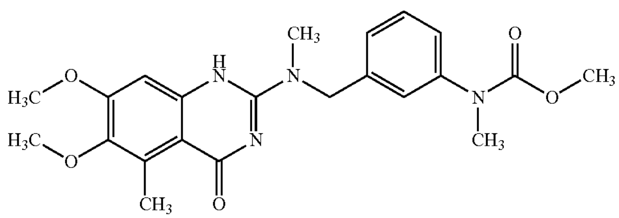 | N-(3-{[(6,7-Dimethoxy-5-methyl-4-oxo-1,4-dihydro-quinazolin-2-yl)-methyl-amino]-methyl}-phenyl)-N-methyl-2-oxo-propionamide | 198.9–201.9 | |

TABLE 11-continued

| # | Structure | Systematic Name | MP ° C. | M + H |
|---|---|---|---|---|
| 180 | 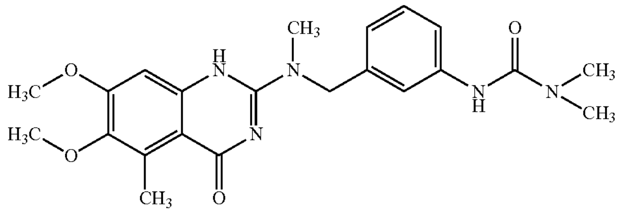 | 3-(3-{[(6,7-Dimethoxy-5-methyl-4-oxo-1,4-dihydro-quinazolin-2-yl)-methyl-amino]-methyl}-phenyl)-1,1-dimethyl-urea | 131.5–168.0 | |
| 181 | 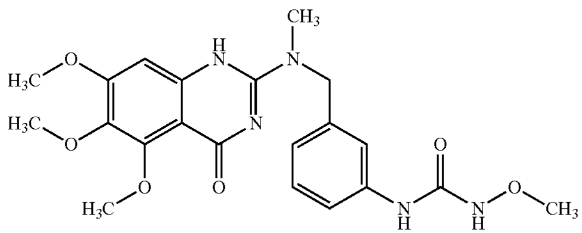 | N-Methoxy-N'-(3-{[methyl-(5,6,7-trimethoxy-4-oxo-1,4-dihydro-quinazolin-2-yl)-amino]-methyl}-phenyl)-urea | 165–7 | |
| 182 | 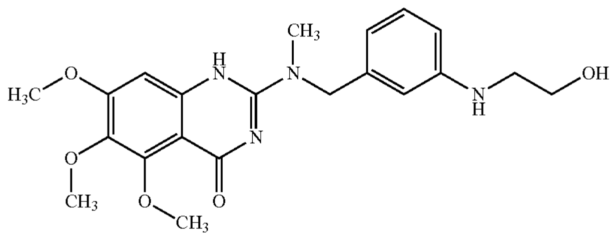 | 2-{[3-(2-Hydroxy-ethylamino)-benzyl]-methyl-amino}-5,6,7-trimethoxy-1H-quinazolin-4-one | 60.5–61.5 | |
| 183 | 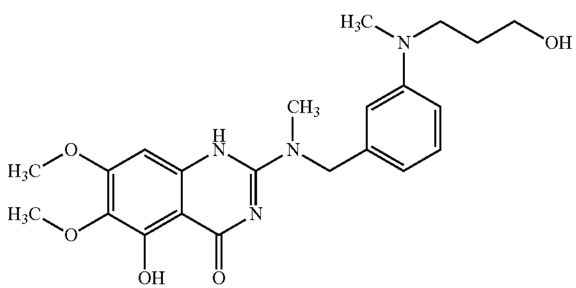 | 5-Hydroxy-2-({3-[(3-hydroxy-propyl)-methyl-amino]-benzyl}-methyl-amino)-6,7-dimethoxy-1H-quinazolin-4-one | | 429 |

TABLE 11-continued

| # | Structure | Systematic Name | MP °C. | M + H |
|---|---|---|---|---|
| 184 | 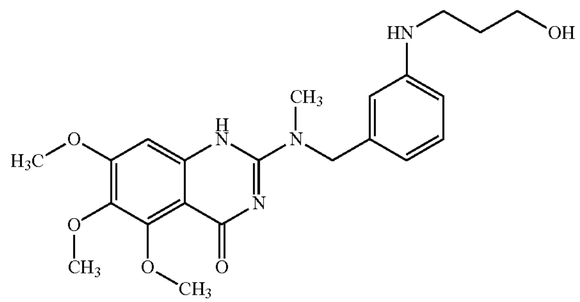 | 2-{[3-(3-Hydroxy-propylamino)-benzyl]-methyl-amino}-5,6,7-trimethoxy-1H-quinazolin-4-one | 47–48.5 | |
| 185 | 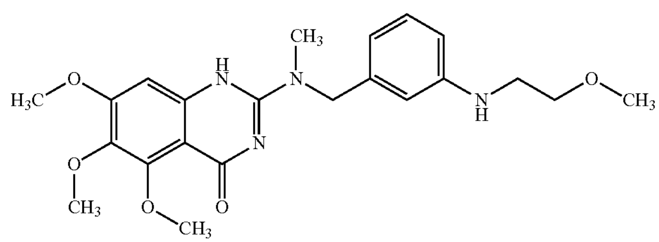 | 5,6,7-Trimethoxy-2-{[3-(2-methoxy-ethylamino)-benzyl]-methyl-amino}-1H-quinazolin-4-one | 178.9–179.9 (HCl Salt) | |
| 186 | 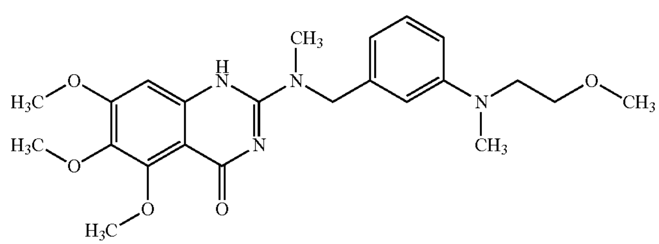 | 5,6,7-Trimethoxy-2-({3-[(2-methoxy-ethyl)-methyl-amino]-benzyl}-methyl-amino)-1H-quinazolin-4-one | 179.3–181.2 (HCl Salt) | |
| 187 | 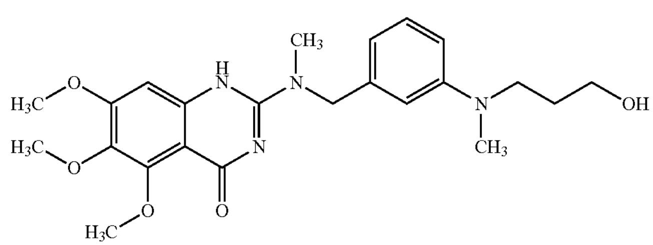 | 2-({3-[(3-Hydroxy-propyl-methyl-amino]-benzyl}-methyl-amino)-5,6,7-trimethoxy-1H-quinazolin-4-one | 156–157.2 (HCl Salt) | |

TABLE 11-continued

| # | Structure | Systematic Name | MP ° C. | M + H |
|---|---|---|---|---|
| 188 | 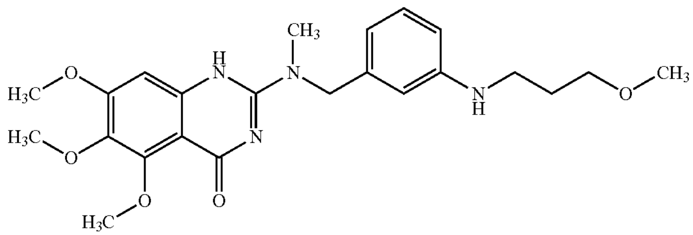 | 5,6,7-Trimethoxy-2-{[3-(3-methoxy-propylamino)-benzyl]-methyl-amino}-1H-quinazolin-4-one | 207.0–209.1 (HCl Salt) | |
| 189 | 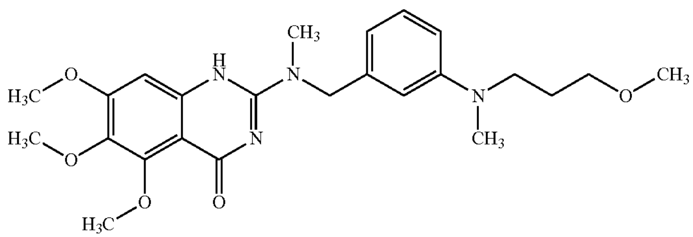 | 5,6,7-Trimethoxy-2-({3-[(3-methoxy-propyl)-methyl-amino]-benzyl}-methyl-amino)-1H-quinazolin-4-one bi | 166.7–168.1 (HCl Salt) | |
| 190 | 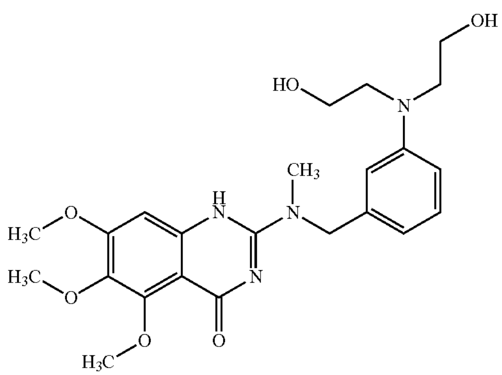 | 2-({3-[Bis(2-hydroxy-ethyl)-amino]-bewnzyl}-methyl-amino)-5,6,7-trimethoxy-1H-quinazolin-4-one | 138.1–141 | |

TABLE 11-continued

| # | Structure | Systematic Name | MP ° C. | M + H |
|---|---|---|---|---|
| 191 | 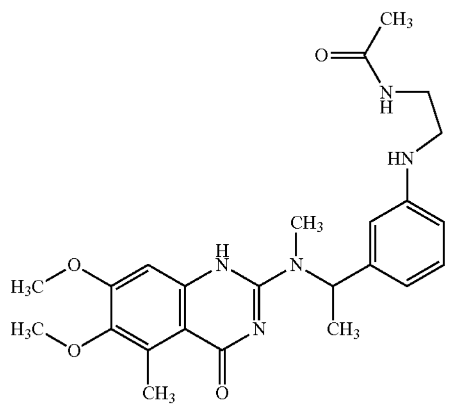 | N-[2-(3-{1-[(6,7-Dimethoxy-5-methyl-4-oxo-1,4-dihydro-quinazolin-2-yl)-methyl-amino]-ethyl}-phenylamino)-ethyl]-acetamide | 220.6–222.4 | |
| 192 | 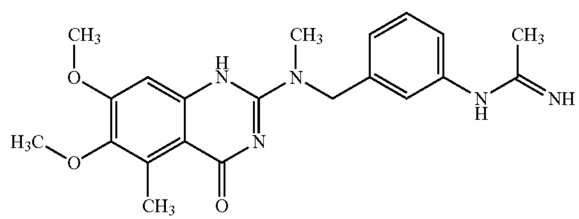 | N-(3-{[(6,7-Dimethoxy-5-methyl-4-oxo-1,4-dihydro-quinazolin-2-yl)-methyl-amino]-methyl}-phenyl)-acetamide | 155–58 | |
| 193 | 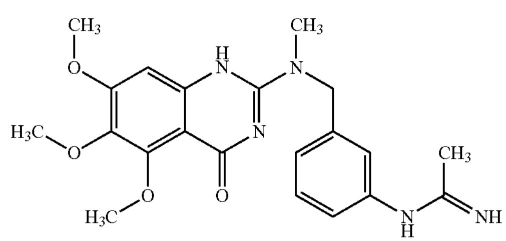 | N-(3-{[Methyl-(5,6,7-trimethoxy-4-oxo-1,4-dihydro-quinazolin-2-yl)-amino]-methyl}-phenyl)-acetamide | | 412 |

TABLE 11-continued

| # | Structure | Systematic Name | MP ° C. | M + H |
|---|---|---|---|---|
| 194 | 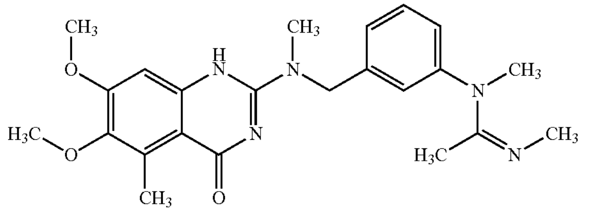 | N-(3-{[(6,7-Dimethoxy-5-methyl-4-oxo-1,4-dihydro-quinazolin-2-yl)-methyl]-amino]-methyl}-phenyl)-N,N'-dimethyl-acetamide | 181.2–186.6 | |
| 195 | 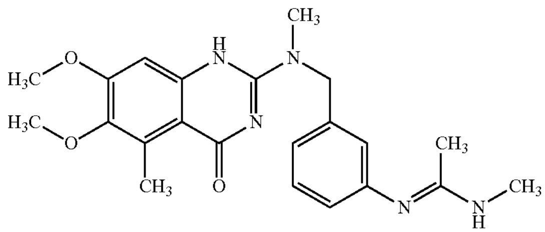 | N-(3-{[(6,7-Dimethoxy-5-methyl-4-oxo-1,4-dihydro-quinazolin-2-yl)-methyl]-amino]-methyl}-phenyl)-N'-methyl-acetamide | 233.1–233.9 | |
| 196 | 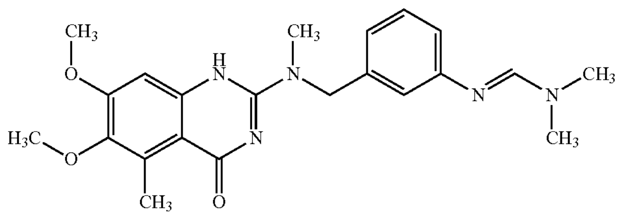 | N'-(3-{[(6,7-Dimethoxy-5-mehtyl-4-oxo-1,4-dihydro-quinazolin-2-yl)-methyl]-amino]-methyl}-phenyl)-N,N-dimethyl-formamidine | 185–86 | |
| 197 | 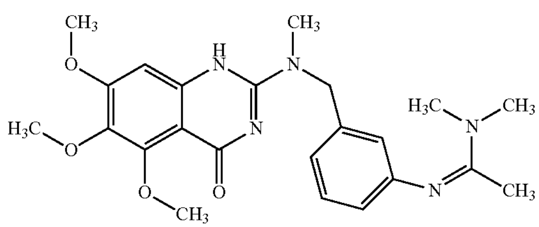 | N,N-Dimethyl-N'-(3-{[methyl-(5,6,7-trimethoxy-4-oxo-1,4-dihydro-quinazolin-2-yl)-amino]-methyl}-phenyl)acetamidine | 199–201 | |

TABLE 11-continued

| # | Structure | Systematic Name | MP °C. | M + H |
|---|---|---|---|---|
| 198 | 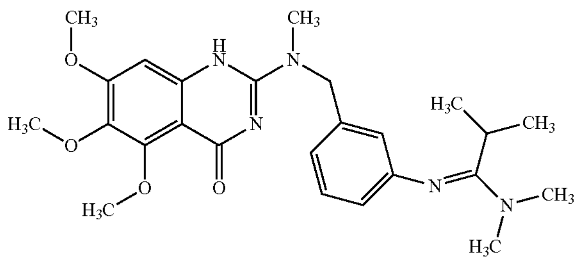 | N,N-Dimethyl-N'-(3-{[methyl-(5,6,7-trimethoxy-4-oxo-1,4-dihydro-quinazolin-2-yl)-amino]-methyl}-phenyl)-isobutyramidine | 148–50 | |
| 199 | 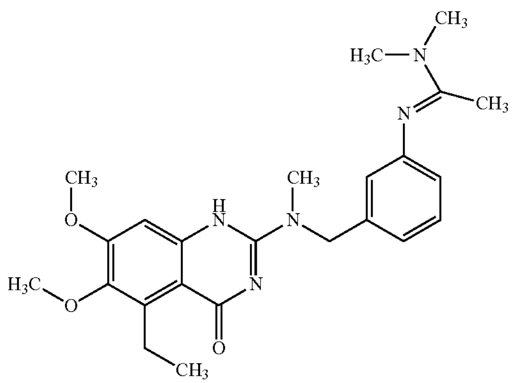 | N'-(3-{[(5-Ethyl-6,7-dimethoxy-4-oxo-1,4-dihydro-quinazolin-2-yl)-methyl-amino]-methyl}-phenyl)-N,N-dimethyl-acetamidine | 224.6–225.5 | |
| 200 | 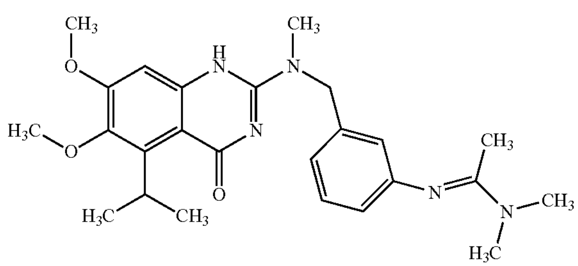 | N'-(3-{[(5-Isopropyl-6,7-dimethoxy-4-oxo-1,4-dihydro-quinazolin-2-yl)-methyl-amino]-methyl}-phenyl)-N,N-dimethyl-acetamide | 235.6–236.5 | |

TABLE 11-continued

| # | Structure | Systematic Name | MP ° C. | M + H |
|---|---|---|---|---|
| 201 | 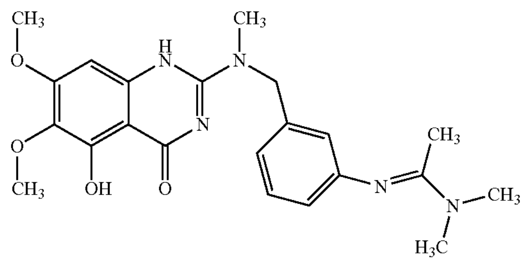 | N'-(3-{[(5-Hydroxy-6,7-dimethoxy-4-oxo-1,4-dihydro-quinazolin-2-yl)-methyl-amino]-methyl}-phenyl)-N,N-dimethyl-acetamidine | | 426 |
| 202 | 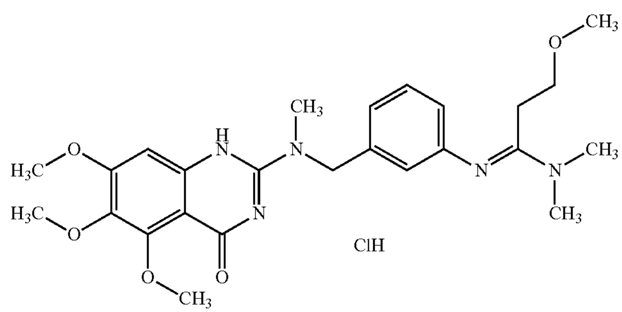 | 3-Methoxy-N,N-dimethyl-N'-(3-{[methyl-(5,6,7-trimethoxy-4-oxo-1,4-dihydro-quinazolin-2-yl)-amino]-methyl}-phenyl)-propionamidine | 145 | |
| 203 | 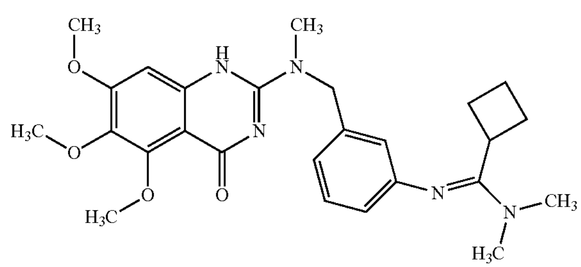 | N,N-Dimethyl-N'-(3-{[methyl-(5,6,7-trimethoxy-4-oxo-1,4-dihydro-quinazolin-2-yl)-amino]-methyl}-phenyl)-cyclobutanecarboxamidine | 164.2–165.7 | |

TABLE 11-continued

| # | Structure | Systematic Name | MP ° C. | M + H |
|---|---|---|---|---|
| 204 | 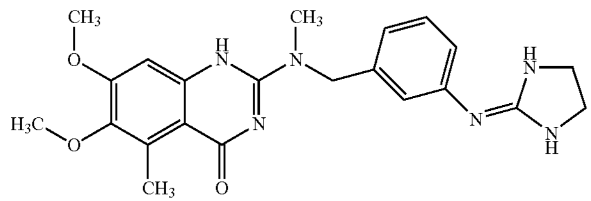 | 2-{[(Imidazolidin-2-ylideneamino)-benzyl]-methyl-amino}-6,7-dimethoxy-5-methyl-1H-quinazolin-4-one | 141.3–144.7 | |
| 205 | 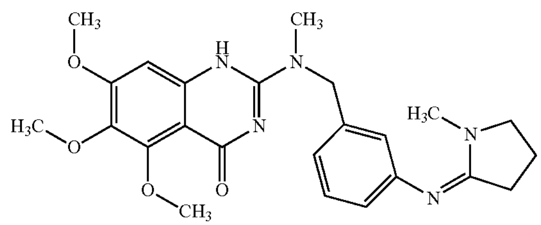 | 5,6,7-Trimethoxy-2-(methyl-{3-[1-methyl-pyrrolidin-(2Z)-ylideneamino]-benzyl}-amino)-1H-quinazolin-4-one | 130–133 | |
| 206 | 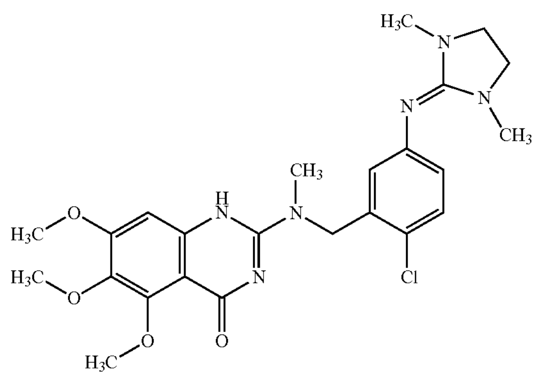 | 2-{[2-Chloro-5-(1,3-dimethyl-imidazolidin-2-ylideneamino)-benzyl]-methyl-amino}-5,6,7-trimethoxy-1H-quinazolin-4-one | | 501, M+ |

TABLE 11-continued

| # | Structure | Systematic Name | MP °C. | M + H |
|---|---|---|---|---|
| 207 | 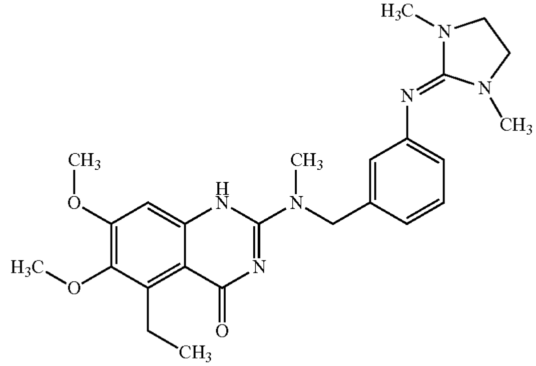 | 2-{[3-(1,3-dimethyl-imidazolidin-2-ylideneamino)-benzyl]-methyl-amino}-5-ethyl-6,7-dimethoxy-1H-quinaolin-4-one | 212.5–219.9 (PF₆ salt) | |
| 208 | 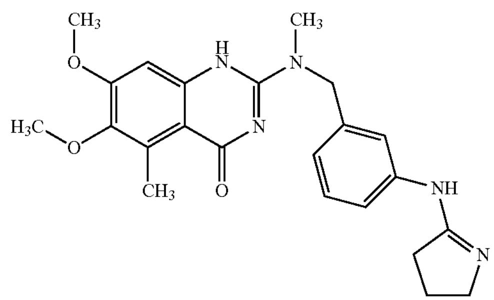 | 2-{[[3-(4,5-Dihydro-3H-pyrrol-2-yl)amino)-benzyl]-methyl-amino}-6,7-dimethoxy-5-methyl-1H-quinaozlin-4-one | 175.4–177.2 | |
| 209 | 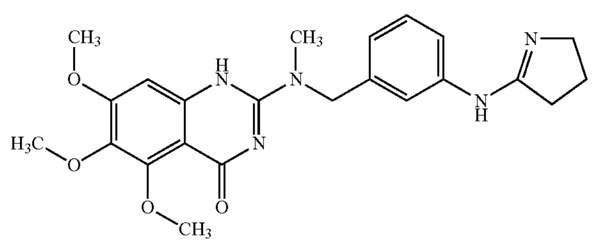 | 2-{[[3-(4,5-Dihydro-3H-pyrrol-2-yl)amino)-benzyl]-methyl-amino}-5,6,7-trimethoxy-1H-quinazolin-4-one | 207–209 | |

TABLE 11-continued

| # | Structure | Systematic Name | MP °C. | M + H |
|---|---|---|---|---|
| 210 | 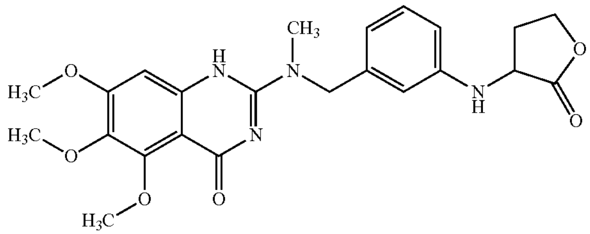 | 5,6,7-Trimethoxy-2-{methyl-[3-(2-oxo-tetrahydro-furan-3-ylamino)-benzyl]-amino}-1H-quinazolin-4-one | | 455 |
| 211 | 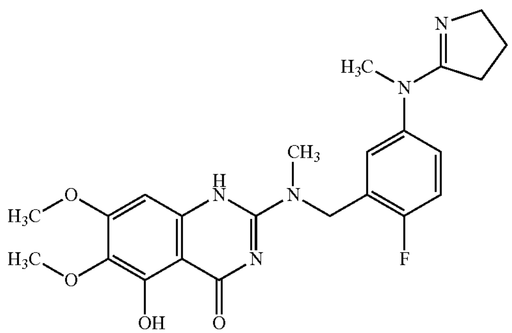 | 2-({[(4,5-Dihydro-3H-pyrrol-2-yl)-methyl-amino]-2-fluoro-benzyl}-methylamino)-5-hydroxy-6,7-dimethoxy-1H-quinazolin-4-one | 264.9–267 | |
| 212 | 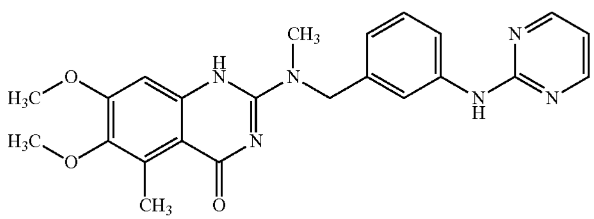 | 6,7-Dimethoxy-5-methyl-2-{methyl-[3-(pyrimidin-2-ylamino)-benzyl]-amino}-1H-quinazolin-4-one | | 433 |
| 213 | 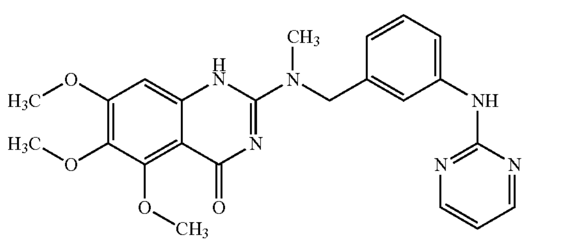 | 5,6,7-Trimethoxy-2-{methyl-[3-(pyrimidin-2-ylamino)-benzyl]-amino}-1H-quinaozlin-4-one | 190.3–191.1 | |

TABLE 11-continued

| # | Structure | Systematic Name | MP ° C. | M + H |
|---|---|---|---|---|
| 214 | 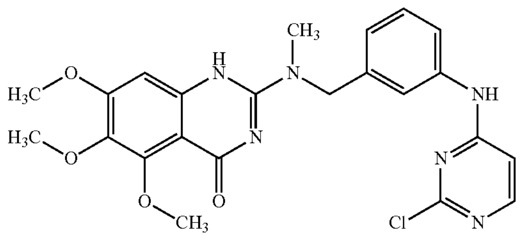 | 2-{[3-(2-Chloro-pyrimidin-4-ylamino)-benzyl]-methyl-amino}-5,6,7-trimethoxy-1H-quinazolin-4-one | 205.9–210.1 | |
| 215 | 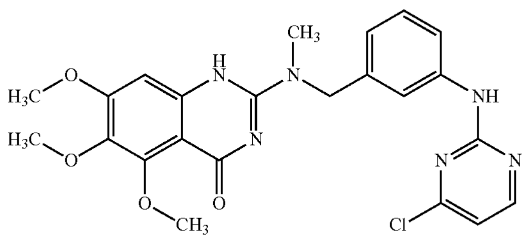 | 2-{[3-(4-Chloro-pyrimidin-2-ylamino)-benzyl]-methyl-amino}-5,6,7-trimethoxy-1H-quinazolin-4-one | 128.9–133.4 | |
| 216 | 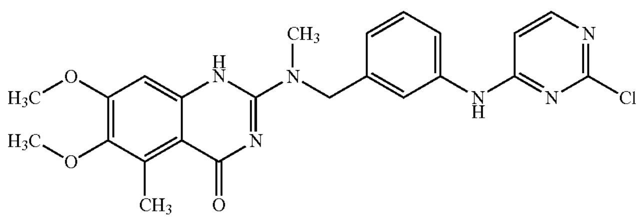 | 2-{[3-(2-Chloro-pyrimidin-4-ylamino)-benzyl]-methyl-amino}-6,7-dimethoxy-5-methyl-1H-quinazolin-4-one | | 467 |
| 217 | 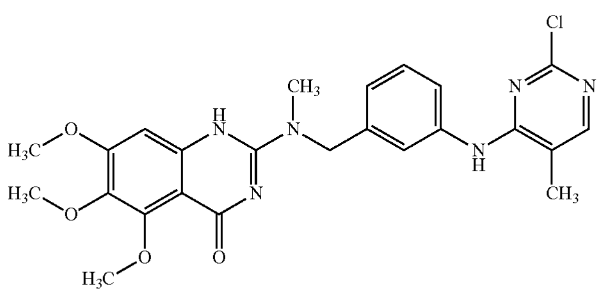 | 2-{[3-(2-Chloro-5-methyl-pyrimidin-4-ylamino)-benzyl]-methyl-amino}-5,6,7-trimethoxy-1H-quinazolin-4-one | 225.9–227.0 | |

TABLE 11-continued

| # | Structure | Systematic Name | MP °C. | M + H |
|---|---|---|---|---|
| 218 | 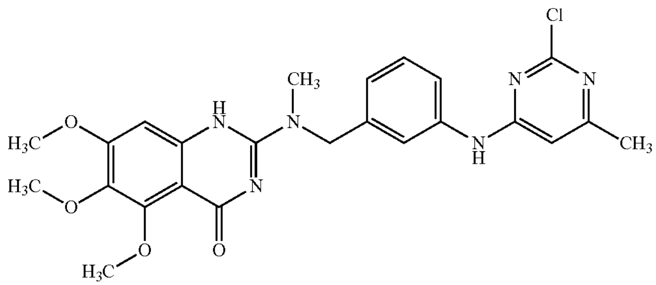 | 2-{[3-(2-Chloro-6-methyl-pyrimidin-4-ylamino)-benzyl]-methyl-amino}-5,6,7-trimethoxy-1H-quinazolin-4-one | 185.5–187.1 | |
| 219 | 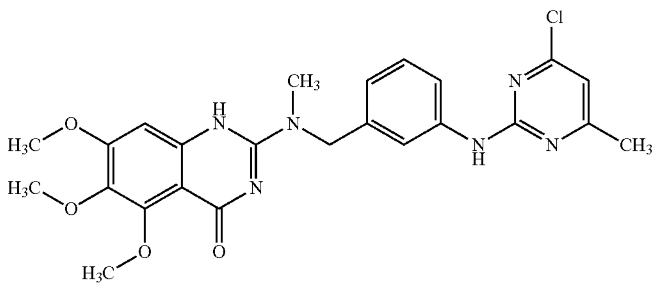 | 2-{[3-(4-Chloro-6-methyl-pyrimidin-2-ylamino)-benzyl]-methyl-amino}-5,6,7-trimethoxy-1H-quinazolin-4-one | 191.3–192.8 | |
| 220 | 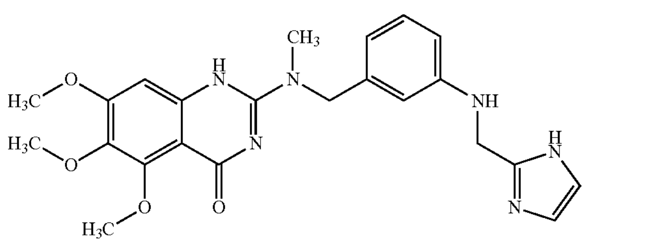 | 2-({3-[(1H-Imidazol-2-ylmethyl)-amino]-benzyl}-methylamino)-5,6,7-trimethoxy-1H-quinazolin-4-one | 125.0–131.0 | |

TABLE 11-continued

| # | Structure | Systematic Name | MP ° C. | M + H |
|---|---|---|---|---|
| 221 | 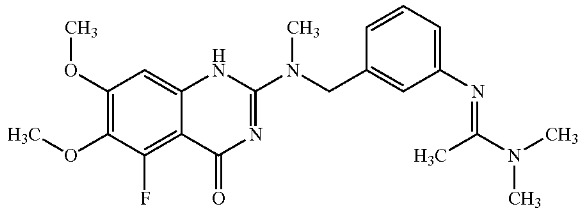 | N'-(3-{[(5-Fluoro-6,7-dimethoxy-4-oxo-1,4-dihydro-quinazolin-2-yl)-methyl-amino]-methyl}-phenyl)-N,N-dimethyl-acetamidine | 199.9–201.9 | |
| 222 | 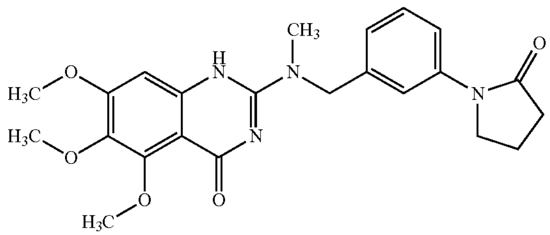 | 5,6,7-Trimethoxy-2-{methyl-[3-(2-oxxo-pyrrolidin-1-yl)-benzyl]amino}-1H-quinazolin-4-one | 165.5–166.5 | 439 |
| 223 | 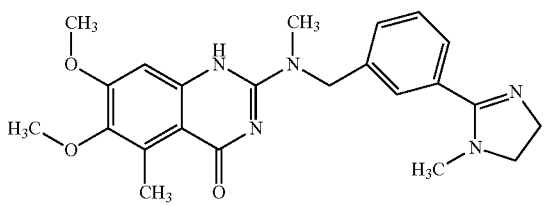 | 6,7-Dimethoxy-5-methyl-2-{methyl-[3-(1-methyl-4,5-dihydro-1H-imidazol-2-yl)-benzyl]-amino}-1H-quinazolin-4-one | 145–148 | 422 |

TABLE 11-continued
| # | Structure | Systematic Name | MP ° C. | M + H |
|---|---|---|---|---|
| 224 | 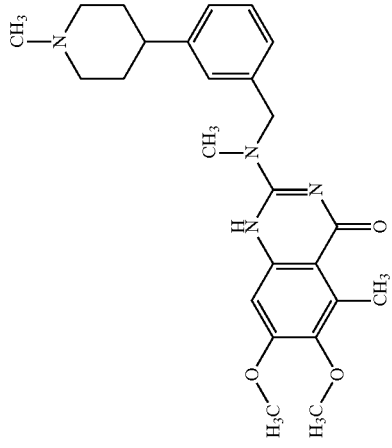 | 6,7-Dimethoxy-5-methyl-2-[methyl-[3-(1-methyl-piperidin-4-yl)-benzyl]-amino]-1H-quinazolin-4-one | 155.7–158.0 | 437 |
| 225 | 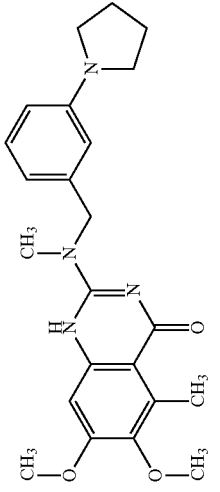 | 6,7-Dimethoxy-5-methyl-2-[methyl-(3-pyrrolidin-1-yl-benzyl)-amino]-1H-quinazolin-4-one | | 409 |
| 226 | 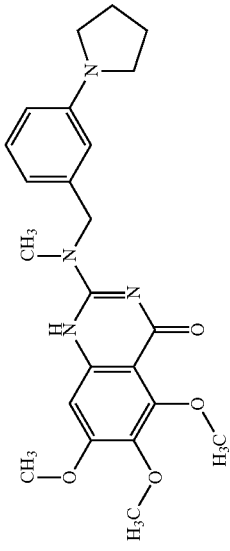 | 5,6,7-Trimethoxy-2-[methyl-(3-pyrrolidin-1-yl-benzyl)-amino]-1H-quinazolin-4-one | | 425 |

TABLE 11-continued

| # | Structure | Systematic Name | MP ° C. | M + H |
|---|---|---|---|---|
| 227 | 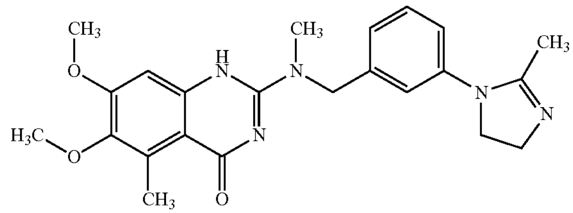 | 6,7-Dimethoxy-5-methyl-2-{methyl-[3-(2-methyl-4,5-dihydro-imidazol-1-yl)-benzyl]-amino}-1H-quinazolin-4-one | 177–180 | |
| 228 | 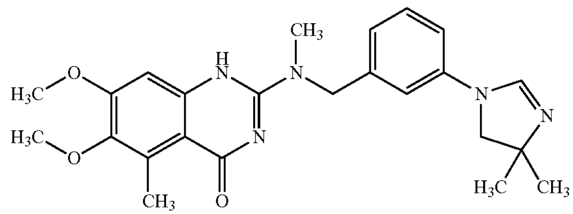 | 2-{[3-(4,4-Dimethyl-4,5-dihydro-imidazol-1-yl)-benzyl]-methyl-amino}-6,7-dimethoxy-5-methyl-1H-quinazolin-4-one | | 437 |
| 229 | 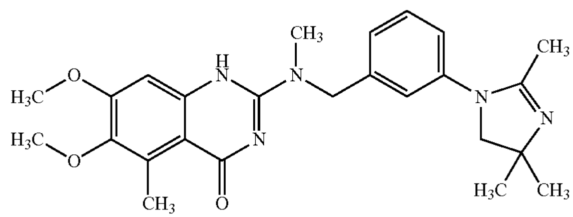 | 6,7-Dimethoxy-5-methyl-2-{methyl-[3-(2,4,4-trimethyl-4,5-dihydro-imidazol-1-yl)-benzyl]-amino}-1H-quinazolin-4-one | | 450 |
| 230 | 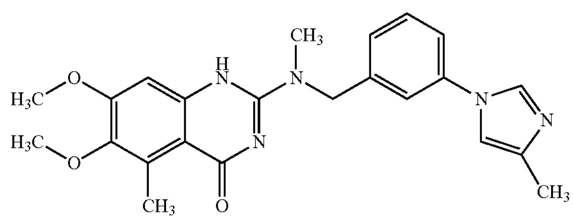 | 6,7-Dimethoxyt-5-methyl-2-{methyl-[3-(4-methyl-imidazol-1-yl)-benzyl]-amino}-1H-quinazolin-4-one | 245–249.5 | |

TABLE 11-continued

| # | Structure | Systematic Name | MP °C. | M + H |
|---|---|---|---|---|
| 231 | 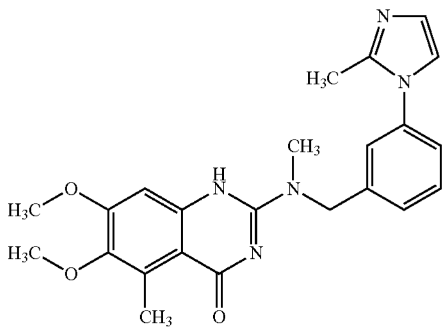 | 6,7-Dimethoxy-5-methyl-2-{methyl-[3-(2-methyl-imidazol-1-yl)-benzyl]-amino}-1H-quinazolin-4-one | | 420 |
| 232 | 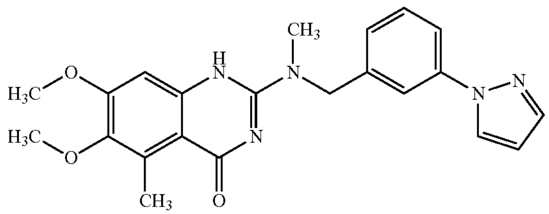 | 6,7-Dimethoxy-5-methyl-2-[methyl-(3-pyrazol-1-yl-benzyl)-amino]-1H-quinazolin-4-one | 220.8–224.1 | |
| 233 | 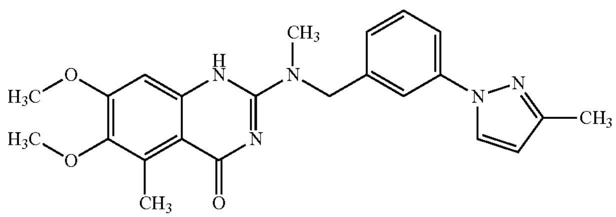 | 6,7-Dimethoxy-5-methyl-2-{methyl-[3-(3-methyl-pyrazol-1-yl)-benzyl]-amino}-1H-quinazolin-4-one | 220–223.5 | |
| 234 | 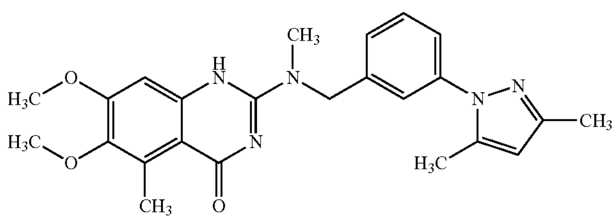 | 2-{[3-(3,5-Dimethyl-pyrazol-1-yl)-benzyl]-methyl-amino}-6,7-dimethoxy-5-methyl-1H-quinazolin-4-one | | 434 |

TABLE 11-continued

| # | Structure | Systematic Name | MP ° C. | M + H |
|---|---|---|---|---|
| 235 | 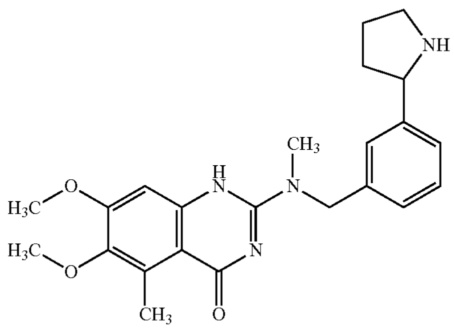 | 6,7-Dimethoxy-5-methyl-2-[methyl-(3-pyrroldin-2-yl-benzyl)-amino]-1H-quinazolin-4-one | | 409 |
| 236 | 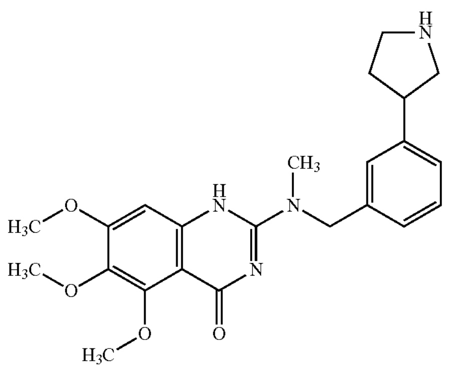 | 5,6,7-Trimethoxy-2-[methyl-(3-pyrrolidin-3-yl-benzyl)-amino]-1H-quinazolin-4-one | | 425 |
| 237 | 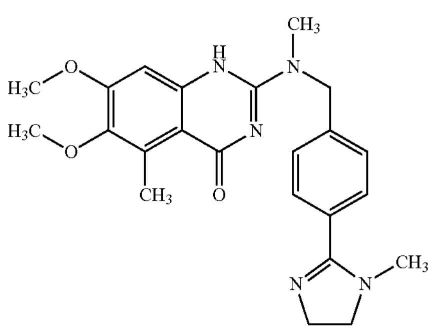 | 6,7-Dimethoxy-5-methyl-2-{methyl[4-(1-methyl-,5-dihydro-1H-imidazol-2-yl)-benzyl]-amino}-1H-quinazolin-4-oine | 179–181 | |

TABLE 11-continued

| # | Structure | Systematic Name | MP °C. | M + H |
|---|---|---|---|---|
| 238 | 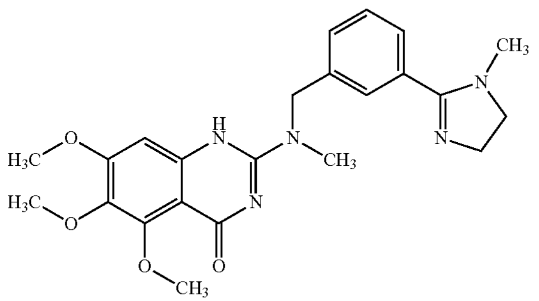 | 5,6,7-Trimethoxy-2-{methyl-[3-(1-methyl-4,5-dihydro-1H-imidazol-2-yl)-benzyl]-amino}-1H-quinazolin-4-one | | 438, M+ |
| 239 | 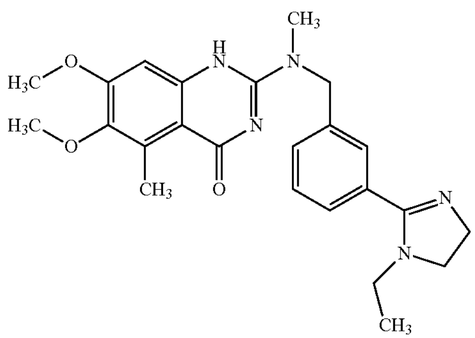 | 2-{[3-(1-Ethyl-4,5-dihydro-1H-imidazol-2-yl)-benzyl]-methyl-amino}-6,7-dimethoxy-5-methyl-1H-quinazolin-4-one | | 436 |
| 240 | 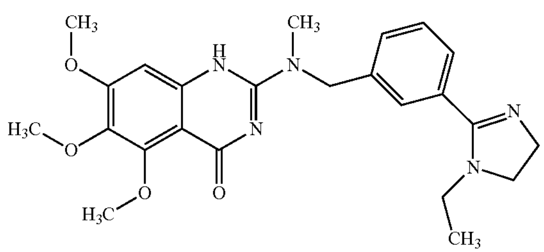 | 2-{[3-(1-Ethyl-4,5-dihydro-1H-imidazol-2-yl)-benzyl]-methyl-amino}-5,6,7-trimethoxy-1H-quinazolin-4-one | | 452 |

TABLE 11-continued

| # | Structure | Systematic Name | MP ° C. | M + H |
|---|---|---|---|---|
| 241 | 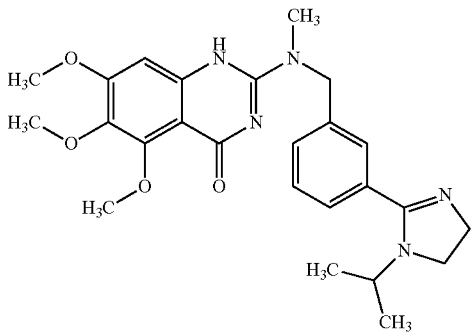 | 2-{[3-(1-Isopropyl-4,5-dihydro-1H-imidazol-2-yl)-benzyl]-methyl-amino}-5,6,7-trimethoxy-1H-quinazolin-4-one | | 466 |
| 242 | 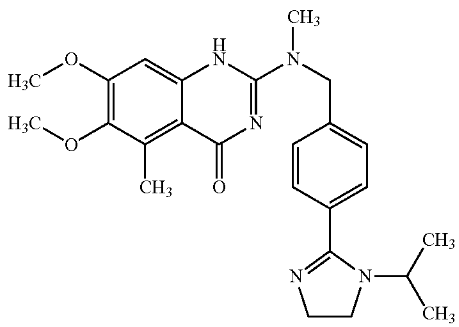 | 2-{[4-(1-Isopropyl-4,5-dihydro-1H-imidazol-2-yl)-benzyl]-methyl-amino}-6,7-dimethoxy-5-methyl-1H-quinazolin-4-one | | 450 |
| 243 | 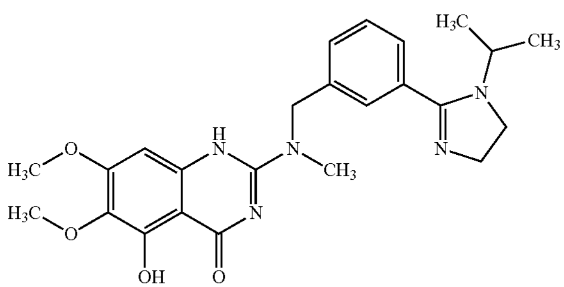 | 5-Hydroxy-2-{[3-(1-isopropyl-4,5-dihydro-1H-imidazol-2-yl)-benzyl]-methyl-amino}-6,7-dimethoxy-1H-quinazolin-4-one | | 453 |

TABLE 11-continued

| # | Structure | Systematic Name | MP °C. | M + H |
|---|---|---|---|---|
| 244 | 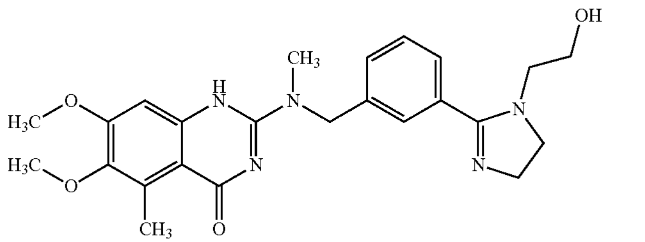 | 2-({3-[1-(2-Hydroxy-ethyl)-4,5-dihydro-1H-imidazol-2-yl]-benzyl}-methyl-amino)-6,7-dimethoxy-5-methyl-1H-quinazolin-4-one | 253–254.9 | |
| 245 | 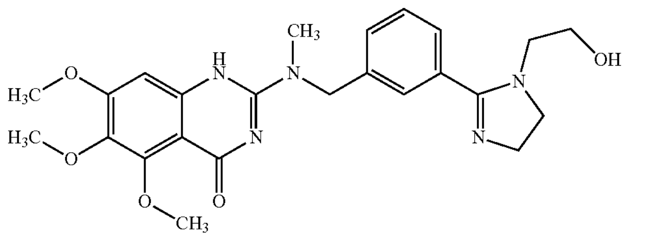 | 2-({3-[1-(2-Hydroxy-ethyl)-4,5-dihydro-1H-imidazol-2-yl]-benzyl}-methyl-amino)-5,6,7-trimethoxy-1H-quinazolin-4-one | 106.1–116.6 (TFA Salt) | |
| 246 | 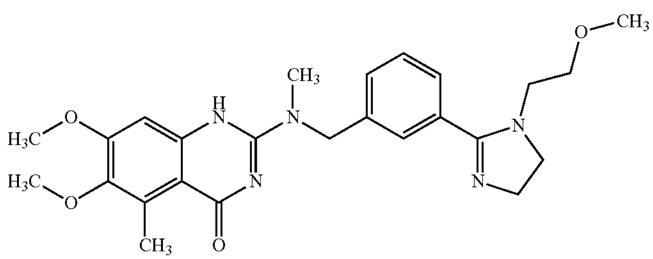 | 6,7-Dimethoxy-2-*{3-[1-(2-methoxy-ethyl)-4,5-dihydro-1H-imidazol-2-yl]-benzyl}-methyla-mino)-5-methyl-1H-quinazolin-4-one | 161–164.4 | |
| 247 | 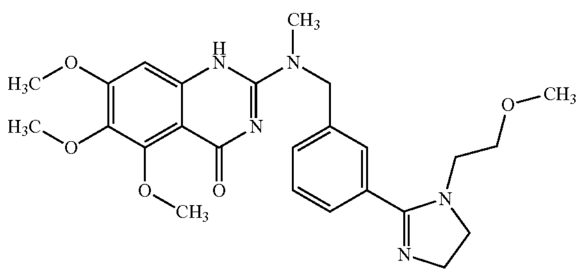 | 5,6,7-Trimethoxy-2-({3-[1-(2-methoxy-ethyl)-4,5-dihydro-1H-imidazol-2-yl]-benzyl}-methyl-amino)-1H-quinazolin-4-one | | 483 |

TABLE 11-continued

| # | Structure | Systematic Name | MP °C. | M + H |
|---|---|---|---|---|
| 248 | 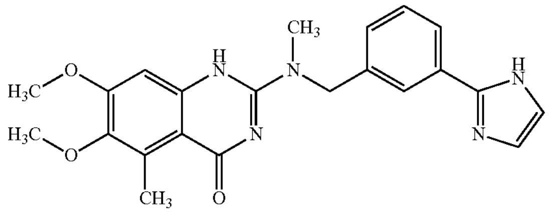 | 2-{[3-(1H-Imidazol-2-yl)-benzyl]-methyl-amino}-6,7-dimethoxy-5-methyl-1H-quinazolin-4-one | 255.5–258.9 | |
| 249 | 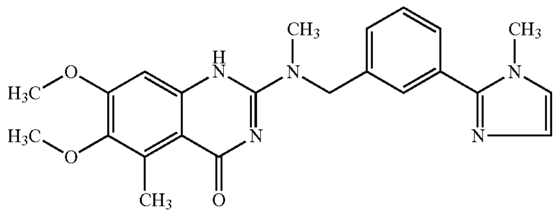 | 6,7-Dimethoxy-5-methyl-2-{methyl-[3-(1-methyl-1H-imidazol-2-yl)-benzyl]-amino}-1H-quinazolin-4-one | 179–182.1 | |
| 250 | 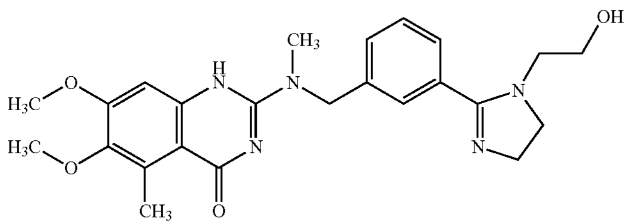 | 2-({3-[1-(2-Hydroxy-ethyl)-1H-imidazol-2-yl]-benzyl}-methyl-amino)-6,7-dimethoxy-5-methyl-1H-quinaozlin-4-one | | 451 |
| 251 | 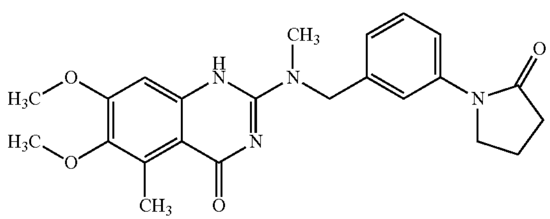 | 6,7-Dimethoxy-5-methyl-2-{methyl-[3-(2-oxo-pyrrolidin-1-yl)-benzyl]-amino}-1H-quinazolin-4-one | 210.9–212.1 | |

TABLE 11-continued
| # | Structure | Systematic Name | MP ° C. | M + H |
|---|---|---|---|---|
| 252 | 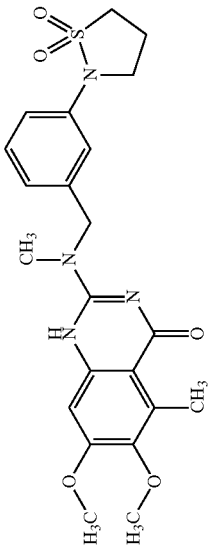 | 2-{[3-(1,1-Dioxo-1λ6-isothiazolidin-2-yl)-benzyl]-methyl-amino}-6,7-dimethoxy-5-methyl-1H-quinazolin-4-one | 226.0–228.5 | |
| 253 | 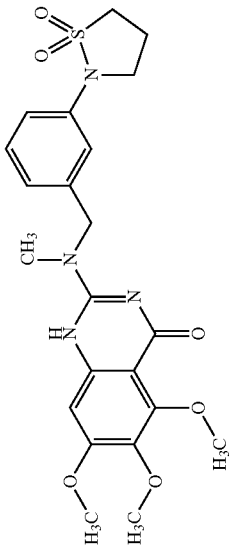 | {[3-(1,1-Dioxo-1λ6-isothiazolidin-2-yl)-benzyl]-methyl-amino}-5,6,7-trimethoxy-1H-quinazolin-4-one | 181.1–183.5 | |
| 254 | 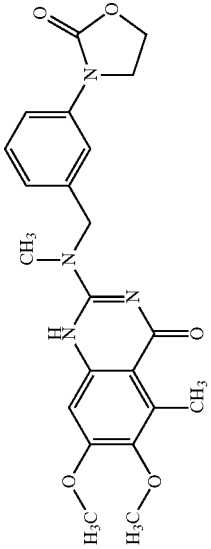 | 6,7-Dimethoxy-2-{methyl-[3-(2-oxo-oxazolidin-3-yl)-benzyl]-amino}-1H-quinazolin-4-one | 254.8–257.1 | |
| 255 | 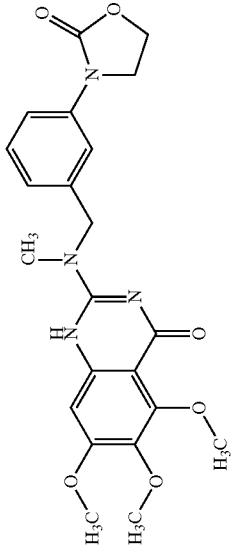 | 5,6,7-2Trimethoxy-2-{methyl-[3-(2-oxo-oxazolidin-3-yl)-benzyl]-amino}-1H-quinazolin-4-one | 226.0–229.5 | |

TABLE 11-continued

| # | Structure | Systematic Name | MP °C. | M + H |
|---|---|---|---|---|
| 256 | 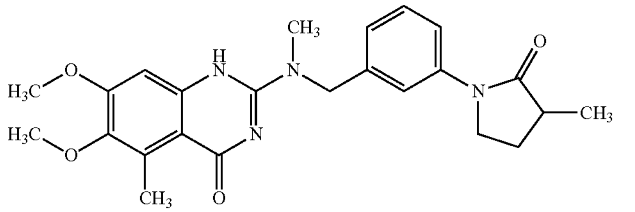 | 6,7-Dimethoxy-5-methyl-2-{methyl-[3-(3-methyl-2-oxo-pyrrolidin-1-yl)-benzyl]-amino}-1H-quinazolin-4-one | 210.8–211.6 | |
| 257 | 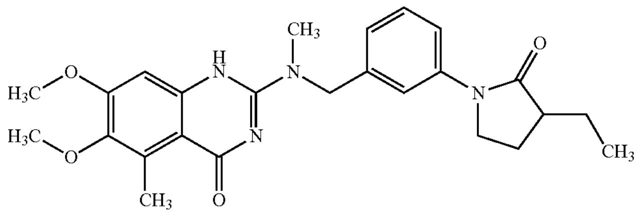 | 2-{[3-(3-Ethyl-2-oxo-pyrrolidin-1-yl)-benzyl]-methyl-amino}-6,7-dimethoxy-5-methyl-1H-quinazolin-4-one | 200.1–202.1 | |
| 258 | 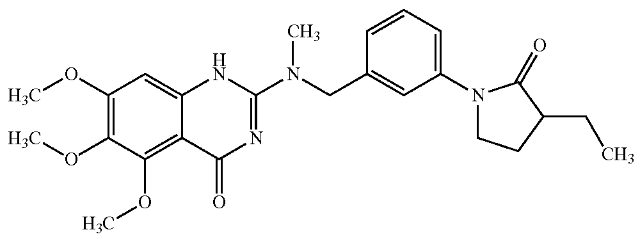 | 2-{[3-(3-Ethyl-2-oxo-pyrrolidin-1-yl)-benzyl]-methyl-amino}-5,6,7-trimethoxy-1H-quinazolin-4-one | | 467 |
| 259 | 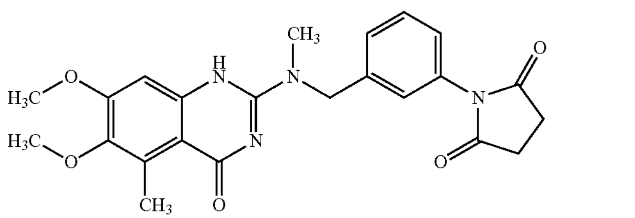 | 1-(3-{[(6,7-Dimethoxy-5-methyl-4-oxo-1,4-dihydro-quinazolin-2-yl)-methyl-amino]-methyl}-phenyl)-pyrrolidin-2,5-dione | 198.6–199.8 | |

TABLE 11-continued

| # | Structure | Systematic Name | MP °C. | M + H |
|---|---|---|---|---|
| 260 | 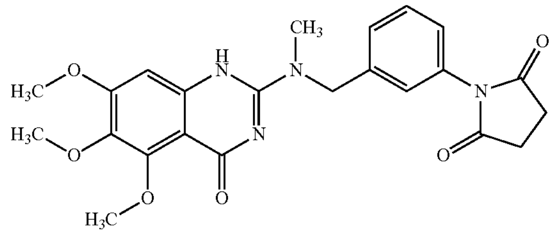 | 1-(3-{[Methyl-(5,6,7-trimethoxy-4-oxo-1,4-dihydro-quinazolin-2-yl)-amino]-methyl}-phenyl)-pyrrolidine-2,5-dione | 125.5–128.5 | |
| 261 | 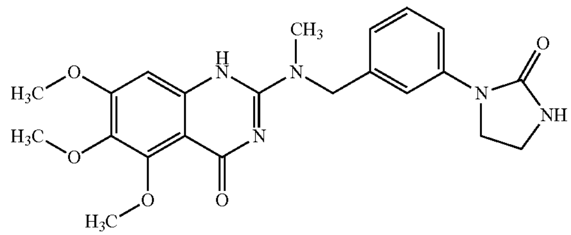 | 5,6,7-Trimethoxy-2-{methyl[3-(2-oxo-imidazolidin-1-yl)-benzyl]-amino}-1H-quinazolin-4-one | 130.0–133.0 | |
| 262 | 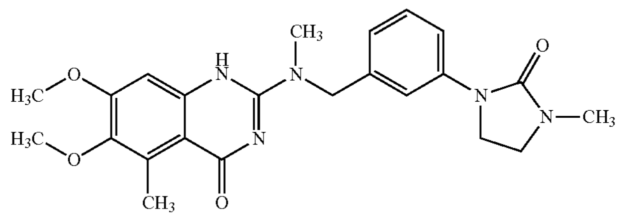 | 6,7-Dimethoxy-5-methyl-2-{methyl-[3-(3-methyl-2-oxo-imidazolidin-1-yl)-benzyl]-amino}-1H-quinazolin-4-one | 230.0–230.5 | |
| 263 | 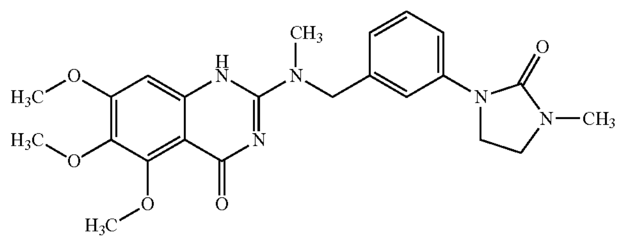 | 5,6,7-Trimethoxy-2-{methyl-[3-(3-methyl-2-oxo-imidazolidin-1-yl)-benzyl]-amino}-1H-quinaozlin-4-one | 205.4–207.8 | |

TABLE 11-continued

| # | Structure | Systematic Name | MP ° C. | M + H |
|---|---|---|---|---|
| 264 | 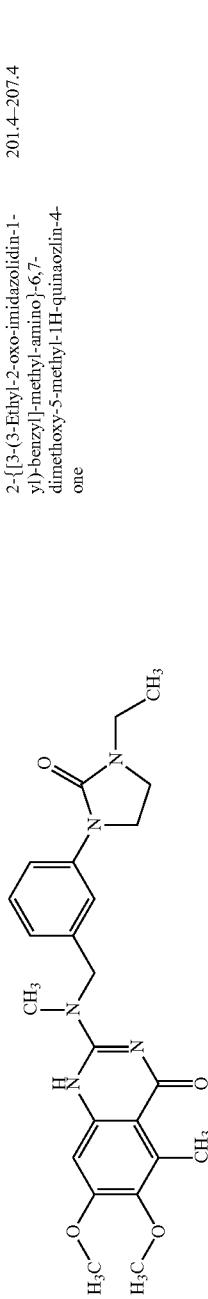 | 2-{[3-(3-Ethyl-2-oxo-imidazolidin-1-yl)-benzyl]-methyl-amino}-6,7-dimethoxy-5-methyl-1H-quinaozlin-4-one | 201.4–207.4 | |
| 265 | 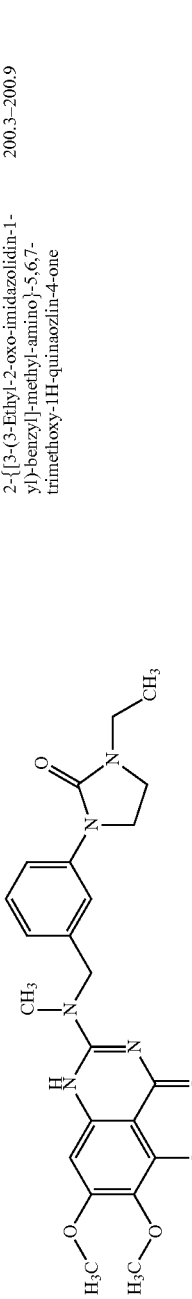 | 2-{[3-(3-Ethyl-2-oxo-imidazolidin-1-yl)-benzyl]-methyl-amino}-5,6,7-trimethoxy-1H-quinaozlin-4-one | 200.3–200.9 | |
| 266 | 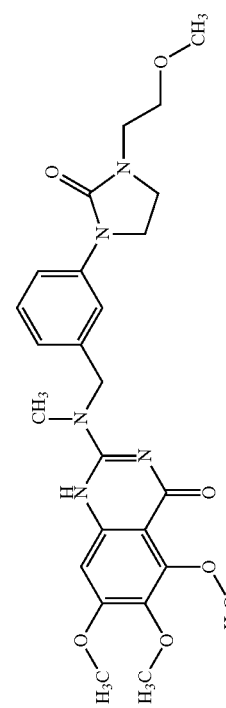 | 5,6,7-Trimethoxy-2-({3-[3-(2-methoxy-ethyl)-2-oxo-imidazllidin-1-yl]-benzyl}-methyl-amino)-1H-quinazolin-4-one | 199.5–202.1 | |
| 267 | 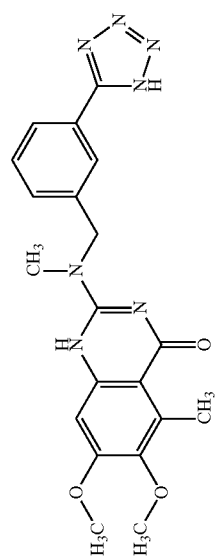 | 6,7-Dimethoxy-5-methyl-2-{methyl-[3-(1-H-tetrazol-5-yl)-benzyl]-amino}-1H-quinazolin-4-one | | 408 |

TABLE 11-continued

| # | Structure | Systematic Name | MP °C. | M + H |
|---|---|---|---|---|
| 268 | 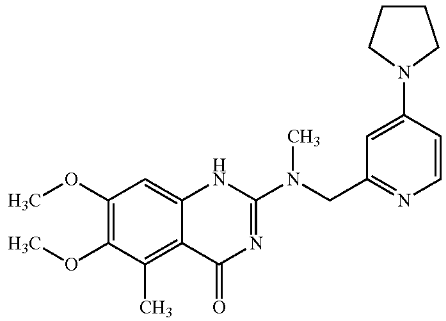 | 6,7-Dimethoxy-5-methyl-2-[methyl-(4-pyrrolidin-1-yl-pyridin-2-ylmethyl)-amino]-1H-quinazolin-4-one | | 410 |
| 269 | 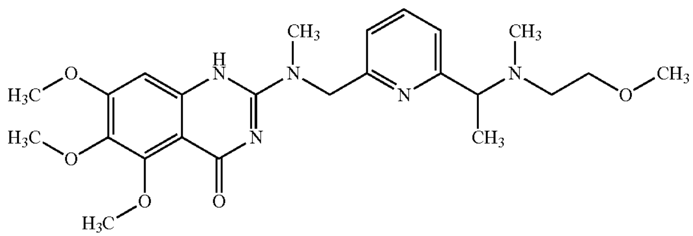 | 5,6,7-Trimethoxy-2-[(6={1-[(2-methoxy-ethyl)-methyl-amino]-ethyl}-pyridin-2-ylmethyl)-methyl-amino]-1H-quinazolin-4-one | | 472 |
| 270 | 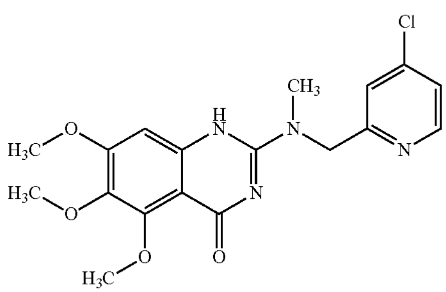 | 2-[(4-Chloro-pyridin-2-ylmethyl)-methyl-amino]-5,6,7-trimethoxy-1H-quinazolin-4-one | | 391, 393 |

TABLE 11-continued

| # | Structure | Systematic Name | MP °C. | M + H |
|---|---|---|---|---|
| 271 | 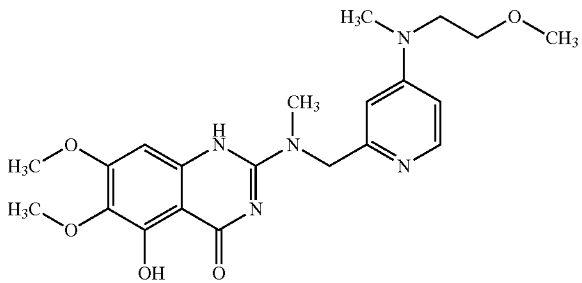 | 5-Hydroxy-6,7-dimethoxy-2-({4-[(2-methoxy-ethyl)-methyl-amino]-pyridin-2-ylmethyl}-methyl-amino)-1H-quinazolin-4-one | | 430.1 |
| 272 | 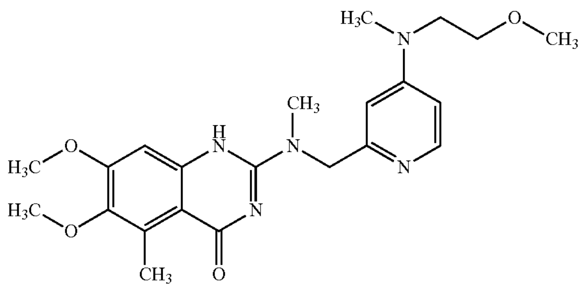 | 6,7-Dimethoxy-2-({4-[(2-methoxy-ethyl)-methyl-amino]-pyridin-2-ylmethyl}-methyl-amino)-5-methyl-1H-quinazolin-4-one | | 428 |
| 273 | 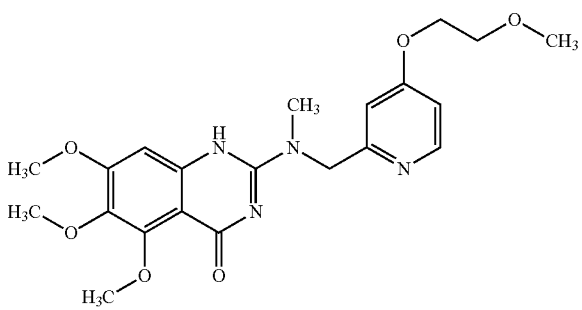 | 5,6,7-Trimethoxy-2-{[4-(2-methoxy-ethoxy)-pyridin-2-ylmethyl]-methyl-amino}-1H-quinaozlin-4-one | | 431 |

TABLE 11-continued

| # | Structure | Systematic Name | MP °C. | M + H |
|---|---|---|---|---|
| 274 | 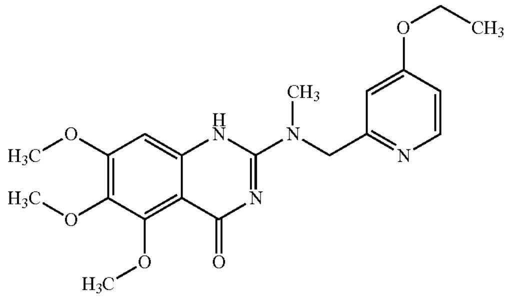 | 2-[(4-Ethoxy-pyridin-2-ylmethyl)-methyl-amino]-5,6,7-trimethoxy-1H-quinazolin-4-one | | 401 |
| 275 | 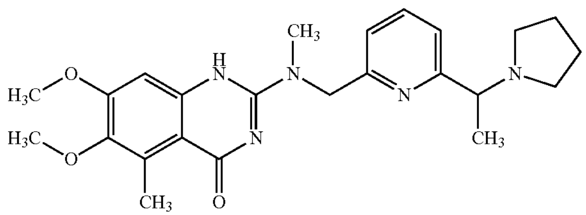 | 6,7-Dimethoxy-5-methyl-2-{methyl-[6-(1-pyrrolidin-1-yl-ethyl)-pyridin-2-ylmethyl]-amino}-1H-quinazolin-4-one | 75.4–85.6 | |
| 276 | 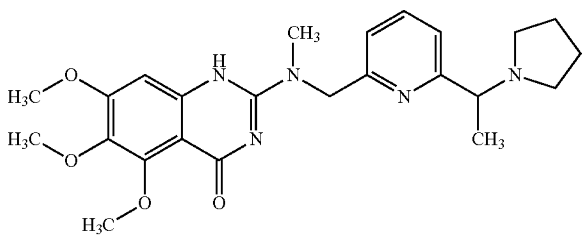 | 5,6,7-Trimethoxy-2-{methyl-[6-(1-pyrrolidin-1-yl-ethyl)-pyridin-2-ylmethyl]-amino}-1H-quinazolin-4-one | | 454 |
| 277 | 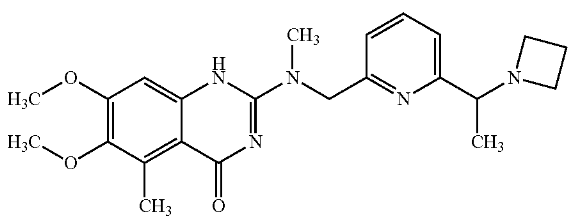 | 2-{[6-(1-Azetidin-1-yl-ethyl)-pyridin-2-ylmethyl]-methyl-amino}-6,7-dimethoxy-5-methyl-1H-quinazolin-4-one | | 424 |

TABLE 11-continued

| # | Structure | Systematic Name | MP ° C. | M + H |
|---|---|---|---|---|
| 278 | 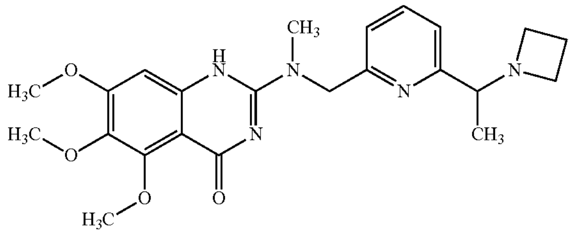 | 2-{[6-(1-Azitidin-1-yl-ethyl)-pyridin-2-ylmethyl]-methyl-amino}-5,6,7-trimethoxy-1H-quinazolin-4-one | 70.8–78.8 | |
| 279 | 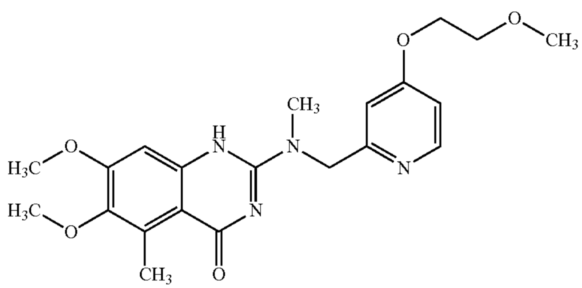 | 6,7-Dimethoxy-2-{[4-(2-methoxy-ethoxy)-pyridin-2-ylmethyl]-methyl-amino}-5-methyl-1H-quinaolin-4-one | | 415 |
| 280 | 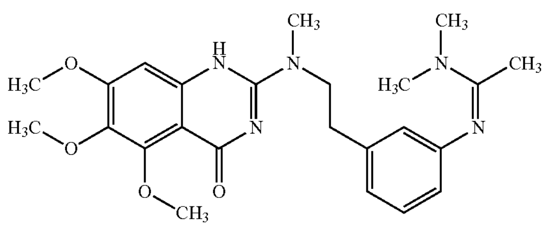 | N,N-Dimethyl-N'-(3-{2-[methyl-(5,6,7-trimethoxy-4-oxo-1,4-dihydro-quinazolin-2-yl)-amino]-ethyl}-phenyl)-acetamidine | | 454 |
| 281 | 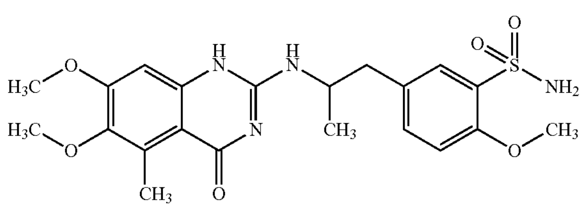 | 5-[2-(6,7-Dimethoxy-5-methyl-4-oxo-1,4-dihydro-quinazolin-2-ylamino)-propyl]-2-methoxy-benzenesulfonamide | | 463 |

TABLE 11-continued

| # | Structure | Systematic Name | MP ° C. | M + H |
|---|---|---|---|---|
| 282 | 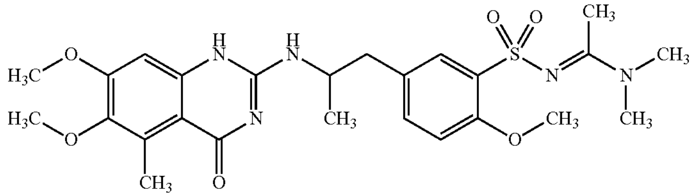 | 5-[2-(6,7-Dimethoxy-5-methyl-4-oxo-1,4-dihydro-quinazoloin-2-ylamino)-propyl]-N-[1-dimethylamino-eth-(E)-ylidene]-2-methoxy-benzenesulfonamide | | 532 |
| 283 | 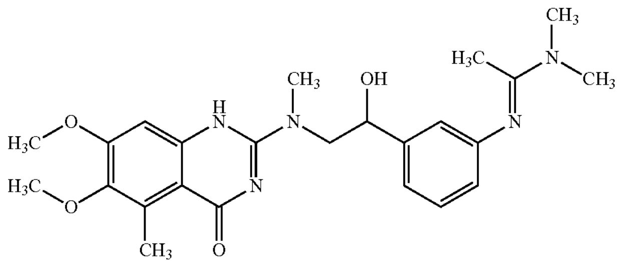 | N'-(3-{2-[(6,7-Dimethoxy-5-methyl-4-oxo-1,4-dihydro-quinazolin-2-yl)-methyl-amino]-1-hydroxy-ethyl}-phenyl)-N,N-dimethyl-acetamidine | | 455 |
| 284 | 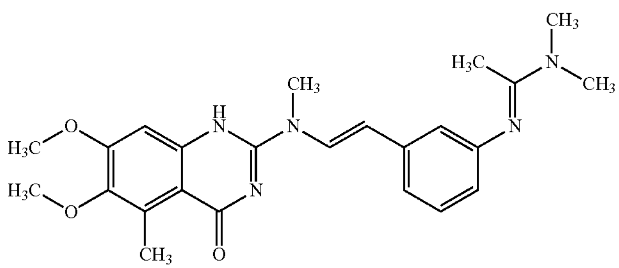 | N'-(3-((E)-2-[(6,7-Dimethoxy-5-methyl-4-oxo-1,4-dihydro-quinazolin-2-yl)-methyl-amino]-vinyl}-phenyl)-N,N-dimethyl-acetamidine | | 436 |
| 285 | 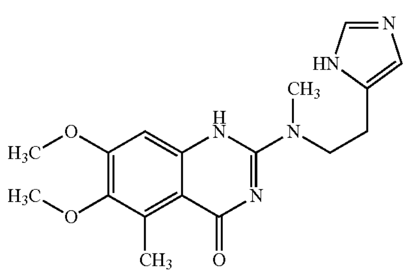 | 2-{[2-(3H-Imidazol-4-yl)-ethyl]-methyl-amino}-6,7-dimethoxy-5-methyl-1H-quinaozlin-4-one | | 344 |

TABLE 11-continued

| # | Structure | Systematic Name | MP °C. | M + H |
|---|---|---|---|---|
| 286 | 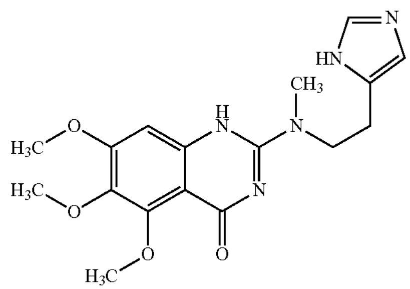 | 2-{[2-(3H-Imidazol-4-yl)-ethyl]-methyl-amino}-5,6,7-trimethoxy-1H-quinazolin-4-one | | 360 |
| 287 | 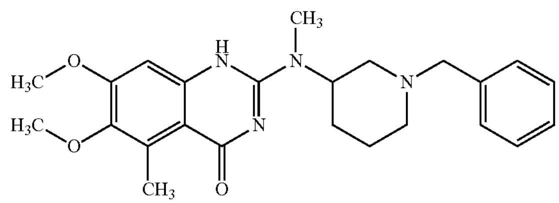 | 2-[(1-Benzyl-piperidin-3-yl)-methyl-amino]-6,7-dimethoxy-5-methyl-1H-quinazolin-4-one | | 423 |
| 288 | 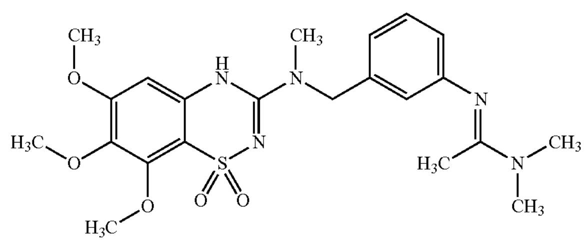 | N,N-Dimethyl-N'-(3-{[methyl-(6,7,8-trimethoxy-1,1-dioxo-1,4-dihydro-1λ6-benzo[1,2,4]thiadiazin-3-yl)-amino]-methyl}-phenyl)-acetamidine | | 477 |

TABLE 11-continued

| # | Structure | Systematic Name | MP ° C. | M + H |
|---|---|---|---|---|
| 289 | 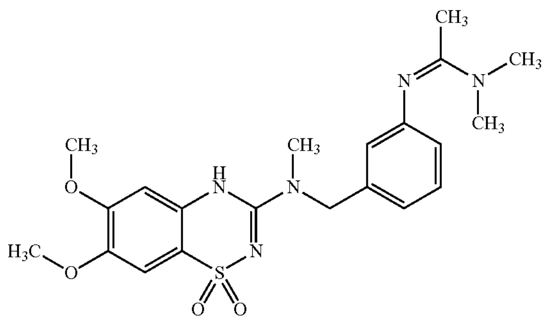 | N'-(3-{[(6,7-Dimethoxy-1,1-dioxo-1,4-dihydro-1λ6-benzo[1,2,4]thiadiazin-3-yl)-methyl-amino]-methyl}-phenyl)-N,N-dimethyl-acetamidine | | 446 |
| 290 | 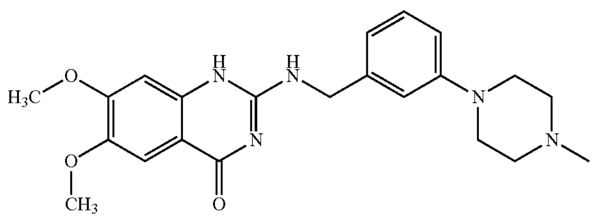 | 6,7-Dimethoxy-2-[3-(4-methyl-piperazin-1-yl)-benzylamino]-1H-quinazolin-4-one | | 410 |
| 291 | 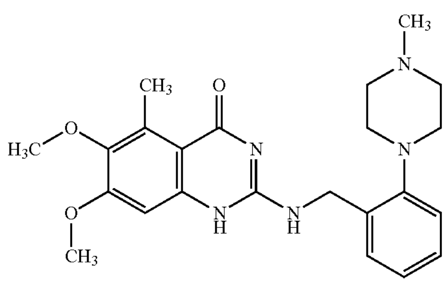 | 6,7-Dimethoxy-5-methyl-2-[2-(4-methyl-piperazin-1-yl)-benzylamino]-1H-quinazolin-4-one | | 424 |

TABLE 11-continued

| # | Structure | Systematic Name | MP ° C. | M + H |
|---|---|---|---|---|
| 292 | 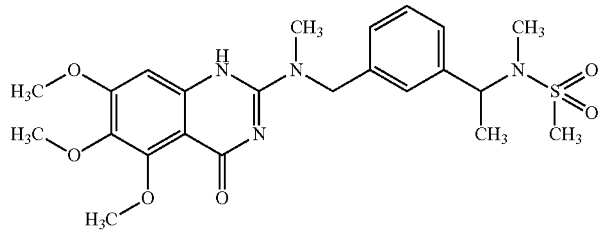 | N-Methyl-N-[1-(3-{[methyl-(5,6,7-trimethoxy-4-oxo-1,4-dihydro-quinazolin-2-yl)-amino]-methyl}-phenyl)-ethyl]-methanesulfonamide | 171.0–172.4 | |
| 293 | 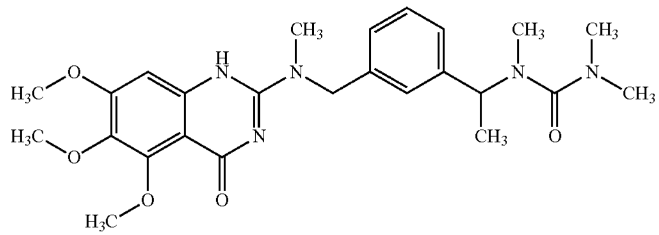 | 1,1,3-Trimethyl-3-[1-(3-{[methyl-(5,6,7-trimethoxy-4-oxxo-1,4-dihydro-quinazolin-2-yl)-amino]-methyl}-phenyl-ethyl]-urea | 68–70 | |
| 294 | 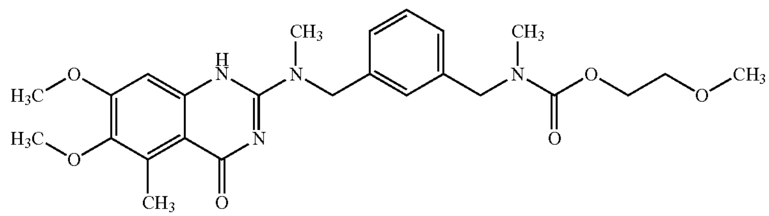 | (3-{[(6,7-Dimethoxy-5-methyl-4-oxo-1,4-dihydro-quinazolin-2-yl)-methyl-amino]-methyl}-benzyl)-methyl-carbamic acid 2-methoxy-ethyl ester | 145.8–146.9 | |

Table 11

ASSAY EXAMPLES

Example L-1

The potency and selectivity of the inventive compounds as α1A/B antagonists was determined with CHO-K1 cells expressing adrenoceptor subtype α1A-215, α1B or α1D by measuring cAMP accumulation using AlphaScreen.

Cell preparation was accomplished by culturing CHO-α1 cloned cells in Ham's F12 nutrient media supplemented with 10% FBS and G418 (25 mg/mL), harvested at 80% confluence, washed with warmed PBS×2, and detached with versene for 5 min. at 37° C. The cultured cells were then resuspended in 40 mL of stimulation buffer (HBSS with 5 mM hepes, 0.1% BSA) and centrifuged at 500–100 rpm for 5 min. The obtained pellet was resuspended in stimulation buffer (with 0.5M IBMX), and the cells were counted. Cells were diluted to the desired number of cells/mL (α1A at $3 \times 10^6$/mL, α1B $15 \times 10^6$/mL, and α1D $20 \times 10^6$/mL).

The compounds being tested were diluted in stimulation buffer (with 0.5M IBMX), from $10^{-5}$ to $10^{-11}$ (final) dilution, 11 points. 5 μl of each compound was dispensed to 96 well ½ area plates in triplicate. 5 μl of stimulation buffer was dispensed to a norepinephrine (NE) plate. 10 μl of cells were added with anti-cAMP Acceptor beads in stimulation buffer to each plate and incubated for 15 min. at RT (in dark or covered with black plate). Then 5 μl of NE was added to the antagonist plates, at 1 μM for α1A and 1B and at 100 nM for α1D, and then 5 μl serial dilution of NE was added to NE plate. Plates were incubated for 30 min. at RT (in dark or covered with black plate) and 10 μl Donor beads+biotin-cAMP in lysis buffer (5 mM Hepes, 0.54% Tween-20, 0.1% BSA) was added. Plates were incubated for 3 h. at RT with gentle shaking (in dark or covered with black plate). Plates were read on an AlphaScreen Fusion analyzer, using reagent pursuant to AlphaSreen cAMP detection kit (PerkinElmer Cat#6760600).

Reference compounds norepinephrine, prazosin and vehicle were run in every experiment. In each plate, on column 12, A–D were loaded with only cells to define total count and E–H were loaded with NE 1 μM, (total—NE 1 μM), to define 100% NE activity. The values determined for each experimental well on the plate were divided by (total count—NE 1 μM), to determine % of NE activity. All data was plotted using non-liner curve fitting by GraphPad Prism to get $pEC_{50}$ ($pEC_{50}$ being the negative logarithm of $EC_{50}$, i.e., the molar concentration of an agonist which produces 50% of the maximum possible response for that agonist) for norepinephrine and pKb (wherein Kb is the equilibrium dissociation for a competitive antagonist, determined in a functional assay, and being equal to the concentration of antagonist which would occupy 50% of the receptors at equilibrium, units=mol $1^{-1}$, and pKb is the negative logarithm of Kb) for prazosin and tested compounds. (AlphaScreen cAMP Detection Kit from PerkinElmer Life Sciences).

Example L-2

Example [$^3$H]prazosin Binding
(Alpha1-Adrenoceptor) Assay

Alpha1A, alpha1B, and alpha1D adrenoceptor transfected CHO-K1 cells, prepared using the methods described by Chang et al., *FEBS Lett.* 1998, 422:279–283, were grown to confluence in T-162 tissue culture flasks in Ham's F-12 culture medium supplemented with 10% fetal bovine serum, geneticin (150 μg/mL) and streptomycin/penicillin (30 μg/mL/30 μg/mL) at 37° C. in 7% $CO_2$. Cells were harvested by incubating with phosphate-buffered saline (PBS) containing 30 μM EDTA for 5–10 min at 37° C. Cells were pelleted by centrifuging at 500×g for 5 min, and the pelleted cells were homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in the homogenizing buffer and rehomogenized. The resulting homogenate was centrifuged at 45,000×g for 20 min. The pellet was resuspended in 50 mM Tris buffer (pH 7.4 at 4° C.), aliquoted, frozen, and stored at –80° C. for further use.

The membranes were thawed at room temperature and diluted in assay buffer (50 mM Tris buffer at pH 4) at 37° C. and homogenized using the Polytron tissue disrupter. The membranes were incubated with the radioligand ([$^3$H]prazosin, NEN, 0.1–0.5 nM) and test compound at 37° C. for 30 min. The membranes were then filtered over polyethyleneimine-treated GF/B unifilter plates using a Packard Filtermate Harvester and washed with ice-cold 50 mM Tris-HCl, 1 mM EDTA buffer (3×3 sec. washes). Scintillation cocktail was added to the filter plates and bound radioligand determined by liquid scintillation spectrophotometry.

For each experiment, total binding (in the absence of any test or reference compounds) and non-specific binding (10 μM phentolamine) were determined. For each sample tested, the concentration producing 50% inhibition of binding ($IC_{50}$) and Hill Slope ($n_H$) was determined using iterative non-linear curve fitting techniques with Kaleidagraph (Synergy Software) or other appropriate software. If the radioligand $K_D$ was known, the inhibition dissociation constant ($K_I$) of each ligand was determined according to the method of Cheng and Prusoff (Cheng, Y-C. and Prusoff, W. H., *Biochem. Pharmacol.*, 1973, 22, 3099–3108).

Proceeding as in Example L-2, compounds of Formula I were tested and found to be selective alpha1A/B-adrenoceptor antagonists.

Example L-3

Dog In Vivo Intraurethral and Blood Pressure Assay

The following describes an in vivo assay for measuring the relative effect of test compounds on hypogastric nerve stimulation-induced increases in intraurethral pressure and phenylephrine-induced increases in diastolic blood pressure in anesthetized dog.

Male Mongrel dogs (10 to 20 kg) were fasted for 12 to 18 hours and anesthetized with phenobarbital sodium (36 mg/kg, i.v.). An endotracheal tube was inserted and thereafter the lungs were mechanically ventilated with room air. The right femoral vein was isolated and cannulated with two polyethylene cannulae, one for the administration of a continuous infusion of phenobarbital sodium (5 to 10 mg/kg/hr) and the other for bolus administration of test substances. The right femoral artery was isolated and cannulated to the abdominal aorta with a fluid filled polyethylene cannula connected to an external pressure transducer for monitoring diastolic aortic pressure (DAP). The bladder was exposed via a ventral midline abdominal incision and emptied of urine through a 22 gauge needle. The bladder was cannulated through a stab incision with a water filled balloon catheter connected to an external pressure transducer for monitoring prostatic intraurethral pressure (IUP). The right hypogastric nerve (HGN) was carefully isolated and attached to a Dastre's electrode for nerve stimulation.

The preparation was allowed to stabilize for at least 20–30 minutes and must have had a stable basal IUP for not less than 15 minutes prior to commencement of the assay protocol. The HGN was stimulated (20–50V, 10 Hz, 10 msec pulse train for 10 sec) to induce a measurable increase in IUP and then phenylephrine (PE) was administered by bolus injection (6 μg/kg, i.v.) to induce a measurable increase in DAP. The HGN stimulation and PE bolus injection were repeated every 5 minutes until three consecutive reproducible increases in IUP and DAP were achieved. Test compound was administered and 10 minutes later the HGN stimulation and PE bolus injection were repeated. Test compound was administered approximately every 20 minutes, increasing the dose until maximal or near maximal inhibition of the increases in IUP and DAP is attained.

Proceeding as in Example L-3, compounds of Formula I were tested and found to selectively inhibit the HGN stimulation-induced increases in IUP. In contrast, prazosin inhibited increases in IUP and DAP in similar fashion.

Compounds of formula I are active in the above assays. For some examplary compounds the following table shows corresponding data.

| Compound | pKi | | |
|---|---|---|---|
| | alpha 1A | alpha 1B | alpha 1D |
| N'-{3-[(6,7-dimethoxy-5-methyl-4-oxo-1,4-dihydroquinazolin-2-ylamino)-methyl]-phenyl}-N,N-dimethyl-acetamidine | 8.13 | 9.05 | 7.16 |
| 2-{[4-(2,3-dihydroxy-propoxy)-benzyl]-methyl-amino}-6,7-dimethoxy-5-methyl-1H-quinazolin-4-one | 8.15 | 8.16 | 6.10 |
| 2-{[3-(4,5-dihydro-oxazol-2-yl)-benzyl]-methyl-amino}-5,6,7-trimethoxy-1H-quinazolin-4-one | 6.09 | 7.83 | 5.58 |
| 2-({4-[(ethyl-methyl-amino)-methyl]-benzyl}-methyl-amino)-5,6,7-trimethoxy-1H-quinazolin-4-one | 8.50 | 8.51 | 6.26 |
| 5,6,7-trimethoxy-2-{[3-(3-methoxy-pyrrolidin-1-ylmethyl)-benzyl]-methyl-amino}-1H-quinazolin-4-one | 8.27 | 8.13 | 5.27 |
| 6,7-Dimethoxy-5-methyl-2-[methyl-(2-methyl-2,3-dihydro-1H-isoindol-5-ylmethyl)-amino]-1H-quinazolin-4-one | 8.49 | 7.83 | 5.58 |
| 2-{[3-(1-Dimethylamino-ethyl)-benzyl]-methyl-amino}-5,6,7-trimethoxy-1H-quinazolin-4-one | 8.81 | 8.43 | 6.85 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound according to Formula (I),

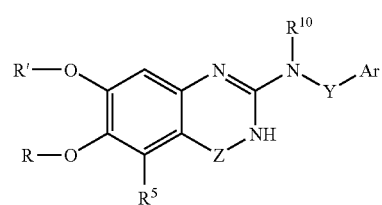

wherein,
Y is $C_{1-4}$alkylene or $C_{2-4}$alkenylene;
Z is —C(═O)—;
R and R' are alkyl;
$R^5$ is selected from halogen, cyano, hydroxy, —$R^6$, and —$OR^6$;
$R^6$ is selected from alkyl, aryl, heteroaryl, cycloalkyl, and heterocyclyl;
$R^{10}$ is selected from hydrogen, alkyl, hydroxyalkyl, aminoalkyl and aralkyl;
Ar is

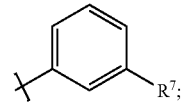

and
$R^7$ is selected from methyl-(3,3,3-trifluoro-propyl)-amino-methyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxy-carbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methyl-amino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxy-ethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyamino-carbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxy-ethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethyl-amino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutane-carboxamidinyl-, imidazolidin-2-ylideneamino-, 1-methyl-pyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-Dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-, 2-oxo-imidazolidin-1-yl-, 3-methyl-2-oxo-imidazolidin-1-yl-, 3-ethyl-2-oxo-imidazolidin-1-yl-, 3-(2-methoxyethyl)-2-oxo-imidazolidin-1-yl-, 1H-tetrazol-5-yl-, ethoxy-, 1-pyrrolidin-1-yl-ethyl-, 1-Azetidin-1-yl-ethyl-, aminosulfonyl-, N,N-dimethylamino-acetamidinesulfonyl-, and 1-methanesulfonyl-methylamino)-ethyl-;

or a pharmaceutically-acceptable salt thereof.

2. The compound of claim 1, wherein R and R' are both CH$_3$.

3. The compound of claim 1, wherein R$^{10}$ is selected from hydrogen, alkyl, hydroxyalkyl, and benzyl.

4. The compound of claim 1, wherein:
R and R' are both CH$_3$;
R$^5$ is selected from methyl, ethyl, n-propyl, isopropyl, halogen, cyano, methoxy, and ethoxy; and
R$^{10}$ is selected from hydrogen and alkyl.

5. A compound of formula (Ib):

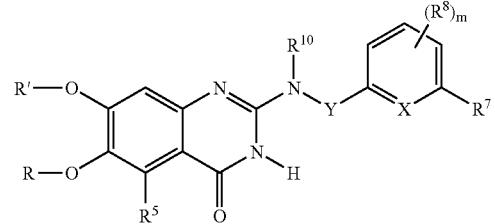

wherein:
m is from 0 to 3;
X is CH;
Y is methylene;
R and R' are methyl;
R$^5$ is methoxy or methyl;
one of R$^7$ and R$^8$ is hydrogen, or methoxy, and the other is selected from methyl-(3,3,3-trifluoro-propyl)-aminomethyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxycarbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methylamino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxyethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyamino-carbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxy-ethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethyl-amino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutane-carboxamidinyl, imidazolidin-2-ylideneamino-, 1-methyl-pyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-2-oxo-imidazolidin-1-yl-, 3-methyl-2-oxo-imidazolidin-1-yl-, 3-ethyl-2-oxo-imidazolidin-1-yl-, 3-(2-methoxy-ethyl)-2-oxo-imidazolidin-1-yl-, 1H-tetrazol-5-yl-, ethoxy-, 1-pyrrolidin-1-yl-ethyl-, 1-Azetidin-1-yl-ethyl-, aminosulfonyl-, N,N-dimethylamino-acetamidinesulfonyl-, and 1-methanesulfonyl-methylamino)-ethyl-; and $R^{10}$ is hydrogen or methyl.

6. A compound selected from the group consisting of:
2-[(3-Bromo-benzyl)-methyl-amino]-5,6,7-trimethoxy-1H-quinazolin-4-one;
2-[(2-Fluoro-benzyl)-(2-hydroxy-ethyl)-amino]-6,7-dimethoxy-5-methyl-1H-quinazolin-4-one;
3-{[Methyl-(5,6,7-trimethoxy-4-oxo-1,4-dihydro-quinazolin-2-yl)-amino]-methyl}-benzonitrile;
6,7-Dimethoxy-5-methyl-2-[methyl-(3-methylamino-benzyl)-amino]-1H-quinazolin-4-one;
2-[(3-Amino-benzyl)-methyl-amino]-5,6,7-trimethoxy-1H-quinazolin-4-one;
2-[(2-Amino-benzyl)-methyl-amino]-5,6,7-trimethoxy-1H-quinazolin-4-one;
6,7-Dimethoxy-5-methyl-2-[methyl-(3-methylaminomethyl-benzyl)-amino]-1H-quinazolin-4-one;
2-[(3-Aminomethyl-benzyl)-methyl-amino]-6,7-dimethoxy-5-methyl-1H-quinazolin-4-one;
(3-{[Methyl-(5,6,7-trimethoxy-4-oxo-1,4-dihydro-quinazolin-2-yl)-amino]-methyl}-phenyl)-acetonitrile;
2-[(3-Hydroxymethyl-benzyl)-methyl-amino]-5,6,7-trimethoxy-1H-quinazolin-4-one;
5-Hydroxy-2-[(3-hydroxymethyl-benzyl)-methyl-amino]-6,7-dimethoxy-1H-quinazolin-4-one;
5,6,7-Trimethoxy-2-[methyl-(3-morpholin-4-ylmethyl-benzyl)-amino]-1H-quinazolin-4-one;
5,6,7-Trimethoxy-2-[methyl-(3-methylaminomethyl-benzyl)-amino]-1H-quinazolin-4-one;
2-[Ethyl-(3-methylaminomethyl-benzyl)-amino]-6,7-dimethoxy-5-methyl-1H-quinazolin-4-one;
2-[(3-Ethylaminomethyl-benzyl)-methyl-amino]-6,7-dimethoxy-5-methyl-1H-quinazolin-4-one;
2-({3-[(Ethyl-methyl-amino)-methyl]-benzyl}-methyl-amino)-5,6,7-trimethoxy-1H-quinazolin-4-one;
6,7-Dimethoxy-5-methyl-2-(methyl-{3-[(2,2,2-trifluoro-ethylamino)-methyl]-benzyl}-amino)-1H-quinazolin-4-one;
2-[(3-{[(2-Hydroxy-ethyl)-methyl-amino]-methyl}-benzyl)-methyl-amino]-5,6,7-trimethoxy-1H-quinazolin-4-one;
5,6,7-Trimethoxy-2-[(3-{[(2-methoxy-ethyl)-methyl-amino]-methyl}-benzyl)-methyl-amino]-1H-quinazolin-4-one;

2-[(3-{[Ethyl-(2-methoxy-ethyl)-amino]-methyl}-benzyl)-methyl-amino]-5,6,7-trimethoxy-1H-quinazolin-4-one;
N-(3-{[(6,7-Dimethoxy-5-methyl-4-oxo-1,4-dihydro-quinazolin-2-yl)-methyl-amino]-methyl}-benzyl)-2-methoxy-N-methyl-acetamide;
2-Methoxy-N-methyl-N-(3-{[methyl-(5,6,7-trimethoxy-4-oxo-1,4-dihydro-quinazolin-2-yl)-amino]-methyl}-benzyl)-acetamide;
2-[(3-{[Ethyl-(2-methoxy-ethyl)-amino]-methyl}-benzyl)-methyl-amino]-6,7-dimethoxy-5-methyl-1H-quinazolin-4-one;
6,7-Dimethoxy-5-methyl-2-[methyl-(3-pyrrolidin-1-ylmethyl-benzyl)-amino]-1H-quinazolin-4-one;
5-Hydroxy-6,7-dimethoxy-2-{methyl-[3-(1-methyl-4,5-dihydro-1H-imidazol-2-ylmethyl)-benzyl]-amino}-1H-quinazolin-4-one;
5,6,7-Trimethoxy-2-{methyl-[3-(1-methyl-4,5-dihydro-1H-imidazol-2-ylmethyl)-benzyl]-amino}-1H-quinazolin-4-one;
5-Hydroxy-2-{[3-(1-isopropyl-4,5-dihydro-1H-imidazol-2-ylmethyl)-benzyl]-methyl-amino}-6,7-dimethoxy-1H-quinazolin-4-one;
2-{[3-(1-Isopropyl-4,5-dihydro-1H-imidazol-2-ylmethyl)-benzyl]-methyl-amino}-5,6,7-trimethoxy-1H-quinazolin-4-one;
5,6,7-Trimethoxy-2-{methyl-[3-(1-methyl-piperidin-4-ylmethyl)-benzyl]-amino}-1H-quinazolin-4-one;
2-[(3-Methanesulfonyl-benzyl)-methyl-amino]-6,7-dimethoxy-5-methyl-1H-quinazolin-4-one;
2-[(3-Methanesulfonyl-benzyl)-methyl-amino]-5,6,7-trimethoxy-1H-quinazolin-4-one;
N,N-Dimethyl-3-{[methyl-(5,6,7-trimethoxy-4-oxo-1,4-dihydro-quinazolin-2-yl)-amino]-methyl}-benzenesulfonamide;
3-{[(6,7-Dimethoxy-5-methyl-4-oxo-1,4-dihydro-quinazolin-2-yl)-methyl-amino]-methyl}-N-(2-methoxy-ethyl)-benzenesulfonamide;
N-(2-Methoxy-ethyl)-3-{[methyl-(5,6,7-trimethoxy-4-oxo-1,4-dihydro-quinazolin-2-yl)-amino]-methyl}-benzenesulfonamide;
3-{[(6,7-Dimethoxy-5-methyl-4-oxo-1,4-dihydro-quinazolin-2-yl)-methyl-amino]-methyl}-N-(3-methoxy-propyl)-benzenesulfonamide;
3-{[(6,7-Dimethoxy-5-methyl-4-oxo-1,4-dihydro-quinazolin-2-yl)-methyl-amino]-methyl}-benzoic acid;
3-{[Methyl-(5,6,7-trimethoxy-4-oxo-1,4-dihydro-quinazolin-2-yl)-amino]-methyl}-benzoic acid;
3-{[(6,7-Dimethoxy-5-methyl-4-oxo-1,4-dihydro-quinazolin-2-yl)-methyl-amino]-methyl}-N-methyl-benzamide;
N-Methyl-3-{[methyl-(5,6,7-trimethoxy-4-oxo-1,4-dihydro-quinazolin-2-yl)-amino]-methyl}-benzamide;
N-(2-Dimethylamino-ethyl)-3-{[methyl-(5,6,7-trimethoxy-4-oxo-1,4-dihydro-quinazolin-2-yl)-amino]-methyl}-benzamide;
N-(2-Dimethylamino-ethyl)-N-methyl-3-{[methyl-(5,6,7-trimethoxy-4-oxo-1,4-dihydro-quinazolin-2-yl)-amino]-methyl}-benzamide;
N-(3-Dimethylamino-propyl)-N-methyl-3-{[methyl-(5,6,7-trimethoxy-4-oxo-1,4-dihydro-quinazolin-2-yl)-amino]-methyl}-benzamide;
N-(2-Hydroxy-ethyl)-3-{[methyl-(5,6,7-trimethoxy-4-oxo-1,4-dihydro-quinazolin-2-yl)-amino]-methyl}-benzamide;
N-(2-Hydroxy-propyl)-3-{[methyl-(5,6,7-trimethoxy-4-oxo-1,4-dihydro-quinazolin-2-yl)-amino]-methyl}-benzamide;
N-(2-Hydroxy-ethyl)-N-methyl-3-{[methyl-(5,6,7-trimethoxy-4-oxo-1,4-dihydro-quinazolin-2-yl)-amino]-methyl}-benzamide;
N-(2-Methoxy-ethyl)-3-{[methyl-(5,6,7-trimethoxy-4-oxo-1,4-dihydro-quinazolin-2-yl)-amino]-methyl}-benzamide;
N-(3-Methoxy-propyl)-3-{[methyl-(5,6,7-trimethoxy-4-oxo-1,4-dihydro-quinazolin-2-yl)-amino]-methyl}-benzamide;
N-Cyanomethyl-3-{[methyl-(5,6,7-trimethoxy-4-oxo-1,4-dihydro-quinazolin-2-yl)-amino]-methyl}-benzamide;
3-{[Methyl-(5,6,7-trimethoxy-4-oxo-1,4-dihydro-quinazolin-2-yl)-amino]-methyl}-N-(tetrahydro-furan-2-ylmethyl)-benzamide;
N-Furan-2-ylmethyl-3-{[methyl-(5,6,7-trimethoxy-4-oxo-1,4-dihydro-quinazolin-2-yl)-amino]-methyl}-benzamide;
3-{[Methyl-(5,6,7-trimethoxy-4-oxo-1,4-dihydro-quinazolin-2-yl)-amino]-methyl}-N-(2-morpholin-4-yl-ethyl)-benzamide;
2-{[3-(4-Hydroxymethyl-piperidine-1-carbonyl)-benzyl]-methyl-amino}-5,6,7-trimethoxy-1H-quinazolin-4-one;
2-{[3-(2-Hydroxy-ethoxy)-benzyl]-methyl-amino}-5,6,7-trimethoxy-1H-quinazolin-4-one;
2-[(3-Methanesulfinylmethoxy-benzyl)-methyl-amino]-6,7-dimethoxy-5-methyl-1H-quinazolin-4-one;
6,7-Dimethoxy-5-methyl-2-{methyl-[3-(pyrimidin-2-yloxy)-benzyl]-amino}-1H-quinazolin-4-one;
2-[(3-Hydroxy-benzyl)-methyl-amino]-6,7-dimethoxy-5-methyl-1H-quinazolin-4-one;
2-[(3-Hydroxy-benzyl)-methyl-amino]-5,6,7-trimethoxy-1H-quinazolin-4-one;
2-[(3-Methanesulfonylmethoxy-benzyl)-methyl-amino]-5,6,7-trimethoxy-1H-quinazolin-4-one;
(3-{[(6,7-Dimethoxy-5-methyl-4-oxo-1,4-dihydro-quinazolin-2-yl)-methyl-amino]-methyl}-phenoxy)-acetic acid;
(3-{[Methyl-(5,6,7-trimethoxy-4-oxo-1,4-dihydro-quinazolin-2-yl)-amino]-methyl}-phenoxy)-acetic acid;
2-{[3-(2-Hydroxy-ethoxy)-benzyl]-methyl-amino}-6,7-dimethoxy-5-methyl-1H-quinazolin-4-one;
6,7-Dimethoxy-2-{[3-(2-methoxy-ethoxy)-benzyl]-methyl-amino}-5-methyl-1H-quinazolin-4-one;
5,6,7-Trimethoxy-2-{[3-(2-methoxy-ethoxy)-benzyl]-methyl-amino}-1H-quinazolin-4-one;
6,7-Dimethoxy-2-{[3-(3-methoxy-propoxy)-benzyl]-methyl-amino}-5-methyl-1H-quinazolin-4-one;
5,6,7-Trimethoxy-2-{[3-(3-methoxy-propoxy)-benzyl]-methyl-amino}-1H-quinazolin-4-one;
2-{[3-(2-Dimethylamino-ethoxy)-benzyl]-methyl-amino}-6,7-dimethoxy-5-methyl-1H-quinazolin-4-one;
2-{[3-(2-Ethylamino-ethoxy)-benzyl]-methyl-amino}-6,7-dimethoxy-5-methyl-1H-quinazolin-4-one;
5,6,7-Trimethoxy-2-{methyl-[3-(pyrimidin-2-yloxy)-benzyl]-amino}-1H-quinazolin-4-one;
N'-(3-{[(6,7-Dimethoxy-5-methyl-4-oxo-1,4-dihydro-quinazolin-2-yl)-methyl-amino]-methyl}-phenyl)-N,N-dimethyl-acetamidine;

N-(3-{[(5-Isopropyl-6,7-dimethoxy-4-oxo-1,4-dihydro-quinazolin-2-yl)-methyl-amino]-methyl}-phenyl)-methanesulfonamide;

N'-(3-{[(6,7-dimethoxy-5-methyl-4-oxo-1,4-dihydro-quinazolin-2-yl)-methyl-amino]-methyl}-phenyl)-N,N-dimethylsulfamide;

N-(3-{[(6,7-dimethoxy-5-methyl-4-oxo-1,4-dihydro-quinazolin-2-yl)-methyl-amino]-methyl}-phenyl)-N,N',N'-trimethylsulfamide;

N,N-Dimethyl-N'-(3-{[methyl-(5,6,7-trimethoxy-4-oxo-1,4-dihydro-quinazolin-2-yl)-amino]-methyl}-phenyl)-sulfamide;

N,N,N'-Trimethyl-N'-(3-{[methyl-(5,6,7-trimethoxy-4-oxo-1,4-dihydro-quinazolin-2-yl)-amino]-methyl}-phenyl)-sulfamide;

N-(3-{[(6,7-Dimethoxy-5-methyl-4-oxo-1,4-dihydro-quinazolin-2-yl)-methyl-amino]-methyl}-phenyl)-acetamide;

N-(3-{[Methyl-(5,6,7-trimethoxy-4-oxo-1,4-dihydro-quinazolin-2-yl)-amino]-methyl}-phenyl)-acetamide;

N-(4-Chloro-3-{[methyl-(5,6,7-trimethoxy-4-oxo-1,4-dihydro-quinazolin-2-yl)-amino]-methyl}-phenyl)-acetamide;

1,1-Dimethyl-3-(3-{[methyl-(5,6,7-trimethoxy-4-oxo-1,4-dihydro-quinazolin-2-yl)-amino]-methyl}-phenyl)-urea;

(3-{[Methyl-(5,6,7-trimethoxy-4-oxo-1,4-dihydro-quinazolin-2-yl)-amino]-methyl}-phenyl)-carbamic acid methyl ester;

(3-{[(6,7-Dimethoxy-5-methyl-4-oxo-1,4-dihydro-quinazolin-2-yl)-methyl-amino]-methyl}-phenyl)-methyl-carbamic acid methyl ester;

N-(3-{[(6,7-Dimethoxy-5-methyl-4-oxo-1,4-dihydro-quinazolin-2-yl)-methyl-amino]-methyl}-phenyl)-N-methyl-2-oxo-propionamide;

3-(3-{[(6,7-Dimethoxy-5-methyl-4-oxo-1,4-dihydro-quinazolin-2-yl)-methyl-amino]-methyl}-phenyl)-1,1-dimethyl-urea;

N-Methoxy-N'-(3-{[methyl-(5,6,7-trimethoxy-4-oxo-1,4-dihydro-quinazolin-2-yl)-amino]-methyl}-phenyl)-urea;

2-{[3-(2-Hydroxy-ethylamino)-benzyl]-methyl-amino}-5,6,7-trimethoxy-1H-quinazolin-4-one;

5-Hydroxy-2-({3-[(3-hydroxy-propyl)-methyl-amino]-benzyl}-methyl-amino)-6,7-dimethoxy-1H-quinazolin-4-one;

2-{[3-(3-Hydroxy-propylamino)-benzyl]-methyl-amino}-5,6,7-trimethoxy-1H-quinazolin-4-one;

5,6,7-Trimethoxy-2-{[3-(2-methoxy-ethylamino)-benzyl]-methyl-amino}-1H-quinazolin-4-one;

5,6,7-Trimethoxy-2-({3-[(2-methoxy-ethyl)-methyl-amino]-benzyl}-methyl-amino)-1H-quinazolin-4-one;

2-({3-[(3-Hydroxy-propyl)-methyl-amino]-benzyl}-methyl-amino)-5,6,7-trimethoxy-1H-quinazolin-4-one;

5,6,7-Trimethoxy-2-{[3-(3-methoxy-propylamino)-benzyl]-methyl-amino}-1H-quinazolin-4-one;

5,6,7-Trimethoxy-2-({3-[(3-methoxy-propyl)-methyl-amino]-benzyl}-methyl-amino)-1H-quinazolin-4-one;

2-({3-[Bis-(2-hydroxy-ethyl)-amino]-benzyl}-methyl-amino)-5,6,7-trimethoxy-1H-quinazolin-4-one;

N-[2-(3-{1-[(6,7-Dimethoxy-5-methyl-4-oxo-1,4-dihydro-quinazolin-2-yl)-methyl-amino]-ethyl}-phenylamino)-ethyl]-acetamide;

N-(3-{[(6,7-Dimethoxy-5-methyl-4-oxo-1,4-dihydro-quinazolin-2-yl)-methyl-amino]-methyl}-phenyl)-acetamidine;

N-(3-{[Methyl-(5,6,7-trimethoxy-4-oxo-1,4-dihydro-quinazolin-2-yl)-amino]-methyl}-phenyl)-acetamidine;

N-(3-{[(6,7-Dimethoxy-5-methyl-4-oxo-1,4-dihydro-quinazolin-2-yl)-methyl-amino]-methyl}-phenyl)-N,N'-dimethyl-acetamidine;

N-(3-{[(6,7-Dimethoxy-5-methyl-4-oxo-1,4-dihydro-quinazolin-2-yl)-methyl-amino]-methyl}-phenyl)-N'-methyl-acetamidine;

N'-(3-{[(6,7-Dimethoxy-5-methyl-4-oxo-1,4-dihydro-quinazolin-2-yl)-methyl-amino]-methyl}-phenyl)-N,N-dimethyl-formamidine;

N,N-Dimethyl-N'-(3-{[methyl-(5,6,7-trimethoxy-4-oxo-1,4-dihydro-quinazolin-2-yl)-amino]-methyl}-phenyl)-acetamidine; and N,N-Dimethyl-N'-(3-{[methyl-(5,6,7-trimethoxy-4-oxo-1,4-dihydro-quinazolin-2-yl)-amino]-methyl}-phenyl)-isobutyramidine.

7. A pharmaceutical composition comprising a therapeutically effective amount of at least one compound of claim 1 and at least one pharmaceutically acceptable carrier.

8. A compound to Formula (I),

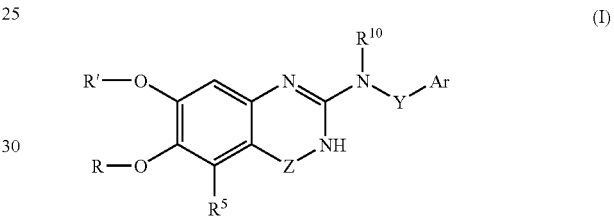

wherein,

Y is $C_{1-4}$alkylene or $C_{2-4}$alkenylene;

Z is —C(=O)—;

R and R' are alkyl;

R and R' are both $CH_3$;

$R^5$ is selected from methyl, ethyl, n-propyl, isopropyl, halogen, cyano, methoxy, and ethoxy; and $R^{10}$ is selected from hydrogen and alkyl;

Ar is

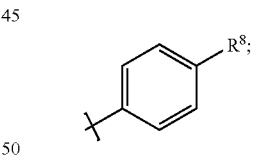

and $R^8$ is selected from methyl-(3,3,3-trifluoro-propyl)-amino-methyl-, 2-hydroxy-3-methoxy-propoxy-, methoxy-, 3-hydroxy-2-hydroxymethyl-propoxy-, 1-(dimethylamino-carbonyl-methylamino)-ethyl-, 1-[(methoxycarbonyl)-methylamino]-ethyl-, 3-hydroxy-2-hydroxymethyl-propoxy-, 2,3-dihydroxypropoxy-, (S)-4-methoxy-2-oxo-pyrrolidin-1-yl-, 2-methoxyethoxy-carbonylaminomethyl-, methanesulfonyl-N-methylamino-methyl-, 4,5-dihydro-oxazol-2-yl-, 2-oxo-pyrrolidin-1-yl-, 2-[(2-hydroxy-ethyl)-methylamino]-ethoxy-, 3-hydroxy-2-oxo-pyrrolidin-1-yl-, 2-methylamino-ethyl-, (S)-4-hydroxy-2-oxo-pyrrolidin-1-yl-, 2-(N-ethyl-N-methyl-amino)-ethoxy-, 1-(methanesulfonyl-N-methylamino)-ethyl-, 2-(N-ethyl-N-methylamino)-ethyl-, 2-methylamino-ethoxy-, ethyl-(2-hydroxyethyl)-amino-methyl-, 2-hydroxyethoxy-, ethyl-(2-methoxyethyl)-aminomethyl-, 2-hydroxy-ethyl-methylamino-methyl-, 3-methoxy-pyrrolidin-1-ylmethyl-, N-ethyl-N-methylamino-methyl-, 2-methoxyethy-laminomethyl-, 4-hydroxy-piperidin-1-ylmethyl-, hydroxy-pyrrolidin-1-ylmethyl-, aminomethyl-, ethylamino-methyl-, 3-dimethylamino-propoxy-, pyrrolidin-1-ylmethyl-, azetidin-1-ylmethyl-, 1,3-dimethyl-imidazolidin-2-ylideneamino)-, 1-(methylamino-methyl-carbonyl-methylamino)-ethyl-, N,N-dimethylacetamidinyl-, 1-[(2-methoxyethyl)-methylamino]-ethyl-, methylamino-methyl-, dimethylamino-methyl-, 3,4-dimethylimidazoline-2,4-dione-1-yl-, 3-methylimidazoline-2,4-dione-1-yl)-, 1-dimethylamino-ethyl-, 1-methylamino-ethyl-, cyclopropylamino-methyl-, isopropylamino-methyl-, N-methyl-N-propylamino-methyl-, methylamino-methyl-, N-ethyl-N-methyl-amino-methyl-, 3-methyl-2-oxo-pyrrolidin-1-yl-, 2-oxo-imidazolidin-1-yl-, 2-methoxyethyl-amino-methyl-, 1-methyl-piperidin-4-yl-, pyrrolidin-1-yl-, 4-methyl-piperazin-1-yl-, 4-methyl-piperazin-1-yl-, N,N-dimethyl-formamidinyl)-, methyl-, 4,5-dihydro-3H-pyrrol-2-ylamino-, acetamidinyl-, 4,5-Dihydro-1H-imidazol-2-ylamino)-, 4,4-dimethyl-4,5-dihydro-imidazol-1-yl)-, pyrimidin-2-ylamino-, (1H-Imidazol-2-ylmethyl)-amino-, amino-, cyano-, bromo-, fluoro, methylamino-, methylaminomethyl-, aminomethyl-, cyanomethyl-, hydroxymethyl-, morpholin-4-ylmethyl-, ethylaminomethyl-, (2,2,2-trifluoro-ethylamino)-methyl-, [(2-hydroxy-ethyl)-methylamino]-methyl-, [(2-methoxy-ethyl)-methylamino]-methyl-, [ethyl-(2-methoxy-ethyl)-amino]-methyl-, methoxymethylcarbonyl-N-methylaminomethyl-, 1-methyl-4,5-dihydro-1H-imidazol-2-ylmethyl-, 1-isopropyl-4,5-dihydro-1H-imidazol-2-ylmethyl-, 1-methyl-piperidin-4-ylmethyl-, methanesulfonyl-, dimethylaminosulfonyl-, 2-methoxyethylaminosulfonyl-, 3-methoxypropylaminosulfonyl-, carboxy-, methyamino-carbonyl-, 2-dimethylamino-ethyl)-aminocarbonyl-, 2-dimethylaminoethyl-methylaminocarbonyl-, 3-dimethylaminopropyl-ethylaminocarbonyl-, 2-hydroxyethylaminocarbonyl-, 2-hydroxypropylaminocarbonyl-, 2-hydroxyethyl-methylaminocarbonyl-, 2-methoxyethylaminocarbonyl-, 3-methoxypropylaminocarbonyl-, cyanomethylaminocarbonyl-, tetrahydrofuran-2-ylmethylaminocarbonyl-, furan-2-ylmethylaminocarbonyl-, (2-morpholin-4-yl)-ethylaminocarbonyl-, (4-hydroxymethyl)-piperidin-1-ylaminocarbonyl-, 2-hydroxyethoxy-, methanesulfinylmethoxy-, pyrimidin-2-yloxy-, hydroxy-, methanesulfonylmethoxy-, carboxymethoxy-, 2-methoxy-ethoxy-, 3-methoxy-propyloxy-, 2-dimethylamino-ethoxy-, 2-ethylamino-ethoxy-, methanesulfonylamino-, dimethylaminosulfonylamino-, dimethylaminosulfonyl-N-methylamino-, methylcarbonylamino-, chloro-, dimethylaminocarbonylamino-, methoxycarbonylamino-, methoxycarbonyl-carbonyl-methylamino-, methoxyaminocarbonylamino-(183), 2-hydroxyethylamino-, 3-hydroxypropyl-methylamino-, 3-hydroxypropyl-amino-, 2-methoxyethyl)-amino-, 2-methoxyethyl)-methylamino-, 3-hydroxypropyl)-methylamino-, (3-methoxypropyl)-amino-, 3-methoxypropyl)-methylamino-, bis-(2-hydroxyethyl)-amino-, (2-methylcarbonylamino)-ethylamino-, acetamidinyl-, N,N'-dimethylacetamidinyl-, N-methylacetamidinyl-, N,N-dimethylaminoformamidyl-, N,N-dimethylaminoisobutyramidinyl-, N,N-dimethylamino-(3-methoxy)-propionamidyl-, N,N-dimethylcyclobutane-carboxamidinyl-, imidazolidin-2-ylideneamino-, 1-methyl-pyrrolidin-(2Z)-ylideneamino-, 2-oxo-tetrahydro-furan-3-ylamino-, (4,5-Dihydro-3H-pyrrol-2-yl)-methyl-amino-, 2-chloro-pyrimidin-4-ylamino-, 4-chloro-pyrimidin-2-ylamino-, 2-chloro-5-methyl-pyrimidin-4-ylamino-, 2-oxo-pyrrolidin-1-yl-, 1-methyl-4,5-dihydro-1H-imidazol-2-yl-, 2-methyl-4,5-dihydro-imidazol-1-yl-, 4,4-dimethyl-4,5-dihydro-imidazol-1-yl-, 2,4,4-trimethyl-4,5-dihydro-imidazol-1-yl-, 4-methyl-imidazol-1-yl-, 4-methyl-imidazol-1-yl-, 2-methyl-imidazol-1-yl-, pyrazol-1-yl-, 3-methyl-pyrazol-1-yl-, 3,5-Dimethyl-pyrazol-1-yl-, pyrrolidin-2-yl-, pyrrolidin-3-yl-, 1-methyl-4,5-dihydro-1H-imidazol-2-yl-, 1-ethyl-4,5-dihydro-1H-imidazol-2-yl-, 1-isopropyl-4,5-dihydro-1H-imidazol-2-yl-, 1-isopropyl-4,5-dihydro-1H-imidazol-2-yl-, 1-(2-hydroxy-ethyl)-4,5-dihydro-1H-imidazol-2-yl-, 1-(2-methoxy-ethyl)-4,5-dihydro-1H-imidazol-2-yl-, 1H-Imidazol-2-yl-, 1-methyl-1H-imidazol-2-yl, 1-(2-hydroxy-ethyl)-1H-imidazol-2-yl-, 1,1-Dioxo-1λ6-isothiazolidin-2-yl-, 2-oxo-oxazolidin-3-yl-, 3-methyl-2-oxo-pyrrolidin-1-yl-, ethyl-2-oxo-pyrrolidin-1-yl)-, pyrrolidine-2,5-dione-1-yl-, 2-oxo-imidazolidin-1-yl-, 3-methyl-2-oxo-imidazolidin-1-yl-, 3-ethyl-2-oxo-imidazolidin-1-yl-, 3-(2-methoxyethyl)-2-oxo-imidazolidin-1-yl-, 1H-tetrazol-5-yl-, ethoxy-, 1-pyrrolidin-1-yl-ethyl-, 1-Azetidin-1-yl-ethyl-, aminosulfonyl-, N,N-dimethylamino-acetamidinesulfonyl-, and 1-methanesulfonyl-methylamino)-ethyl-.

9. A pharmaceutical composition comprising a therapeutically effective amount of at least one compound of claim 5 and at least one pharmaceutically acceptable carrier.

10. A pharmaceutical composition comprising a therapeutically effective amount of at least one compound of claim 8 and at least one pharmaceutically acceptable carrier.

11. The compound of claim 5, wherein m is 0 or 1.

* * * * *